(12) United States Patent
Buettelmann et al.

(10) Patent No.: US 10,618,897 B2
(45) Date of Patent: Apr. 14, 2020

(54) SPIROINDOLINONES AS DDR1 INHIBITORS

(71) Applicant: Hoffmann-La Roche Inc., Little Falls, NJ (US)

(72) Inventors: Bernd Buettelmann, Basel (CH); Buelent Kocer, Basel (CH); Bernd Kuhn, Basel (CH); Marco Prunotto, Basel (CH); Hans Richter, Basel (CH); Martin Ritter, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/057,436

(22) Filed: Aug. 7, 2018

(65) Prior Publication Data

US 2019/0071444 A1 Mar. 7, 2019

Related U.S. Application Data

(63) Continuation of application No. PCT/EP2017/052489, filed on Feb. 6, 2017.

(30) Foreign Application Priority Data

Feb. 8, 2016 (EP) ..................... 16154716

(51) Int. Cl.
  *C07D 471/10* (2006.01)
  *C07D 487/10* (2006.01)
  *C07D 519/00* (2006.01)

(52) U.S. Cl.
  CPC ......... *C07D 471/10* (2013.01); *C07D 487/10* (2013.01); *C07D 519/00* (2013.01)

(58) Field of Classification Search
  CPC ... C07D 471/10; C07D 487/10; C07D 519/00
  USPC ...................................... 514/234.5
  See application file for complete search history.

(56) References Cited

U.S. PATENT DOCUMENTS

| | | | |
|---|---|---|---|
| 3,839,340 A | 10/1974 | Scharpf et al. | |
| 3,839,342 A | 10/1974 | Scharpf et al. | |
| 4,329,353 A | 5/1982 | Stokbroekx et al. | |
| 5,635,510 A | 6/1997 | Burkholder et al. | |
| 2014/0371219 A1 | 12/2014 | Bae et al. | |
| 2015/0152047 A1 | 6/2015 | Murata et al. | |
| 2018/0148450 A1 | 5/2018 | Buettelmann et al. | |
| 2019/0071444 A1 | 3/2019 | Buettelmann et al. | |

FOREIGN PATENT DOCUMENTS

| | | |
|---|---|---|
| EP | 0 921 125 A1 | 6/1999 |
| EP | 1 329 451 A1 | 7/2003 |
| WO | 99/65494 A1 | 12/1999 |
| WO | 01/94346 | 12/2001 |
| WO | 01 94346 A1 | 12/2001 |
| WO | 2007/039438 A1 | 4/2007 |
| WO | 2010/037081 A1 | 4/2010 |
| WO | 2011/160084 A1 | 12/2011 |
| WO | WO-2014060411 A1 * | 4/2014 |
| WO | 2017/005583 | 1/2017 |
| WO | 2017/137334 | 8/2017 |

OTHER PUBLICATIONS (ISR and WO for PCTEP2017/052489), 2017.
EMBL Database, 97504014, Dec. 11, 2015.
ISR and Written Opinion of PCT/EP2016/065231, dated as of actual completion of the international search dated Aug. 1, 2016.
NCBI Database, 69162822, Nov. 30, 2012.
NCBI Database, 97400085, Dec. 11, 2015.
NCBI Database, 97400124, Dec. 11, 2015.
NCBI Database, 97400131, Dec. 11, 2015.
NCBI Database, 97412879, Dec. 11, 2015.
NCBI Database, 97452620, Dec. 11, 2015.
NCBI Database, 97504009, Dec. 11, 2015.
NCBI Database, 97504034, Dec. 11, 2015.
NCBI Database, 97504035, Dec. 11, 2015.
NCBI Database, 97504036, Dec. 11, 2015.
NCBI Database, 97504037, Dec. 11, 2015.
NCBI Database, 97504038, Dec. 11, 2015.
NCBI Database, 97504040, Dec. 11, 2015.
Petr Vachal et al., "1,3,8-Triazaspiro (4.5)decane-2,4-diones as Efficacious Pan-Inhibitors of Hypoxia-Inducible Factor Prolyl Hydroxylase 1-3 (HIF PHD1-3) for the Treatment of Anemia" Journal of Medicinal Chemistry 55(7):2945-2959 (Apr. 12, 2012).

* cited by examiner

*Primary Examiner* — Kristin A Vajda
(74) *Attorney, Agent, or Firm* — Todd M. Crissey

(57) ABSTRACT

The present invention relates to compounds of formula (I):

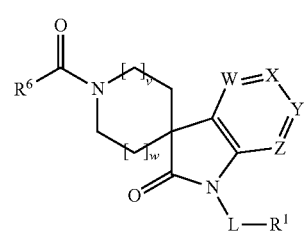

(I)

or pharmaceutically acceptable salts thereof, as well as processes for their manufacture, pharmaceutical compositions comprising them, and their use as medicaments.

34 Claims, No Drawings

SPIROINDOLINONES AS DDR1 INHIBITORS

CROSS-REFERENCE TO RELATED APPLICATIONS

This application is a Continuation of International Application No. PCT/EP2017/052489, filed Feb. 6, 2017, claiming priority to EP Application No. 16154716.1, filed Feb. 8, 2016, each of which are incorporated herein by reference in its entirety.

The present invention relates to a compound of formula (I):

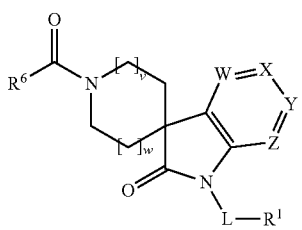

or a pharmaceutically acceptable salt thereof, wherein L, W, X, Y, Z, v, w, $R^1$ and $R^6$ are as described herein, as well as processes for their manufacture, pharmaceutical compositions comprising them, and their use as medicaments.

BACKGROUND OF THE INVENTION

Discoidin Domain Receptors (DDRs) are type I transmembrane glycoproteins, which are represented by two receptors DDR1 and DDR2. DDR1 is mainly expressed in epithelial cells and DDR2 in stroma. The DDR1 subfamily includes five isoforms generated by alternative splicing with DDR1a and DDR1b as the most common isoforms and DDR1d and DDR1e being either truncated or inactive kinases, respectively. A single protein represents the DDR2 subtype. DDR1 is a collagen-activated receptor tyrosine kinase (RTK). DDR1 is widely expressed during embryonic development and in adult tissues, particularly in epithelia of skin, lung, liver, kidney, gut, colon and brain. Among the collagen-receptor families, the DDRs are the only RTKs that undergo autophosphorylation in response to various collagens.

Structurally, the ectodomain of DDRs is composed of a discoidin (DS) domain, a DS-like domain, and an extracellular juxtamembrane (EJXM) region, which are followed by a single-pass transmembrane segment. The intracellular portion of the receptor is composed of a relatively long intracellular juxtamembrane (IJXM) region and a C-terminal kinase domain (KD). DDRs display an atypical activation kinetics manifested by a slow and sustained phosphorylation, which suggests a unique mechanism of receptor activation that differentiates DDRs from other members of the RTK family. DDRs initiate signaling pathways that are critical for cell-collagen interactions and thus play key roles in many physiological and pathological conditions involving collagen remodeling [Leitinger, B., *Discoidin domain receptor functions in physiological and pathological conditions. International review of cell and molecular biology*, 2014. 310: p. 39-87; Hohenester, E., *Signalling complexes at the cell-matrix interface. Current opinion in structural biology*, 2014. 29C: p. 10-16].

Some light on the physiological function of DDR1 can be indirectly deduced by the DDR1-knockout mouse phenotype [Vogel, W F., et al., *Discoidin domain receptor 1 tyrosine kinase has an essential role in mammary gland development. Molecular and cellular biology*, 2001. 21(8): p. 2906-17]. DDR1-knockout mice survived gestation but are smaller in size than control littermates showing defects in the development of certain organs, such as impaired mammary gland development, poorly calcified fibula bone, and a narrower pelvis. In addition to the above defects present in DDR1-knockout mice, mutant females are unable to lactate because of the failure of alveolar epithelium to secrete milk proteins. DDR1-null female mice during pregnancy showed hyperproliferation and aberrant differentiation of lobulo-alveolar epithelial cells. At birth, the alveoli showed intracellular lipid production and deposition but failure to secrete milk into the central lumen. In the early pubertal stage, the mammary gland development defect was manifest as a delay in mammary duct outgrowth, enlargement in primary ducts, and the terminal end buds due to a marked increase in cell proliferation rate in the mutant mice. In addition, a substantial deposition of collagen was shown in and around mammary gland epithelial cells in DDR1-knockout mice.

The DDR1-knockout adult mice exhibit proteinuria and urinary acanthocytes. Results from electron microscopy demonstrate thickening of subepithelial glomerular basement membrane as well as a focal loss of the podocyte slit diaphragms. These data suggest that the loss of cell-matrix communication in DDR1-deficient podocytes appears to result in excess accumulation of basement membrane proteins, which leads to disturbed anchorage of foot processes and disruption of the slit diaphragm. In other words, the interaction between type IV collagen and DDR1 plays an important role in maintaining the structural integrity of the glomerular basement membrane [Gross, O., et al., *DDR1-deficient mice show localized subepithelial GBM thickening with focal loss of slit diaphragms and proteinuria. Kidney International*, 2004. 66(1): p. 102-11].

Despite some of the developmental defects found in DDR1-null mice, these mice have been valuable in understating the role of these receptors in various diseases, including cancer, atherosclerosis, lung and liver fibrosis, renal injury, and osteoarthritis.

Many cancers are characterized by dysregulated kinome expression and activation. DDRs play a key role in cancer progression and metastatisation processes, in part by regulating the interaction of cancer cells with collagens [Valiathan, R. R., et al., *Discoidin domain receptor tyrosine kinases: new players in cancer progression. Cancer metastasis reviews*, 2012. 3](1-2): p. 295-321]. Both DDRs are overexpressed in a large number of different types of cancer, ranging from lung, breast, brain, esophagus, head and neck, liver, and prostate cancers to lymphomas and leukemias. Dysregulated DDR expression has been shown in a number of studies to correlate with unfavorable outcomes for patients and altered functions of DDR1 and DDR2 likely contribute to tumorigenesis. Moreover, DDR1 can confer resistance to chemotherapy and mediate prosurvival signals in breast cancer and lymphoma cell lines [Cader, F. Z., et al., *The EBV oncogene LMP1 protects lymphoma cells from cell death through the collagen-mediated activation of DDR1. Blood*, 2013, 122(26): p. 4237-45; Ongusaha, P. P., et al., *p53 induction and activation of DDR1 kinase counteract p53-mediated apoptosis and influence p53 regulation through a positive feedback loop. The EMBO journal*, 2003. 22(6): p. 1289-301] and may be involved in the recurrence of certain types of cancer [Jian, Z. X., et al., *Involvement of discoidin domain 1 receptor in recurrence of hepatocellular carcinoma by genome-wide analysis. Medical oncology,* 2012. 29(5): p. 3077-82]. However, the molecular mechanisms underlying the roles of the DDRs in various steps of cancer progression are largely undefined.

Screening of non-small cell lung carcinoma (NSCLC) tissue samples showed that DDR1 is significantly upregulated in these patients and that expression of DDR1 is significantly associated with overall and disease-free survival. Multivariate analysis revealed that expression of DDR1 is independent of tumor differentiation, stage, histology, and patient age. A screening for DDR mutations revealed one polymorphism with synonymous change at S495, unlikely to be of functional importance [Ford, C. E., et al., *Expression and mutation analysis of the discoidin domain receptors 1 and 2 in non-small cell lung carcinoma. British journal of cancer,* 2007. 96(5): p. 808-14]. Other studies underlined the relevance and role of DDR1 in metastatisation process. Screening of NSCLC samples, encompassing 86 squamous cell carcinomas, 69 adenocarcinomas, and 16 pure bronchioloalveolar carcinomas (BAC), indicated that DDR1 upregulation was more frequent in invasive adenocarcinoma (64%) compared with BAC (38%; 83). In addition, DDR1 expression was significantly correlated with lymph node metastasis in invasive NSCLC. Overexpression of DDR1 in lung cancer cells resulted in a significant increase in cell motility and invasiveness, which may correlate with the induction of matrix metalloproteinase-9 [Yang, S. H., et al., *Discoidin domain receptor 1 is associated with poor prognosis of non-small cell lung carcinomas. Oncology reports,* 2010. 24(2): p. 311-9; Miao, L., et al., *Discoidin domain receptor 1 is associated with poor prognosis of non-small cell lung cancer and promotes cell invasion via epithelial-to-mesenchymal transition. Medical oncology,* 2013. 30(3): p. 626]. These results indicate that up-regulation of DDR1 may contribute to the progression and poor prognosis of certain types of NSCLC and that this effect may be attributed to increased invasiveness.

Even if not totally understood, DDR1 seems to play a central role in modulation of inflammation and fibrosis. As fibrosis is frequently the result of an earlier inflammation event, it's not clear if the main role of DDR1 resides in the direct blockage of fibrosis processes (e.g., myofibroblast activation, collagen deposition) or more in inflammation modulation. Unfortunately, in vivo experiments performed using the DDR1 null mice do not allow to untangle these two biological processes. Modulation of fibrosis and inflammation has been demonstrated in several organs, namely lung and kidney. DDR1-deficient mice show reduced bleomycin-induced pulmonary injury characterized by reduced collagen and tenascin-C levels [Avivi-Green, C., M Singal, and W. F. Vogel, *Discoidin domain receptor 1-deficient mice are resistant to bleomycin-induced lung fibrosis. American journal of respiratory and critical care medicine,* 2006. 174(4): p. 420-7]. Authors reported two possible reasons for the decreased fibrotic response in DDR1-null mice are decreased inflammation, with reduced CD3-positive lymphocytes and F4/80-positive cells infiltrating the lungs, and decreased activation of the p38 MAPK, a kinase involved in lung fibrosis. In kidney, DDR1 expression is elevated in patients with lupus nephritis and Goodpasture's syndrome as well as in a mouse model of crescentic glomerulonephritis [Kerroch, M., et al., *Genetic inhibition of discoidin domain receptor 1 protects mice against crescentic glomerulonephritis. FASEB journal: official publication of the Federation of American Societies for Experimental Biology,* 2012. 26(10): p. 4079-91]. Similarly, DDR1 expression increases in the glomeruli of rats that have undergone partial renal ablation [Lee, R., et al., *Localization of discoidin domain receptors in rat kidney. Nephron Exp Nephrol,* 2004. 97(2): p. e62-70] and in tubules of mice that have undergone unilateral ureteral obstruction [Guerrot, D., et al., *Discoidin domain receptor 1 is a major mediator of inflammation and fibrosis in obstructive nephropathy. Am J Pathol,* 2011. 179(1): p. 83-91]. Use of DDR1-null mice in several mouse models of kidney injury showed that compared to wild type mice DDR1-null mice have improved renal function, reduced fibrosis and reduced inflammation. In this context, DDR1-null mice are protected from angiotensin II-mediated proteinuria, glomerular fibrosis, and inflammation, and show reduced collagen deposition, tubular macrophage infiltration and pro-inflammatory cytokine levels following unilateral ureteral obstruction. Moreover, COL4A3 KO mice, the mouse model for human Alport syndrome, crossed onto the DDR1-null mice have reduced renal fibrosis and inflammation due to reduced TGF-β-mediated signaling and reduced levels of the pro-inflammatory cytokine IL6 [Gross, O., et al., *Loss of collagen-receptor DDR1 delays renal fibrosis in hereditary type IV collagen disease. Matrix Biol.* 29(5): p. 346-56]. Finally, DDR1-null mice have increased survival and improved renal function in a model of crescentic glomerulonephritis induced by injection of alloimmune sheep nephrotoxic serum. In that respect, finding that older DDR1-null mice show focal swelling of the glomerular basement membrane (GBM) and mild proteinuria [Gross, O., et al., *DDR1-deficient mice show localized subepithelial GBM thickening with focal loss of slit diaphragms and proteinuria. Kidney Int.,* 2004. 66(1): p. 102-11] suggests that DDR1 might play a very different role in physiological conditions. Again, as we mentioned before in the case of the lung fibrosis, hallmark of protection conferred by DDR1 deletion in all these renal experimental studies showed reduced macrophage infiltration supporting the pro-inflammatory role of DDR1.

Despite the progress made in understanding the role of DDR1, there remains an unmet need of potent and selective compounds suitable to modulate the DDR1 receptor to treat diseases related to DDR1 overexpression. Present invention provides novel compounds which exhibit high affinity and selectivity to the DDR1 receptor and are thus suitable for the treatment or prevention of diseases related to DDR1 upregulation.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this Application is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

The definitions described herein apply irrespective of whether the terms in question appear alone or in combination. It is contemplated that the definitions described herein can be appended to form chemically-relevant combinations, such as e.g. "heterocycloalkylaryl", "haloalkylheteroaryl", "arylalkylheterocycloalkyl", or "alkoxyalkyl". The last member of the combination is the radical which is binding to the rest of the molecule. The other members of the combination are attached to the binding radical in reversed order in respect of the literal sequence, e.g. the combination arylalkylheterocycloalkyl refers to a heterocycloalkyl-radical which is substituted by an alkyl which is substituted by an aryl.

The term "moiety" refers to an atom or group of chemically bonded atoms that is attached to another atom or molecule by one or more chemical bonds thereby forming part of a molecule. For example, the variables $R^1$, $R^2$ and $R^3$ of formula (I) refer to moieties that are attached to the core structure of formula I by a covalent bond.

When indicating the number of substituents, the term "one or more" refers to the range from one substituent to the highest possible number of substitution, i.e. replacement of one hydrogen up to replacement of all hydrogens by substituents.

The term "optional" or "optionally" denotes that a subsequently described event or circumstance can but need not occur, and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "compound(s) of this invention" and "compound(s) of the present invention" refers to compounds as disclosed herein and stereoisomers, tautomers, solvates, and salts (e.g., pharmaceutically acceptable salts) thereof.

When the compounds of the invention are solids, it is understood by those skilled in the art that these compounds, and their solvates and salts, may exist in different solid forms, particularly different crystal forms, all of which are intended to be within the scope of the present invention and specified formulas.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog. (Cahn et al. Angew. Chem. Inter. Edit. 1966, 5, 385; errata 511). The prefixes D and L or (+) and (–) are employed to designate the sign of rotation of plane-polarized light by the compound, with (–) or L designating that the compound is levorotatory. A compound prefixed with (+) or D is dextrorotatory.

The term "halo", "halogen", and "halide" are used interchangeably herein and denote fluoro, chloro, bromo, or iodo, particularly fluoro, chloro or bromo, most particularly fluoro.

The term "hydrogen" and "hydro" are used interchangeably to denote a hydrogen radical (—H).

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl. Particular examples of alkyl are methyl, ethyl, iso-propyl and tert-butyl.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms. Particular examples of haloalkyl are trifluoro-methyl and trifluoro-ethyl.

The term "alkoxy" denotes a group of the formula —O—R', wherein R' is an alkyl group.

Examples of alkoxy moieties include methoxy, ethoxy, isopropoxy, and tert-butoxy. Particular alkoxy is methoxy.

The term "alkylene" denotes a linear saturated divalent hydrocarbon group of 1 to 7 carbon atoms or a divalent branched saturated divalent hydrocarbon group of 3 to 7 carbon atoms.

Examples of alkylene groups include methylene, ethylene, propylene, 2-methylpropylene, butylene, 2-ethylbutylene, pentylene, hexylene. Particular alkylene is ethylene.

The term "annelated" denotes the attachment of a further ring to an existing ring via a common single or double bond, i.e. both rings share one single or double bond.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl. Particular examples of cycloalkyl are cyclopropyl, cyclopentyl and cyclohexyl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Particular examples for heterocycloalkyl are azetidinyl, oxetanyl, pyrrolidinyl, piperidinyl, piperazinyl, morpholinyl, 3-oxa-8-azabicyclo[3.2.1]octanyl, 3,3a,4,5,6,6a-hexahydro-2H-cyclopenta[b]pyrrolyl, octahydro-cyclopenta[b]pyrrolyl, octahydro-cyclopenta[c]pyrrolyl, hexahydro-furo[3,4-b]pyrrolyl, hexahydro-furo[3,4-c]pyrrolyl, hexahydro-furo[2,3-c]pyrrolyl, octahydro-pyrrolo[1,2-a]pyrazinyl, 4-oxa-7-aza-spiro[2.5]octanyl, and 2-oxa-6-aza-spiro[3.5]nonanyl.

Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Particular examples of monocyclic saturated heterocycloalkyl are azetidinyl, oxetanyl, pyrrolidinyl, piperidinyl, piperazinyl, and morpholinyl.

Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Particular examples of for bicyclic saturated heterocycloalkyl are 3-oxa-8-azabicyclo[3.2.1]octanyl, 3,3a,4,5,6,6a-hexahydro-2H-cyclopenta[b]pyrrolyl, octahydro-cyclopenta[b]pyrrolyl, octahydro-cyclopenta[c]pyrrolyl, hexahydro-furo[3,4-b]pyrrolyl, hexahydro-furo[3,4-c]pyrrolyl, hexahydro-furo[2,3-c]pyrrolyl, octahydro-pyrrolo[1,2-a]pyrazinyl, 4-oxa-7-aza-spiro[2.5]octanyl, and 2-oxa-6-aza-spiro[3.5]nonanyl. Examples for partly unsaturated heterocycloalkyl are dihydrofuryl, imidazolinyl, dihydro-oxazolyl, tetrahydro-pyridinyl, or dihydropyranyl.

The term "heterocycloalkyl bound via C-atom" denotes a heterocycloalkyl as described herein which is linked to the rest of the molecule via a C ring atom and not via a ring heteroatom.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "aryl" denotes a monovalent aromatic carbocyclic mono- or bicyclic ring system comprising 6 to 10 carbon ring atoms. Examples of aryl moieties include phenyl and naphthyl, most particularly phenyl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

Particular examples for heteroaryl are oxadiazolyl, pyridinyl, indazolyl, pyrazolo[3,4-b]pyridinyl, pyrazolo[3,4-c]pyridinyl, and pyrazolo[4,3-b]pyridinyl.

Particular examples for monocyclic heteroaryl are oxadiazolyl and pyridinyl.

Particular examples for bicyclic heteroaryl are indazolyl, pyrazolo[3,4-b]pyridinyl, pyrazolo[3,4-c]pyridinyl, and pyrazolo[4,3-b]pyridinyl.

The term "aryl annelated to cycloalkyl" denotes an aryl as defined herein and a cycloalkyl as defined herein which are annelated together sharing two adjacent ring atoms. Examples of aryl annelated to heterocycloalkyl include 2,3-dihydro-1H-inden-1-yl and 1,2,3,4-tetrahydronaphthalen-1-yl.

The term "aryl annelated to heterocycloalkyl" denotes an aryl as defined herein and a heterocycloalkyl as defined herein which are annelated together sharing two adjacent ring atoms.

Examples of aryl annelated to heterocycloalkyl include benzodioxolyl particularly 2H-benzo[b][1,4]oxazin-4(3H)-yl and 3,4-Dihydro-2H-benzo[1,4]oxazinyl.

The term "heteroaryl annelated to heterocycloalkyl" denotes an heteroaryl as defined herein and a heterocycloalkyl as defined herein which are annelated together sharing two adjacent ring atoms. Examples of aryl annelated to heterocycloalkyl include 4,5,6,7-tetrahydro-1H-pyrrolo[3,2-c]pyridinyl.

The term "amino" denotes a group of the formula —NR'R" wherein R' and R" are independently hydrogen, alkyl, alkoxy, cycloalkyl, haloalkyl, heterocycloalkyl, aryl or heteroaryl. Alternatively, R' and R", together with the nitrogen to which they are attached, can form a heterocycloalkyl. The term "primary amino" denotes a group wherein both R' and R" are hydrogen. The term "secondary amino" denotes a group wherein R' is hydrogen and R" is not. The term "tertiary amino" denotes a group wherein both R' and R" are not hydrogen. Particular secondary and tertiary amines are methylamine, ethylamine, propylamine, isopropylamine, phenylamine, benzylamine, dimethylamine, diethylamine, dipropylamine and diisopropylamine. Most particular example for amino is dimethylamine.

The term "oxo" denotes a divalent oxygen atom =O.

The term "carbonyl" denotes a —C(O)— group.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups.

The term "amino-protecting group" denotes groups intended to protect an amino group and includes benzyl, benzyloxycarbonyl (carbobenzyloxy, CBZ), Fmoc (9-Fluorenylmethyloxycarbonyl), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting groups.

The term "carboxy-protecting group" denotes groups intended to protect a carboxy group and includes ester groups and heterocycloalkyl groups. Examples of such ester groups include substituted arylalkyl esters, including esters with substituted benzyls, such as 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, esters with alkyl or substituted alkyl such as methyl, ethyl, t-butyl allyl or t-amyl, triphenylmethyl (trityl), 4-methoxytrityl, 4,4'-dimethoxytrityl, 4,4',4"-trimethoxytrityl, 2-phenylprop-2-yl, thioesters such as t-butyl thioester, silyl esters such as trimethylsilyl, t-butyldimethylsilyl esters, phenacyl, 2,2,2-trichloroethyl, beta-(trimethylsilyl)ethyl, beta-(di(n-butyl)methylsilyl)ethyl, p-toluenesulfonylethyl, 4-nitrob enzyl sulfonylethyl, allyl, cinnamyl, and 1-(trimethylsilylmethyl)prop-1-en-3-yl. Another example of carboxy-protecting groups are heterocycloalkyl groups such as 1,3-oxazolinyl. Further examples of these groups are found in T. W. Greene and P. G. M. Wuts, "Protective Groups in Organic Synthesis", 2nd ed., John Wiley & Sons, Inc., New York, N.Y., 1991, chapter 5; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy group" denotes a carboxy group substituted by a carboxy-protecting group.

The term "deprotection" or "deprotecting" denotes the process by which a protective group is removed after the selective reaction is completed. Deprotecting reagents include acids, bases or hydrogen, in particular potassium or sodium carbonates, lithium hydroxide in alcoholic solutions, zinc in methanol, acetic acid, trifluoroacetic acid, palladium catalysts, or boron tribromide.

The term "leaving group" denotes the group with the meaning conventionally associated with it in synthetic organic chemistry, i.e., an atom or group displaceable under substitution reaction conditions. Examples of leaving groups include halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, and acyloxy.

The term "active pharmaceutical ingredient" (or "API") denotes the compound or molecule in a pharmaceutical composition that has a particular biological activity.

The terms "pharmaceutical composition" and "pharmaceutical formulation" (or "formulation") are used interchangeably and denote a mixture or solution comprising a therapeutically effective amount of an active pharmaceutical ingredient together with pharmaceutically acceptable excipients to be administered to a mammal, e.g., a human in need thereof.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "half maximal inhibitory concentration" (IC50) denotes the concentration of a particular compound or molecule required for obtaining 50% inhibition of a biological process in vitro. IC50 values can be converted logarithmically to pIC50 values (−log IC50), in which higher values indicate exponentially greater potency. The IC50 value is not an absolute value but depends on experimental conditions e.g. concentrations employed. The IC50 value can be converted to an absolute inhibition constant (Ki) using the Cheng-Prusoff equation (Biochem. Pharmacol. (1973) 22:3099).

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "treating" or "treatment" of a disease state includes inhibiting the disease state, i.e., arresting the development of the disease state or its clinical symptoms, or relieving the disease state, i.e., causing temporary or permanent regression of the disease state or its clinical symptoms.

The term "preventing" or "prevention" of a disease state denotes causing the clinical symptoms of the disease state not to develop in a subject that can be exposed to or predisposed to the disease state, but does not yet experience or display symptoms of the disease state.

In detail, the present invention relates to a compound of formula (I)

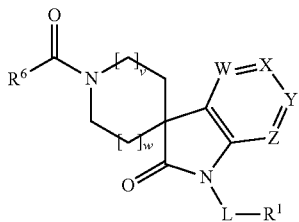

wherein
W is $CHR^2$ or N;
X is $CHR^3$ or N;
Y is $CHR^4$ or N;
Z is $CHR^5$ or N;
with the proviso that not more than two of W, X, Y and Z are N,
L is $-(CHR^7)_m-(CHR^8)_n-(CO)_q-$;
$R^1$ is $-NR^9R^{10}$, aryl, heteroaryl, $C_{3-7}$ cycloalkyl, heterocycloalkyl, aryl annelated to cycloalkyl, aryl annelated to heterocycloalkyl, or heteroaryl annelated to heterocycloalkyl, wherein each of aryl, heteroaryl, $C_{3-7}$ cycloalkyl and heterocycloalkyl are optionally substituted with one or more $R^{1'}$;
each $R^{1'}$ is independently selected from halogen, cyano, $C_{1-7}$ alkyl, halo-$C_{1-7}$ alkyl, $C_{3-7}$ cycloalkyl, $C_{3-7}$ cycloalkyl-$C_{1-7}$ alkyl, heterocycloalkyl, heterocycloalkyl-$C_{1-7}$ alkyl, phenyl, benzyl, heteroaryl, amino, hydroxy, $C_{1-7}$ alkoxy, halo-$C_{1-7}$ alkoxy, $C_{1-7}$ alkoxy-$C_{1-7}$ alkyl, oxo, $-CH_2-OR^{11}$, $-C(O)-OR^{11}$, and $-C(O)-NHR^{11}$;
or if $R^1$ is $C_{3-7}$ cycloalkyl or heterocycloalkyl then two $R^1$ together are forming $-(CR^{12}R^{13})_s-$ or $-(CR^{12}R^{13})_t-O-(CR^{14}R^{15})_u-$;
$R^2$ is hydrogen, halogen, cyano, $C_{1-7}$ alkyl, halo-$C_{1-7}$ alkyl, hydroxy-$C_{1-7}$ alkyl, $C_{3-7}$ cycloalkyl, $C_{3-7}$ cycloalkyl-$C_{1-7}$ alkyl, amino, hydroxy, $C_{1-7}$ alkoxy, halo-$C_{1-7}$ alkoxy, $C_{1-7}$ alkoxy-$C_{1-7}$ alkyl, $-C(O)-C_{1-7}$ alkoxy or $-C(O)$-amino;
$R^3$ is hydrogen, halogen, cyano, $C_{1-7}$ alkyl, halo-$C_{1-7}$ alkyl, hydroxy-$C_{1-7}$ alkyl, $C_{3-7}$ cycloalkyl, $C_{3-7}$ cycloalkyl-$C_{1-7}$ alkyl, amino, hydroxy, $C_{1-7}$ alkoxy, halo-$C_{1-7}$ alkoxy, $C_{1-7}$ alkoxy-$C_{1-7}$ alkyl, $-C(O)-C_{1-7}$ alkoxy or $-C(O)$-amino;
$R^4$ is hydrogen, halogen, cyano, $C_{1-7}$ alkyl, halo-$C_{1-7}$ alkyl, hydroxy-$C_{1-7}$ alkyl, $C_{3-7}$ cycloalkyl, $C_{3-7}$ cycloalkyl-$C_{1-7}$ alkyl, amino, hydroxy, $C_{1-7}$ alkoxy, halo-$C_{1-7}$ alkoxy, $C_{1-7}$ alkoxy-$C_{1-7}$ alkyl, $-C(O)-C_{1-7}$ alkoxy or $-C(O)$-amino;
$R^5$ is hydrogen, halogen, cyano, $C_{1-7}$ alkyl, halo-$C_{1-7}$ alkyl, hydroxy-$C_{1-7}$ alkyl, $C_{3-7}$ cycloalkyl, $C_{3-7}$ cycloalkyl-$C_{1-7}$ alkyl, amino, hydroxy, $C_{1-7}$ alkoxy, halo-$C_{1-7}$ alkoxy, $C_{1-7}$ alkoxy-$C_{1-7}$ alkyl, $-C(O)-C_{1-7}$ alkoxy or $-C(O)$-amino;
$R^6$ is mono- or bicyclic heteroaryl comprising 2 to 5 heteroatoms selected from N, O or S, wherein $R^6$ is optionally substituted with one or more $R^{6'}$;
each $R^{6'}$ is independently selected from halogen, cyano, $C_{1-7}$ alkyl, halo-$C_{1-7}$ alkyl, $C_{3-7}$ cycloalkyl, amino, hydroxy, $C_{1-7}$ alkoxy, $-C(O)OH$, $-C(O)OCH_3$ and $-C(O)NH_2$;
$R^7$ is hydrogen, $C_{1-7}$ alkyl, hydroxy-$C_{1-7}$ alkyl, $C_{1-7}$ alkoxy-$C_{1-7}$ alkyl, halo-$C_{1-7}$ alkoxy-$C_{1-7}$ alkyl, $-(CH_2)_r$-phenyl, $-(CH_2)_r$-heteroaryl, $-(CH_2)_x-NR^{16}R^{17}$ or $R^7$ is forming $C_{1-7}$ alkylene with $R^{10}$;
$R^8$ is hydrogen, $C_{1-7}$ alkyl, or halo-$C_{1-7}$ alkyl;
$R^9$ is, $C_{1-7}$ alkyl, $C_{3-7}$ cycloalkyl, heterocycloalkyl, heterocycloalkyl-$C_{1-7}$ alkyl, aryl, aryl annelated to $C_{5-6}$ cycloalkyl, heteroaryl, or $-CH_2-CH_2-N^{18}R^{19}$, wherein $C_{1-7}$ alkyl, is optionally substituted with one or more $R^{9'}$, and wherein $C_{3-7}$ cycloalkyl, heterocycloalkyl, aryl annelated to $C_{5-6}$ cycloalkyl, aryl, benzyl, and heteroaryl are optionally substituted with one or more $R^{9''}$;
each $R^{9'}$ is independently selected from halogen, cyano, amino, hydroxy, $C_{1-7}$ alkoxy, $C_{1-7}$ alkyl, halo-$C_{1-7}$ alkoxy, $C_{3-7}$ cycloalkyl, halo-$C_{37}$ cycloalkyl, heterocycloalkyl, phenyl, and heteroaryl;
each $R^{9''}$ is independently selected from halogen, cyano, $C_{1-7}$ alkyl, halo-$C_{1-7}$ alkyl, $C_{3-7}$ cycloalkyl, amino, hydroxy, $C_{1-7}$ alkoxy, halo-$C_{1-7}$ alkoxy, $C_{1-7}$ alkoxy-$C_{1-7}$ alkyl, oxo, $-CH_2-C(O)-NHC_{1-7}$ alkyl, heterocycloalkyl, phenyl, benzyl, heteroaryl and $C_{1-7}$ alkyl-heteroaryl;
$R^{10}$ is hydrogen, $C_{1-7}$ alkyl, $C_{3-7}$ cycloalkyl, halo-$C_{1-7}$ alkyl, or $R^{10}$ is forming $C_{1-7}$ alkylene with $R^7$;
$R^{11}$ is hydrogen, $C_{1-7}$ alkyl, halo-$C_{1-7}$ alkyl, $C_{3-7}$ cycloalkyl, or heterocycloalkyl bound via C-atom;
$R^{12}$, $R^{13}$, $R^{14}$ and $R^{15}$ are each independently selected from hydrogen, halogen and $C_{1-7}$ alkyl;
$R^{16}$ and $R^{17}$ are independently selected from hydrogen and $C_{1-7}$ alkyl or $R^{16}$ and $R^{17}$ together with the nitrogen to which they are bound form heterocycloalkyl optionally substituted by $R^{21}$;
$R^{18}$ and $R^{19}$ are independently selected from hydrogen and $C_{1-7}$ alkyl or $R^{18}$ and $R^{19}$ together with the nitrogen to which they are bound form heterocycloalkyl;
$R^{21}$ is $C_{1-7}$alkyl, $C_{3-7}$ cycloalkyl, halo-$C_{1-7}$ alkyl;
m is 0, 1 or 2;
n is 0, 1 or 2;
q is 0 or 1;
r is 0, 1 or 2;
s is 2, 3 or 4;
t is 1 or 2;
u is 1 or 2;
v is 0 or 1;
w is 0 or 1;
x is 1 or 2;
or a pharmaceutically acceptable salt thereof;
with the proviso that if m=n=q=0 then $R^1$ is not heterocycloalkyl bound via a nitrogen ring atom or $-NR^9R^{10}$;
with the proviso that if $R^1$ is heterocycloalkyl bound to L via a nitrogen ring atom or $R^1$ is $-NR^9R^{10}$ then m+n≥2 if q=0;
with the proviso that 1'-(1-methylimidazole-2-carbonyl)-1-(3-quinolyl)spiro[indoline-3,4'-piperidine]-2-one and salts thereof are excluded.

One embodiment of present invention relates to a compound of formula (I) wherein
W is $CHR^2$ or N;
X is $CHR^3$;
Y is $CHR^4$;
Z is $CHR^5$;

L is —(CHR$^7$)$_m$—(CHR$^8$)$_n$—(CO)$_q$—;
R$^1$ is —NR$^9$R$^{10}$, aryl, heteroaryl, heterocycloalkyl, aryl annelated to heterocycloalkyl or heteroaryl annelated to heterocycloalkyl, wherein each of aryl, heteroaryl and heterocycloalkyl are optionally substituted with one or more R$^{1'}$;
each R$^{1'}$ is independently selected from halogen, cyano, C$_{1-7}$ alkyl, halo-C$_{1-7}$ alkyl, C$_{3-7}$ cycloalkyl, heterocycloalkyl-C$_{1-7}$ alkyl, C$_{1-7}$ alkoxy, C$_{1-7}$ alkoxy-C$_{1-7}$ alkyl, hydroxy, oxo andamino;
R$^2$ is hydrogen, halogen, cyano, C$_{1-7}$ alkyl, halo-C$_{1-7}$ alkyl, hydroxy-C$_{1-7}$ alkyl, C$_{3-7}$ cycloalkyl, hydroxy, C$_{1-7}$ alkoxy or —C(O)—C$_{1-7}$ alkoxy;
R$^3$ is hydrogen, halogen, or C$_{1-7}$ alkoxy;
R$^4$ is hydrogen or halogen;
R$^5$ is hydrogen or halogen;
R$^6$ is bicyclic heteroaryl comprising 2 to 4 heteroatoms selected from N, wherein R$^6$ is optionally substituted by one R$^{6'}$;
R$^{6'}$ is —NH$_2$, —C(O)NH$_2$, —C(O)OH, or —C(O)OCH$_3$
R$^7$ is hydrogen or —CH$_2$-morpholinyl or R$^7$ is forming C$_{1-7}$ alkylene with R$^{10}$;
R$^8$ is hydrogen;
R$^9$ is cyano, C$_{1-7}$ alkyl, C$_{3-7}$ cycloalkyl, heterocycloalkyl, heterocycloalkyl-C$_{1-7}$ alkyl, heteroaryl or aryl annelated to C$_{5-6}$ cycloalkyl, wherein C$_{1-7}$ alkyl, is optionally substituted with one or more R$^{9'}$, and wherein C$_{3-7}$ cycloalkyl, heterocycloalkyl and aryl annelated to C$_{5-6}$ cycloalkyl are optionally substituted with one or more R$^{9''}$;
each R$^{9'}$ is independently selected from halogen, cyano and hydroxy;
each R$^{9''}$ is independently selected from halogen, C$_{1-7}$ alkyl and halo-C$_{1-7}$ alkyl;
R$^{10}$ is hydrogen or C$_{1-7}$ alkyl or R$^{10}$ is forming C$_{1-7}$ alkylene with R$^7$;
R$^{11}$ is C$_{1-7}$alkyl
m is 0 or 1;
n is 1;
q is 0 or 1;
v is 0 or 1;
w is 0 or 1;
or a pharmaceutically acceptable salt thereof;
with the proviso that if R$^1$ is heterocycloalkyl bound to L via a nitrogen ring atom or R$^1$ is —NR$^9$R$^{10}$ then m+n≥2 if q=0.

A particular embodiment of the invention relates to a compound of formula (Ia)

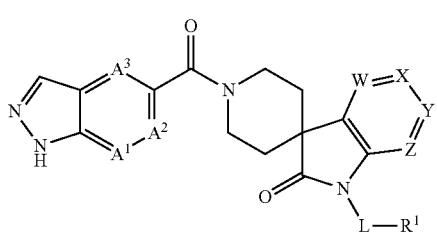

(Ia)

wherein one of A$^1$, A$^2$ and A$^3$ is N and the other two are CH; and L, R$^1$, W, X, Y and Z are as described above; or a pharmaceutically acceptable salt thereof.

A particular embodiment of the invention relates to a compound of formula (Ib)

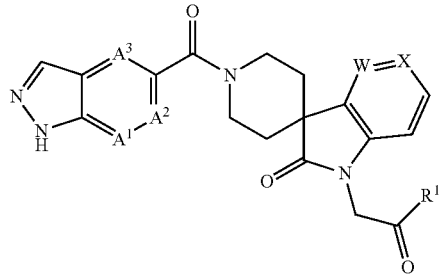

(Ib)

wherein one of A$^1$, A$^2$ and A$^3$ is N and the other two are CH; and R$^1$, W and X are as described above; or a pharmaceutically acceptable salt thereof. In a particular embodiment of the invention W is CR$^2$.

In a particular embodiment of the invention W is CR$^2$.
In a particular embodiment of the invention W is N.
In a particular embodiment of the invention X is CR$^3$.
In a particular embodiment of the invention Y is CR$^4$.
In a particular embodiment of the invention Z is CR$^5$.
In a particular embodiment of the invention L is —CH$_2$—, —CH$_2$—C(O)—, —CH(CH$_2$-morpholinyl)-C(O)—, —CH(R$^7$)—C(O)— or —CH$_2$—CH$_2$—C(O)—; wherein R$^7$ is forming ethylene with R$^{10}$.

In a particular embodiment of the invention L is —CH$_2$—, —CH$_2$—C(O)— or —CH$_2$—CH$_2$—C(O)—.

In a particular embodiment of the invention L is —CH$_2$—C(O)—.

In a particular embodiment of the invention R$^1$ is —NR$^9$R$^{10}$, aryl, heteroaryl, heterocycloalkyl, aryl annelated to heterocycloalkyl, or heteroaryl annelated to heterocycloalkyl, wherein each of aryl, heteroaryl, and heterocycloalkyl are optionally substituted with one or more R$^{1'}$.

In a particular embodiment of the invention R$^1$ is —NR$^9$R$^{10}$, phenyl, oxadiazolyl, pyridinyl, azetidinyl, pyrrolidinyl, piperidinyl, piperazinyl, morpholinyl, thiomorpholinyl, 3-oxa-8-azabicyclo[3.2.1]octanyl, hexahydrocyclopenta[b]pyrrolyl, hexahydrocyclopenta[c]pyrrolyl, hexahydropyrrolo[1,2-a]pyrazinyl, 2-azaspiro[3.3]heptanyl, 5-azaspiro[2.5]octanyl, 2-oxa-7-azaspiro[3.4]octanyl, dihydroindolyl, benzo[b][1,4]oxazinyl, dihydropyrrolo[1,2-a]pyrazinyl, or tetrahydropyrrolo[3,2-c]pyridinyl, each except —NR$^9$R$^{10}$ optionally substituted with one, two, three or four R$^{1'}$.

In a particular embodiment of the invention R$^1$ is —NR$^9$R$^{10}$, phenyl, oxadiazolyl, pyridinyl, azetidinyl, pyrrolidinyl, piperidinyl, piperazinyl, morpholinyl, thiomorpholinyl, 3-oxa-8-azabicyclo[3.2.1]octan-8-yl, hexahydrocyclopenta[b]pyrrol-1-yl, hexahydrocyclopenta[c]pyrrol-2-yl, hexahydropyrrolo[1,2-a]pyrazin-2-yl, 2-azaspiro[3.3]heptan-2-yl, 5-azaspiro[2.5]octan-5-yl, 2-oxa-7-azaspiro[3.4]octan-7-yl, dihydroindol-1-yl, benzo[b][1,4]oxazin-4(3H)-yl, dihydropyrrolo[1,2-a]pyrazin-2-yl, or tetrahydropyrrolo[3,2-c]pyridin-5-yl, each except —NR$^9$R$^{10}$ optionally substituted with one, two, three or four R$^{1'}$.

In a particular embodiment of the invention R$^1$ is —NR$^9$R$^{10}$, pyrrolidinyl, or morpholinyl, wherein pyrrolidinyl and morpholinyl are optionally substituted with one, two, three or four R$^{1'}$.

In a particular embodiment of the invention R$^1$ is —NR$^9$R$^{10}$ or pyrrolidinyl, wherein pyrrolidinyl is optionally substituted with one, two or three R$^{1'}$.

In a particular embodiment of the invention each $R^{1'}$ is independently selected from halogen, cyano, $C_{1-7}$ alkyl, halo-$C_{1-7}$ alkyl, $C_{3-7}$ cycloalkyl, heterocycloalkyl-$C_{1-7}$ alkyl, hydroxy, $C_{1-7}$ alkoxy, $C_{1-7}$ alkoxy-$C_{1-7}$ alkyl, oxo, amino and —C(O)—$OR^{11}$.

In a particular embodiment of the invention each $R^{1'}$ is independently selected from halogen, cyano, $C_{1-7}$ alkyl, halo-$C_{1-7}$ alkyl, $C_{3-7}$ cycloalkyl, heterocycloalkyl-$C_{1-7}$ alkyl, hydroxy, oxo, and —C(O)—$OR^1$.

In a particular embodiment of the invention each $R^{1'}$ is independently selected from halogen, halo-$C_{1-7}$ alkyl and hydroxy.

In a particular embodiment of the invention each $R^{1'}$ is independently selected from fluoro, cyano, methyl, —$CH_2F$, —$CF_3$, —$CH_2$—$CF_3$, cyclopropyl, morpholinyl-$CH_2$—, hydroxy, methoxy, methoxy-methyl, oxo, dimethylamino and —C(O)—$OCH_3$.

In a particular embodiment of the invention each $R^{1'}$ is independently selected from fluoro, cyano, methyl, —$CF_3$, —$CH_2$—$CF_3$, cyclopropyl, morpholinyl-$CH_2$—, hydroxy, oxo and —C(O)—$OCH_3$.

In a particular embodiment of the invention each $R^{1'}$ is independently selected from fluoro, cyano, methyl, —$CF_3$, —$CH_2$—$CF_3$, cyclopropyl, morpholinyl-$CH_2$—, hydroxy, and —C(O)—$OCH_3$.

In a particular embodiment of the invention each $R^{1'}$ is independently selected from fluoro, —$CF_3$, and hydroxy.

In a particular embodiment of the invention $R^2$ is hydrogen, halogen, cyano, $C_{1-7}$ alkyl, halo-$C_{1-7}$ alkyl, hydroxy-$C_{1-7}$ alkyl, $C_{3-7}$ cycloalkyl, hydroxy, $C_{1-7}$ alkoxy, and —C(O)—$C_{1-7}$ alkoxy.

In a particular embodiment of the invention $R^2$ is halogen or $C_{1-7}$ alkyl.

In a particular embodiment of the invention $R^2$ is hydrogen, fluoro, chloro, bromo, cyano, methyl, ethyl, —$CF_3$, —$CH_2OH$, cyclopropyl, hydroxy, methoxy, ethoxy, and —C(O)—$OCH_3$.

In a particular embodiment of the invention $R^2$ is chloro, bromo or methyl.

In a particular embodiment of the invention $R^3$ is hydrogen, halogen, or $C_{1-7}$ alkoxy.

In a particular embodiment of the invention $R^3$ is hydrogen or halogen.

In a particular embodiment of the invention $R^3$ is hydrogen, fluoro, chloro, bromo, or methoxy.

In a particular embodiment of the invention $R^3$ is hydrogen, fluoro or chloro.

In a particular embodiment of the invention $R^4$ is hydrogen or halogen.

In a particular embodiment of the invention $R^4$ is hydrogen or fluoro.

In a particular embodiment of the invention $R^4$ is hydrogen.

In a particular embodiment of the invention $R^5$ is hydrogen or halogen.

In a particular embodiment of the invention $R^5$ is hydrogen or fluoro.

In a particular embodiment of the invention $R^5$ is hydrogen.

In a particular embodiment of the invention $R^6$ is bicyclic heteroaryl comprising 2, 3 or 4 nitrogen atoms, wherein $R^6$ is optionally substituted with one or more $R^{6'}$.

In a particular embodiment of the invention $R^6$ is bicyclic heteroaryl comprising 2 or 3 nitrogen atoms, wherein $R^6$ is optionally substituted with one or more $R^{6'}$.

In a particular embodiment of the invention $R^6$ is bicyclic heteroaryl comprising 2, 3 or 4 nitrogen atoms.

In a particular embodiment of the invention $R^6$ is bicyclic heteroaryl comprising 2 or 3 nitrogen atoms.

In a particular embodiment of the invention $R^6$ is indazolyl, pyrazolo[3,4-b]pyridinyl, pyrazolo[3,4-c]pyridinyl, pyrazolo[4,3-b]pyridinyl, or 1H-pyrazolo[4,3-d]pyrimidinyl.

In a particular embodiment of the invention $R^6$ is indazole-5-yl, indazole-6-yl, pyrazolo[3,4-b]pyridine-5-yl, pyrazolo[3,4-c]pyridine-5-yl, pyrazolo[4,3-b]pyridine-5-yl, or 1H-pyrazolo[4,3-d]pyrimidin-5-yl.

In a particular embodiment of the invention $R^{6'}$ is —$NH_2$, —C(O)$NH_2$, —C(O)OH, or —C(O)$OCH_3$.

In a particular embodiment of the invention $R^7$ is hydrogen, —$CH_2$-morpholinyl, or $R^7$ is forming $C_{1-7}$ alkylene with $R^{10}$ In a particular embodiment of the invention $R^7$ is hydrogen.

In a particular embodiment of the invention $R^8$ is hydrogen.

In a particular embodiment of the invention $R^9$ is $C_{1-7}$ alkyl, $C_{3-7}$ cycloalkyl, heterocycloalkyl, heterocycloalkyl-alkyl, heteroaryl or aryl annelated to $C_{5-6}$ cycloalkyl, wherein $C_{1-7}$ alkyl is optionally substituted with one, two or three $R^{9'}$, and wherein $C_{3-7}$ cycloalkyl, heterocycloalkyl, and aryl annelated to $C_{5-6}$ cycloalkyl are optionally substituted with one or two $R^{9''}$.

In a particular embodiment of the invention $R^9$ is $C_{1-7}$ alkyl optionally substituted with one, two or three $R^{9'}$.

In a particular embodiment of the invention $R^9$ is $C_{1-7}$ alkyl substituted with three halo.

In a particular embodiment of the invention $R^9$ is methyl, ethyl, n-propyl, isopropyl, tert-butyl, cyclopropyl, cyclohexyl, oxetanyl, oxetanyl-methyl, oxazolyl, dihydroindenyl or tetrahydronaphthalenyl, wherein methyl, ethyl, n-propyl, isopropyl and tert-butyl are optionally substituted with one, two or three $R^{9'}$, and wherein cyclopropyl, cyclohexyl, oxetanyl, oxazolyl, dihydroindenyl and tetrahydronaphthalenyl are optionally substituted with one or two $R^{9''}$.

In a particular embodiment of the invention each $R^{9'}$ is independently selected from halogen, cyano, heterocycloalkyl or hydroxy, more particularly halogen.

In a particular embodiment of the invention each $R^{9'}$ is independently selected from fluoro, cyano, oxetanyl or hydroxy, more particularly fluoro.

In a particular embodiment of the invention each $R^{9''}$ is independently selected from halogen, cyano, $C_{1-7}$ alkyl and halo-$C_{1-7}$ alkyl.

In a particular embodiment of the invention each $R^{9''}$ is independently selected from fluoro, cyano, methyl and trifluoromethyl.

In a particular embodiment of the invention $R^{10}$ is hydrogen, $C_{1-7}$ alkyl, or $R^{10}$ is forming $C_{1-7}$ alkylene with $R^7$.

In a particular embodiment of the invention $R^{10}$ is hydrogen or methyl.

In a particular embodiment of the invention $R^{10}$ is hydrogen.

In a particular embodiment of the invention $R^{11}$ is $C_{1-7}$ alkyl.

In a particular embodiment of the invention $R^{11}$ is methyl.

In a particular embodiment of the invention $R^{16}$ and $R^{17}$ together with the nitrogen to which they are bound form morpholinyl.

In a particular embodiment of the invention m is 1.

In a particular embodiment of the invention n is 0 or 1, particularly 0.

In a particular embodiment of the invention q is 0 or 1, particularly 1.

In a particular embodiment of the invention v is 1 and w is 1.

In a particular embodiment of the invention v is 0 and w is 1.

In a particular embodiment of the invention v is 0 and w is 0.

In a particular embodiment of the invention x is 1.

Particular compounds of formula (I) of the present invention are those selected from the group consisting of:

2-[1'-(1H-Indazole-5-carbonyl)-2-oxospiro[indole-3,4'-piperidine]-1-yl]-N-(2,2,2-trifluoroethyl)acetamide;

2-[1'-(1H-Indazole-5-carbonyl)-4-methyl-2-oxospiro[indole-3,4'-piperidine]-1-yl]-N-(2,2,2-trifluoroethyl)acetamide;

2-[4-Bromo-1'-(1H-indazole-5-carbonyl)-2-oxospiro[indole-3,4'-piperidine]-1-yl]-N-(2,2,2-trifluoroethyl)acetamide;

2-[4-Fluoro-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[1-(1H-Indazole-5-carbonyl)-5'-methoxy-2'-oxospiro[piperidine-4,3'-pyrrolo[3,2-b]pyridine]-1'-yl]-N-(2,2,2-trifluoroethyl)acetamide;

2-[4-Chloro-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[5-Bromo-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[5-Fluoro-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[4-Methoxy-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[4-Bromo-2-oxo-1'-(1H-pyrazolo[3,4-b]pyridine-5-carbonyl)spiro[indole-3,4'-piperidine]-1-yl]-N-(2,2,2-trifluoroethyl)acetamide;

Methyl 2-oxo-1-(2-oxo-2-((2,2,2-trifluoroethyl)amino)ethyl)-1'-(1H-pyrazolo[3,4-b]pyridine-5-carbonyl)spiro[indoline-3,4'-piperidine]-4-carboxylate;

2-[4-Ethyl-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[4,5-Difluoro-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[4-Methyl-2-oxo-1'-(1H-pyrazolo[3,4-b]pyridine-5-carbonyl)spiro[indole-3,4'-piperidine]-1-yl]-N-(2,2,2-trifluoroethyl)acetamide;

Methyl 1'-(1H-indazole-5-carbonyl)-2-oxo-1-(2-oxo-2-((2,2,2-trifluoroethyl)amino)ethyl)spiro[indoline-3,4'-piperidine]-4-carboxylate;

(S)-4-Methyl-1-(2-oxo-2-(2-(trifluoromethyl)pyrrolidin-1-yl)ethyl)-1'-(1H-pyrazolo[3,4-b]pyridine-5-carbonyl)spiro[indoline-3,4'-piperidin]-2-one;

2-[4-Cyano-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[5-Chloro-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[6-Fluoro-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[4-Bromo-7-fluoro-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[4,5-Dichloro-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[4-Bromo-2-oxo-1'-(1H-pyrazolo[3,4-c]pyridine-5-carbonyl)spiro[indole-3,4'-piperidine]-1-yl]-N-(2,2,2-trifluoroethyl)acetamide;

2-[4-Bromo-2-oxo-1'-(1H-pyrazolo[4,3-b]pyridine-5-carbonyl)spiro[indole-3,4'-piperidine]-1-yl]-N-(2,2,2-trifluoroethyl)acetamide;

4-Methyl-1-(2-oxo-2-(2-(trifluoromethyl)morpholino)ethyl)-1'-(1H-pyrazolo[3,4-b]pyridine-5-carbonyl)spiro[indoline-3,4'-piperidin]-2-one;

2-[1'-(1H-Indazole-5-carbonyl)-4-methyl-2-oxospiro[indole-3,4'-piperidine]-1-yl]-N-[1-(trifluoromethyl)cyclopropyl]acetamide;

N-tert-Butyl-2-[1'-(1H-indazole-5-carbonyl)-4-methyl-2-oxospiro[indole-3,4'-piperidine]-1-yl]acetamide;

N-(1-Hydroxy-2-methylpropan-2-yl)-2-[1'-(1H-indazole-5-carbonyl)-4-methyl-2-oxospiro[indole-3,4'-piperidine]-1-yl]acetamide;

(rac, cis)-1-[2-[2,6-Dimethylmorpholin-4-yl]-2-oxoethyl]-1'-(1H-indazole-5-carbonyl)-4-methylspiro[indole-3,4'-piperidine]-2-one;

N-tert-Butyl-2-[1'-(1H-indazole-5-carbonyl)-4-methyl-2-oxospiro[indole-3,4'-piperidine]-1-yl]-N-methylacetamide;

2-[1'-(1H-Indazole-5-carbonyl)-4-methyl-2-oxospiro[indole-3,4'-piperidine]-1-yl]-N-[(2R)-1,1,1-trifluoropropan-2-yl]acetamide;

2-[4,5-Dichloro-2-oxo-1'-(1H-pyrazolo[3,4-c]pyridine-5-carbonyl)spiro[indole-3,4'-piperidine]-1-yl]-N-(2,2,2-trifluoroethyl)acetamide;

2-[4-Chloro-5-fluoro-2-oxo-1'-(1H-pyrazolo[3,4-c]pyridine-5-carbonyl)spiro[indole-3,4'-piperidine]-1-yl]-N-(2,2,2-trifluoroethyl)acetamide;

2-[4-Chloro-5-fluoro-1'-(1H-indazole-5-carbonyl)-2-oxospiro[indole-3,4'-piperidine]-1-yl]-N-(2,2,2-trifluoroethyl)acetamide;

2-[4,5-Dichloro-2-oxo-1'-(1H-pyrazolo[4,3-b]pyridine-5-carbonyl)spiro[indole-3,4'-piperidine]-1-yl]-N-(2,2,2-trifluoroethyl)acetamide;

2-[4-Chloro-5-fluoro-2-oxo-1'-(1H-pyrazolo[4,3-b]pyridine-5-carbonyl)spiro[indole-3,4'-piperidine]-1-yl]-N-(2,2,2-trifluoroethyl)acetamide;

2-[4-Chloro-5-fluoro-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[4,5-Dichloro-1'-(1H-indazole-5-carbonyl)-2-oxospiro[indole-3,4'-piperidine]-1-yl]-N-(2,2,2-trifluoroethyl)acetamide;

2-[2-Oxo-1'-(1H-pyrazolo[3,4-b]pyridine-5-carbonyl)-4-(trifluoromethyl)spiro[indole-3,4'-piperidine]-1-yl]-N-(2,2,2-trifluoroethyl)acetamide;

1-[2-(4-Hydroxy-3,3-dimethylpyrrolidin-1-yl)-2-oxoethyl]-1'-(1H-indazole-5-carbonyl)-4-methylspiro[indole-3,4'-piperidine]-2-one;

1-[2-(3,3-Difluoro-4-hydroxypyrrolidin-1-yl)-2-oxoethyl]-1'-(1H-indazole-5-carbonyl)-4-methylspiro[indole-3,4'-piperidine]-2-one;

1-[2-(3,3-Difluoropyrrolidin-1-yl)-2-oxoethyl]-1'-(1H-indazole-5-carbonyl)-4-methylspiro[indole-3,4'-piperidine]-2-one;

1-[2-(3-Fluoro-3-methylpyrrolidin-1-yl)-2-oxoethyl]-1'-(1H-indazole-5-carbonyl)-4-methylspiro[indole-3,4'-piperidine]-2-one;

1-[2-[3-Hydroxy-3-(trifluoromethyl)pyrrolidin-1-yl]-2-oxoethyl]-1'-(1H-indazole-5-carbonyl)-4-methylspiro[indole-3,4'-piperidine]-2-one;

(S)-Methyl 4,4-difluoro-1-(2-(4-methyl-2-oxo-1'-(1H-pyrazolo[3,4-b]pyridine-5-carbonyl)spiro[indoline-3,4'-piperidin]-1-yl)acetyl)pyrrolidine-2-carboxylate;

(S)-4-Bromo-1'-(1H-indazole-5-carbonyl)-1-(2-oxo-2-(2-(trifluoromethyl)pyrrolidin-1-yl)ethyl)spiro[indoline-3,4'-piperidin]-2-one;

(S)-4-Methyl-1-(2-oxo-2-(2-(trifluoromethyl)pyrrolidin-1-yl)ethyl)-1'-(1H-pyrazolo[4,3-b]pyridine-5-carbonyl)spiro[indoline-3,4'-piperidin]-2-one;

2-[1'-(1H-Indazole-5-carbonyl)-4-methyl-2-oxospiro[indole-3,4'-piperidine]-1-yl]-N-[(2S)-1,1,1-trifluoropropan-2-yl]acetamide;

2-[1'-(1H-Indazole-5-carbonyl)-4-methyl-2-oxospiro[indole-3,4'-piperidine]-1-yl]-N-(3-methyloxetan-3-yl)acetamide;

1-[(3-Cyclopropyl-1,2,4-oxadiazol-5-yl)methyl]-1'-(1H-indazole-5-carbonyl)-4-methylspiro[indole-3,4'-piperidine]-2-one;

2-(4-Methyl-2-oxo-1'-(1H-pyrazolo[4,3-b]pyridine-5-carbonyl)spiro[indoline-3,4'-piperidin]-1-yl)-N-(2,2,2-trifluoroethyl)acetamide;

N-(2-Cyanopropan-2-yl)-2-[1'-(1H-indazole-5-carbonyl)-4-methyl-2-oxospiro[indole-3,4'-piperidine]-1-yl]acetamide;

(S)-4-Methyl-1-(2-oxo-2-(2-(trifluoromethyl)pyrrolidin-1-yl)ethyl)-1'-(1H-pyrazolo[3,4-c]pyridine-5-carbonyl)spiro[indoline-3,4'-piperidin]-2-one;

2-(4-(Hydroxymethyl)-1'-(1H-indazole-5-carbonyl)-2-oxospiro[indoline-3,4'-piperidin]-1-yl)-N-(2,2,2-trifluoroethyl)acetamide;

N-(2,3-Dihydro-1H-inden-1-yl)-2-[1'-(1H-indazole-5-carbonyl)-4-methyl-2-oxospiro[indole-3,4'-piperidine]-1-yl]acetamide;

2-[1'-(1H-Indazole-5-carbonyl)-4-methyl-2-oxospiro[indole-3,4'-piperidine]-1-yl]-N-(1,2,3,4-tetrahydronaphthalen-1-yl)acetamide;

N-(2,2-Difluorocyclohexyl)-2-[1'-(1H-indazole-5-carbonyl)-4-methyl-2-oxospiro[indole-3,4'-piperidine]-1-yl]acetamide;

1-[2-[1'-(1H-Indazole-5-carbonyl)-4-methyl-2-oxospiro[indole-3,4'-piperidine]-1-yl]acetyl]pyrrolidine-3-carbonitrile;

2-[4-Chloro-1'-(1H-indazole-5-carbonyl)-2-oxospiro[indole-3,4'-piperidine]-1-yl]-N-(2,2,2-trifluoroethyl)acetamide;

2-[4-Cyclopropyl-1'-(1H-indazole-5-carbonyl)-2-oxospiro[indole-3,4'-piperidine]-1-yl]-N-(2,2,2-trifluoroethyl)acetamide;

4-Chloro-1'-(1H-indazole-5-carbonyl)-1-[2-oxo-2-[(2S)-2-(trifluoromethyl)pyrrolidin-1-yl]ethyl]spiro[indole-3,4'-piperidine]-2-one;

1-(2-(3-Oxa-8-azabicyclo[3.2.1]octan-8-yl)-2-oxoethyl)-4-bromo-1'-(1H-indazole-5-carbonyl)spiro[indoline-3,4'-piperidin]-2-one;

4-Bromo-1'-(1H-indazole-5-carbonyl)-1-(2-oxo-2-(2-(trifluoromethyl)morpholino)ethyl)spiro[indoline-3,4'-piperidin]-2-one;

4-Bromo-1-(2-(3,3-difluoropyrrolidin-1-yl)-2-oxoethyl)-1'-(1H-indazole-5-carbonyl)spiro[indoline-3,4'-piperidin]-2-one;

4-Bromo-1'-(1H-indazole-5-carbonyl)-1-(2-oxo-2-(3-(trifluoromethyl)pyrrolidin-1-yl)ethyl)spiro[indoline-3,4'-piperidin]-2-one;

4-Bromo-1-(2-oxo-2-(3-(trifluoromethyl)pyrrolidin-1-yl)ethyl)-1'-(1H-pyrazolo[4,3-b]pyridine-5-carbonyl)spiro[indoline-3,4'-piperidin]-2-one;

4-Bromo-1-(2-(3,3-difluoropyrrolidin-1-yl)-2-oxoethyl)-1'-(1H-pyrazolo[4,3-b]pyridine-5-carbonyl)spiro[indoline-3,4'-piperidin]-2-one;

4-Bromo-1-(2-oxo-2-(3-(trifluoromethyl)pyrrolidin-1-yl)ethyl)-1'-(1H-pyrazolo[3,4-b]pyridine-5-carbonyl)spiro[indoline-3,4'-piperidin]-2-one;

4-Bromo-1-(2-(3,3-difluoropyrrolidin-1-yl)-2-oxoethyl)-1'-(1H-pyrazolo[3,4-b]pyridine-5-carbonyl)spiro[indoline-3,4'-piperidin]-2-one;

4-Bromo-1-(2-oxo-2-(3-(trifluoromethyl)pyrrolidin-1-yl)ethyl)-1'-(1H-pyrazolo[3,4-c]pyridine-5-carbonyl)spiro[indoline-3,4'-piperidin]-2-one;

4-Bromo-1-(2-(3,3-difluoropyrrolidin-1-yl)-2-oxoethyl)-1'-(1H-pyrazolo[3,4-c]pyridine-5-carbonyl)spiro[indoline-3,4'-piperidin]-2-one;

(S)-4-Bromo-1-(2-oxo-2-(2-(trifluoromethyl)pyrrolidin-1-yl)ethyl)-1'-(1H-pyrazolo[3,4-c]pyridine-5-carbonyl)spiro[indoline-3,4'-piperidin]-2-one;

(S)-4-Bromo-1-(2-oxo-2-(2-(trifluoromethyl)pyrrolidin-1-yl)ethyl)-1'-(1H-pyrazolo[4,3-b]pyridine-5-carbonyl)spiro[indoline-3,4'-piperidin]-2-one;

4-Bromo-1-(2-oxo-2-(2-(trifluoromethyl)morpholino)ethyl)-1'-(1H-pyrazolo[4,3-b]pyridine-5-carbonyl)spiro[indoline-3,4'-piperidin]-2-one;

4-Bromo-1-[2-(3-oxa-8-azabicyclo[3.2.1]octan-8-yl)-2-oxoethyl]-1'-(1H-pyrazolo[4,3-b]pyridine-5-carbonyl)spiro[indole-3,4'-piperidine]-2-one;

(S)-4-Bromo-1-(2-oxo-2-(2-(trifluoromethyl)pyrrolidin-1-yl)ethyl)-1'-(1H-pyrazolo[3,4-b]pyridine-5-carbonyl)spiro[indoline-3,4'-piperidin]-2-one;

4-Bromo-1-(2-oxo-2-(2-(trifluoromethyl)morpholino)ethyl)-1'-(1H-pyrazolo[3,4-b]pyridine-5-carbonyl)spiro[indoline-3,4'-piperidin]-2-one;

1-(2-(3-Oxa-8-azabicyclo[3.2.1]octan-8-yl)-2-oxoethyl)-4-bromo-1'-(1H-pyrazolo[3,4-b]pyridine-5-carbonyl)spiro[indoline-3,4'-piperidin]-2-one;

4-Chloro-1-[[(3-cyclopropyl-1,2,4-oxadiazol-5-yl)methyl]-1'-(1H-indazole-5-carbonyl)spiro[indole-3,4'-piperidine]-2-one;

4-Bromo-1'-(1H-indazole-5-carbonyl)-1-(2-oxo-2-(3,3,4-trimethylpiperazin-1-yl)ethyl)spiro[indoline-3,4'-piperidin]-2-one;

1-(1H-Indazole-5-carbonyl)-5'-methoxy-1'-[2-oxo-2-[(2S)-2-(trifluoromethyl)pyrrolidin-1-yl]ethyl]spiro[piperidine-4,3'-pyrrolo[3,2-b]pyridine]-2'-one;

2-[1'-(1H-Indazole-5-carbonyl)-4-methyl-2-oxospiro[indole-3,4'-piperidine]-1-yl]-N-methyl-N-[(2S)-1,1,1-trifluoropropan-2-yl]acetamide;

2-[4-Bromo-5-fluoro-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[4-Bromo-5-fluoro-1'-(1H-indazole-5-carbonyl)-2-oxospiro[indole-3,4'-piperidine]-1-yl]-N-(2,2,2-trifluoroethyl)acetamide;

4-Bromo-1-(2-(3,3-dimethylmorpholino)-2-oxoethyl)-1'-(1H-indazole-5-carbonyl)spiro[indoline-3,4'-piperidin]-2-one;

1-(2-(2H-Benzo[b][1,4]oxazin-4(3H)-yl)-2-oxoethyl)-4-bromo-1'-(1H-indazole-5-carbonyl)spiro[indoline-3,4'-piperidin]-2-one;

2-(4-Bromo-1'-(1H-indazole-5-carbonyl)-2-oxospiro[indoline-3,4'-piperidin]-1-yl)-N-(pyridin-2-yl)acetamide;

2-(4-Bromo-1'-(1H-indazole-5-carbonyl)-2-oxospiro[indoline-3,4'-piperidin]-1-yl)-N-(2-(morpholinomethyl)phenyl)acetamide;

2-(4-Bromo-1'-(1H-indazole-5-carbonyl)-2-oxospiro[indoline-3,4'-piperidin]-1-yl)-N-phenylacetamide;

2-[4-Ethoxy-1'-(1H-indazole-5-carbonyl)-2-oxospiro[indole-3,4'-piperidine]-1-yl]-N-(2,2,2-trifluoroethyl)acetamide;

2-[1'-(1H-Indazole-5-carbonyl)-4-methyl-2-oxospiro[indole-3,4'-piperidine]-1-yl]-N-(3,3,3-trifluoropropyl)acetamide;

2-[1'-(1H-Indazole-5-carbonyl)-4-methyl-2-oxospiro[indole-3,4'-piperidine]-1-yl]-N-methyl-N-[(2R)-1,1,1-trifluoropropan-2-yl]acetamide;

3-[1'-(1H-Indazole-5-carbonyl)-4-methyl-2-oxospiro[indole-3,4'-piperidine]-1-yl]-N-(2,2,2-trifluoroethyl)propanamide;

2-[4-Hydroxy-1'-(1H-indazole-5-carbonyl)-2-oxospiro[indole-3,4'-piperidine]-1-yl]-N-(2,2,2-trifluoroethyl)acetamide;

5'-Chloro-1-(1H-indazole-5-carbonyl)-1'-[2-oxo-2-[(2S)-2-(trifluoromethyl)pyrrolidin-1-yl]ethyl]spiro[piperidine-4,3'-pyrrolo[3,2-b]pyridine]-2'-one;

4-Bromo-1'-(1H-indazole-5-carbonyl)-1-[2-oxo-2-[2-(2,2,2-trifluoroethyl)pyrrolidin-1-yl]ethyl]spiro[indoline-3,4'-piperidine]-2-one;

4-Bromo-1-[2-(4,4-difluoro-1-piperidyl)-2-oxo-ethyl]-1'-(1H-indazole-5-carbonyl)spiro[indoline-3,4'-piperidine]-2-one;

4-Bromo-1'-(1H-indazole-5-carbonyl)-1-[2-oxo-2-(1-piperidyl)ethyl]spiro[indoline-3,4'-piperidine]-2-one;

1-[2-(3,3a,4,5,6,6a-Hexahydro-2H-cyclopenta[b]pyrrol-1-yl)-2-oxo-ethyl]-4-bromo-1'-(1H-indazole-5-carbonyl)spiro[indoline-3,4'-piperidine]-2-one;

4-Chloro-5-fluoro-1-[2-oxo-2-[2-(2,2,2-trifluoroethyl)pyrrolidin-1-yl]ethyl]-1'-(1H-pyrazolo[4,3-b]pyridine-5-carbonyl)spiro[indoline-3,4'-piperidine]-2-one;

1-[2-(3,3a,4,5,6,6a-Hexahydro-2H-cyclopenta[b]pyrrol-1-yl)-2-oxo-ethyl]-4-chloro-5-fluoro-1'-(1H-pyrazolo[4,3-b]pyridine-5-carbonyl)spiro[indoline-3,4'-piperidine]-2-one;

4-Chloro-5-fluoro-1-[2-oxo-2-[(2S)-2-(trifluoromethyl)pyrrolidin-1-yl]ethyl]-1'-(1H-pyrazolo[4,3-b]pyridine-5-carbonyl)spiro[indoline-3,4'-piperidine]-2-one;

4-Chloro-5-fluoro-1-[2-oxo-2-[2-(trifluoromethyl)morpholin-4-yl]ethyl]-1'-(1H-pyrazolo[4,3-b]pyridine-5-carbonyl)spiro[indoline-3,4'-piperidine]-2-one;

2-[1'-(3-Amino-1H-indazole-6-carbonyl)-4-chloro-5-fluoro-2-oxospiro[indole-3,4'-piperidine]-1-yl]-N-(2,2,2-trifluoroethyl)acetamide;

(−)-4-Chloro-1-[2-oxo-1-(2,2,2-trifluoroethyl)piperidin-3-yl]-1'-(1H-pyrazolo[3,4-b]pyridine-5-carbonyl)spiro[indole-3,4'-piperidine]-2-one;

(+)-4-Chloro-1-[2-oxo-1-(2,2,2-trifluoroethyl)piperidin-3-yl]-1'-(1H-pyrazolo[3,4-b]pyridine-5-carbonyl)spiro[indole-3,4'-piperidine]-2-one;

4-Bromo-1'-(1H-indazole-5-carbonyl)-1-[2-(2-methylthiomorpholin-4-yl)-2-oxoethyl]spiro[indole-3,4'-piperidine]-2-one;

1-[2-(5-Azaspiro[2.5]octan-5-yl)-2-oxoethyl]-4-bromo-1'-(1H-indazole-5-carbonyl)spiro[indole-3,4'-piperidine]-2-one;

4-Bromo-1'-(1H-indazole-5-carbonyl)-1-[2-oxo-2-(4-oxo-1,3,6,7,8,8a-hexahydropyrrolo[1,2-a]pyrazin-2-yl)ethyl]spiro[indole-3,4'-piperidine]-2-one;

4-Bromo-1-[2-(3-fluoropyrrolidin-1-yl)-2-oxoethyl]-1'-(1H-indazole-5-carbonyl)spiro[indole-3,4'-piperidine]-2-one;

(−)-4,5-Dichloro-1-[2-oxo-2-[2-(2,2,2-trifluoroethyl)pyrrolidin-1-yl]ethyl]-1'-(1H-pyrazolo[4,3-b]pyridine-5-carbonyl)spiro[indole-3,4'-piperidine]-2-one;

(+)-4,5-Dichloro-1-[2-oxo-2-[2-(2,2,2-trifluoroethyl)pyrrolidin-1-yl]ethyl]-1'-(1H-pyrazolo[4,3-b]pyridine-5-carbonyl)spiro[indole-3,4'-piperidine]-2-one;

(−)-4-Chloro-5-fluoro-1-[2-oxo-2-[2-(2,2,2-trifluoroethyl)pyrrolidin-1-yl]ethyl]-1'-(1H-pyrazolo[4,3-b]pyridine-5-carbonyl)spiro[indole-3,4'-piperidine]-2-one;

(+)-4-Chloro-5-fluoro-1-[2-oxo-2-[2-(2,2,2-trifluoroethyl)pyrrolidin-1-yl]ethyl]-1'-(1H-pyrazolo[4,3-b]pyridine-5-carbonyl)spiro[indole-3,4'-piperidine]-2-one;

(+)-1-[2-[3,3a,4,5,6,6a-Hexahydro-2H-cyclopenta[b]pyrrol-1-yl]-2-oxoethyl]-4-chloro-5-fluoro-1'-(1H-pyrazolo[4,3-b]pyridine-5-carbonyl)spiro[indole-3,4'-piperidine]-2-one;

(−)-1-[2-[3,3a,4,5,6,6a-Hexahydro-2H-cyclopenta[b]pyrrol-1-yl]-2-oxoethyl]-4-chloro-5-fluoro-1'-(1H-pyrazolo[4,3-b]pyridine-5-carbonyl)spiro[indole-3,4'-piperidine]-2-one;

(+) or (−)-4-Chloro-5-fluoro-1-[2-oxo-2-[2-(trifluoromethyl)morpholin-4-yl]ethyl]-1'-(1H-pyrazolo[4,3-b]pyridine-5-carbonyl)spiro[indole-3,4'-piperidine]-2-one;

(−) or (+)-4-Chloro-5-fluoro-1-[2-oxo-2-[2-(trifluoromethyl)morpholin-4-yl]ethyl]-1'-(1H-pyrazolo[4,3-b]pyridine-5-carbonyl)spiro[indole-3,4'-piperidine]-2-one;

2-[4'-Bromo-1-(1H-indazole-5-carbonyl)-2'-oxospiro[azetidine-3,3'-indole]-1'-yl]-N-(2,2,2-trifluoroethyl)acetamide;

2-[4-Bromo-2-oxo-1'-(1H-pyrazolo[4,3-d]pyrimidine-5-carbonyl)spiro[indole-3,4'-piperidine]-1-yl]-N-(2,2,2-trifluoroethyl)acetamide;

2-[4-Chloro-5-fluoro-2-oxo-1'-(1H-pyrazolo[4,3-d]pyrimidine-5-carbonyl)spiro[indole-3,4'-piperidine]-1-yl]-N-(2,2,2-trifluoroethyl)acetamide;

2-[4-Bromo-1'-(1H-indazole-5-carbonyl)-2-oxospiro[indole-3,4'-piperidine]-1-yl]-N-methyl-N-(oxetan-3-ylmethyl)acetamide;

2-[4-Bromo-1'-(1H-indazole-5-carbonyl)-2-oxospiro[indole-3,4'-piperidine]-1-yl]-N-(cyanomethyl)-N-methylacetamide;

2-[4-Bromo-1'-(1H-indazole-5-carbonyl)-2-oxospiro[indole-3,4'-piperidine]-1-yl]-N-methyl-N-(5-methyl-1,2-oxazol-3-yl)acetamide;

4-Bromo-1'-(1H-indazole-5-carbonyl)-1-[2-oxo-2-(1,4,6,7-tetrahydropyrrolo[3,2-c]pyridin-5-yl)ethyl]spiro[indole-3,4'-piperidine]-2-one;

4-Bromo-1'-(1H-indazole-5-carbonyl)-1-[2-(3-methyl-2,3-dihydroindol-1-yl)-2-oxoethyl]spiro[indole-3,4'-piperidine]-2-one;

4-Bromo-1-[2-(5-fluoro-2,3-dihydroindol-1-yl)-2-oxoethyl]-1'-(1H-indazole-5-carbonyl)spiro[indole-3,4'-piperidine]-2-one;

(2S)-1-[2-[4-Bromo-1'-(1H-indazole-5-carbonyl)-2-oxospiro[indole-3,4'-piperidine]-1-yl]acetyl]pyrrolidine-2-carbonitrile;

2-[4-Chloro-2-oxo-1'-(1H-pyrazolo[3,4-b]pyridine-5-carbonyl)spiro[indole-3,4'-piperidine]-1-yl]-3-morpholin-4-yl-N-(2,2,2-trifluoroethyl)propanamide;

4-Chloro-1-[2-(2,2-dimethylpyrrolidin-1-yl)-2-oxoethyl]-5-fluoro-1'-(1H-pyrazolo[4,3-b]pyridine-5-carbonyl)spiro[indole-3,4'-piperidine]-2-one;

4-Chloro-5-fluoro-1-[2-oxo-2-[3-(trifluoromethyl)azetidin-1-yl]ethyl]-1'-(1H-pyrazolo[4,3-b]pyridine-5-carbonyl)spiro[indole-3,4'-piperidine]-2-one;

1-[2-[(3aR,6aS)-3,3a,4,5,6,6a-Hexahydro-1H-cyclopenta[c]pyrrol-2-yl]-2-oxoethyl]-4-chloro-5-fluoro-1'-(1H-pyrazolo[4,3-b]pyridine-5-carbonyl)spiro[indole-3,4'-piperidine]-2-one;

1-[2-[(3aR,6aS)-3,3a,4,5,6,6a-Hexahydro-1H-cyclopenta[c]pyrrol-2-yl]-2-oxoethyl]-4-bromo-1'-(1H-indazole-5-carbonyl)spiro[indole-3,4'-piperidine]-2-one;

1-[2-(3,4,6,7,8,8a-Hexahydro-1H-pyrrolo[1,2-a]pyrazin-2-yl)-2-oxoethyl]-4-bromo-1'-(1H-indazole-5-carbonyl)spiro[indole-3,4'-piperidine]-2-one;

1-[2-(3,4,6,7,8,8a-Hexahydro-1H-pyrrolo[1,2-a]pyrazin-2-yl)-2-oxoethyl]-4-chloro-5-fluoro-1'-(1H-pyrazolo[4,3-b]pyridine-5-carbonyl)spiro[indole-3,4'-piperidine]-2-one;

4-Chloro-1-[2-(7,7-difluoro-2-azaspiro[3.3]heptan-2-yl)-2-oxoethyl]-5-fluoro-1'-(1H-pyrazolo[4,3-b]pyridine-5-carbonyl)spiro[indole-3,4'-piperidine]-2-one;

2-[1-(3-Amino-1H-indazole-6-carbonyl)-4'-bromo-2'-oxospiro[azetidine-3,3'-indole]-1'-yl]-N-(2,2,2-trifluoroethyl)acetamide;

2-[4'-Bromo-2'-oxo-1-(1H-pyrazolo[4,3-b]pyridine-5-carbonyl)spiro[azetidine-3,3'-indole]-1'-yl]-N-(2,2,2-trifluoroethyl)acetamide;

4-Chloro-1-[2-(3,3-difluoroazetidin-1-yl)-2-oxoethyl]-5-fluoro-1'-(1H-indazole-5-carbonyl)spiro[indole-3,4'-piperidine]-2-one;

4-Bromo-1-[2-(2,3-dihydroindol-1-yl)-2-oxoethyl]-1'-(1H-indazole-5-carbonyl)spiro[indole-3,4'-piperidine]-2-one;

5-[4-Chloro-2-oxo-1-[2-oxo-2-(2,2,2-trifluoroethylamino)ethyl]spiro[indole-3,4'-piperidine]-1'-carbonyl]-1H-indazole-3-carboxamide;

4-Chloro-5-fluoro-1'-(1H-indazole-5-carbonyl)-1-[2-oxo-2-(3,3,4,4-tetrafluoropyrrolidin-1-yl)ethyl]spiro[indole-3,4'-piperidine]-2-one;

4-Chloro-5-fluoro-1'-(1H-indazole-5-carbonyl)-1-[2-(3-methoxypyrrolidin-1-yl)-2-oxoethyl]spiro[indole-3,4'-piperidine]-2-one;

1-[2-[4-Chloro-5-fluoro-1'-(1H-indazole-5-carbonyl)-2-oxospiro[indole-3,4'-piperidine]-1-yl]acetyl]pyrrolidine-2-carbonitrile;

1-[2-(3,3a,4,5,6,6a-Hexahydro-1H-cyclopenta[c]pyrrol-2-yl)-2-oxoethyl]-4-chloro-5-fluoro-1'-(1H-indazole-5-carbonyl)spiro[indole-3,4'-piperidine]-2-one;

2-[4-Chloro-5-fluoro-1'-(1H-indazole-5-carbonyl)-2-oxospiro[indole-3,4'-piperidine]-1-yl]-N-(1-cyanocyclopropyl)acetamide;

4-Chloro-5-fluoro-1'-(1H-indazole-5-carbonyl)-1-[2-[2-(methoxymethyl)pyrrolidin-1-yl]-2-oxoethyl]spiro[indole-3,4'-piperidine]-2-one;

4-Chloro-5-fluoro-1-[2-(3-fluoropyrrolidin-1-yl)-2-oxoethyl]-1'-(1H-indazole-5-carbonyl)spiro[indole-3,4'-piperidine]-2-one;

4-Chloro-5-fluoro-1'-(1H-indazole-5-carbonyl)-1-[2-oxo-2-[(2S)-2-(trifluoromethyl)pyrrolidin-1-yl]ethyl]spiro[indole-3,4'-piperidine]-2-one;

4-Chloro-5-fluoro-1'-(1H-indazole-5-carbonyl)-1-[2-oxo-2-[(2R)-2-(trifluoromethyl)pyrrolidin-1-yl]ethyl]spiro[indole-3,4'-piperidine]-2-one;

(−)-2-[4-Chloro-2-oxo-1'-(1H-pyrazolo[3,4-b]pyridine-5-carbonyl)spiro[indole-3,4'-piperidine]-1-yl]-3-morpholin-4-yl-N-(2,2,2-trifluoroethyl)propanamide;

(+)-2-[4-Chloro-2-oxo-1'-(1H-pyrazolo[3,4-b]pyridine-5-carbonyl)spiro[indole-3,4'-piperidine]-1-yl]-3-morpholin-4-yl-N-(2,2,2-trifluoroethyl)propanamide;

(+) or (−)-4-Bromo-1'-(1H-indazole-5-carbonyl)-1-[2-[3-methyl-2,3-dihydroindol-1-yl]-2-oxoethyl]spiro[indole-3,4'-piperidine]-2-one;

(−) or (+)-4-Bromo-1'-(1H-indazole-5-carbonyl)-1-[2-[3-methyl-2,3-dihydroindol-1-yl]-2-oxoethyl]spiro[indole-3,4'-piperidine]-2-one;

4-Chloro-1-[2-[(3R,4S)-3-(dimethylamino)-4-fluoropyrrolidin-1-yl]-2-oxoethyl]-5-fluoro-1'-(1H-pyrazolo[4,3-b]pyridine-5-carbonyl)spiro[indole-3,4'-piperidine]-2-one;

2-[4-Chloro-5-fluoro-1'-(1H-indazole-5-carbonyl)-2-oxospiro[indole-3,4'-piperidine]-1-yl]-N-(2,2-difluorocyclopropyl)acetamide;

4-Bromo-1-[2-[3-(fluoromethyl)-4-(trifluoromethyl)pyrrolidin-1-yl]-2-oxoethyl]-1'-(1H-indazole-5-carbonyl)spiro[indole-3,4'-piperidine]-2-one;

4-Chloro-5-fluoro-1'-(1H-indazole-5-carbonyl)-1-[2-(2-oxa-7-azaspiro[3.4]octan-7-yl)-2-oxoethyl]spiro[indole-3,4'-piperidine]-2-one;

4-Bromo-1-[2-[(3R,4S)-3,4-difluoropyrrolidin-1-yl]-2-oxoethyl]-1'-(1H-indazole-5-carbonyl)spiro[indole-3,4'-piperidine]-2-one;

4-Bromo-1-[2-(3,4-dihydro-1H-pyrrolo[1,2-a]pyrazin-2-yl)-2-oxoethyl]-1'-(1H-indazole-5-carbonyl)spiro[indole-3,4'-piperidine]-2-one;

4-Bromo-1-[2-[(2S)-4,4-difluoro-2-(fluoromethyl)pyrrolidin-1-yl]-2-oxoethyl]-1'-(1H-indazole-5-carbonyl)spiro[indole-3,4'-piperidine]-2-one;

Methyl 5-[4-chloro-5-fluoro-2-oxo-1-[2-oxo-2-(2,2,2-trifluoroethylamino)ethyl]spiro[indole-3,4'-piperidine]-1'-carbonyl]-1H-indazole-3-carboxylate;

5-[4-Chloro-5-fluoro-2-oxo-1-[2-oxo-2-(2,2,2-trifluoroethylamino)ethyl]spiro[indole-3,4'-piperidine]-1'-carbonyl]-1H-indazole-3-carboxylic acid;

2-[4-Chloro-2-oxo-1'-(1H-pyrazolo[3,4-b]pyridine-5-carbonyl)spiro[indole-3,3'-pyrrolidine]-1-yl]-N-(2,2,2-trifluoroethyl)acetamide;

2-[4-Chloro-1'-(1H-indazole-5-carbonyl)-2-oxospiro[indole-3,3'-pyrrolidine]-1-yl]-N-(2,2,2-trifluoroethyl)acetamide;

2-[4-Chloro-2-oxo-1'-(1H-pyrazolo[4,3-b]pyridine-5-carbonyl)spiro[indole-3,3'-pyrrolidine]-1-yl]-N-(2,2,2-trifluoroethyl)acetamide;

(+) or (−)-2-[4-Chloro-1'-(1H-indazole-5-carbonyl)-2-oxospiro[indole-3,3'-pyrrolidine]-1-yl]-N-(2,2,2-trifluoroethyl)acetamide;

(−) or (+)-2-[4-Chloro-1'-(1H-indazole-5-carbonyl)-2-oxospiro[indole-3,3'-pyrrolidine]-1-yl]-N-(2,2,2-trifluoroethyl)acetamide 4,5-Dichloro-1-(2-oxo-2-(2-(2,2,2-trifluoroethyl)pyrrolidin-1-yl)ethyl)-1'-(1H-pyrazolo[4,3-b]pyridine-5-carbonyl)spiro[indoline-3,4'-piperidin]-2-one and pharmaceutically acceptable salts thereof.

Particular compounds of formula (I) of the present invention are those selected from the group consisting of:

2-[1'-(1H-Indazole-5-carbonyl)-4-methyl-2-oxospiro[indole-3,4'-piperidine]-1-yl]-N-(2,2,2-trifluoroethyl)acetamide;

2-[4-Bromo-1'-(1H-indazole-5-carbonyl)-2-oxospiro[indole-3,4'-piperidine]-1-yl]-N-(2,2,2-trifluoroethyl)acetamide;

2-[4-Chloro-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[4-Bromo-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[4,5-Dichloro-2-oxo-1'-(1H-pyrazolo[3,4-b]pyridine-5-carbonyl)spiro[indole-3,4'-piperidine]-1-yl]-N-(2,2,2-trifluoroethyl)acetamide;
2-[4-Bromo-2-oxo-1'-(1H-pyrazolo[4,3-b]pyridine-5-carbonyl)spiro[indole-3,4'-piperidine]-1-yl]-N-(2,2,2-trifluoroethyl)acetamide;
2-[4,5-Dichloro-2-oxo-1'-(1H-pyrazolo[3,4-c]pyridine-5-carbonyl)spiro[indole-3,4'-piperidine]-1-yl]-N-(2,2,2-trifluoroethyl)acetamide;
2-[4-Chloro-5-fluoro-2-oxo-1'-(1H-pyrazolo[3,4-c]pyridine-5-carbonyl)spiro[indole-3,4'-piperidine]-1-yl]-N-(2,2,2-trifluoroethyl)acetamide;
2-[4-Chloro-5-fluoro-1'-(1H-indazole-5-carbonyl)-2-oxospiro[indole-3,4'-piperidine]-1-yl]-N-(2,2,2-trifluoroethyl)acetamide;
2-[4-Chloro-5-fluoro-2-oxo-1'-(1H-pyrazolo[4,3-b]pyridine-5-carbonyl)spiro[indole-3,4'-piperidine]-1-yl]-N-(2,2,2-trifluoroethyl)acetamide;
2-[4-Chloro-5-fluoro-2-oxo-1'-(1H-pyrazolo[3,4-b]pyridine-5-carbonyl)spiro[indole-3,4'-piperidine]-1-yl]-N-(2,2,2-trifluoroethyl)acetamide;
2-[4,5-Dichloro-1'-(1H-indazole-5-carbonyl)-2-oxospiro[indole-3,4'-piperidine]-1-yl]-N-(2,2,2-trifluoroethyl)acetamide;
1-[2-(3,3-Difluoropyrrolidin-1-yl)-2-oxoethyl]-1'-(1H-indazole-5-carbonyl)-4-methylspiro[indole-3,4'-piperidine]-2-one;
4-Bromo-1-(2-oxo-2-(2-(trifluoromethyl)morpholino)ethyl)-1'-(1H-pyrazolo[3,4-b]pyridine-5-carbonyl)spiro[indoline-3,4'-piperidin]-2-one;
2-[4-Bromo-5-fluoro-2-oxo-1'-(1H-pyrazolo[3,4-b]pyridine-5-carbonyl)spiro[indole-3,4'-piperidine]-1-yl]-N-(2,2,2-trifluoroethyl)acetamide;
5'-Chloro-1-(1H-indazole-5-carbonyl)-1'-[2-oxo-2-[(2S)-2-(trifluoromethyl)pyrrolidin-1-yl]ethyl]spiro[piperidine-4,3'-pyrrolo[3,2-b]pyridine]-2'-one; and
pharmaceutically acceptable salts thereof.

Compounds of formula (III) are suitable as intermediates in the manufacture of compounds of formula (I).

Another embodiment of the invention relates to a compound of formula (III)

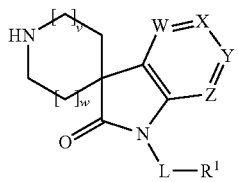

wherein L, $R^1$, W, X, Y, Z, v and w are as described herein;
and salts thereof.

Manufacturing Process

One embodiment of the invention relates to a process for the manufacture of a compound of formula (I) comprising the amide coupling of a compound of formula (III) with an optionally protected carboxylic acid of formula $R^6COOH$ to yield a compound of formula (I), wherein L, W, X, Y, Z, v, w, $R^1$ and $R^6$ are as described herein.

One embodiment of the invention relates to a process for the manufacture of a compound of formula (I) comprising the deprotection step of a compound of formula (II) to a compound of formula (III) followed by the amide coupling step of a compound of formula (III) with an optionally protected carboxylic acid of formula $R^6COOH$ to yield a compound of formula (I), wherein PG is a protecting group, particularly an amino-protecting group, most particularly a benzyl or tert-butyloxycarbonyl group, and L, W, X, Y, Z, v, w, $R^1$ and $R^6$ are as described herein.

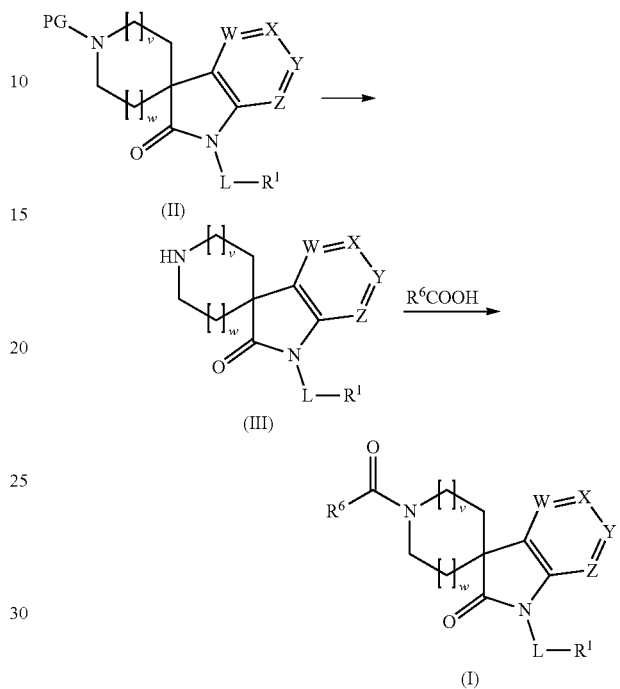

If one of the starting materials, intermediates or compounds of formula (I) contain one or more functional groups which are not stable or are reactive under the reaction conditions of one or more reaction steps, appropriate protecting groups (as described e.g., in "Protective Groups in Organic Chemistry" by T. W. Greene and P. G. M. Wutts, 5$^{th}$ Ed., 2014, John Wiley & Sons, N.Y.) can be introduced before the critical step applying methods well known in the art. Such protecting groups can be removed at a later stage of the synthesis using standard methods described in the literature.

If starting materials or intermediates contain stereogenic centers, compounds of formula (I) can be obtained as mixtures of diastereomers or enantiomers, which can be separated by methods well known in the art e.g., (chiral) HPLC or crystallization. Racemic compounds can e.g., be separated into their antipodes via diastereomeric salts by crystallization with optically pure acids or by separation of the antipodes by specific chromatographic methods using either a chiral adsorbent or a chiral eluent.

A person skilled in the art will acknowledge that in the synthesis of compounds of formula (I)—insofar not desired otherwise—an "orthogonal protection group strategy" will be applied, allowing the cleavage of several protective groups one at a time each without affecting other protecting groups in the molecule. The principle of orthogonal protection is well known in the art and has also been described in literature (e.g. Barany and R. B. Merrifield, *J Am. Chem. Soc.* 1977, 99, 7363; H. Waldmann et al., *Angew. Chem. Int. Ed. Engl.* 1996, 35, 2056).

A person skilled in the art will acknowledge that the sequence of reactions may be varied depending on reactivity and nature of the intermediates.

Compounds of formula IA-IE wherein o is 1, 2 or 3, p is 0 or 1, PG is a protecting group, $R^{20}$ is $C_{1-7}$alkyl, halo-$C_{1-7}$alkyl, $C_{3-7}$ cycloalkyl, $C_{3-7}$ alkyl-$C_{3-7}$ cycloalkyl, aryl; and $R^2$ to $R^{10}$, W, X, Y, Z, v, w, m, n and q are as described herein can be synthesized according to literature procedures and as depicted in Scheme 1.

Compounds of formula IA can be prepared for example by alkylation of intermediates 1 in which PG signifies a suitable protecting group such as a benzyl or tert-butyloxycarbonyl group with compounds of the type $LG(CHR^7)_m(CHR^8)_nC(O)NHR^9$ (LG signifies a leaving group such as Cl, Br, I, $OSO_2$alkyl, $OSO_2$fluoroalkyl or $OSO_2$aryl) in an appropriate solvent such as DMF and using an appropriate base such as cesium carbonate at temperatures ranging from 0° C. to the reflux temperature of the solvent to give intermediates 2 (step a).

Removal of the protecting group from intermediates 2 by methods known to those skilled in the art and as described in literature, for example in "Protective Groups in Organic Chemistry" by T. W. Greene and P. G. M. Wutts, 5$^{th}$ Ed., 2014, John Wiley & Sons, N.Y. (e.g., a benzyl group by hydrogenation using a suitable catalyst such as palladium on carbon in an appropriate solvent such as MeOH, EtOH, EtOAc or mixtures thereof, or using 1-chloroethyl chloroformate with a suitable base and solvent such as DIPEA in DCE; a Boc group by reaction with TFA in DCM) furnishes intermediates 3 (step b).

Reaction of intermediates 3 with carboxylic acids of the type $R^6COOH$, furnishes compounds IA (step c). Amide couplings of this type are widely described in the literature and can be accomplished by the usage of coupling reagents such as CDI, DCC, HATU, HBTU, HOBT, TBTU or Mukaiyama reagent in a suitable solvent e.g., DMF, DMA, DCM or dioxane, optionally in the presence of a base (e.g., $NEt_3$, DIPEA (Huenig's base) or DMAP). Alternatively, the optionally protected carboxylic acids $R^6COOH$ can be converted into their acid chlorides by treatment with, e.g. thionyl chloride, neat or optionally in a solvent such as DCM. Reaction of the acid chloride with intermediates 3 in an appropriate solvent such as DCM or DMF and a base, e.g. $NEt_3$, Huenig's base, pyridine, DMAP or lithium bis(trimethylsilyl)amide at temperatures ranging from 0° C. to the reflux temperature of the solvent or solvent mixture yields compounds IA (step c).

Compounds of formula IB can be prepared in for example by alkylation of intermediates 1 in which PG signifies a suitable protecting group such as a benzyl or tert-butyloxycarbonyl group with compounds of the type $LG(CHR^7)_m(CHR^8)_nC(O)NR^9R^{10}$ in which LG signifies a leaving group such as Cl, Br, I, $OSO_2$alkyl, $OSO_2$fluoroalkyl or $OSO_2$aryl in an appropriate solvent such as DMF and using an appropriate base such as cesium carbonate at temperatures ranging from 0° C. to the reflux temperature of the solvent or solvent mixture to give intermediates 4 (step d).

Removal of the protecting group from intermediates 4 for example applying the methods described under Scheme 1, step b, furnishes intermediates 5 (step e).

Reaction of intermediates 5 with carboxylic acids of the type $R^6COOH$ applying for example the methods described in Scheme 1, step c, furnishes compounds IB (step f).

Scheme 1

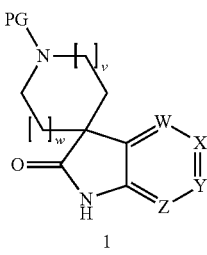

1

PG = Protective group

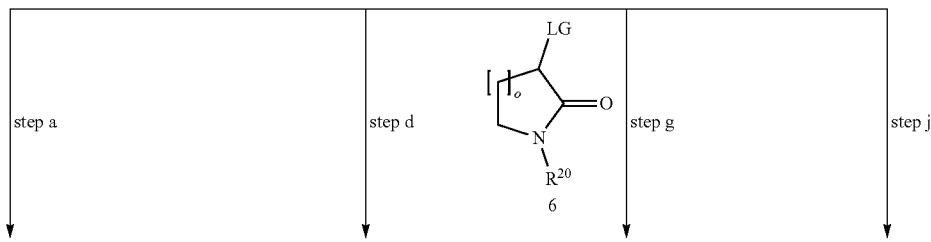

-continued

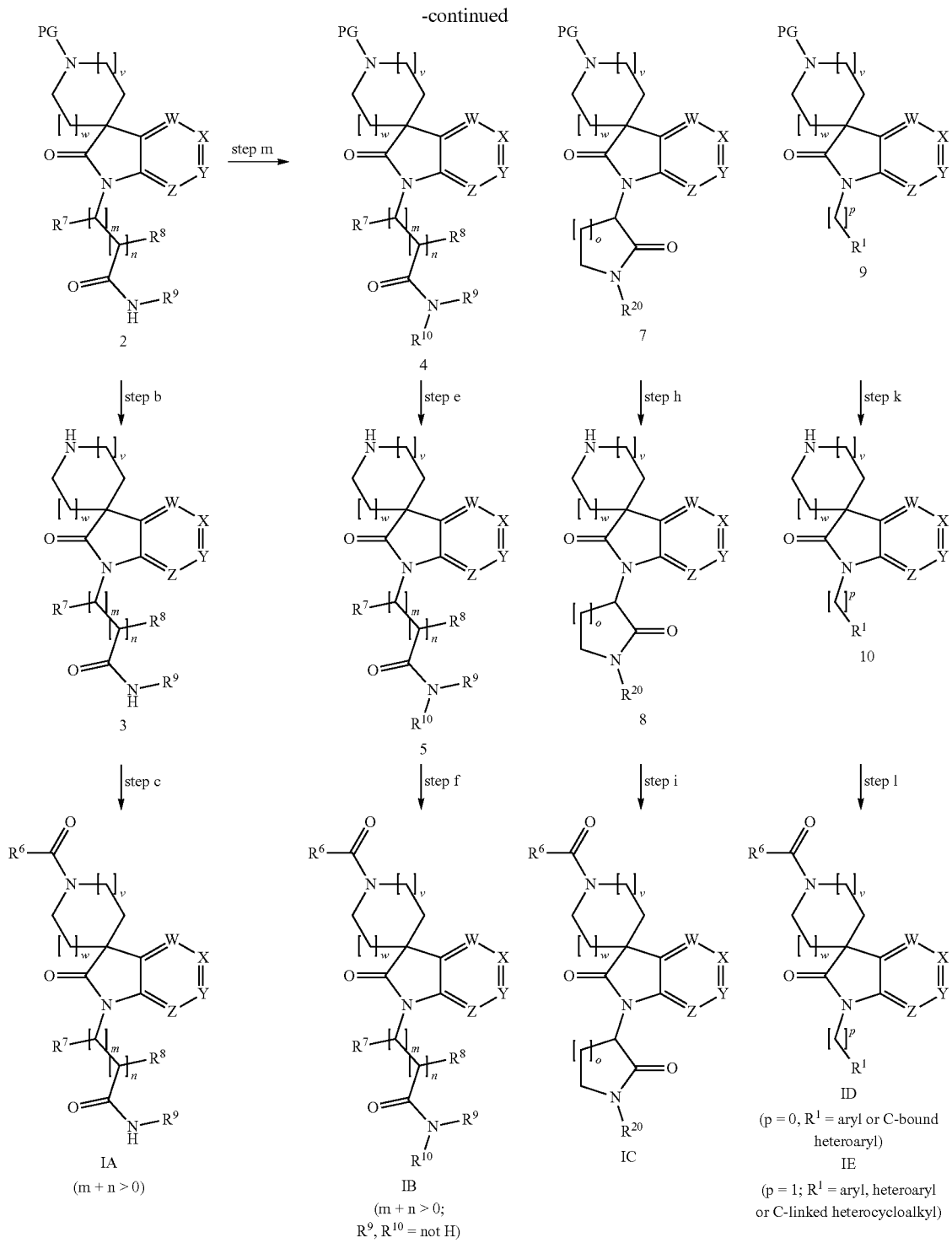

Compounds IB can alternatively be prepared by alkylation of intermediates 2 with compounds $R^{10}$-LG in which LG signifies a suitable leaving group such as bromo (or another leaving group such as chloro, iodo or OSO$_2$alkyl, OSO$_2$fluoroalkyl, OSO$_2$aryl) using an appropriate base and solvent such as sodium hydride in THF to furnish intermediates 4 (step m). Subsequent deprotection and acylation as described before in Scheme 1, step b and step c, respectively furnishes compounds IB.

Compounds of formula IC can be prepared for example by alkylation of intermediates 1 with γ-, δ- or ε-lactams 6 (o=1, 2 or 3, respectively; either commercially available or prepared by methods known in the art) in which LG signifies a suitable leaving group such as bromo (or another leaving group such as chloro, iodo or OSO$_2$alkyl, OSO$_2$fluoroalkyl, OSO$_2$aryl) using an appropriate base and solvent such as sodium hydride in THF to furnish compounds 7 (step g).

Removal of the protecting group from intermediates 7 as described for example under Scheme 1, step b, furnishes intermediates 8 (step h).

Reaction of intermediates 8 with carboxylic acids of the type $R^6COOH$ using for example the methods described under Scheme 1, step c, furnishes compounds IC (step i).

Compounds of formula ID in which p=0 and $R^1$ signifies a optionally substituted phenyl or optionally substituted heteroaryl ring linked via carbon atom can be prepared for example from intermediates 1 as described in Scheme 1. Reaction of intermediates 1 with compounds $R^1LG$ in which LG represents a suitable leaving group such iodo or bromo (or another leaving group such as $OSO_2$alkyl, $OSO_2$fluoroalkyl or $OSO_2$aryl) using an appropriate base and solvent such as $K_2CO_3$ in dioxane in the presence of DMEDA and Cu(I) at temperatures between RT and the boiling point of the solvent yields compounds 9 (p=0, step i). Microwave heating may be applied to accelerate the reaction or drive the reaction to completion.

Removal of the protecting group in intermediates 9 for example applying the methods described under Scheme 1, step b, furnishes intermediates 10 (p=0, step k).

Reaction of intermediates 10 with carboxylic acids of the type $R^6COOH$ using for example the methods described under Scheme 1, step c, furnishes compounds ID (p=0, step 1).

Compounds of formula IE in which p=1 and $R^1$ signifies an optionally substituted phenyl or via carbon linked optionally substituted heteroaryl ring can be prepared from intermediates 1 as depicted in Scheme 1. Alkylation of intermediates 1 with compounds $R^1CH_2LG$ in which LG represents a suitable leaving group such as chloro, bromo, iodo (or another leaving group such as $OSO_2$alkyl, $OSO_2$fluoroalkyl or $OSO_2$aryl) using an appropriate base and solvent such as sodium hydride in THF yields compounds 9 (p=1, step i).

Removal of the protecting group in intermediates 9 for example using the methods described under Scheme 1, step b, furnishes intermediates 10 (p=1, step k).

Acylation of intermediates 10 with carboxylic acids of the type $R^6COOH$ applying for example the methods described under Scheme 1, step c, furnishes compounds IE (p=1, step 1).

Scheme 2

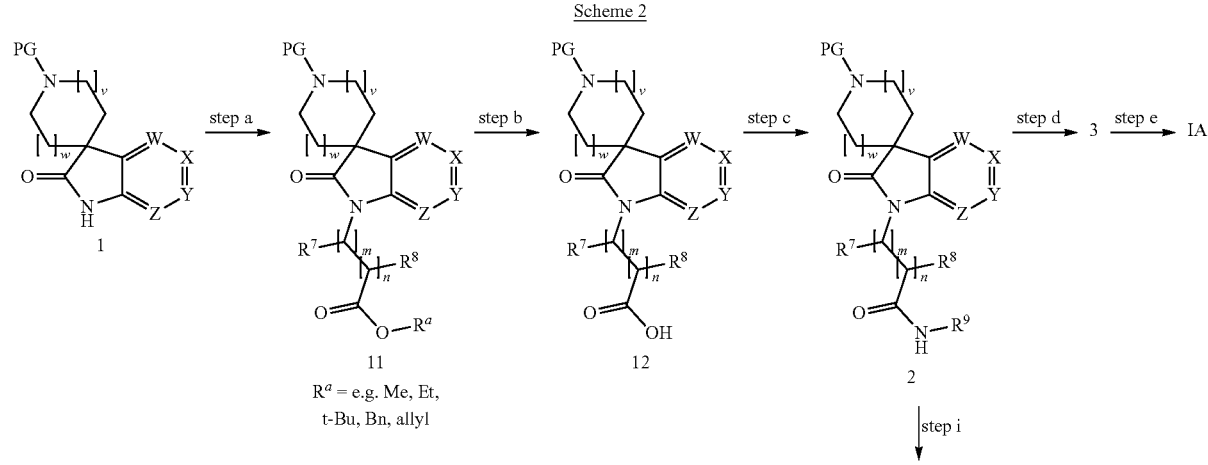

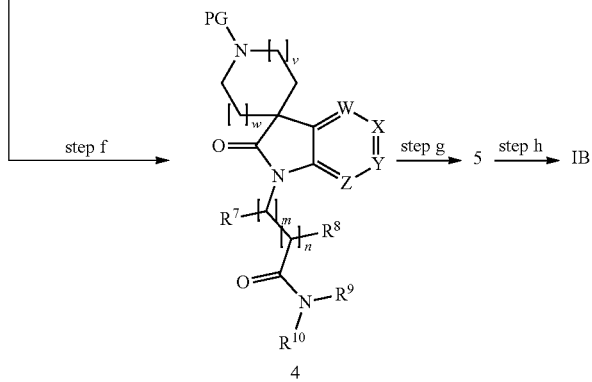

Compounds formula IA and IB can be alternatively synthesized from intermediates 12 as depicted in Scheme 2, wherein PG is a protecting group, $R^a$ signifies a group such as methyl, ethyl, benzyl, tert-butyl or allyl that can be cleaved without affecting PG, $R^7$ to $R^{10}$, W, X, Y, Z, v, w, m and n and are as described herein.

Alkylation of intermediates 1 in which PG signifies a suitable protecting group such as a benzyl or tert-butyloxycarbonyl group with compounds of the type $LG(CHR^7)_m(CHR^8)_nC(O)OR^a$ (LG signifies a leaving group such as Cl, Br, I, $OSO_2alkyl$, $OSO_2fluoroalkyl$ or $OSO_2aryl$), either commercially available or prepared by literature methods, in an appropriate solvent such as DMF and using an appropriate base such as $Cs_2CO_3$ at temperatures ranging from 0° C. to the reflux temperature of the solvent yields intermediates 11 (step a).

Cleavage of the ester functionality in intermediates 11 by methods known in the art and as described for example in "Protective Groups in Organic Chemistry" by T. W. Greene and P. G. M. Wutts, 5th Ed., 2014, John Wiley & Sons, N.Y. (e.g., a methyl or ethyl ester under basic (e.g. lithium or sodium hydroxide in polar solvents such as methanol, $H_2O$ or THF or mixtures of said solvents) or under acidic conditions (e.g. a tert-butyl ester using TFA in $CH_2Cl_2$, concentrated hydrochloric acid in THF or formic acid in an appropriate solvent such as alcohols like isopropanol)) furnishes intermediates 12 (step b). Further esters include, but are not limited to, e.g. benzyl esters that can be cleaved for example by hydrogenation using a suitable catalyst such as palladium on carbon in an appropriate solvent such as MeOH, EtOH, EtOAc or mixtures thereof, or using 1-chloroethyl chloroformate with a suitable base and solvent such as DIPEA in DCE.

Amide coupling of intermediates 12 with amines $R^9NH_2$ (either commercially available or prepared by methods well known in the art) yields intermediates 2 (step c). Amide couplings of this type are widely described in the literature and can be accomplished by the usage of coupling reagents such as, e.g. CDI, DCC, HATU, HBTU, HOBT, TBTU or Mukaiyama reagent in a suitable solvent, e.g., DMF, DMA, DCM or dioxane, optionally in the presence of a base (e.g. $NEt_3$, DIPEA or DMAP). Alternatively, the carboxylic acid functionality in compounds 12 can be converted into an acid chloride by treatment with, e.g. thionyl chloride, neat or optionally in a solvent such as DCM. Reaction of the acid chloride with amines $R^9NH_2$ in an appropriate solvent such as DCM or DMF in the presence of an appropriate base, e.g. $NEt_3$, Huenig's base, pyridine, DMAP or lithium bis(trimethylsilyl)amide at temperatures ranging from 0° C. to the reflux temperature of the solvent or solvent mixture yields intermediates 2 (step c).

Intermediates 2 can be converted into intermediates 3 (step d) and further into compounds IA (step e) by methods known in the art and using the reagents and applying the reaction conditions described before, e.g. in Scheme 1 step b and step c.

Compounds IB can be prepared from intermediates 12 and secondary amines $R^9R^{10}NH$ (either commercially available or prepared by methods well known in the art) by literature methods using the reagents and applying the reaction conditions described before under Scheme 2, stec to give intermediates 4 (step f).

Intermediates 4 can then be transformed into intermediates 5 (step g) that can be further converted into compounds IB (step h) by methods known in the art and using the reagents and applying the reaction conditions described before, e.g. in Scheme 1 step e and step f.

Intermediates 4 can alternatively be prepared from intermediates 2 applying methods known in the art and using the reagents and applying the reaction conditions described before, e.g. in Scheme 1 step k (step i).

Subsequent deprotection followed by acylation as described for example under Scheme 1, step e and step f furnishes compounds IB (step g and step h).

Scheme 3

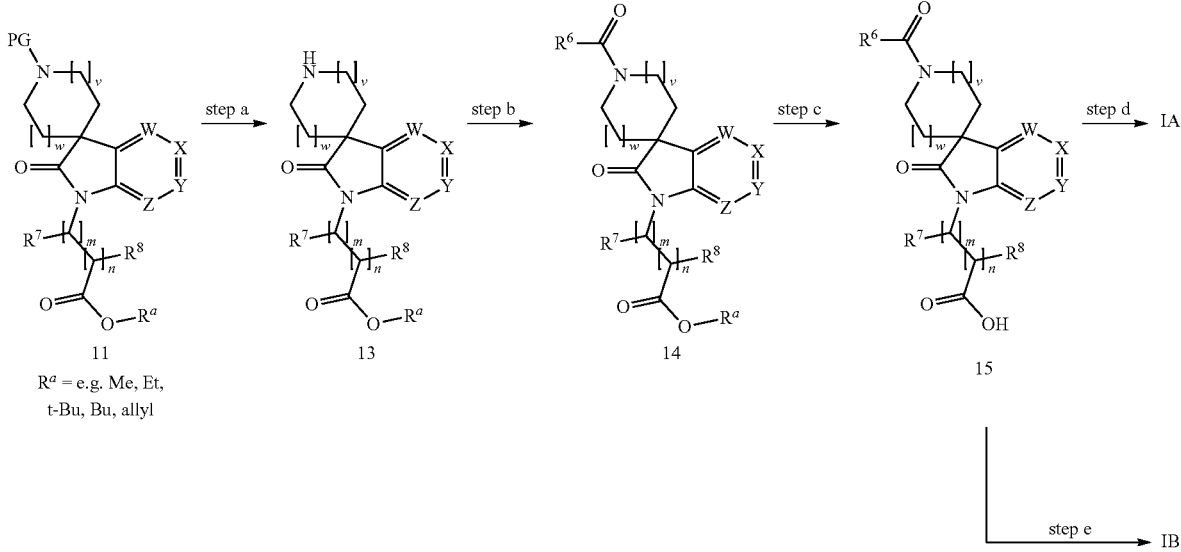

11
$R^a$ = e.g. Me, Et, t-Bu, Bu, allyl

Compounds of formula IA and IB can be alternatively synthesized from intermediates 11 as depicted in Scheme 3, wherein PG is a protecting group, $R^a$ signifies a cleavable group such as methyl, ethyl, benzyl, tert-butyl or allyl and $R^6$ to $R^8$, W, X, Y, Z, v, w, m and n are as described herein.

Removal of the protecting group in intermediates 11 by methods described in literature, e.g. in "Protective Groups in Organic Chemistry" by T. W. Greene and P. G. M. Wutts, 5$^{th}$ Ed., 2014, John Wiley & Sons, N.Y. and as described under Scheme 1, step b, yields intermediates 13 (step a).

Amide coupling of intermediates 13 with carboxylic acids R$^6$COOH applying methods described in literature and as described under Scheme 1, step c, gives intermediates 14 (step b).

Cleavage of the ester functionality in intermediates 14 using methods known in the art and as described under Scheme 2, step b, furnishes intermediates 15 (step c).

Amide coupling of intermediates 15 with amines of the type R$^9$NH$_2$ and R$^9$R$^{10}$NH applying the reaction conditions described in literature and as described under Scheme 2, step c and step f, yields compounds IA and IB, respectively (step d and step e).

In case one or more substituents in compounds IA-IE carry protecting groups these can be removed by methods known to those skilled in the art and as described for example in "Protective Groups in Organic Chemistry" by T. W. Greene and P. G. M. Wutts, 5$^{th}$ Ed., 2014, John Wiley & Sons, N.Y. to furnish the final compounds.

A person skilled in the art will acknowledge that the sequence of reactions steps as depicted in Schemes 1 to 3 may be varied depending on reactivity and nature of the intermediates.

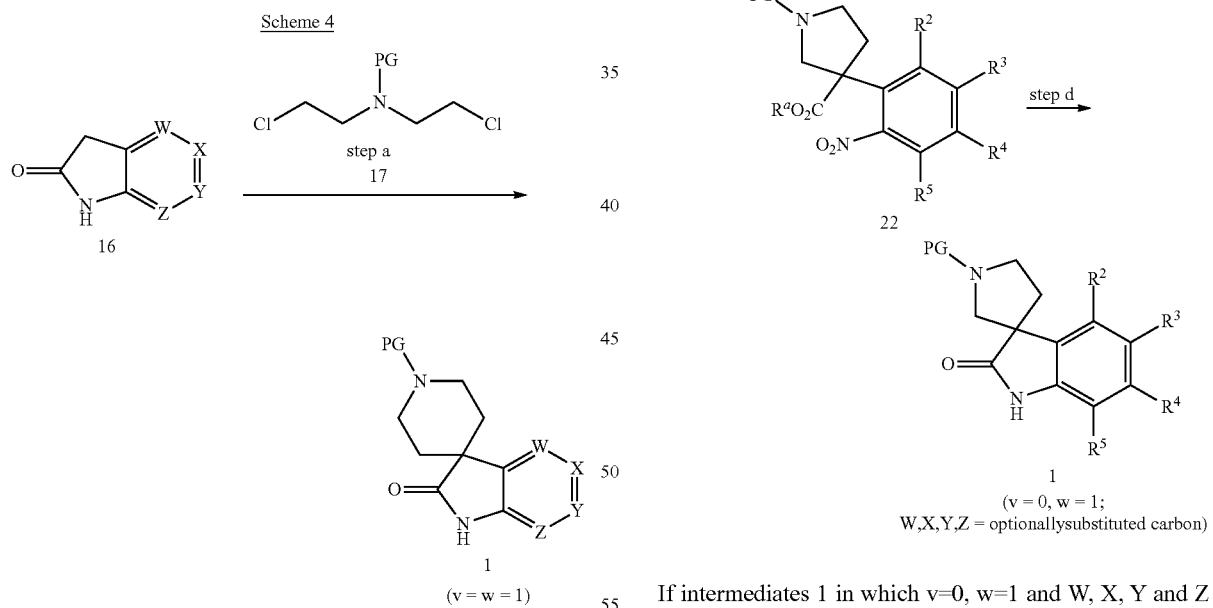

Scheme 4

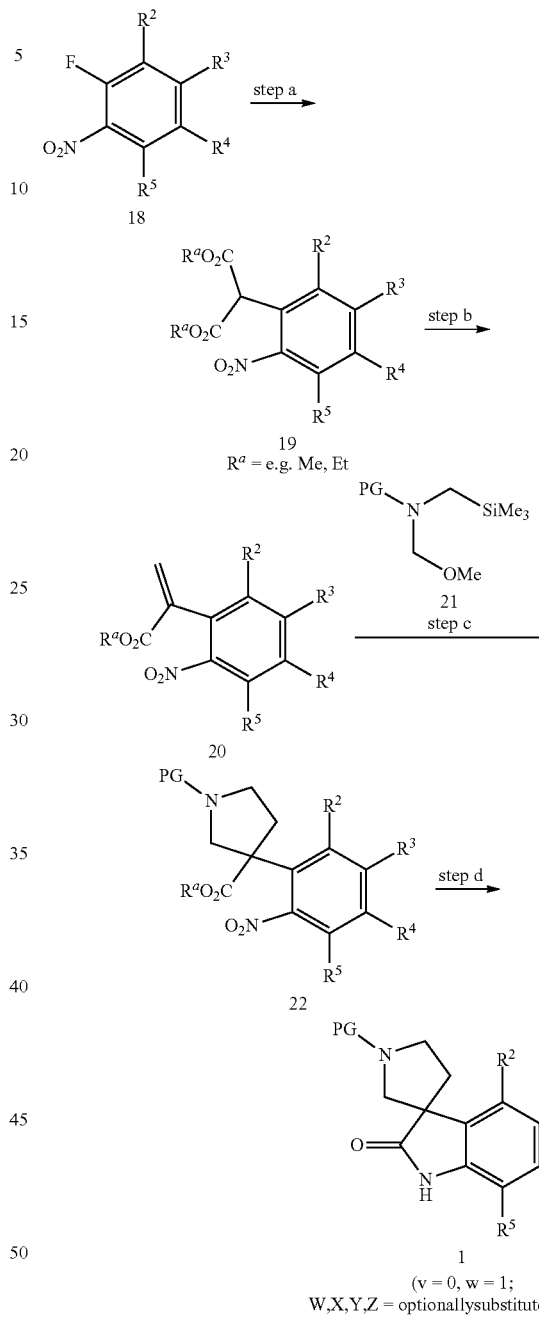

Scheme 5

If intermediates 1 in which v=w=1 are commercially not available they can be prepared by methods known in the art and as described in literature, for example in WO2004/069256 or WO2009/089454, and as depicted in Scheme 4, by reacting intermediates 16 with commercially available N,N-bis(2-chloroethyl)amines 17 in which PG is a protective group such as benzyl or Boc using a suitable base and solvent such as lithium or sodium bis(trimethylsilyl)amide in THF at temperatures ranging from −78° C. to the boiling point of the solvent (step a).

If intermediates 1 in which v=0, w=1 and W, X, Y and Z are optionally substituted carbon are commercially not available they can be prepared for example as depicted in Scheme 5. Several steps of this synthetic sequence have also been described in literature (e.g. J. E. Murray et al., *J. Org. Chem.*, 42, 1977; Selvakumar et al., *Tetrahedron Lett.* 2002, 43, 9175; S. Comesse et al., *Org. Biomol. Chem.* 2013, 11, 1818).

1-Fluoro-2-nitro benzenes 18, either commercially available or prepared by methods known in the art, can be reacted for example with dimethyl or diethyl malonate using a suitable base and solvent such as sodium hydride in THF to give intermediates 19 (step a).

Reaction of intermediates 19 with formalin using for example potassium carbonate as a base in H₂O at temperatures ranging from room temperature to the boiling point of the solvent affords the propenoic acid intermediates 20 (step b).

Reaction of intermediates 20 with commercially available benzyl(methoxymethyl)(trimethylsilylmethyl)amine 21 in the presence of an acid (e.g. trifluoroacetic acid in toluene or DCM) or fluoride source (e.g. LiF in ACN) provides intermediates 22 (step c). Reactions of that type have also been described in literature (e.g.

WO2007/060526, WO2012/093109 or M. J. Fray et al., Tetrahedron Lett. 2010, 51, 1026).

Reduction of the nitro functionality in intermediates 22 and cyclization of the amine onto the ester group applying literature procedures, for example iron in a mixture of THF and H₂O in the presence of ammonium chloride at temperatures ranging from room temperature to the boiling point of the solvent furnishes intermediates 1 in which v=0, w=1 and W, X, Y and Z are optionally substituted carbon (step d).

The hydroxyl functionalities in intermediates 25 can be converted into a suitable leaving group such as a trifluoromethanesulfonate group by methods known to those skilled in the art, for example by reacting intermediates 25 with trifluoromethanesulfonic anhydride in the presence of a base such as Huenig's base in a solvent such as ACN and DCM to give intermediates 26 (step c).

Depending on the stability, intermediates 26 can be isolated or converted in situ into intermediates 27 by reaction with a primary amine of the type PG'-NH₂ in which PG' signifies a suitable protecting group such as benzyl, 2,4-dimethoxybenzyl or allyl in a solvent such as ACN (step d).

Removal of the protecting group PG in intermediates 27 by methods known to those skilled in the art and as described for example in "Protective Groups in Organic Chemistry" by T. W. Greene and P. G. M. Wutts, 5th Ed., 2014, John Wiley & Sons, N.Y. furnishes intermediates 1 in which v=w=0 and W, X, Y and Z are optionally substituted carbon (step e).

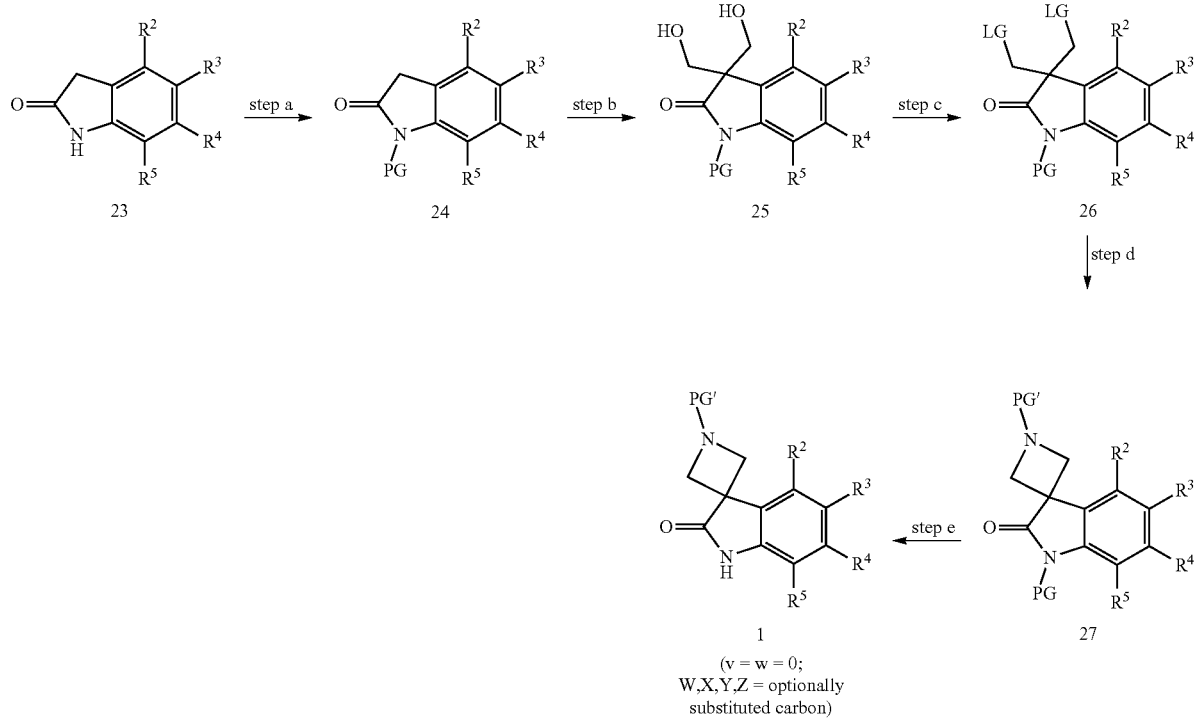

If intermediates 1 in which v=w=0 and W, X, Y and Z are optionally substituted carbon and are commercially not available they can be prepared for example as depicted in Scheme 6.

Intermediates 23 can be protected according to methods known in the art and as described for example in "Protective Groups in Organic Chemistry" by T. W. Greene and P. G. M. Wutts, 5th Ed., 2014, John Wiley & Sons, N.Y. to furnish intermediates 24 (step a).

Intermediates 24 can be transformed into intermediates 25 for example by reacting intermediates 24 with paraformaldehyde using a suitable base and solvent such as K₂CO₃ in THF (step b).

Scheme 7

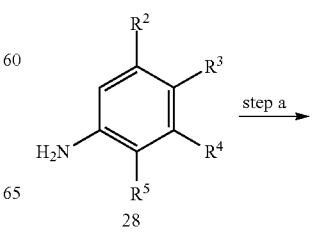

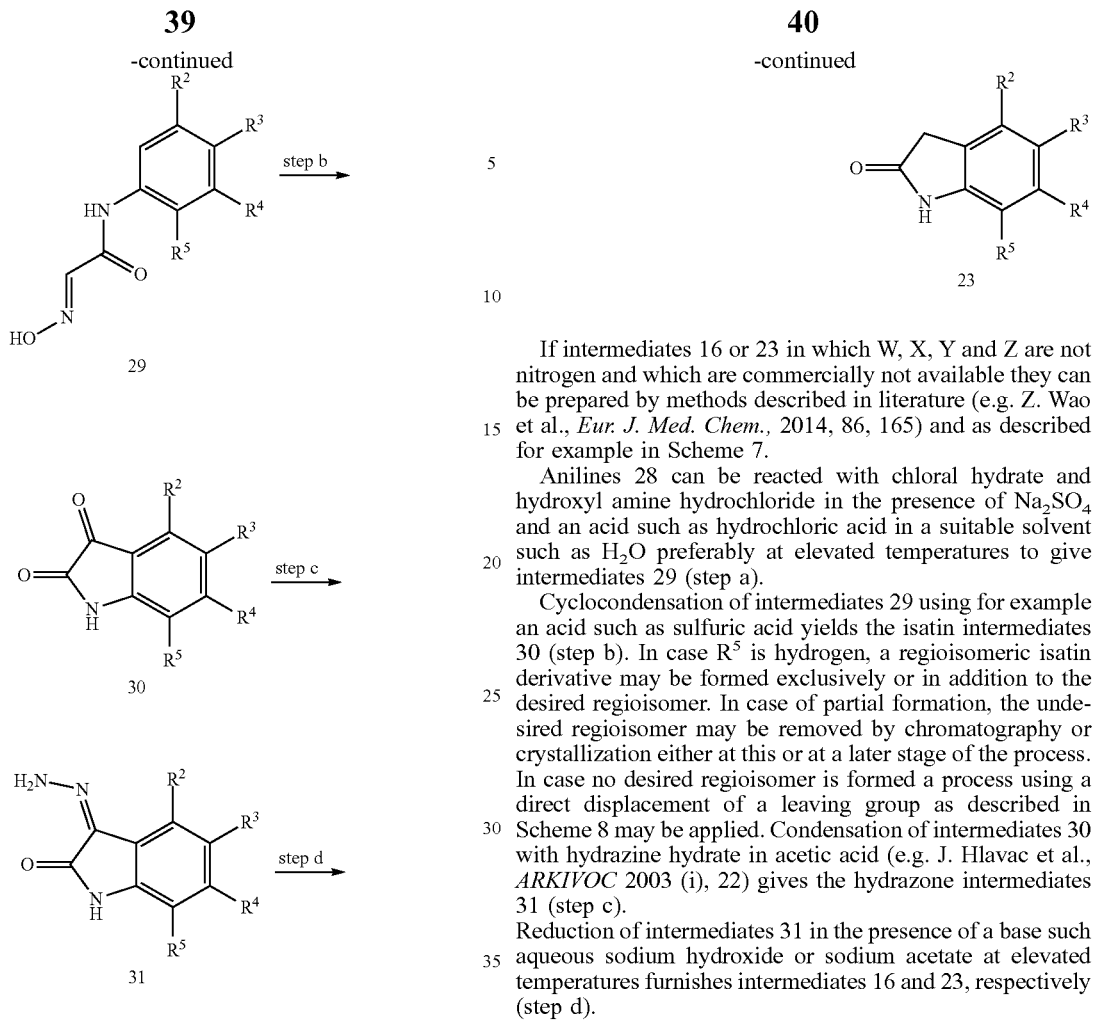

If intermediates 16 or 23 in which W, X, Y and Z are not nitrogen and which are commercially not available they can be prepared by methods described in literature (e.g. Z. Wao et al., *Eur. J. Med. Chem.*, 2014, 86, 165) and as described for example in Scheme 7.

Anilines 28 can be reacted with chloral hydrate and hydroxyl amine hydrochloride in the presence of $Na_2SO_4$ and an acid such as hydrochloric acid in a suitable solvent such as $H_2O$ preferably at elevated temperatures to give intermediates 29 (step a).

Cyclocondensation of intermediates 29 using for example an acid such as sulfuric acid yields the isatin intermediates 30 (step b). In case $R^5$ is hydrogen, a regioisomeric isatin derivative may be formed exclusively or in addition to the desired regioisomer. In case of partial formation, the undesired regioisomer may be removed by chromatography or crystallization either at this or at a later stage of the process. In case no desired regioisomer is formed a process using a direct displacement of a leaving group as described in Scheme 8 may be applied. Condensation of intermediates 30 with hydrazine hydrate in acetic acid (e.g. J. Hlavac et al., *ARKIVOC* 2003 (i), 22) gives the hydrazone intermediates 31 (step c).

Reduction of intermediates 31 in the presence of a base such aqueous sodium hydroxide or sodium acetate at elevated temperatures furnishes intermediates 16 and 23, respectively (step d).

Scheme 8

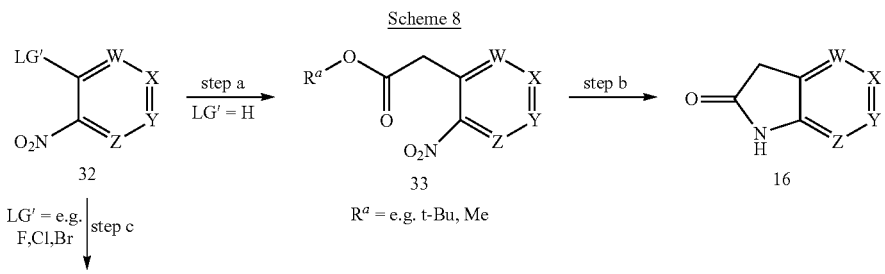

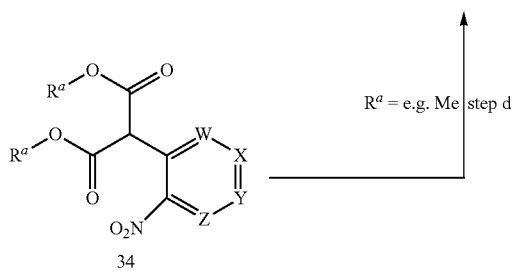

Intermediates 16 can be alternatively synthesized from intermediates 33 as depicted in Scheme 8.

In case intermediates 33 are commercially not available they can be prepared by methods well known in the art, for example applying the "vicarious nucleophilic substitution reaction", reacting nitroarenes 32 in which LG' is hydrogen with compounds of the type $LGCH_2COOR^a$ in which LG is a leaving group selected from, but not limited to, chloro, bromo or trimethylsilyl and $R^a$ signifies for example a methyl, ethyl or tert-butyl group in the presence of a suitable base such as sodium hydride or potassium tert-butylate in a solvent such as DMF or THF (step a).

Reduction of the nitro functionality in intermediates 33 and cyclization of the resulting amine on the ester group applying literature procedures, for example iron in acetic acid or in a mixture of THF and $H_2O$ in the presence of ammonium chloride, at temperatures ranging from room temperature to the boiling point of the solvent furnishes intermediates 16 (step b).

Alternatively, nitroarenes 32 in which LG' is a suitable leaving group such as F, Cl or Br can be reacted with dimethyl malonate using for example sodium hydride as a base in a solvent such as DMSO to give intermediates 34 (step c).

Decarboxylation of intermediates 34 using for example lithium chloride in DMSO, provides intermediates 33 (step d).

Reactions of this type are well known in the art and described in literature (e.g. J. A. Joule, Science of Synthesis 2001, 10, 361; B. Mudryk et al., Synthesis 1988, 12, 1007; G. J. Quallich et al., Synthesis, 1993, 1, 51).

Compounds of formula IF wherein $R^{10}$ is H, m is 1, n is 0, Q signifies O, S, SO, $SO_2$, NH or $NR^{21}$, PG is a protecting group, and $R^6$ to $R^{10}$, W, X, Y, Z, v and w are as described herein can be synthesized according to literature procedures and as depicted in Scheme 9.

Intermediates 1 can be reacted for example with propargylic acid tert-butyl ester in the presence of triphenylphosphine in a solvent like DCM to give intermediates 35 (step a).

Reaction of intermediates 35 with compounds 36 in a solvent such as DMF yields intermediates 37 (step b).

Removal of the tert-butyl group by methods known to those skilled in the art and as described for example in "Protective Groups in Organic Chemistry" by T. W. Greene and P. G. M. Wutts, 5th Ed., 2014, John Wiley & Sons, N.Y., e.g. by reaction with TFA in DCM, furnishes intermediates 38 (step c).

Intermediates 38 can be transformed into the amide intermediates 39 by methods known in literature and as described under Scheme 2, step c (step d).

Removal of the protecting group from intermediates 39 by methods known to those skilled in the art and as described for example in "Protective Groups in Organic Chemistry" by T. W. Greene and P. G. M. Wutts, 5th Ed., 2014, John Wiley & Sons, N.Y. gives intermediates 40 (step e).

Scheme 9

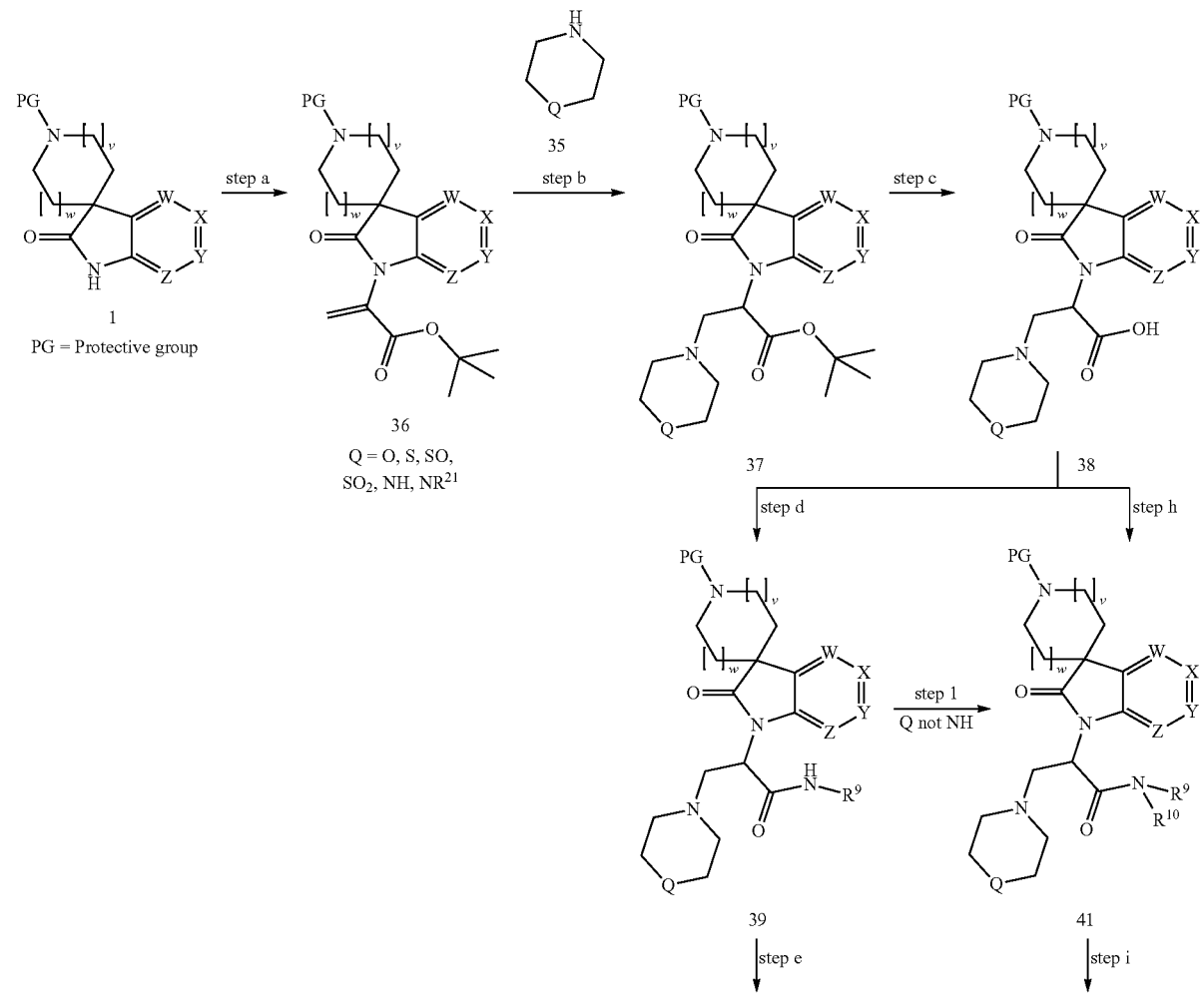

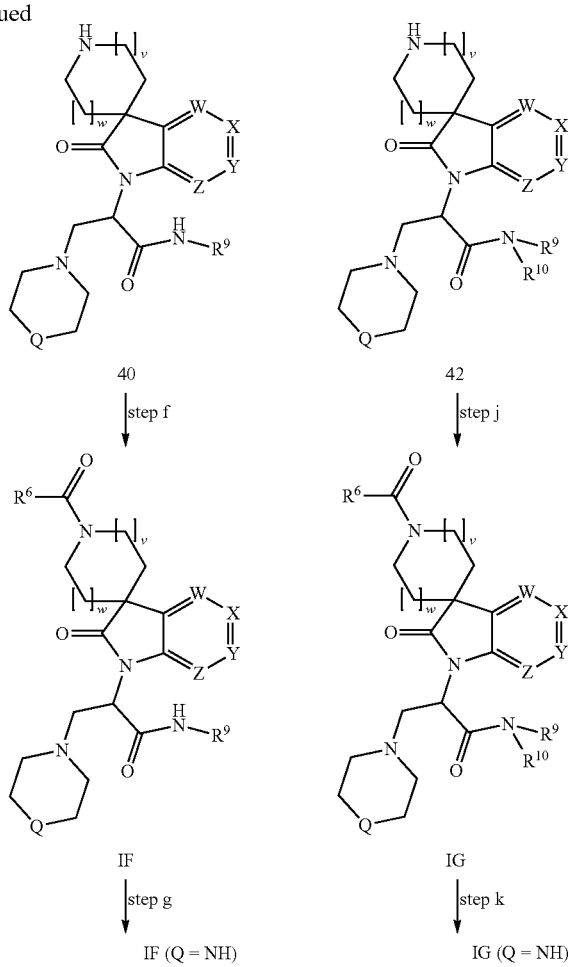

Acylation of intermediates 40 with acids R⁶COOH using methods known in the art and as described under Scheme 1, step c, furnishes compounds IF (step f).

Compounds IF in which Q is nitrogen substituted by hydrogen, compounds IF can be prepared according to the methods described above and using piperazines 36 in which one of the two nitrogen atoms is protected with a suitable protecting group and removing the protecting group as the final reaction step (step g) by methods known in the art and as described for example in "Protective Groups in Organic Chemistry" by T. W. Greene and P. G. M. Wutts, 5th Ed., 2014, John Wiley & Sons, N.Y.

Compounds of formula IG wherein $R^9$ and $R^{10}$ are not H, m is 1, n is 0, Q signifies O, S, SO, $SO_2$, NH or $NR^{21}$, PG is a protecting group and v and w are as described herein can be synthesized according to literature procedures and as depicted in Scheme 9 from intermediates 38.

Intermediates 38 can be transformed into tertiary amide intermediates 41 by reaction with secondary amines $R^9R^{10}NH$ (either commercially available or prepared by methods well known in the art) applying methods known in literature and as described under Scheme 2, step f (step h).

Removal of the protecting group in intermediates 41 by methods known to those skilled in the art and as described for example in "Protective Groups in Organic Chemistry" by T. W. Greene and P. G. M. Wutts, 5th Ed., 2014, John Wiley & Sons, N.Y. gives intermediates 42 (step i).

Acylation of intermediates 42 with acids R⁶COOH using methods known in the art and as described for example under Scheme 1, step c, furnishes compounds IG (step i).

Compounds IG in which Q in is nitrogen substituted by hydrogen can be prepared according to the methods described above using piperazines 36 in which one of the two nitrogen atoms is protected with a suitable protecting group and removing the protecting group on the final reaction step (step k) by methods known in the art and as described for example in "Protective Groups in Organic Chemistry" by T. W. Greene and P. G. M. Wutts, 5th Ed., 2014 Wiley & Sons, N.Y.

Intermediates 41 in which Q ≠ NH for the preparation of compounds IG may alternatively be prepared by alkylation of intermediates 39 with compounds $R^{10}$-LG in which LG signifies a suitable leaving group such as bromo (or another leaving group such as chloro, iodo or $OSO_2$alkyl, $OSO_2$fluoroalkyl, $OSO_2$aryl) using the conditions as described under Scheme 1, step k (step l). Subsequent deprotection and acylation as described before under step i and step i, respectively furnishes compounds IB.

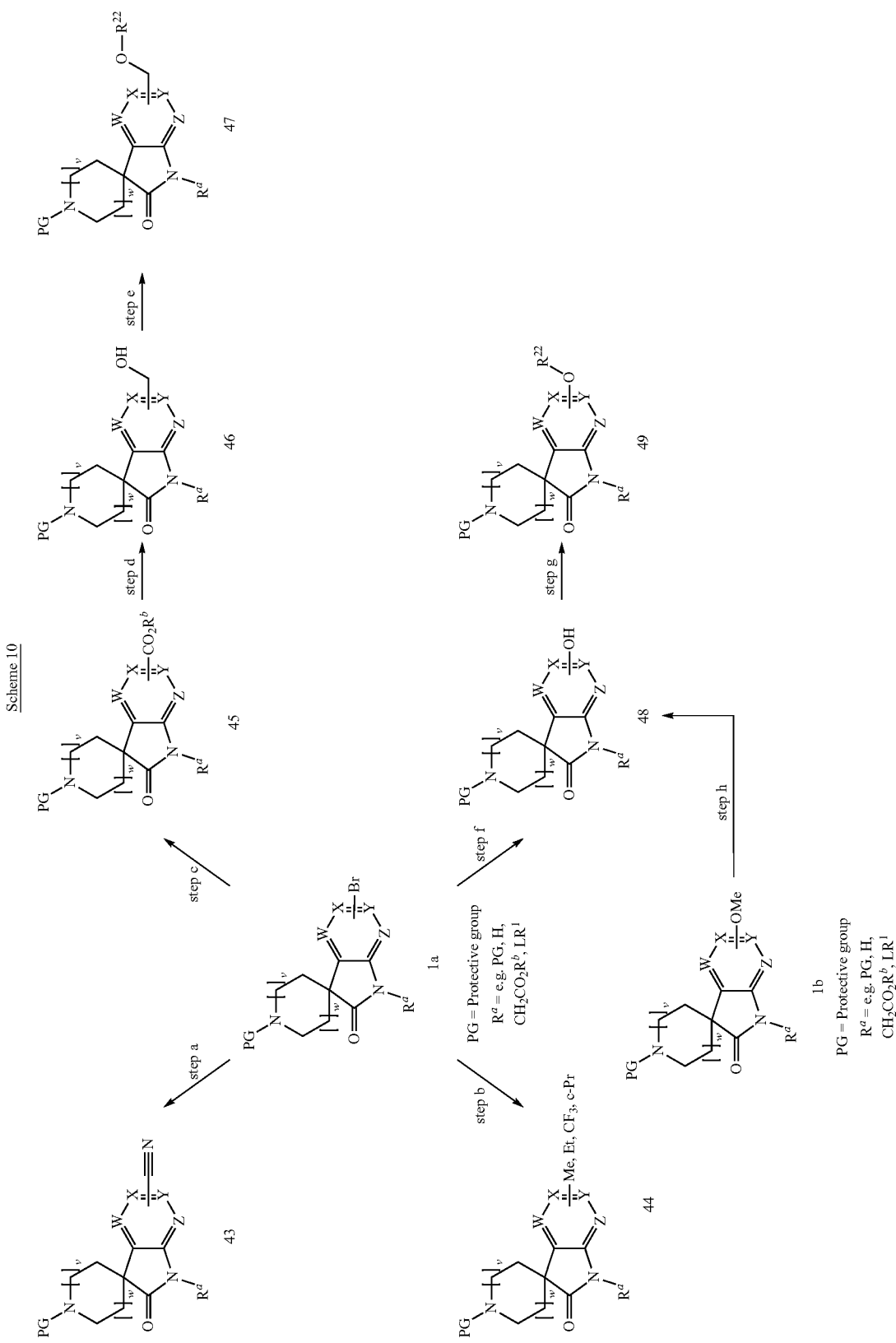
Scheme 10

Compounds of the general formula (I) may be also prepared by functional group conversion on different intermediates of type 1a and 1b as exemplified in Scheme 10, wherein $R^a$—depending on the reaction conditions applied—is hydrogen, a suitable protecting group, $LR^1$ or $CH_2CO_2R^b$. $R^b$ in intermediates 1a is a group such as methyl, ethyl or tert-butyl that can be cleaved off without affecting PG after the desired transformation, liberating an acid functionality that can be subjected for example to amide couplings with amines $H_2NR^9$ or $HNR^9R^{10}$ applying the reaction conditions outlined before. In intermediates 45, $R^b$ signifies a group such as methyl or ethyl that can be selectively reduced to the alcohol. $R^{22}$ is $C_{1-7}$alkyl, $C_{3-7}$cycloalkyl, halo-$C_{1-7}$ alkyl, PG is a protective group, W, X, Y, Z, v and w are as described herein.

A person skilled in the art will acknowledge that other intermediates or different groups $R^a$ and PG compatible with the chemical transformation may be used applying protective group strategy and/or changing the sequence of steps. The transformations outlined below are exemplary, known in literature and others may be applied.

Compounds 43 in which one of $R^2$ to $R^5$ is a cyano group can be prepared from intermediates 1a, prepared according to the procedures described before, for example using a cyanating agent such as zinc(II) cyanide, potassium hexacyanoferrate(II) or copper(I) cyanide with tetraethylammonium cyanide, a suitable catalyst such as Palladium(II) acetate or tris(dibenzylideneacetone)dipalladium(0) optionally in the presence of 1,1'-bis(diphenylphosphino)ferrocene in a suitable solvent such as DMF, NMP or dioxane, optionally using a base such as sodium, potassium or cesium carbonate at temperatures ranging from 0° C. to the boiling point of the solvent (step a).

Compounds 44 in which one of $R^2$ to $R^5$ is a methyl group can be prepared from intermediates 1a, for example by cross-coupling reaction with trimethylboroxinex in the presence of a suitable catalyst such as tetrakis(triphenylphosphine)palladium(0) or [1,1'-bis(diphenylphosphino)ferrocene]dichloropalladium(II), complex with DCM, and using a suitable base such as potassium or sodium carbonate in a solvent or solvent mixture such as dioxane or dimethoxyethane and $H_2O$ at temperatures ranging from room temperature up to the boiling point of the solvent (step b).

Compounds 44 in which one of $R^2$ to $R^5$ is a trifluoromethyl substituent can be prepared for example by reaction of intermediates 1a with, e.g. sodium trifluoroacetate or methyl 3-oxo-co-fluorosulfonylperfluoropentanoate and copper(I) iodide in an appropriate solvent like, e.g. DMF or NMP at temperatures ranging from room temperature up to the boiling point of the solvent (step b).

Compounds 44 in which one of $R^2$ to $R^5$ is a cyclopropyl substituent can be prepared for example by reaction of intermediates 1a with cyclopropylboronic acid in the presence of a suitable catalyst system such as palladium(II) acetate and tricyclohexylphosphine using a suitable base and solvent such as potassium carbonate in a mixture of toluene and $H_2O$ (step b).

Alternatively a cyclopropyl substituent can be introduced for example through palladium-catalyzed (e.g. tetrakis(triphenylphosphine)palladium(0)) reaction of intermediates 1a with a pre-formed complex of 9-borabicyclo[3.3.1]nonane and propargylbromide in the presence of an appropriate base such as sodium hydroxide in an appropriate solvent like THF (step b).

Compounds 44 in which one of $R^2$ to $R^5$ is an ethyl group can be prepared for example by reaction of intermediates 1a with tributyl(vinyl)tin and LiCl in the presence of a suitable catalyst like $Pd(PPh_3)_4$ in a solvent such as toluene at temperatures ranging from room temperature to the boiling point of the solvent to give the corresponding vinyl intermediate. Subsequent reduction of the vinyl double bond for example by hydrogenation using a catalyst such as $Pd(PPh_3)_4$ in a solvent such as methanol yields intermediates 44 in which one of $R^2$ to $R^5$ is an ethyl group (step b). In case PG is a benzyl protective group this method allows concomitant removal of the protective group.

Compounds 45 in which one of $R^2$ to $R^5$ is a carboxylic ester group and $R^a$ signifies an alkyl group like methyl or ethyl can be prepared from intermediates 1a via bromine-lithium exchange, quenching the lithium intermediate with carbon dioxide and esterification of the resulting carboxylic acid (step d). Alternatively, intermediates 1a can be subjected to carbonylation reactions under a carbon monoxide atmosphere using a suitable catalyst like bis(triphenylphosphine)palladium(II) dichloride in methanol or ethanol (formation of methyl and ethyl ester, respectively) in the presence of a base like triethylamine (step c).

The ester functionality in intermediates 45 can be reduced to deliver the benzylic alcohol intermediates 46, for example using lithium aluminium hydride or di-isobutylaluminium hydride in an appropriate solvent such as diethyl ether or THF (step d).

The alcohol group in intermediates 46 can be alkylated with reagents of the type $R^{22}LG$ in which LG signifies a suitable leaving group such as Cl, Br, I, $OSO_2$alkyl, $OSO_2$fluoroalkyl or $OSO_2$aryl in an appropriate solvent such as DMF and using an appropriate base such as potassium or cesium carbonate at temperatures ranging from 0° C. to the reflux temperature of the solvent to give compounds 47 (step e).

Compounds 49 in which one of $R^2$ to $R^5$ is a $C_{1-7}$ alkoxy or halo-$C_{1-7}$ alkoxy group can be synthesized for example by reaction of intermediates 1a with n-butyl lithium and boron trimethoxide or boron triisopropoxide in a solvent such as THF and oxidizing the resulting boronic acid after isolation or in situ with hydrogen peroxide in $H_2O$, or using copper sulfate with 1,10-phenanthroline and a base such as KOH to give the hydroxy intermediates 48 (step f).

Alkylation of intermediates 48 with alkylating agents of the type $R^{22}LG$ in which LG signifies a leaving group such as Cl, Br, I, $OSO_2$alkyl, $OSO_2$fluoroalkyl or $OSO_2$aryl in an appropriate solvent such as DMF and using an appropriate base such as potassium or cesium carbonate at temperatures ranging from 0° C. to the reflux temperature of the solvent yields compounds 49 (step g).

Intermediates 48 can be also synthesized from intermediates Ib, prepared according to the procedures described for example under Scheme 1 before, by demethylation of the methoxy group, for example using boron tribromide in a solvent such as DMF (step h).

Intermediates 43, 44, 47 and 49 can be further converted into compounds (I) applying the reaction steps and methods described for example in Scheme 1.

Scheme 11

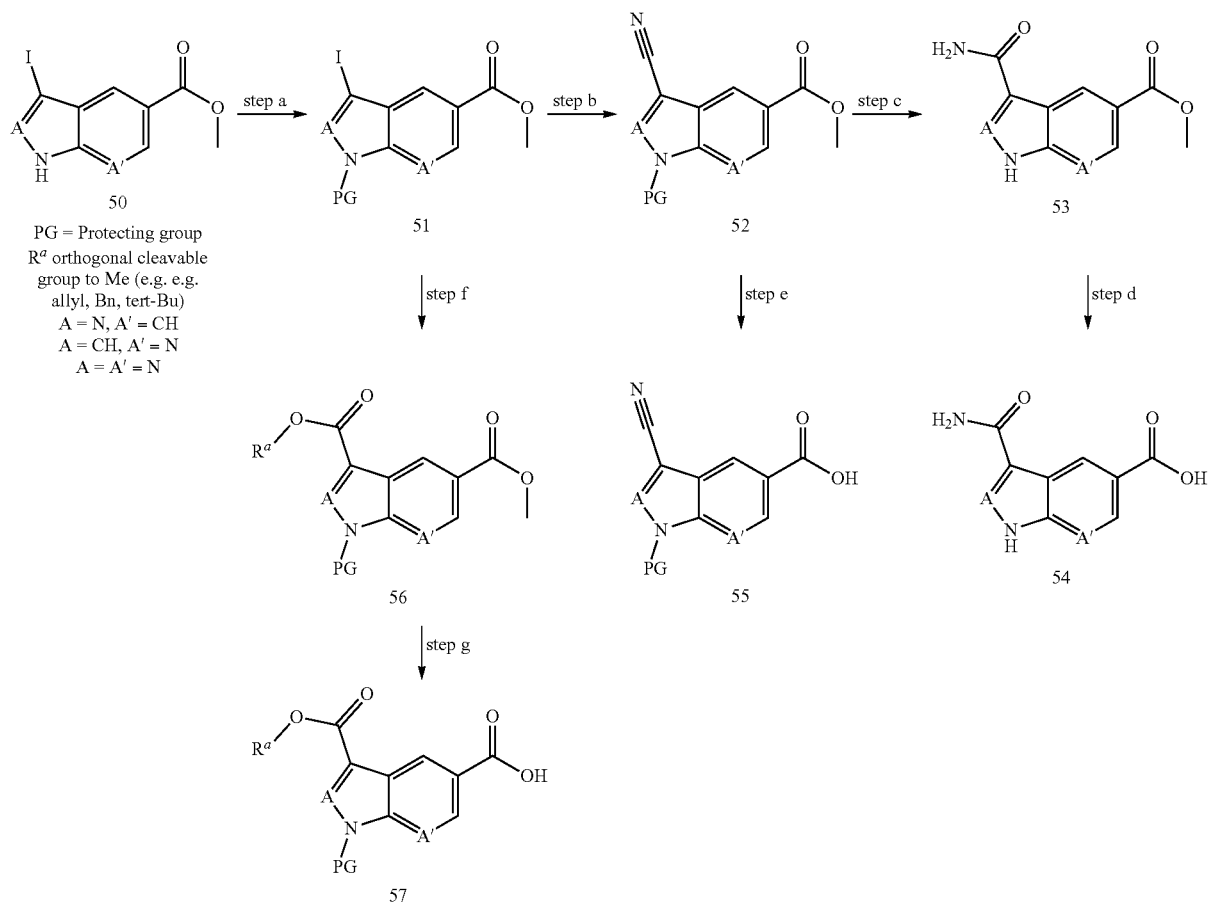

In case the carboxylic acid R⁶COOH is an 1H-pyrrolo[2,3-b]pyridine-5-carboxylic acid, 1H-indazole-5-carboxylic acid or 1H-pyrazolo[3,4-b]pyridine-5-carboxylic acid substituted in the 3-position with a cyano, carboxamido, carboxylic acid or carboxylic acid ester group and which are not commercially available they can be prepared by methods known in the art and as exemplified in Scheme 11, applying an orthogonal protecting group strategy.

A person skilled in the art will acknowledge that other intermediates, different sequence of steps or different groups $R^a$ and PG, compatible with the chemical transformations, may be used.

Commercially available intermediates 50 can be optionally protected by methods as described for example in "Protective Groups in Organic Chemistry" by T. W. Greene and P. G. M. Wutts, 5th Ed., 2014 Wiley & Sons, N.Y. to give intermediates 51 (step a).

Reaction of intermediates 51 with a cyanating agent applying the conditions described in Scheme 10, step a, yields intermediates 52 (step b).

Hydrolysis of the cyano group in intermediates 52 under acidic (e.g. sulfuric acid) or basic (e.g. sodium hydroxide) conditions gives carboxamide intermediates 53 (step c). Heating may be applied to accelerate the reaction or drive it to completion. Depending on the nature of the protecting group PG and the reaction conditions applied concomitant hydrolysis to the amide and cleavage of the protecting group may occur (step c).

Cleavage of the methyl ester in intermediates 53, for example using lithium hydroxide in H₂O and THF or using methods as described for example in "Protective Groups in Organic Chemistry" by T. W. Greene and P. G. M. Wutts, 5th Ed., 2014 Wiley & Sons, N.Y. furnishes intermediates 54 (step d).

Intermediates 52 can be converted into intermediates 55 applying the method described under step d above or as described for example in "Protective Groups in Organic Chemistry" by T. W. Greene and P. G. M. Wutts, 5th Ed., 2014 Wiley & Sons, N.Y. (step e).

Intermediates 51 may be converted into intermediates 56, for example by the methods described under Scheme 10, step c (step f).

Cleavage of the methyl ester in intermediates 56 by literature methods, for example as described for example in "Protective Groups in Organic Chemistry" by T. W. Greene and P. G. M. Wutts, 5th Ed., 2014 Wiley & Sons, N.Y., leaving the second ester functionality ($R^a$) in intermediates 56 intact, furnishes intermediates 57 (step g).

Intermediates 54, 55 and 57 can be further transformed into compounds of formula (I) by methods known in literature and as described for example under Scheme 1, step c. In case of intermediates 57, removal of $R^a$ and PG by methods known in literature will furnish the final compounds.

Scheme 12

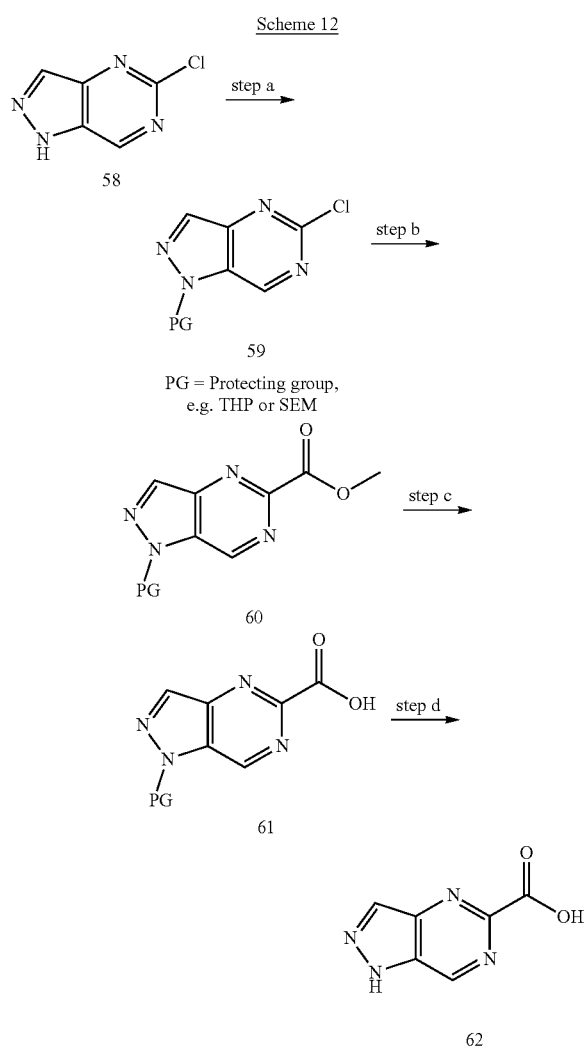

PG = Protecting group,
e.g. THP or SEM

In case the carboxylic acid $R^6COOH$ is 1H-pyrazolo[4,3-d]pyrimidine-5-carboxylic acid it can be prepared by methods known in the art and as exemplified in Scheme 12.

Commercially available 5-chloro-1H-pyrazolo[4,3-d]pyrimidine 58 can be protected for example with a tetrahydropyran (THP) or 2-(trimethylsilyl)ethoxymethyl (SEM) protecting group by methods known in the art and as described for example in "Protective Groups in Organic Chemistry" by T. W. Greene and P. G. M. Wutts, 5$^{th}$ Ed., 2014 Wiley & Sons, N.Y. (e.g. a THP group using 3,4-dihydro-2H-pyran and p-toluenesulfonic acid in a solvent like DCM or THF; a SEM group using SEMCl in the presence of a suitable base and solvent such sodium hydride in DMF) to give intermediates 59 (step a).

Intermediates 59 can be subjected to a palladium-catalyzed carbonylation reaction using for example carbon monoxide, methanol (in case of a methyl ester), palladium(II) acetate and 1,3-bis(diphenylphosphino)propane as catalyst and ligand, respectively, and trimethylamine as a base in a solvent such as DMF to yield intermediates 60 (step b). Elevated carbon monoxide pressures and temperatures up to the boiling point of the solvent may be applied to accelerate the reaction or drive it to completion (step b).

Cleavage of the ester functionality in intermediates 60 according to the methods described under Scheme 11, step d, gives intermediates 61 (step c).

Removal of the protective group using literature methods, for example under acidic conditions (e.g. aqueous HCl or HCl/dioxane in DCM) furnishes intermediates 62 (step d).

Intermediates 62 in turn can be further transformed into compounds of formula (I) by methods known in literature and as described for example under Scheme 1, step c. Alternatively intermediates 61 can be further transformed into compounds of formula (I) by methods described before, removing the protecting group PG by methods described in literature and as outlined before as final step.

Pharmaceutical Compositions

Another embodiment provides pharmaceutical compositions or medicaments comprising the compounds of the invention and a therapeutically inert carrier, diluent or pharmaceutically acceptable excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may comprise components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical formulation is prepared by mixing a compound of the present invention and a carrier or excipient. Suitable carriers and excipients are well known to those skilled in the art and are described in detail in, e.g., Ansel H. C. et al., Ansel's Pharmaceutical Dosage Forms and Drug Delivery Systems (2004) Lippincott, Williams & Wilkins, Philadelphia; Gennaro A. R. et al., Remington: The Science and Practice of Pharmacy (2000) Lippincott, Williams & Wilkins, Philadelphia; and Rowe R. C, Handbook of Pharmaceutical Excipients (2005) Pharmaceutical Press, Chicago. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which compounds of the invention can be administered can vary within wide limits and will, of course, be fitted to the individual requirements in each particular case. In general, in the case of oral administration a daily dosage of about 0.01 to 1000 mg per person of a compound of general formula (I) should be appropriate, although the above upper limit can also be exceeded when necessary.

An example of a suitable oral dosage form is a tablet comprising about 100 mg to 500 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol formulation can be prepared by dissolving the compound, for example 10 to 100 mg, of the invention in a suitable buffer solution, e.g. a phosphate buffer, adding a tonicifier, e.g. a salt such as sodium chloride, if desired. The solution may be filtered, e.g., using a 0.2 μm filter, to remove impurities and contaminants.

Therapeutic Uses

As described above, the compounds of formula (I) and their pharmaceutically acceptable salts possess valuable pharmacological properties and have been found to be inhibitors of the Discoidin Domain Receptor 1 (DDR1).

The compounds of the present invention can be used, either alone or in combination with other drugs, for the treatment or prevention of diseases related to DDR1. These diseases include, but are not limited to renal conditions, liver conditions, inflammatory conditions, vascular conditions, cardiovascular conditions, fibrotic diseases, cancer and acute and chronic organ transplant rejection.

Renal conditions include, but are not limited to, acute kidney injury and chronic renal disease with and without proteinuria including end-stage renal disease (ESRD). In more detail, this includes decreased creatinine clearance and decreased glomerular filtration rate, micro-albuminuria, albuminuria and proteinuria, glomerulosclerosis with expansion of reticulated mesangial matrix with or without significant hypercellularity (particularly diabetic nephropathy and amyloidosis), focal thrombosis of glomerular capillaries (particularly thrombotic microangiopathies), global fibrinoid necrosis, ischemic lesions, malignant nephrosclerosis (such as ischemic retraction, reduced renal blood flow and renal arteriopathy), swelling and proliferation of intracapillary (endothelial and mesangial) and/or extracapillary cells (crescents) like in glomerular nephritis entities, focal segmental glomerular sclerosis, IgA nephropathy, vasculitis/systemic diseases as well as acute and chronic kidney transplant rejection. Renal conditions also includes early and advanced Alport syndrome.

Inflammatory conditions include, but are not limited to, arthritis, osteoarthritis, multiple sclerosis, systemic lupus erythematodes, inflammatory bowel disease, abnormal evacuation disorder and the like as well as inflammatory airways diseases such as idiopathic pulmonary fibrosis (IPF), chronic obstructive pulmonary disease (COPD) or chronic asthma. Further conditions of the respiratory system include, but are not limited to, other diffuse parenchymal lung diseases of different etiologies including iatrogenic drug-induced fibrosis, occupational and/or environmental induced fibrosis, systemic diseases and vasculitis, granulomatous diseases (sarcoidosis, hypersensitivity pneumonia), collagen vascular disease, radiation induced fibrosis.

Vascular conditions include, but are not limited to, atherosclerosis, thrombotic vascular disease as well as thrombotic microangiopathies, proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction and the like.

Cardiovascular conditions include, but are not limited to, acute coronary syndrome, coronary heart disease, myocardial infarction, arterial and pulmonary hypertension, cardiac arrhythmia such as atrial fibrillation, stroke and other vascular damage.

Fibrotic diseases include, but are not limited to myocardial and vascular fibrosis, renal fibrosis, liver fibrosis, pulmonary fibrosis, skin fibrosis, scleroderma and encapsulating peritonitis.

Cancer and cancer metastasis include, but are not limited to, breast cancer, non-small cell lung carcinoma, lymphoma, ovarian cancer, pancreatic cancer, lung cancer, prostate cancer, mesothelioma, glioma, glioblastoma, hepatic carcinoma, renal carcinoma, cancer of the esophagus, head and neck cancer and leukemias, squamous cell carcinoma, adenocarcinoma, bronchioloalveolar carcinoma and progression and metastatic aggressiveness thereof.

In a particular embodiment, the renal condition is selected from the group consisting of acute kidney injury, chronic kidney disease, diabetic nephropathy, acute kidney transplant rejection and chronic allograft nephropathy.

In another particular embodiment, the renal condition is acute kidney injury.

In another particular embodiment, the renal condition is chronic kidney disease.

In a further particular embodiment, the renal condition is diabetic nephropathy.

In another particular embodiment, the renal condition is acute kidney transplant rejection.

In another particular embodiment, the renal condition is chronic allograft nephropathy.

In a particular embodiment, the liver condition is acute and chronic liver transplant rejection In a particular embodiment, the compounds of formula (I) or their pharmaceutically acceptable salts and esters can be used for the treatment or prophylaxis of organ or skin fibrosis.

In a particular embodiment, the fibrotic disease is renal tubulo-interstitial fibrosis or glomerulosclerosis.

In a particular embodiment, the fibrotic disease is early or progressive renal tubule-interstitial fibrosis and glomerular damage induced by Alport syndrome.

In a particular embodiment, the fibrotic disease induce by patients affected by Alport syndrome.

In a particular embodiment of the invention, the compounds of the present invention are used for the treatment or prevention of early or advanced Alport syndrome.

In a particular embodiment, the fibrotic disease is non-alcoholic liver steatosis, liver fibrosis or liver cirrhosis.

In a particular embodiment, the fibrotic disease is idiopathic pulmonary fibrosis.

In a particular embodiment, the fibrotic disease is encapsulating peritonitis

In a particular embodiment, the cancer includes, but is not limited to, breast cancer, non-small cell lung carcinoma, lymphoma, ovarian cancer, pancreatic cancer, lung cancer, prostate cancer, mesothelioma, glioma, glioblastoma, hepatic carcinoma, renal carcinoma, cancer of the esophagus, head and neck cancer and leukemias, squamous cell carcinoma, adenocarcinoma, bronchioloalveolar carcinoma and progression and metastatic aggressiveness thereof.

Compounds of formula (I) as described herein can also be used in combination with any other cancer drug even if the compound on its own might not be tumor static or induce cancer regression but as a combination treatment to reduce metastasis and prevent cancer drug resistance.

A particular embodiment of the invention also relates to a pharmaceutical composition comprising a compound of formula (I) as described herein and at least one pharmaceutically acceptable excipient.

A particular embodiment of the invention also relates to a compound of formula (I) as described herein for use as therapeutically active substances.

A particular embodiment of the invention also relates to a compound of formula (I) as described herein for use in the treatment or prevention of diseases which are related to DDR1, particularly for use in the treatment or prevention of renal conditions, liver conditions, inflammatory conditions, vascular conditions, cardiovascular conditions, fibrotic diseases, cancer and acute and chronic organ transplant rejection.

A particular embodiment of the invention also relates to a compound of formula (I) as described herein for use in the treatment or prevention of acute kidney injury, chronic kidney disease, contrast agent-induced nephropathy, diabetic nephropathy, acute kidney transplant rejection, chronic allograft nephropathy, acute and chronic liver transplant rejection, organ fibrosis, skin fibrosis, renal tubulo-interstitial fibrosis, glomerulosclerosis, rapid progressive crescentic glomerulonephritis, crescentic glomerulonephritis, Goodpasture syndrome, granulomatous tubulointerstitial nephritis, Wegener's granulomatosis, glomerular damage induced by Alport syndrome, non-alcoholic liver steatosis, liver fibrosis, liver cirrhosis idiopathic pulmonary fibrosis, encapsulating peritonitis, breast cancer, non-small cell lung carcinoma, lymphoma, ovarian cancer, pancreatic cancer, lung cancer, prostate cancer, mesothelioma, glioma, glioblastoma, hepatic carcinoma, renal carcinoma, cancer of the esophagus, head and neck cancer and leukemias, squamous cell carcinoma, adenocarcinoma, bronchioloalveolar carcinoma or progression and metastatic aggressiveness thereof.

In another embodiment, the invention relates to a method for the treatment or prevention of diseases which are related to DDR1, which method comprises administering a compound of formula (I) as described herein to a human being or animal.

In another embodiment, the invention relates to a method for the treatment or prevention of renal conditions, liver conditions, inflammatory conditions, vascular conditions, cardiovascular conditions, fibrotic diseases, cancer and acute and chronic organ transplant rejection, which method comprises administering a compound of formula (I) as described herein to a human being or animal.

In another embodiment, the invention relates to a method for the treatment or prevention of acute kidney injury, chronic kidney disease, contrast agent-induced nephropathy, diabetic nephropathy, acute kidney transplant rejection, chronic allograft nephropathy, acute and chronic liver transplant rejection, organ fibrosis, skin fibrosis, renal tubulo-interstitial fibrosis, glomerulosclerosis, rapid progressive crescentic glomerulonephritis, crescentic glomerulonephritis, Goodpasture syndrome, granulomatous tubulointerstitial nephritis, Wegener's granulomatosis, glomerular damage induced by Alport syndrome, non-alcoholic liver steatosis, liver fibrosis, liver cirrhosis idiopathic pulmonary fibrosis, encapsulating peritonitis, breast cancer, non-small cell lung carcinoma, lymphoma, ovarian cancer, pancreatic cancer, lung cancer, prostate cancer, mesothelioma, glioma, glioblastoma, hepatic carcinoma, renal carcinoma, cancer of the esophagus, head and neck cancer and leukemias, squamous cell carcinoma, adenocarcinoma, bronchioloalveolar carcinoma or progression and metastatic aggressiveness thereof, which method comprises administering a compound of formula (I) as described herein to a human being or animal.

The invention also embraces the use of a compound of formula (I) as described herein for the treatment or prevention of diseases which are related to DDR1.

The invention also embraces the use of a compound of formula (I) as described herein for the treatment or prevention of renal conditions, liver conditions, inflammatory conditions, vascular conditions, cardiovascular conditions, fibrotic diseases, cancer and acute and chronic organ transplant rejection.

The invention also embraces the use of a compound of formula (I) as described herein for the treatment or prevention of acute kidney injury, chronic kidney disease, contrast agent-induced nephropathy, diabetic nephropathy, acute kidney transplant rejection, chronic allograft nephropathy, acute and chronic liver transplant rejection, organ fibrosis, skin fibrosis, renal tubulo-interstitial fibrosis, glomerulosclerosis, rapid progressive crescentic glomerulonephritis, crescentic glomerulonephritis, Goodpasture syndrome, granulomatous tubulointerstitial nephritis, Wegener's granulomatosis, glomerular damage induced by Alport syndrome, non-alcoholic liver steatosis, liver fibrosis, liver cirrhosis idiopathic pulmonary fibrosis, encapsulating peritonitis, breast cancer, non-small cell lung carcinoma, lymphoma, ovarian cancer, pancreatic cancer, lung cancer, prostate cancer, mesothelioma, glioma, glioblastoma, hepatic carcinoma, renal carcinoma, cancer of the esophagus, head and neck cancer and leukemias, squamous cell carcinoma, adenocarcinoma, bronchioloalveolar carcinoma or progression and metastatic aggressiveness thereof.

The invention also relates to the use of a compound of formula (I) as described herein for the preparation of medicaments useful for the treatment or prevention of diseases which are related to DDR1.

The invention also relates to the use of a compound of formula (I) as described herein for the preparation of medicaments useful for the treatment or prevention of renal conditions, liver conditions, inflammatory conditions, vascular conditions, cardiovascular conditions, fibrotic diseases, cancer and acute and chronic organ transplant rejection.

The invention also relates to the use of a compound of formula (I) as described herein for the preparation of medicaments useful for the treatment or prevention of acute kidney injury, chronic kidney disease, contrast agent-induced nephropathy, diabetic nephropathy, acute kidney transplant rejection, chronic allograft nephropathy, acute and chronic liver transplant rejection, organ fibrosis, skin fibrosis, renal tubulo-interstitial fibrosis, glomerulosclerosis, rapid progressive crescentic glomerulonephritis, crescentic glomerulonephritis, Goodpasture syndrome, granulomatous tubulointerstitial nephritis, Wegener's granulomatosis, glomerular damage induced by Alport syndrome, non-alcoholic liver steatosis, liver fibrosis, liver cirrhosis idiopathic pulmonary fibrosis, encapsulating peritonitis, breast cancer, non-small cell lung carcinoma, lymphoma, ovarian cancer, pancreatic cancer, lung cancer, prostate cancer, mesothelioma, glioma, glioblastoma, hepatic carcinoma, renal carcinoma, cancer of the esophagus, head and neck cancer and leukemias, squamous cell carcinoma, adenocarcinoma, bronchioloalveolar carcinoma or progression and metastatic aggressiveness thereof.

EXAMPLES

The following examples 1-168 are provided for illustration of the invention. They should not be considered as limiting the scope of the invention, but merely as being representative thereof.

Abbreviations

AcOH=acetic acid, ACN=acetonitrile, $BBr_3$=boron tribromide, Boc=tert-butyloxycarbonyl, nBuLi=n-butyllithium, CAS RN=chemical abstracts registration number, CO=carbon monoxide, $Cs_2CO_3$=cesium carbonate, CuCl=copper (I) chloride, CuCN=copper (I) cyanide, DCM=dichloromethane, DMAP=4-dimethylaminopyridine, DME=1,2-dimethoxyethane, DMEDA=N,N'-dimethylethylenediamine, DMF=N,N-dimethylformamide, DIPEA=N,N-diisopropylethylamine, dppf=1,1 bis(diphenylphosphino)ferrocene, EDC=3-(ethyliminomethyleneamino)-N,N-dimethylpropan-1-amine, EI=electron impact, ESI=electrospray ionization, EtOAc=ethyl acetate, EtOH=ethanol, h=hour, $H_2O$=water, HBTU=O-(Benzotriazol-1-yl)-N,N,N',N'-tetramethyluronium hexafluorophosphate, HOBt=N-Hydroxybenzotriazole, HATU=1-[bis(dimethylamino)methylene]-1H-1,2,3-triazolo[4,5-b]pyridinium-3-oxide hexafluorophosphate, HCl=hydrogen chloride, prep. HPLC=preparative high performance liquid chromatography, $I_2$=iodine, iPrMgCl=isopropylmagnesium chloride, ISP=ion spray positive (mode), ISN=ion spray negative (mode), min=minutes, $K_2CO_3$=potassium carbonate, $KHCO_3$=potassium bicarbonate, KI=potassium iodide, KOH=potassium hydroxide, $K_3PO_4$=potassium phosphate, $LiAlH_4$ or LAH=lithium aluminium hydride, LiF=lithium fluoride, LiHMDS=lithium bis(trimethylsilyl)amide, LiOH=lithium hydroxide, MeOH=methanol, $MgSO_4$=magnesium sulfate, MPLC=medium performance liquid chromatography, MS=mass spectrum, $N_2$=nitrogen, $Na_2CO_3$=sodium carbonate, $Na_2SO_4$=sodium sulfate, $Na_2S_2O_3$=sodium thiosulfate, NaH=sodium hydride, $NaHCO_3$=sodium hydrogen carbonate, $NaNO_2$=sodium nitrite, NaOH=sodium hydroxide, $NEt_3$=triethylamine, $NH_4OAc$=ammonium acetate, $NH_4Cl$=ammonium chloride, $NH_4HCO_3$=ammonium bicarbonate, NMP=1-methyl-2-pyrrolidinone, PG=protecting group, Pd—C=palladium on activated carbon, $PdCl_2(dppf)-CH_2Cl_2$=1,1'-bis(diphenylphosphino)ferrocene-palladium(II)dichloride dichloromethane complex, $Pd(OAc)_2$=palladium(II) acetate, $Pd(OH)_2$=palladium hydroxide, $Pd(PPh_3)_4$=tetrakis(triphenylphosphine)palladium(0), PyBOP=(benzotriazol-1-yloxy)tripyrrolidinophosphonium hexafluorophosphate, R=any group, RT=room temperature, S-PHOS=2-dicyclohexylphosphino-2',6'-dimethoxybiphenyl, T3P=propylphosphonic anhydride, TBAI=tetrabutylammonium iodide, TEA=triethylamine, TFA=trifluroacetic acid, THF=tetrahydrofuran, TMEDA=N,N,N',N'-tetramethylethylenediamine, X=halogen, $ZnCl_2$=zinc chloride, $Zn(CN)_2$=zinc cyanide.

Intermediates

Intermediate INT1a (Method K)

2-{2-Oxo-1,2-dihydrospiro[indole-3,4'-piperidine]-1-yl}-N-(2,2,2-trifluoroethyl)acetamide

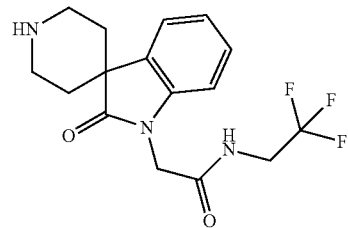 [SMILES: O=C(CN1C(=O)C2(CCNCC2)c2ccccc21)NCC(F)(F)F]

To a solution of tert-butyl 2-oxo-1-{[(2,2,2-trifluoroethyl)carbamoyl]methyl}-1,2-dihydrospiro[indole-3,4'-piperidine]-1'-carboxylate (200 mg, 0.45 mmol, intermediate INT5b) in dioxane (15 mL) was added HCl (4N) in dioxane (2 mL) and the reaction mixture was stirred at 25° C. for 6 h. The reaction mixture was evaporated off to get the title product as colourless liquid (150 mg, 97%) which was used in the next step without further purification. MS (ESI): m/z=341.8 $[M+H]^+$.

Intermediate INT3a (Method L)

2-{4-Bromo-2-oxo-1,2-dihydrospiro[indole-3,4'-piperidine]-1-yl}-N-(2,2,2-trifluoroethyl)acetamide

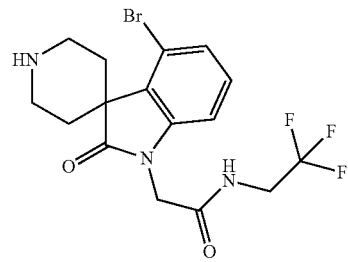 [SMILES: O=C(CN1C(=O)C2(CCNCC2)c2c(Br)cccc21)NCC(F)(F)F]

To a solution of 2-{1'-benzyl-4-bromo-2-oxo-1,2-dihydrospiro[indole-3,4'-piperidine]-1-yl}-N-(2,2,2-trifluoroethyl)acetamide (220 mg, 0.43 mmol, intermediate INT7b) in 1,2-dichloroethane (15 mL) were added 1-chloroethyl chloroformate (0.13 mL, 1.18 mmol, CAS RN 50893-53-3) and DIPEA (0.10 mL, 0.64 mmol, CAS RN 7087-68-5) at 0° C. The reaction mixture was heated to reflux for 16 h. The solvent was evaporated, MeOH (10 mL) was added and the reaction mixture was again refluxed for 3 h. The solvent was evaporated off to get the title product (160 mg, 88%) as a brown liquid which was used in the next step without further purification. MS (EI): m/z=519.8 $[M+H]^+$.

Intermediate INT10a (Method M)

2-{4-Ethyl-2-oxo-1,2-dihydrospiro[indole-3,4'-piperidine]-1-yl}-N-(2,2,2-trifluoroethyl)-acetamide

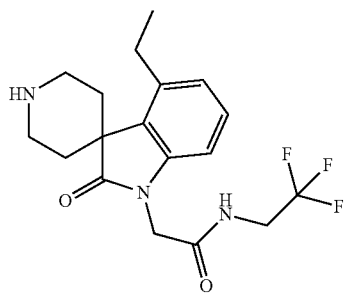 [SMILES: CCc1cccc2c1C1(CCNCC1)C(=O)N2CC(=O)NCC(F)(F)F]

A solution of 2-{1'-benzyl-4-ethenyl-2-oxo-1,2-dihydrospiro[indole-3,4'-piperidine]-1-yl}-N-(2,2,2-trifluoroethyl)acetamide (200 mg, 0.44 mmol, intermediate INT13b) in anhydrous MeOH (20 mL) was purged with $N_2$ for 15 min. Pd/C (160 mg, CAS RN 7440-05-3) was then added and the reaction mixture was stirred under a $H_2$ atmosphere at 25° C. for 16 h. The reaction mixture was filtered off and the filtrate was stripped off to get the title compound (150 mg, 93%). MS (EI): m/z=370.0 $[M+H]^+$.

Intermediate INT37a

2-{4'-Bromo-2'-oxo-1',2'-dihydrospiro[azetidine-3,3'-indole]-1'-yl}-N-(2,2,2-trifluoroethyl) acetamide

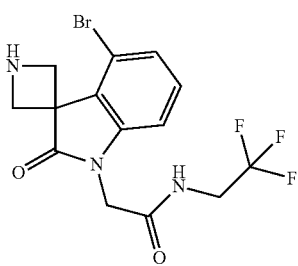 [SMILES: O=C(CN1C(=O)C2(CNC2)c2c(Br)cccc21)NCC(F)(F)F]

To a stirred solution of 2-{4'-bromo-1-[(2,4-dimethoxyphenyl)methyl]-2'-oxo-1',2'-dihydrospiro[azetidine-3,3'-indole]-1'-yl}-N-(2,2,2-trifluoroethyl)acetamide (300 mg, 0.554 mmol) in ACN (3 mL) at 25° C. was added a solution of ceric ammonium nitrate (668 mg, 1.218 mmol, CAS RN 16774-21-3) in $H_2O$ (3 mL) and the reaction mixture was stirred at 25° C. for 3 h. The reaction mixture was quenched with saturated aqueous $NaHCO_3$ solution (10 mL) and extracted with 10% MeOH in DCM (3×100 mL). The combined organic layers were dried over $Na_2SO_4$, filtered and filtrate was evaporated under reduced pressure. The crude product was purified over silica gel column chromatography (10-12% MeOH/DCM) to furnish the desired compound as an off-white solid (73 mg, 34%). MS (ESI): m/z=392.1 $[M+H]^+$.

a) tert-Butyl 4-bromo-2-oxo-2,3-dihydro-1H-indole-1-carboxylate

To a stirred solution of 4-bromo-2,3-dihydro-1H-indol-2-one (6 g, 28.30 mmol, CAS RN 99365-48-7) in THF (300 mL) were added $NaHCO_3$ (21.4 g, 254.717 mmol, CAS RN 144-55-8) and di-tert-butyl dicarbonate (16.4 mL, 71.32 mmol, CAS RN 24424-99-5) at 25° C. and the reaction mixture was stirred at 80° C. for 2.5 h. The reaction mixture was filtered through a sintered funnel and washed with EtOAc (50 mL). The filtrate was washed with $H_2O$ (100 mL), dried over $Na_2SO_4$, filtered and concentrated. The crude product was purified by column chromatography over silica gel (2-4% EtOAc/n-hexane) to yield the desired compound as an off-white solid (6.7 g, 76%). MS (ESI): m/z=312.2 $[M+H]^+$.

b) tert-Butyl 4-bromo-3,3-bis(hydroxymethyl)-2-oxo-2,3-dihydro-1H-indole-1-carboxylate To a stirred solution of tert-butyl 4-bromo-2-oxo-2,3-dihydro-1H-indole-1-carboxylate (3.3 g, 10.577 mmol) in THF (83 mL) were added potassium carbonate (4.39 g, 31.731 mmol) and para formaldehyde (7.62 g, 253.85 mmol, CAS RN 30525-89-4) at 20° C. and the reaction mixture was stirred at 20° C. for 30 min. The reaction mixture was poured onto ice and extracted with EtOAc (2×200 mL). The combined organic layers were dried over $Na_2SO_4$, filtered and evaporated under reduced pressure. The crude product was purified by column chromatography over silica gel (30-33% EtOAc/hexane) to yield the desired compound as an off-white solid (1.57 g, 40%). MS (ESI): m/z=372.2 $[M+H]^+$.

c) Tert-butyl 4'-bromo-1-[(2,4-dimethoxyphenyl)methyl]-2'-oxo-1',2'-dihydrospiro[azetidine-3,3'-indole]-1'-carboxylate To a stirred solution of tert-butyl 4-bromo-3,3-bis(hydroxymethyl)-2-oxo-2,3-dihydro-1H-indole-1-carboxylate (1.05 g, 2.823 mmol) in ACN (20 mL) were added DIPEA (3 mL, 16.935 mmol, CAS RN 7087-68-5) followed by triflic anhydride (1 mL, 5.93 mmol, CAS RN 358-23-6) in DCM (10 mL) at −25° C. and the reaction mixture was stirred at −25° C. for 1 h. Then 2,4-dimethoxy benzyl amine (0.43 mL, 2.823 mmol, CAS RN 20781-20-8) in ACN (10 mL) was added to the reaction mixture at −25° C. The reaction mixture was stirred at −25° C. for 15 min and then at 25° C. for 16 h. The solvent was evaporated and the resulting crude product purified by column chromatography over silica gel (15-20% EtOAc/n-hexane) to provide the title compound as a pale yellow liquid (395 mg, 28%). The product was used as is for the next step.

d) 4'-Bromo-1-[(2,4-dimethoxyphenyl)methyl]-1',2'-dihydrospiro[azetidine-3,3'-indole]-2'-one To a stirred solution of tert-butyl 4'-bromo-1-[(2,4-dimethoxyphenyl)methyl]-2'-oxo-1',2'-dihydrospiro[azetidine-3,3'-indole]-1'-carboxylate (590 mg, 1.173 mmol) in DCM (6 mL) was added HCl in dioxane (6 mL) at 0° C. and reaction mixture was stirred at 25° C. for 4 h. The solvent was evaporated and the resulting residue was diluted with DCM (50 mL) and washed with saturated aqueous $NaHCO_3$ solution (30 mL). The organic layer was dried over $Na_2SO_4$, filtered and the filtrate was evaporated to yield the desired compound as an off-white solid (359 mg, 76%). MS (ESI): m/z=403.0 $[M+H]^+$.

e) 2-{4'-Bromo-1-[(2,4-dimethoxyphenyl)methyl]-2'-oxo-1',2'-dihydrospiro[azetidine-3,3'-indole]-1'-yl}-N-(2,2,2-trifluoroethyl)acetamide To a solution of 4'-bromo-1-[(2,4-dimethoxyphenyl)methyl]-1',2'-dihydrospiro[azetidine-3,3'-indole]-2'-one (350 mg, 0.868 mmol) in DMF (7 mL) was added sodium hydride (60% in mineral oil) (25 mg, 1.042 mmol, CAS RN 7646-69-7) at 0° C. and the reaction mixture was stirred at 25° C. for 1 h. Then 2-chloro-N-(2,2,2-trifluoroethyl)acetamide (153 mg, 0.868 mmol, CAS RN 170655-44-4) was added at 25° C. and the reaction mixture was stirred at 25° C. for 4 h. The reaction mixture was quenched with saturated aqueous NH$_4$Cl solution (20 mL) and extracted with EtOAc (2×100 mL). The combined organic layers were dried over Na$_2$SO$_4$, filtered and evaporated. The crude product was purified by column chromatography over silica gel (3-5% MeOH/DCM) to provide the title compound as an off-white solid (301 mg, 64%). MS: (ESI): m/z=541.9 [M+H]$^+$.

Intermediate INT38a 2-(4-Chloro-2-oxo-spiro[indole-3,3'-pyrrolidin]-1-yl)-N-(2,2,2-trifluoro-ethyl)-acetamide

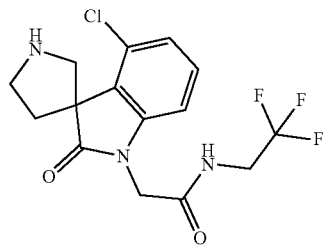 [SMILES: O=C(CN1C(=O)C2(CCNC2)c2c(Cl)cccc21)NCC(F)(F)F]

To a solution of 2-{1'-benzyl-4-chloro-2-oxo-1,2-dihydrospiro[indole-3,3'-pyrrolidine]-1-yl}-N-(2,2,2-trifluoroethyl)acetamide (3 g, 6.64 mmol) in 1,2-dichloroethane (30 mL, CAS RN 107-06-2) were added 1-chloroethyl chloroformate (2.88 mL, 26.60 mmol, CAS RN 50893-53-3) and DIPEA (1.65 mL, 9.978 mmol, CAS RN 7087-68-5) at 0° C. The reaction mixture was heated at 85° C. for 16 h. The solvent was evaporated, MeOH (30 mL) was added and the reaction mixture was refluxed for 3 h. The solvent was evaporated and the crude product was purified using an amine functionalized silica gel chromatography (2-3% MeOH/DCM) to get the desired compound as a brown solid (1.8 g, 75%). MS: (EI): m/z=360.1 [M−H]$^-$.

a) 1,3-Dimethyl 2-(2-chloro-6-nitrophenyl)propanedioate

To a stirred solution of dimethyl malonate (0.39 mL, 3.429 mmol, CAS RN 108-59-8) in THF (5 mL) was added sodium hydride (60% in mineral oil) (171.4 mg, 4.286 mmol, CAS RN 7646-69-7) at 0° C. The reaction mixture was stirred at 25° C. for 30 min., then cooled again to 0° C. and 1-chloro-2-fluoro-3-nitrobenzene (500 mg, 2.86 mmol, CAS RN 2106-49-2) was added. The reaction mixture was stirred at 25° C. for 16 h. After completion of the reaction, it was quenched with saturated aqueous NH$_4$Cl solution (10 mL) and was extracted with EtOAc (2×50 mL). The organic layer washed with brine, dried over Na$_2$SO$_4$ and concentrated under reduced pressure. The crude product was purified using silica gel column chromatography (10-12% EtOAc/n-hexane) to get the title compound as an off-white solid (550 mg, 67%). MS: (EI): m/z=286.0 [M−H]$^-$.

b) Methyl 2-(2-chloro-6-nitrophenyl)prop-2-enoate

To a mixture of 1,3-dimethyl 2-(2-chloro-6-nitrophenyl) propanedioate (300 mg, 1.045 mmol) in formalin (37-41%, 3 mL, CAS RN 50-00-0) was added a solution of K$_2$CO$_3$ (216.69 mg, 1.568 mmol) in water (1 mL). The resultant mixture was heated to 60° C. for 16 h. After completion of reaction, the mixture was diluted with H$_2$O (10 mL) and extracted with EtOAc (2×50 mL). The organic layer was washed with brine, dried over Na$_2$SO$_4$ and concentrated. The crude product was purified by column chromatography (5-7% EtOAc/n-hexane) to get the desired compound as an off white-solid (210 mg, 83%). MS (EI): m/z=242.0 [M+H]$^+$.

c) Methyl 1-benzyl-3-(2-chloro-6-nitrophenyl)pyrrolidine-3-carboxylate

To a stirred solution of methyl 2-(2-chloro-6-nitrophenyl) prop-2-enoate (5 g, 20.747 mmol) and benzyl-methoxymethyl-trimethylsilanylmethyl-amine (7.96 mL, 31.12 mmol, CAS RN 111300-06-2) in ACN (50 mL) was added LiF (0.54 g, 20.747 mmol, CAS RN 7789-24-4) at 0° C. The reaction was warmed to 25° C. and stirred for 16 h. After completion of the reaction, it was diluted with EtOAc (100 mL) and washed with 5N HCl (20 mL) and saturated NaHCO$_3$ solution (20 mL). The combined organic layer was washed with brine, dried over Na$_2$SO$_4$ and was concentrated under reduced pressure. The crude product was purified over silica gel column chromatography (5-7% EtOAc/n-hexane) to yield the desired compound (3.5 g, 45.1%). MS (EI): m/z=375.2 [M+H]$^+$.

d) 1'-Benzyl-4-chloro-1,2-dihydrospiro[indole-3,3'-pyrrolidine]-2-one

To a stirred solution of methyl 1-benzyl-3-(2-chloro-6-nitrophenyl)pyrrolidine-3-carboxylate (3.5 g, 9.35 mmol) in THF (175 mL) was added H$_2$O (85 mL), iron powder (5.22 g, 93.46 mmol, CAS RN 7439-89-6), NH$_4$Cl (5 g, 93.47 mmol) and the reaction mixture heated at 80° C. for 4 h. After cooling, the reaction mixture was filtered through a celite bed and washed with EtOAc (2×100 mL). The filtrate was washed with brine, dried over Na$_2$SO$_4$ and concentrated under vacuum to get the desired compound as an off-white solid (2.8 g, 96%). MS (EI): m/z=313.2 [M+H]$^+$.

e) 2-{1'-Benzyl-4-chloro-2-oxo-1,2-dihydrospiro [indole-3,3'-pyrrolidine]-1-yl}-N-(2,2,2-trifluoroethyl)acetamide To a stirred solution of 1'-benzyl-4-chloro-1,2-dihydrospiro[indole-3,3'-pyrrolidine]-2-one (2.8 g, 8.974 mmol) in DMF (40 mL) was added sodium hydride (60% in mineral oil) (430 mg, 10.769 mmol) at 0° C. and the reaction mixture was stirred at 25° C. for 1 h. Then 2-chloro-N-(2,2,2-trifluoro-ethyl)-acetamide (1.42 g, 8.077 mmol, CAS RN 170655-44-4) was added at 0° C. and the reaction mixture was stirred at 25° C. for 3 h. The reaction mixture was quenched with saturated aqueous NH$_4$Cl solution and extracted with EtOAc (2×100 mL). The combined organic layers were washed with water (3×50 mL) and brine, dried over Na$_2$SO$_4$, filtered and evaporated, and the resulting crude product was purified by silica gel column chromatography (20-25% EtOAc/n-hexane) to afford the title compound as an off-white solid (2.8 g, 77%). MS (EI): m/z=452.2 [M+H]$^+$.

TABLE 1

The following intermediates were synthesized from the suitable building blocks/intermediates in analogy to the methods K to M as described before.

| Int. | Systematic Name | Building blocks/intermediates | Method | MS, m/z |
|---|---|---|---|---|
| INT2a | 2-{4-Methyl-2-oxo-1,2-dihydrospiro[indole-3,4'-piperidine]-1-yl}-N-(2,2,2-trifluoroethyl)acetamide | INT6b | L | MS (EI): m/z = 519.8 [M + H]$^+$ |
| INT4a | 2-{4-Fluoro-2-oxo-1,2-dihydrospiro[indole-3,4'-piperidine]-1-yl}-N-(2,2,2-trifluoroethyl)acetamide | INT8b | L | MS (EI): m/z = 359.8 [M + H]$^+$ |
| INT5a | 2-{4-Chloro-2-oxo-1,2-dihydrospiro[indole-3,4'-piperidine]-1-yl}-N-(2,2,2-trifluoroethyl)acetamide | INT9b | L | MS (EI): m/z = 376.2 [M + H]$^+$ |
| INT6a | 2-{5-Bromo-2-oxo-1,2-dihydrospiro[indole-3,4'-piperidine]-1-yl}-N-(2,2,2-trifluoroethyl)acetamide | INT10b | L | MS (EI): m/z = 422.1 [M + H]$^+$ |

TABLE 1-continued

*The following intermediates were synthesized from the suitable building blocks/intermediates in analogy to the methods K to M as described before.*

| Int. | Systematic Name | Building blocks/intermediates | Method | MS, m/z |
|---|---|---|---|---|
| INT7a | 2-{5-Fluoro-2-oxo-1,2-dihydrospiro[indole-3,4'-piperidine]-1-yl}-N-(2,2,2-trifluoroethyl)acetamide | INT11b | L | MS (EI): m/z = 360.2 [M + H]+ |
| INT8a | 2-{4-Methoxy-2-oxo-1,2-dihydrospiro[indole-3,4'-piperidine]-1-yl}-N-(2,2,2-trifluoroethyl)acetamide | 2-{1'-Benzyl-4-methoxy-2-oxo-1,2-dihydro-spiro[indole-3,4'-piperidine]-1-yl}-N-(2,2,2-trifluoro-ethyl)acetamide INT12b | L | MS (EI): m/z = 371.9 [M + H]+ |
| INT9a | Methyl 2-oxo-1-(2-oxo-2-((2,2,2-trifluoroethyl)amino)ethyl)spiro[indoline-3,4'-piperidine]-4-carboxylate | INT22b | M | MS (ESI): m/z = 400.2 [M + H]+ |

TABLE 1-continued

The following intermediates were synthesized from the suitable building blocks/intermediates in analogy to the methods K to M as described before.

| Int. | Systematic Name | Building blocks/ intermediates | Method | MS, m/z |
|---|---|---|---|---|
| INT11a | 2-{4,5-Difluoro-2-oxo-1,2-dihydrospiro[indole-3,4'-piperidine]-1-yl}-N-(2,2,2-trifluoroethyl)acetamide | INT14b | L | MS (EI): m/z = 377.8 [M + H]$^+$ |
| INT12a | 2-{4-Cyano-2-oxo-1,2-dihydrospiro[indole-3,4'-piperidine]-1-yl}-N-(2,2,2-trifluoroethyl)acetamide | INT15b | L | MS (EI): m/z = 367.2 [M + H]$^+$ |
| INT13a | 2-{5-Chloro-2-oxo-1,2-dihydrospiro[indole-3,4'-piperidine]-1-yl}-N-(2,2,2-trifluoroethyl)-acetamide | INT16b | L | MS (EI): m/z = 375.6 [M + H]$^+$ |
| INT14a | 2-{6-Fluoro-2-oxo-1,2-dihydrospiro[indole-3,4'-piperidine]-1-yl}-N-(2,2,2-trifluoroethyl)-acetamide | INT17b | L | MS (EI): m/z = 359.6 [M + H]$^+$ |

TABLE 1-continued

The following intermediates were synthesized from the suitable building blocks/intermediates in analogy to the methods K to M as described before.

| Int. | Systematic Name | Building blocks/intermediates | Method | MS, m/z |
|---|---|---|---|---|
| INT15a | 2-(4-Bromo-7-fluoro-2-oxo-spiro[indoline-3,4'-piperidine]-1-yl)-N-(2,2,2-trifluoroethyl)acetamide | INT24b | L | MS (ESI): m/z = 437.9 [M + H]+ |
| INT16a | 2-(4,5-Dichloro-2-oxo-spiro[indoline-3,4'-piperidine]-1-yl)-N-(2,2,2-trifluoroethyl)acetamide | INT25b | L | MS (EI): m/z = 410.3 [M + H]+ |
| INT17a | 2-(4-Chloro-5-fluoro-2-oxo-spiro[indoline-3,4'-piperidine]-1-yl)-N-(2,2,2-trifluoroethyl)acetamide | INT30b | L | MS (EI): m/z = 394.1 [M + H]+ |
| INT18a | 2-[2-Oxo-4-(trifluoromethyl)spiro[indoline-3,4'-piperidine]-1-yl]-N-(2,2,2-trifluoroethyl)acetamide | INT26b | L | MS (ESI): m/z = 410.1 [M + H]+ |

TABLE 1-continued

*The following intermediates were synthesized from the suitable building blocks/intermediates in analogy to the methods K to M as described before.*

| Int. | Systematic Name | Building blocks/ intermediates | Method | MS, m/z |
|---|---|---|---|---|
| INT19a | tert-Butyl 2-{4-methyl-2-oxo-1,2-dihydrospiro[indole-3,4'-piperidine]-1-yl}acetate | INT3b | M | MS (EI): m/z = 331.3 [M + H]$^+$ |
| INT20a | Ethyl 2-(4-chloro-2-oxospiro[indole-3,4'-piperidine]-1-yl)acetate | INT4b | L | MS (ESI): m/z = 323.12 [M + H]$^+$ |
| INT21a | 2-{4-Cyclopropyl-2-oxo-1,2-dihydrospiro[indole-3,4'-piperidine]-1-yl}-N-(2,2,2-trifluoroethyl)acetamide | INT18b | L | MS (EI): m/z = 382.2 [M + H]$^+$ |
| INT22a | 4-Chloro-1-[(3-cyclopropyl-1,2,4-oxadiazol-5-yl)methyl]spiro[indole-3,4'-piperidine]-2-one | INT19b | L | MS (ESI): m/z = 359.13 [M + H]$^+$ |

TABLE 1-continued

*The following intermediates were synthesized from the suitable building blocks/intermediates in analogy to the methods K to M as described before.*

| Int. | Systematic Name | Building blocks/intermediates | Method | MS, m/z |
|---|---|---|---|---|
| INT23a | N-Methyl-2-{4-methyl-2-oxo-1,2-dihydrospiro[indole-3,4'-piperidine]-1-yl}-N-[(2S)-1,1,1-trifluoropropan-2-yl]acetamide | INT20b | M | MS (EI): m/z = 384.2 [M + H]+ |
| INT24a | Methyl 2-(4-methyl-2-oxospiro[indoline-3,4'-piperidin]-1-yl)acetate | INT23b | M | MS (ESI): m/z = 289.2 [M + H]+ |
| INT25a | Methyl 2-(4-bromo-2-oxo-spiro[indoline-3,4'-piperidine]-1-yl)acetate | INT27b | L | MS (ESI): m/z = 367.1 [M + H]+ |
| INT26a | 2-(4-Bromo-5-fluoro-2-oxo-spiro[indoline-3,4'-piperidine]-1-yl)-N-(2,2,2-trifluoroethyl)acetamide | INT28b | L | MS (EI): m/z = 438.0 [M + H]+ |

TABLE 1-continued

The following intermediates were synthesized from the suitable building blocks/intermediates in analogy to the methods K to M as described before.

| Int. | Systematic Name | Building blocks/ intermediates | Method | MS, m/z |
|---|---|---|---|---|
| INT27a | Methyl 2-(4-chloro-5-fluoro-2-oxo-spiro[indoline-3,4'-piperidine]-1-yl)acetate | INT29b | L | MS (ESI): m/z = 394.2 [M + H]⁺ |
| INT28a | 2-(4-Hydroxy-2-oxo-spiro[indoline-3,4'-piperidine]-1-yl)-N-(2,2,2-trifluoroethyl)acetamide | INT5g | M | MS (EI): m/z = 358.2 [M + H]⁺ |
| INT29a | 2-(4-Ethoxy-2-oxo-spiro[indoline-3,4'-piperidine]-1-yl)-N-(2,2,2-trifluoroethyl)acetamide | INT6g | L | MS (EI): m/z = 386.3 [M + H]⁺ |
| INT30a | tert-Butyl 3-(4-methyl-2-oxo-spiro[indoline-3,4'-piperidine]-1-yl)propanoate | INT31b | M | MS (EI): m/z = 345.1 [M + H]⁺ |

TABLE 1-continued

*The following intermediates were synthesized from the suitable building blocks/intermediates in analogy to the methods K to M as described before.*

| Int. | Systematic Name | Building blocks/ intermediates | Method | MS, m/z |
|---|---|---|---|---|
| INT31a | N-Methyl-2-(4-methyl-2-oxo-spiro[indoline-3,4′-piperidine]-1-yl)-N-[(1R)-2,2,2-trifluoro-1-methyl-ethyl]acetamide | INT32b | M | MS (EI): m/z = 384.2 [M + H]+ |
| INT32a | tert-Butyl 2-(5′-chloro-2′-oxo-spiro[piperidine-4,3′-pyrrolo[3,2-b]pyridine]-1′-yl)acetate | INT33b | L | MS (EI): m/z = 352.4 [M + H]+ |
| INT33a | Methyl 2-(4,5-dichloro-2-oxospiro[indole-3,4′-piperidine]-1-yl)acetate | INT37b | L | MS (EI): m/z = 342.9 [M + H]+ |

TABLE 1-continued

The following intermediates were synthesized from the suitable building blocks/intermediates in analogy to the methods K to M as described before.

| Int. | Systematic Name | Building blocks/ intermediates | Method | MS, m/z |
|---|---|---|---|---|
| INT34a | (−)-4-Chloro-1-[2-oxo-1-(2,2,2-trifluoroethyl)piperidin-3-yl]-1,2-dihydrospiro[indole-3,4′-piperidine]-2-one | INT35b | L | MS (EI): m/z = 416.0 [M + H]$^+$ |
| INT35a | (+)-4-Chloro-1-[2-oxo-1-(2,2,2-trifluoroethyl)piperidin-3-yl]-1,2-dihydrospiro[indole-3,4′-piperidine]-2-one | INT36b | L | MS (EI): m/z = 416.2 [M + H]$^+$ |
| INT36a | 2-{4-Chloro-2-oxo-1,2-dihydrospiro[indole-3,4′-piperidine]-1-yl}-3-(morpholin-4-yl)-N-(2,2,2-trifluoroethyl)propanamide | INT18d | L | MS (EI): m/z = 475.1 [M + H]$^+$ |

Intermediate INT1b (Method P)

2-(1-Benzyl-5'-methoxy-2'-oxospiro[piperidine-4,3'-pyrrolo[3,2-b]pyridine]-1'-yl)-N-(2,2,2-trifluoroethyl)acetamide

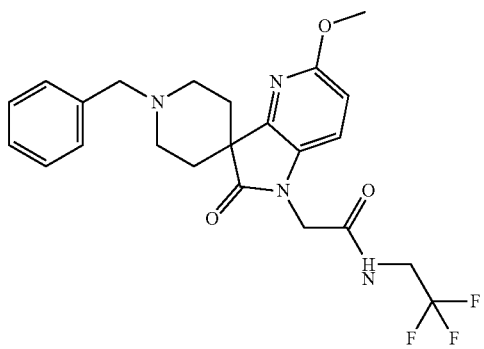 [SMILES: COc1ccc2c(n1)C1(CCN(Cc3ccccc3)CC1)C(=O)N2CC(=O)NCC(F)(F)F]

To a suspension of 1-benzyl-5'-methoxyspiro[piperidine-4,3'-pyrrolo[3,2-b]pyridin]-2'(1'H)-one (68 mg, 210 µmol, intermediate INT1c) in dioxane (1 mL) was added sodium hydride (10.1 mg, 231 µmol; 55% in mineral oil) and the mixture was stirred at RT for 1 h. To the dark solution was added 2-chloro-N-(2,2,2-trifluoroethyl)acetamide (40.6 mg, 231 µmol, CAS RN 170655-44-4) and stirring was continued at RT for 5 hours. The reaction mixture was poured on saturated aqueous $NH_4Cl$ solution and EtOAc and the layers were separated. The aqueous layer was extracted twice with EtOAc. The organic layers were dried over $MgSO_4$, filtered, treated with silica gel and evaporated. The compound was purified by silica gel chromatography on a 12 g column using an MPLC system eluting with a gradient of DCM: MeOH (100:0 to 90:10) to afford the title product as a brown gum (0.050 g; 51.4%). MS (ESI): m/z=461.18 [M−H]⁻.

Intermediate INT29b (Method Q)

Methyl 2-(1'-benzyl-4-chloro-5-fluoro-2-oxo-spiro[indoline-3,4'-piperidine]-1-yl)acetate 1'-Benzyl-4-chloro-5-fluorospiro[indoline-3,4'-piperidin]-2-one (1 g, 2.9 mmol, intermediate INT12c), methyl 2-bromoacetate (466 mg, 288 µL, 3.05 mmol, CAS RN 96-32-2) and $Cs_2CO_3$ (2.7 g, 8.29 mmol) were dissolved in DMF (15 mL) and stirred at RT under an argon atmosphere for 15 h. The reaction mixture was diluted with EtOAc and washed with water (3×100 mL). The organic phase was washed with brine, dried over $MgSO_4$ and filtered. The filtrate was treated with silica gel and concentrated. The crude compound was purified by silica gel chromatography on a 40 g column using a MPLC system eluting with a gradient of DCM:MeOH (100:0 to 90:10). The fractions were collected and concentrated in vacuo to give a yellow solid (1.07 g, 88.5%). MS (ESI): m/z=417.3 [M+H]⁻.

TABLE 2

The following intermediates were synthesized from the suitable building blocks/intermediates in analogy to methods P, Q and X as described before.

| Int. | Systematic Name | Building blocks/ intermediates | Method | MS, m/z |
|---|---|---|---|---|
| INT2b | 1'-Benzyl-1-[(3-cyclopropyl-1,2,4-oxadiazol-5-yl)methyl]-4-methylspiro[indole-3,4'-piperidine]-2-one | 5-(Chloromethyl)-3-cyclopropyl-1,2,4-oxadiazole INT2c | P | MS (ESI): m/z = 429.2 [M + H]⁺ |

TABLE 2-continued

*The following intermediates were synthesized from the suitable building blocks/intermediates in analogy to methods P, Q and X as described before.*

| Int. | Systematic Name | Building blocks/ intermediates | Method | MS, m/z |
|---|---|---|---|---|
| INT3b | tert-Butyl 2-{1'-benzyl-4-methyl-2-oxo-1,2-dihydrospiro[indole-3,4'-piperidine]-1-yl}-acetate | Bromo-acetic acid tert-butyl ester (CAS RN 5292-43-3) INT2c | P using DMF as solvent | MS (EI): m/z = 421.7 [M + H]$^+$ |
| INT4b | Ethyl 2-(1'-benzyl-4-chloro-2-oxospiro[indole-3,4'-piperidine]-1-yl)acetate | Ethyl 2-iodoacetate (CAS RN 623-48-3) INT5c | P | MS (ESI): m/z = 413.16 [M + H]$^+$ |
| INT5b | tert-Butyl 2-oxo-1-{[(2,2,2-trifluoroethyl)carbamoyl]methyl}-1,2-dihydrospiro[indole-3,4'-piperidine]-1'-carboxylate | 2-Chloro-N-(2,2,2-trifluoro-ethyl)acetamide (CAS RN 170655-44-4) tert-Butyl 2-oxo-1,2-dihydro-spiro[indole-3,4'-piperidine]-1'-carboxylate (CAS RN 252882-60-3) | P using DMF as solvent | MS (ESI): m/z = 442.1 [M + H]$^+$ |
| INT6b | 2-{1'-Benzyl-4-methyl-2-oxo-1,2-dihydrospiro[indole-3,4'-piperidine]-1-yl}-N-(2,2,2-trifluoroethyl)acetamide | 2-Chloro-N-(2,2,2-trifluoro-ethyl)acetamide (CAS RN 170655-44-4) INT2c | P using DMF as solvent | MS (EI): m/z = 445.7 [M + H]$^+$ |

TABLE 2-continued

*The following intermediates were synthesized from the suitable building blocks/intermediates in analogy to methods P, Q and X as described before.*

| Int. | Systematic Name | Building blocks/ intermediates | Method | MS, m/z |
|---|---|---|---|---|
| INT7b | 2-{1'-Benzyl-4-bromo-2-oxo-1,2-dihydrospiro[indole-3,4'-piperidine]-1-yl}-N-(2,2,2-trifluoroethyl)acetamide | 2-Chloro-N-(2,2,2-trifluoroethyl)acetamide (CAS RN 170655-44-4) INT3c | P using DMF as solvent | MS (EI): m/z = 509.7 [M + H]+ |
| INT8b | 2-{1'-Benzyl-4-fluoro-2-oxo-1,2-dihydrospiro[indole-3,4'-piperidine]-1-yl}-N-(2,2,2-trifluoroethyl)acetamide | 2-Chloro-N-(2,2,2-trifluoroethyl)acetamide (CAS RN 170655-44-4) INT4c | P using DMF as solvent | MS (EI): m/z = 449.7 [M + H]+ |
| INT9b | 2-{1'-Benzyl-4-chloro-2-oxo-1,2-dihydrospiro[indole-3,4'-piperidine]-1-yl}-N-(2,2,2-trifluoroethyl)acetamide | 2-Chloro-N-(2,2,2-trifluoroethyl)acetamide (CAS RN 170655-44-4) INT5c | P using DMF as solvent | MS (EI): m/z = 465.9 [M + H]+ |
| INT10b | 2-{1'-Benzyl-5-bromo-2-oxo-1,2-dihydrospiro[indole-3,4'-piperidine]-1-yl}-N-(2,2,2-trifluoroethyl)acetamide | 2-Chloro-N-(2,2,2-trifluoroethyl)acetamide (CAS RN 170655-44-4) INT6c | P using DMF as solvent | MS (EI): m/z = 509.9 [M + H]+ |

TABLE 2-continued

The following intermediates were synthesized from the suitable building blocks/intermediates in analogy to methods P, Q and X as described before.

| Int. | Systematic Name | Building blocks/intermediates | Method | MS, m/z |
|---|---|---|---|---|
| INT11b | 2-{1'-Benzyl-5-fluoro-2-oxo-1,2-dihydrospiro[indole-3,4'-piperidine]-1-yl}-N-(2,2,2-trifluoroethyl)acetamide | 2-Chloro-N-(2,2,2-trifluoro-ethyl)acetamide (CAS RN 170655-44-4) INT7c | P using DMF as solvent | MS (EI): m/z = 450.1 [M + H]$^+$ |
| INT12b | 2-{1'-Benzyl-4-methoxy-2-oxo-1,2-dihydrospiro[indole-3,4'-piperidine]-1-yl}-N-(2,2,2-trifluoroethyl)acetamide | 2-Chloro-N-(2,2,2-trifluoro-ethyl)acetamide (CAS RN 170655-44-4) INT8c | P using DMF as solvent | MS (EI): m/z = 461.7 [M + H]$^+$ |
| INT13b | 2-{1'-Benzyl-4-ethenyl-2-oxo-1,2-dihydrospiro[indole-3,4'-piperidine]-1-yl}-N-(2,2,2-trifluoroethyl)acetamide | 2-Chloro-N-(2,2,2-trifluoro-ethyl)acetamide (CAS RN 170655-44-4) INT1g | P using DMF as solvent | MS (EI): m/z = 457.7 [M + H]$^+$ |
| INT14b | 2-{1'-Benzyl-4,5-difluoro-2-oxo-1,2-dihydrospiro[indole-3,4'-piperidine]-1-yl}-N-(2,2,2-trifluoroethyl)acetamide | 2-Chloro-N-(2,2,2-trifluoro-ethyl)acetamide (CAS RN 170655-44-4) INT9c | P using DMF as solvent | MS (EI): m/z = 467.8 [M + H]$^+$ |

TABLE 2-continued

The following intermediates were synthesized from the suitable building blocks/intermediates in analogy to methods P, Q and X as described before.

| Int. | Systematic Name | Building blocks/ intermediates | Method | MS, m/z |
|---|---|---|---|---|
| INT15b | 2-{1'-Benzyl-4-cyano-2-oxo-1,2-dihydrospiro[indole-3,4'-piperidine]-1-yl}-N-(2,2,2-trifluoroethyl)acetamide | 2-Chloro-N-(2,2,2-trifluoroethyl)acetamide (CAS RN 170655-44-4) Int2g | P using DMF as solvent | MS (EI): m/z = 457.1 [M + H]+ |
| INT16b | 2-{1'-Benzyl-5-chloro-2-oxo-1,2-dihydrospiro[indole-3,4'-piperidine]-1-yl}-N-(2,2,2-trifluoroethyl)acetamide | 2-Chloro-N-(2,2,2-trifluoroethyl)acetamide (CAS RN 170655-44-4) INT10c | P using DMF as solvent | MS (EI): m/z = 465.8 [M + H]+ |
| INT17b | 2-{1'-Benzyl-6-fluoro-2-oxo-1,2-dihydrospiro[indole-3,4'-piperidine]-1-yl}-N-(2,2,2-trifluoroethyl)acetamide | 2-Chloro-N-(2,2,2-trifluoroethyl)acetamide (CAS RN 170655-44-4) INT11c | P using DMF as solvent | MS (EI): m/z = 449.4 [M + H]+ |
| INT18b | 2-{1'-Benzyl-4-cyclopropyl-2-oxo-1,2-dihydrospiro[indole-3,4'-piperidine]-1-yl}-N-(2,2,2-trifluoroethyl)acetamide | 2-Chloro-N-(2,2,2-trifluoroethyl)acetamide (CAS RN 170655-44-4) INT3g | P using DMF as solvent | MS (EI): m/z = 472.1 [M + H]+ |

TABLE 2-continued

The following intermediates were synthesized from the suitable building blocks/intermediates in analogy to methods P, Q and X as described before.

| Int. | Systematic Name | Building blocks/ intermediates | Method | MS, m/z |
|---|---|---|---|---|
| INT19b | 1'-Benzyl-4-chloro-1-[(3-cyclopropyl-1,2,4-oxadiazol-5-yl)methyl]spiro[indole-3,4'-piperidine]-2-one | 5-(Chloromethyl)-3-cyclopropyl-1,2,4-oxadiazole (CAS RN 119223-01-7) INT5c | P using DMF as solvent | MS (ESI): m/z = 449.1 [M + H]$^+$ |
| INT20b | 2-{1'-Benzyl-4-methyl-2-oxo-1,2-dihydrospiro[indole-3,4'-piperidine]-1-yl}-N-methyl-N-[(2S)-1,1,1-trifluoropropan-2-yl]acetamide | Iodomethane (CAS RN 74-88-4) INT4d | P using DMF as solvent | MS (EI): m/z = 474.0 [M + H]$^+$ |
| INT21b | Ethyl 2-(1-benzyl-5'-methoxy-2'-oxospiro[piperidine-4,3'-pyrrolo[3,2-b]pyridine]-1'-yl)acetate | Ethyl 2-iodoacetate (CAS RN 623-48-3) INT1c | P | MS (ESI): m/z = 410.3 [M + H]$^+$ |
| INT22b | Methyl 1'-benzyl-2-oxo-1-[2-oxo-2-(2,2,2-trifluoroethylamino)ethyl]spiro[indoline-3,4'-piperidine]-4-carboxylate | 2-Chloro-N-(2,2,2-trifluoro-ethyl)acetamide (CAS RN 170655-44-4) INT4g | P using DMF as solvent | MS (ESI): m/z = 490.2 [M + H]$^+$ |

TABLE 2-continued

The following intermediates were synthesized from the suitable building blocks/intermediates in analogy to methods P, Q and X as described before.

| Int. | Systematic Name | Building blocks/ intermediates | Method | MS, m/z |
|---|---|---|---|---|
| INT23b | Methyl 2-(1'-benzyl-4-methyl-2-oxospiro[indoline-3,4'-piperidin]-1-yl)acetate | Methyl 2-bromoacetate (CAS RN 96-32-2) INT2c | P using DMF as solvent | MS (ESI): m/z = 379.2 [M + H]$^+$ |
| INT24b | 2-(1'-Benzyl-4-bromo-7-fluoro-2-oxo-spiro[indoline-3,4'-piperidine]-1-yl)-N-(2,2,2-trifluoroethyl)acetamide | 2-Chloro-N-(2,2,2-trifluoro-ethyl)acetamide (CAS RN 170655-44-4) INT13c | P using DMF as solvent | MS: (ESI): m/z = 527.3 [M + H]$^+$ |
| INT25b | 2-(1'-Benzyl-4,5-dichloro-2-oxo-spiro[indoline-3,4'-piperidine]-1-yl)-N-(2,2,2-trifluoroethyl)acetamide | 2-Chloro-N-(2,2,2-trifluoro-ethyl)acetamide (CAS RN 170655-44-4) INT14c | P using DMF as solvent | MS (EI): m/z = 500.3 [M + H]$^+$ |

TABLE 2-continued

The following intermediates were synthesized from the suitable building blocks/intermediates in analogy to methods P, Q and X as described before.

| Int. | Systematic Name | Building blocks/ intermediates | Method | MS, m/z |
|---|---|---|---|---|
| INT26b | 2-[1'-Benzyl-2-oxo-4-(trifluoromethyl)spiro[indoline-3,4'-piperidine]-1-yl]-N-(2,2,2-trifluoroethyl)acetamide | 2-Chloro-N-(2,2,2-trifluoro-ethyl)acetamide (CAS RN 170655-44-4) INT15c | P using DMF as solvent | MS (EI): m/z = 500.1 [M + H]$^+$ |
| INT27b | Methyl 2-(1'-benzyl-4-bromo-2-oxo-spiro[indoline-3,4'-piperidine]-1-yl)acetate | Methyl 2-bromoacetate (CAS RN 96-32-2) INT3c | P using DMF as solvent | MS (ESI): m/z = 443.1 [M + H]$^+$ |
| INT28b | 2-(1'-Benzyl-4-bromo-5-fluoro-2-oxo-spiro[indoline-3,4'-piperidine]-1-yl)-N-(2,2,2-trifluoroethyl)acetamide | 2-Chloro-N-(2,2,2-trifluoro-ethyl)acetamide (CAS RN 170655-44-4) INT16c | P using DMF as solvent | MS (EI): m/z = 527.8 [M + H]$^+$ |
| INT30b | 2-(1'-Benzyl-4-chloro-5-fluoro-2-oxo-spiro[indoline-3,4'-piperidine]-1-yl)-N-(2,2,2-trifluoroethyl)acetamide | 2-Chloro-N-(2,2,2-trifluoro-ethyl)acetamide (CAS RN 170655-44-4) INT12c | P using DMF as solvent | MS (EI): m/z = 484.4 [M + H]$^+$ |

TABLE 2-continued

*The following intermediates were synthesized from the suitable building blocks/intermediates in analogy to methods P, Q and X as described before.*

| Int. | Systematic Name | Building blocks/intermediates | Method | MS, m/z |
|---|---|---|---|---|
| INT31b | tert-Butyl 3-(1'-benzyl-4-methyl-2-oxo-spiro[indoline-3,4'-piperidine]-1-yl)propanoate | tert-Butyl acrylate (CAS RN 1663-39-4) INT2c | P using DMF as solvent | MS (EI): m/z = 435.0 [M + H]+ |
| INT32b | 2-(1'-Benzyl-4-methyl-2-oxo-spiro[indoline-3,4'-piperidine]-1-yl)-N-methyl-N-[(1R)-2,2,2-trifluoro-1-methyl-ethyl]acetamide | Iodomethane (CAS RN 74-88-4) INT14d | P using DMF as solvent | MS (EI): m/z = 474.3 [M + H]+ |
| INT33b | tert-Butyl 2-(1-benzyl-5'-chloro-2'-oxo-spiro[piperidine-4,3'-pyrrolo[3,2-b]pyridine]-1'-yl)acetate | Bromo-acetic acid tert-butyl ester (CAS RN 5292-43-3) INT17c | P using DMF as solvent | MS (EI): m/z = 442.2 [M + H]+ |

TABLE 2-continued

*The following intermediates were synthesized from the suitable building blocks/intermediates in analogy to methods P, Q and X as described before.*

| Int. | Systematic Name | Building blocks/ intermediates | Method | MS, m/z |
|---|---|---|---|---|
| INT34b | 1'-Benzyl-4-chloro-1-[2-oxo-1-(2,2,2-trifluoro-ethyl)piperidin-3-yl]-1,2-dihydrospiro[indole-3,4'-piperidine]-2-one | 2-Bromo-1-(2,2,2-trifluoro-ethyl)-piperidin-2-one (MFCD19678916) INT5c | P using DMF as solvent | MS (EI): m/z = 505.7 [M + H]$^+$ |
| INT35b | (−)-1'-Benzyl-4-chloro-1-[2-oxo-1-(2,2,2-trifluoroethyl)piperidin-3-yl]-1,2-dihydrospiro[indole-3,4'-piperidine]-2-one | INT34b | X | MS (EI): m/z = 505.7 [M + H]$^+$ |
| INT36b | (+)-1'-Benzyl-4-chloro-1-[2-oxo-1-(2,2,2-trifluoroethyl)piperidin-3-yl]-1,2-dihydrospiro[indole-3,4'-piperidine]-2-one | INT34b | X | MS (EI): m/z = 505.7 [M + H]$^+$ |

TABLE 2-continued

The following intermediates were synthesized from the suitable building
blocks/intermediates in analogy to methods P, Q and X as described before.

| Int. | Systematic Name | Building blocks/intermediates | Method | MS, m/z |
|---|---|---|---|---|
| INT37b | Methyl 2-{1'-benzyl-4,5-dichloro-2-oxo-1,2-dihydrospiro[indole-3,4'-piperidine]-1-yl} acetate 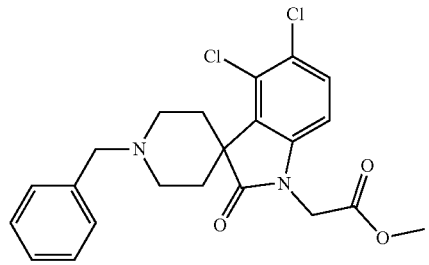 | Methyl bromoacetate (CAS RN 96-32-2) INT14c | P | MS (EI): m/z = 433.0 [M + H]$^+$ |

Intermediate INT1c (Method T)

1'-Benzyl-5-methoxyspiro[1H-pyrrolo[3,2-b]pyridine-3,4'-piperidine]-2-one

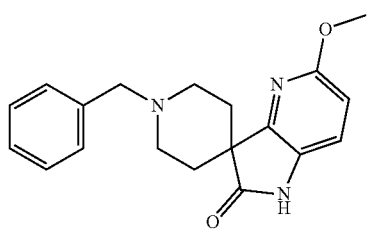 [SMILES: COc1ccc2c(n1)C1(CCN(Cc3ccccc3)CC1)C(=O)N2]

To a suspension of 5-methoxy-1H-pyrrolo[3,2-b]pyridin-2(3H)-one (1.85 g, 11.3 mmol, CAS RN 178393-14-1) in THF (80 mL) at −78° C. was added dropwise LiHMDS (50.3 mL, 50.3 mmol, 1M solution in THF) and the brown solution was stirred at this temperature over 30 min. before N-benzyl-2-chloro-N-(2-chloroethyl)ethanamine hydrochloride (3 g, 11.2 mmol, CAS RN 10429-82-0) was added in one portion. The cooling bath was then removed and the mixture was allowed to warm up to RT. Heating was installed and the light brown suspension was stirred at reflux for 24 hours. The light brown reaction mixture was poured on saturated aqueous NH$_4$Cl solution and EtOAc and the layers were separated. The aqueous layer was twice extracted with EtOAc. The organic layer was dried over MgSO$_4$, filtered, treated with silica gel and evaporated. The compound was purified by silica gel chromatography on a 40 g column using an MPLC system eluting with a gradient of n-heptane:EtOAc (100:0 to 0:100). The product containing fractions were combined. The precipitate formed during evaporation was filtered off to afford the title product as a light brown solid (0.288 g; 8%). MS (ESI): m/z=324.17 [M+H]$^+$.

TABLE 3

The following intermediates were synthesized from the suitable building blocks/intermediates in
analogy to method T described before.

| Int. | Systematic Name | Building blocks/intermediates | Method | MS, m/z |
|---|---|---|---|---|
| INT2c | 1'-Benzyl-4-methyl-1,2-dihydrospiro[indole-3,4'-piperidine]-2-one 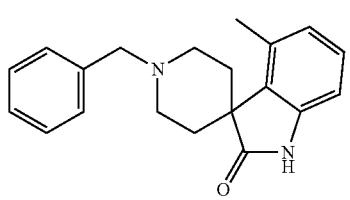 | 4-Methylindolin-2-one (CAS RN 13220-46-7) N-Benzyl-2-chloro-N-(2-chloroethyl)ethanamine hydrochloride (CAS RN 10429-82-0) | T | MS (EI): m/z = 306.9 [M + H]$^+$ |

TABLE 3-continued

The following intermediates were synthesized from the suitable building blocks/intermediates in analogy to method T described before.

| Int. | Systematic Name | Building blocks/intermediates | Method | MS, m/z |
|---|---|---|---|---|
| INT3c | 1'-Benzyl-4-bromo-1,2-dihydrospiro[indole-3,4'-piperidine]-2-one | 4-Bromo-1,3-dihydro-indol-2-one (CAS RN 99365-48-7) N-Benzyl-2-chloro-N-(2-chloroethyl)ethanamine hydrochloride (CAS RN 10429-82-0) | T using NaHDMS as base | MS (EI): m/z = 373.0 [M + H]+ |
| INT4c | 1'-Benzyl-4-fluoro-1,2-dihydrospiro[indole-3,4'-piperidine]-2-one | 4-Fluoro-1,3-dihydro-indol-2-one (CAS RN 138343-94-9) N-Benzyl-2-chloro-N-(2-chloroethyl)ethanamine hydrochloride (CAS RN 10429-82-0) | T using NaHDMS as base | MS (EI): m/z = 311.0 [M + H]+ |
| INT5c | 1'-Benzyl-4-chloro-1,2-dihydrospiro[indole-3,4'-piperidine]-2-one | 4-Chloro-1,3-dihydro-indol-2-one (CAS RN 20870-77-3) N-Benzyl-2-chloro-N-(2-chloroethyl)ethanamine hydrochloride (CAS RN 10429-82-0) | T using NaHDMS as base | MS (EI): m/z = 326.8 [M + H]+ |
| INT6c | 1'-Benzyl-5-bromo-1,2-dihydrospiro[indole-3,4'-piperidine]-2-one | 5-Bromo-1,3-dihydro-indol-2-one (CAS RN 20870-78-4) N-Benzyl-2-chloro-N-(2-chloroethyl)ethanamine hydrochloride (CAS RN 10429-82-0) | T using NaHDMS as base | MS (EI): m/z = 372.9 [M + H]+ |
| INT7c | 1'-Benzyl-5-fluoro-1,2-dihydrospiro[indole-3,4'-piperidine]-2-one | 5-Fluoro-1,3-dihydro-indol-2-one (CAS RN 56341-41-4) N-Benzyl-2-chloro-N-(2-chloroethyl)ethanamine hydrochloride (CAS RN 10429-82-0) | T using NaHDMS as base | MS (EI): m/z = 310.0 [M + H]+ |

TABLE 3-continued

The following intermediates were synthesized from the suitable building blocks/intermediates in analogy to method T described before.

| Int. | Systematic Name | Building blocks/ intermediates | Method | MS, m/z |
|---|---|---|---|---|
| INT8c | 1'-Benyl-4-methoxy-1,2-dihydrospiro[indole-3,4'-piperidine]-2-one | 4-Methoxy-1,3-dihydro-indol-2-one (CAS RN 7699-17-4) N-Benzyl-2-chloro-N-(2-chloroethyl) ethanamine hydrochloride (CAS RN 10429-82-0) | T using NaHDMS as base | MS (EI): m/z = 323.1 [M + H]⁺ |
| INT9c | 1'-Benzyl-4,5-difluoro-1,2-dihydrospiro[indole-3,4'-piperidine]-2-one | 4,5-Difluorooxindole (CAS RN 850429-64-0) N-Benzyl-2-chloro-N-(2-chloroethyl) ethanamine hydrochloride (CAS RN 10429-82-0) | T using NaHDMS as base | MS (EI): m/z = 329.0 [M + H]⁺ |
| INT10c | 1'-Benzyl-5-chloro-1,2-dihydrospiro[indole-3,4'-piperidine]-2-one | 5-Chloro-1,3-dihydro-indol-2-one (CAS RN 17630-75-0) N-Benzyl-2-chloro-N-(2-chloroethyl) ethanamine hydrochloride (CAS RN 10429-82-0) | T using NaHDMS as base | MS (EI): m/z = 324.9 [M − H]⁻ |
| INT11c | 1'-Benzyl-6-fluoro-1,2-dihydrospiro[indole-3,4'-piperidine]-2-one | 6-Fluorooxindole (CAS RN 56341-39-0) N-Benzyl-2-chloro-N-(2-chloroethyl) ethanamine hydrochloride (CAS RN 10429-82-0) | T using NaHDMS as base | MS (EI): m/z = 311.1 [M + H]⁺ |

TABLE 3-continued

The following intermediates were synthesized from the suitable building blocks/intermediates in analogy to method T described before.

| Int. | Systematic Name | Building blocks/ intermediates | Method | MS, m/z |
|---|---|---|---|---|
| INT12c | 1'-Benzyl-4-chloro-5-fluoro-spiro[indoline-3,4'-piperidine]-2-one | N-Benzyl-2-chloro-N-(2-chloroethyl)ethanamine hydrochloride (CAS RN 10429-82-0) INT5f | T using NaHDMS as base | MS (EI): m/z = 345.1 [M + H]+ |
| INT13c | 1'-Benzyl-4-bromo-7-fluoro-spiro[indoline-3,4'-piperidine]-2-one | N-Benzyl-2-chloro-N-(2-chloroethyl)ethanamine hydrochloride (CAS RN 10429-82-0) INT1f | T using NaHDMS as base | MS: (ESI): m/z = 389.0 [M + H]+ |
| INT14c | 1'-Benzyl-4,5-dichloro-spiro[indoline-3,4'-piperidine]-2-one | N-Benzyl-2-chloro-N-(2-chloroethyl)ethanamine hydrochloride (CAS RN 10429-82-0) INT4f | T using NaHDMS as base | MS (EI): m/z = 361.0 [M + H]+ |
| INT15c | 1'-Benzyl-4-(trifluoromethyl)spiro[indoline-3,4'-piperidine]-2-one | N-Benzyl-2-chloro-N-(2-chloroethyl)ethanamine hydrochloride (CAS RN 10429-82-0) INT2f | T using NaHDMS as base | MS (EI): m/z = 361.3 [M + H]+ |
| INT16c | 1'-Benzyl-4-bromo-5-fluoro-spiro[indoline-3,4'-piperidine]-2-one | N-Benzyl-2-chloro-N-(2-chloroethyl)ethanamine hydrochloride (CAS RN 10429-82-0) INT3f | T using NaHDMS as base | MS (EI): m/z = 389.0 [M + H]+ |

TABLE 3-continued

The following intermediates were synthesized from the suitable building blocks/intermediates in analogy to method T described before.

| Int. | Systematic Name | Building blocks/ intermediates | Method | MS, m/z |
|---|---|---|---|---|
| INT17c | 1'-Benzyl-5-chloro-spiro[1H-pyrrolo[3,2-b]pyridine-3,4'-piperidine]-2-one 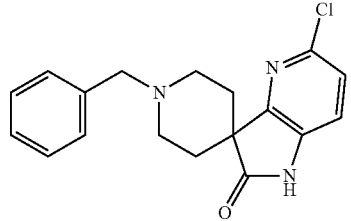 | N-Benzyl-2-chloro-N-(2-chloroethyl)ethanamine hydrochloride (CAS RN 10429-82-0) 5-Chloro-1,3-dihydro-pyrrolo[3,2-b]pyridin-2-one (CAS RN 136888-08-9) | T using NaHDMS as base | MS (EI): m/z = 328.3 [M + H]+ |

Intermediate INT18d

2-{1'-Benzyl-4-chloro-2-oxo-1,2-dihydrospiro[indole-3,4'-piperidine]-1-yl}-3-(morpholin-4-yl)-N-(2,2,2-trifluoroethyl)propanamide

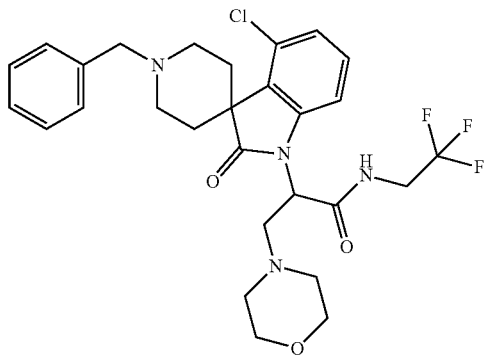 [SMILES: O=C(NCC(F)(F)F)C(CN1CCOCC1)N1C(=O)C2(CCN(Cc3ccccc3)CC2)c2c(Cl)cccc21]

To a solution of 2-{1'-benzyl-4-chloro-2-oxo-1,2-dihydrospiro[indole-3,4'-piperidine]-1-yl}-3-(morpholin-4-yl)propanoic acid (230 mg, 0.48 mmol) and 2,2,2-trifluoroethylamine hydrochloride (128 mg, 0.95 mmol, CAS RN 373-88-6) in anhydrous THF (30 mL) were added T$_3$P (0.60 mL, 0.95 mmol, 50% solution in EtOAc, CAS RN 68957-94-8) and DIPEA (0.23 mL, 1.43 mmol, CAS RN 7087-68-5) under nitrogen atmosphere at 25° C. The reaction mixture was stirred at 80° C. for 16 h, then diluted with EtOAc (60 mL) and washed with H$_2$O (40 mL) and brine (30 mL). The organic layer was dried over Na$_2$SO$_4$, filtered and concentrated. The resulting crude product was purified by column chromatography over silica gel (20-30% EtOAc/n-hexane) to afford the title product (250 mg, 93%) as a yellow sticky liquid. MS (EI): m/z=565.2 [M+H]+.

a) tert-Butyl 2-{1'-benzyl-4-chloro-2-oxo-1,2-dihydrospiro[indole-3,4'-piperidine]-1-yl}prop-2-enoate To a stirred solution of 1'-benzyl-4-chloro-1,2-dihydrospiro[indole-3,4'-piperidine]-2-one (600 mg, 1.83 mmol, INT5c) and 2-propynoic acid tert-butyl ester (0.27 mL, 2.02 mmol, CAS RN 13831-03-3) in DCM (70 mL) was added dropwise to a solution of PPh$_3$ (530 mg, 2.02 mmol, CAS RN 603-35-0) in DCM (10 mL) at 0° C. The reaction mixture was then allowed to warm up to 25° C. and stirred for 16 h. The solvent was removed under reduced pressure and the resulting crude product was purified by column chromatography over silica gel (20-30% EtOAc/n-hexane) to yield the title product (370 mg, 44%) as a yellow solid. MS (EI): m/z=453.0 [M+H]+.

b) tert-Butyl 2-{1'-benzyl-4-chloro-2-oxo-1,2-dihydrospiro[indole-3,4'-piperidine]-1-yl}-3-(morpholin-4-yl)propanoate To a stirred solution of tert-butyl 2-{1'-benzyl-4-chloro-2-oxo-1,2-dihydrospiro[indole-3,4'-piperidine]-1-yl}prop-2-enoate (370 mg, 0.82 mmol) in DMF (15 mL) was added morpholine (0.14 mL, 1.64 mmol, CAS RN 868689-63-8) and the reaction mixture was stirred at 25° C. for 16 h. The solvent was evaporated off and the resulting residue was purified by column chromatography (50-60% EtOAc/n-hexane) to give the title product (320 mg, 72%) as a yellow liquid. MS (EI): m/z=540.2 [M+H]+.

c) 2-{1'-Benzyl-4-chloro-2-oxo-1,2-dihydrospiro[indole-3,4'-piperidine]-1-yl}-3-(morpholin-4-yl)propanoic acid To a solution of tert-butyl 2-{1'-benzyl-4-chloro-2-oxo-1,2-dihydrospiro[indole-3,4'-piperidine]-1-yl}-3-(morpholin-4-yl)propanoate (320 mg, 0.59 mmol) in dry DCM (20 mL) was added TFA (4 mL, CAS RN 407-25-0) at 0° C. under argon atmosphere and reaction mixture was stirred at 25° C. for 16 h. TFA and DCM were evaporated off to furnish the title product (250 mg, 87%) as a brown liquid which was used in the next step with out further purification. MS (EI): m/z=584.0 [M+H]+.

TABLE 4

The following intermediates were synthesized from the suitable building blocks/intermediates in analogy to the methods A, C, D and F as described before.

| Int. | Systematic Name | Building blocks/ intermediates | Method | MS, m/z |
|---|---|---|---|---|
| INT1d | tert-Butyl 2-{1'-[(1H-indazol-5-yl)carbonyl]-4-methyl-2-oxo-1,2-dihydrospiro[indole-3,4'-piperidine]-1-yl}acetate | 1H-Indazole-5-carboxylic acid (CAS RN 61700-61-6) INT19a | A | MS (EI): m/z = 473.4 [M − H]⁻ |
| INT2d | Ethyl 2-[4-chloro-1'-(1H-indazole-5-carbonyl)-2-oxospiro[indole-3,4'-piperidine]-1-yl]acetate | 1H-Indazole-5-carboxylic acid (CAS RN 61700-61-6) INT20a | A | MS (ESI): m/z = 467.15 [M + H]⁺ |
| INT3d | (S)-1-Benzyl-5'-methoxy-1'-(2-oxo-2-(2-(trifluoromethyl)pyrrolidin-1-yl)ethyl)spiro[piperidine-4,3'-pyrrolo[3,2-b]pyridin]-2'(1'H)-one | (S)-2-(trifluoromethyl) pyrrolidine (CAS RN 119580-41-5) INT4e | D | MS (ESI): m/z = 503.23 [M + H]⁺ |
| INT4d | 2-{1'-Benzyl-4-methyl-2-oxo-1,2-dihydrospiro[indole-3,4'-piperidine]-1-yl}-N-[(2S)-1,1,1-trifluoropropan-2-yl]acetamide | (S)-2,2,2-Trifluoro-1-methyl-ethylamine hydrochloride (CAS RN 125353-44-8) INT3e | D | MS (EI): m/z = 460.3 [M + H]⁺ |

TABLE 4-continued

The following intermediates were synthesized from the suitable building blocks/intermediates in analogy to the methods A, C, D and F as described before.

| Int. | Systematic Name | Building blocks/ intermediates | Method | MS, m/z |
|---|---|---|---|---|
| INT5d | Methyl 2-(4-methyl-2-oxo-1'-(1H-pyrazolo[3,4-b]pyridine-5-carbonyl)spiro[indoline-3,4'-piperidin]-1-yl)acetate | 1H-Pyrazolo[3,4-b]pyridine-5-carboxylic acid (CAS RN 952182-02-4) INT24a | F | MS (ESI): m/z = 434.2 [M + H]+ |
| INT6d | Methyl 2-[4-methyl-2-oxo-1'-(1H-pyrazolo[4,3-b]pyridine-5-carbonyl)spiro[indoline-3,4'-piperidine]-1-yl]acetate | 1H-Pyrazolo[4,3-b]pyridine-5-carboxylic acid (CAS RN 1260670-03-8) INT24a | F | MS (ESI): m/z = 434.2 [M + H]+ |
| INT7d | Methyl 2-[4-methyl-2-oxo-1'-(1H-pyrazolo[3,4-c]pyridine-5-carbonyl)spiro[indoline-3,4'-piperidine]-1-yl]acetate | 1H-Pyrazolo[3,4-b]pyridine-5-carboxylic acid (CAS RN 1256824-45-9) INT24a | F | MS (ESI): m/z = 434.1 [M + H]+ |
| INT8d | Methyl 2-[4-bromo-1'-(1H-indazole-5-carbonyl)-2-oxo-spiro[indoline-3,4'-piperidine]-1-yl]acetate | 1H-Indazole-5-carboxylic acid (CAS RN 61700-61-6) INT25a | A TEA instead of DIPEA | MS (ESI): m/z = 497.2 [M + H]+ |

TABLE 4-continued

The following intermediates were synthesized from the suitable building blocks/intermediates in analogy to the methods A, C, D and F as described before.

| Int. | Systematic Name | Building blocks/ intermediates | Method | MS, m/z |
|---|---|---|---|---|
| INT9d | Methyl 2-[4-bromo-2-oxo-1'-(1H-pyrazolo[3,4-b]pyridine-5-carbonyl)spiro[indoline-3,4'-piperidine]-1-yl]acetate | 1H-Pyrazolo[3,4-b]pyridine-5-carboxylic acid (CAS RN 952182-02-4) INT25a | A | MS (ESI): m/z = 500.0 [M + H]+ |
| INT10d | Methyl 2-[4-bromo-2-oxo-1'-(1H-pyrazolo[4,3-b]pyridine-5-carbonyl)spiro[indoline-3,4'-piperidine]-1-yl]acetate | 1H-Pyrazolo[4,3-b]pyridine-5-carboxylic acid (CAS RN 1260670-03-8) INT25a | A TEA instead of DIPEA | MS (ESI): m/z = 498.3 [M + H]+ |
| INT11d | Methyl 2-[4-bromo-2-oxo-1'-(1H-pyrazolo[3,4-c]pyridine-5-carbonyl)spiro[indoline-3,4'-piperidine]-1-yl]acetate | 1H-Pyrazolo[3,4-c]pyridine-5-carboxylic acid (CAS RN 1256824-45-9) INT25a | C TEA instead of DIPEA | MS (ESI): m/z = 500.2 [M + H]+ |
| INT12d | Methyl 2-[4-chloro-5-fluoro-2-oxo-1'-(1H-pyrazolo[4,3-b]pyridine-5-carbonyl)spiro[indoline-3,4'-piperidine]-1-yl]acetate | 1H-Pyrazolo[4,3-b]pyridine-5-carboxylic acid (CAS RN 1260670-03-8) INT27a | C TEA instead of DIPEA | MS (ESI): m/z = 472.2 [M + H]+ |

TABLE 4-continued

The following intermediates were synthesized from the suitable building blocks/intermediates in analogy to the methods A, C, D and F as described before.

| Int. | Systematic Name | Building blocks/ intermediates | Method | MS, m/z |
|---|---|---|---|---|
| INT13d | tert-Butyl 3-[1'-(1H-indazole-5-carbonyl)-4-methyl-2-oxo-spiro[indoline-3,4'-piperidine]-1-yl]propanoate | 1H-Indazole-5-carboxylic acid (CAS RN 61700-61-6) INT30a | C | MS (EI): m/z = 489.4 [M + H]⁺ |

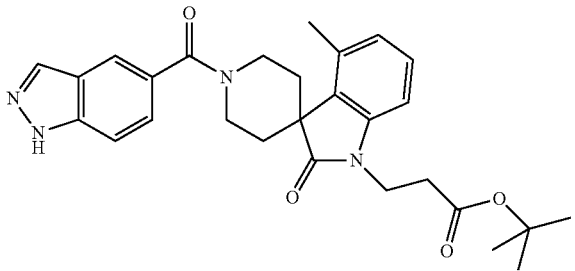

| INT14d | 2-{1'-Benzyl-4-methyl-2-oxo-1,2-dihydrospiro[indole-3,4'-piperidine]-1-yl}-N-[(2R)-1,1,1-trifluoropropan-2-yl]acetamide | (R)-2,2,2-Trifluoro-1-methyl-ethylamine hydrochloride (CAS RN 177469-12-4) INT3e | D | MS (EI): m/z = 460.3 [M + H]⁺ |

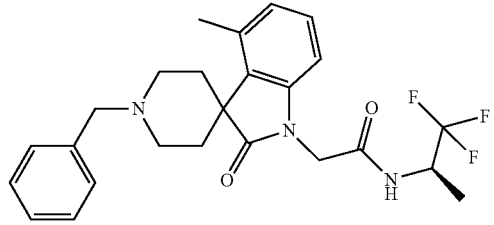

| INT15d | tert-Butyl 2-[5'-chloro-1-(1H-indazole-5-carbonyl)-2'-oxo-spiro[piperidine-4,3'-pyrrolo[3,2-b]pyridine]-1'-yl]acetate | 1H-Indazole-5-carboxylic acid (CAS RN 61700-61-6) INT32a | C | MS (EI): m/z = 469.2 [M + H]⁺ |

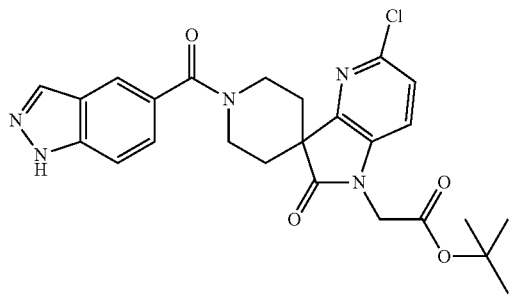

TABLE 4-continued

The following intermediates were synthesized from the suitable building blocks/intermediates in analogy to the methods A, C, D and F as described before.

| Int. | Systematic Name | Building blocks/ intermediates | Method | MS, m/z |
|---|---|---|---|---|
| INT16d | Methyl 2-[4,5-dichloro-2-oxo-1'-(1H-pyrazolo[4,3-b]pyridine-5-carbonyl)spiro[indoline-3,4'-piperidine]-1-yl]acetate | 1H-Pyrazolo[4,3-b]pyridine-5-carboxylic acid (CAS RN 1260670-03-8) INT33a | C | MS (EI): m/z = 488.2 [M + H]⁺ |
| INT17d | Methyl 2-{4-chloro-5-fluoro-1'-[(1H-indazol-5-yl)carbonyl]-2-oxo-1,2-dihydrospiro [indole-3,4'-piperidine]-1-yl}acetate | 1H-Indazole-5-carboxylic acid (CAS RN 61700-61-6) INT27a | C | MS (EI): m/z = 470.9 [M + H]⁺ |

Intermediate INT1e (Method S)

2-{1'-[(1H-Indazol-5-yl)carbonyl]-4-methyl-2-oxo-1,2-dihydrospiro[indole-3,4'-piperidine]-1-yl}acetic acid

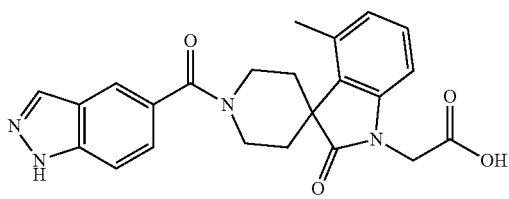 [SMILES: Cc1cccc2c1C1(CCN(C(=O)c3ccc4[nH]ncc4c3)CC1)C(=O)N2CC(=O)O]

To a solution of tert-butyl 2-{1'-[(1H-indazol-5-yl)carbonyl]-4-methyl-2-oxo-1,2-dihydrospiro[indole-3,4'-piperidine]-1-yl}acetate (690 mg, 1.45 mmol, intermediate INT1d) in DCM (30 mL) was added TFA (4 mL, CAS RN 76-05-1) and the reaction mixture was stirred at 25° C. for 16 h. The solvent was evaporated off and the resultant solid was triturated with ether and dried under vacuum to get the title product (590 mg, 97%) as a brown sticky solid. MS (EI): m/z=419.2 [M+H]⁺.

Intermediate INT2e (Method U)

2-(4-Chloro-1'-(1H-indazole-5-carbonyl)-2-oxospiro [indoline-3,4'-piperidin]-1-yl)acetic acid

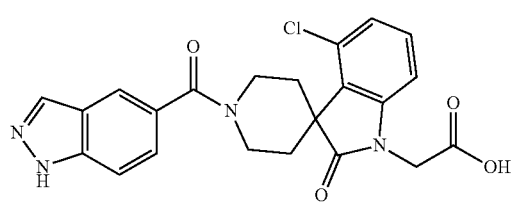 [SMILES: O=C(O)CN1C(=O)C2(CCN(C(=O)c3ccc4[nH]ncc4c3)CC2)c2c(Cl)cccc21]

To a solution of ethyl 2-(4-chloro-1'-(1H-indazole-5-carbonyl)-2-oxospiro[indoline-3,4'-piperidin]-1-yl)acetate (240 mg, 514 μmol, intermediate INT2d) in dioxane (2 mL)

and water (2 mL) was added lithium hydroxide monohydrate (27 mg, 643 μmol) and the clear, yellow solution was stirred at RT for 2.75 h. Dioxane was removed by evaporation and the remaining aqueous solution was diluted with water (2 mL) before 1M HCl in water (643 μL, 643 μmol) was added dropwise. The suspension was filtered, the filter cake washed with water to afford the title product as a colorless solid (0.146 g; 64.7%). MS (ESI): m/z=439.12 [M+H]$^+$.

TABLE 5

The following intermediates were synthesized from the suitable building blocks/intermediates in analogy to the methods S and U as described before.

| Int. | Systematic Name | Building blocks / intermediates | Method | MS, m/z |
|---|---|---|---|---|
| INT3e | 2-{1'-Benzyl-4-methyl-2-oxo-1,2-dihydrospiro[indole-3,4'-piperidine]-1-yl}acetic acid | INT3b | S | MS (EI): m/z = 365.2 [M + H]$^+$ |
| INT4e | 2-(1-Benzyl-5'-methoxy-2'-oxospiro[piperidine-4,3'-pyrrolo[3,2-b]pyridine]-1'-yl)acetic acid | INT21b | U | MS (ESI): m/z = 382.2 [M + H]$^+$ |
| INT5e | 2-(4-Methyl-2-oxo-1'-(1H-pyrazolo[3,4-b]pyridine-5-carbonyl)spiro[indoline-3,4'-piperidin]-1-yl)acetic acid | INT5d | U THF as solvent | MS (ESI): m/z = 420.2 [M + H]$^+$ |
| INT6e | 2-[4-Bromo-1'-(1H-indazole-5-carbonyl)-2-oxo-spiro[indoline-3,4'-piperidine]-1-yl]acetic acid | INT8d | U | MS (ESI): m/z = 485.2 [M + H]$^+$ |

TABLE 5-continued

The following intermediates were synthesized from the suitable building
blocks/intermediates in analogy to the methods S and U as described before.

| Int. | Systematic Name | Building blocks / intermediates | Method | MS, m/z |
|---|---|---|---|---|
| INT7e | 2-[4-Methyl-2-oxo-1'-(1H-pyrazolo[4,3-b]pyridine-5-carbonyl)spiro[indoline-3,4'-piperidine]-1-yl]acetic acid | INT6d | U THF as solvent | MS (ESI): m/z = 420.2 [M + H]$^+$ |
| INT8e | 2-[4-Methyl-2-oxo-1'-(1H-pyrazolo[3,4-c]pyridine-5-carbonyl)spiro[indoline-3,4'-piperidine]-1-yl]acetic acid | INT7d | U THF as solvent | MS (ESI): m/z = 420.2 [M + H]$^+$ |
| INT9e | 2-[4-Bromo-2-oxo-1'-(1H-pyrazolo[3,4-b]pyridine-5-carbonyl)spiro[indoline-3,4'-piperidine]-1-yl]acetic acid | INT9d | U | MS (ESI): m/z = 486.1 [M + H]$^+$ |
| INT10e | 2-[4-Bromo-2-oxo-1'-(1H-pyrazolo[3,4-c]pyridine-5-carbonyl)spiro[indoline-3,4'-piperidine]-1-yl]acetic acid | INT11d | U | MS (ESI): m/z = 486.2 [M + H]$^+$ |

TABLE 5-continued

*The following intermediates were synthesized from the suitable building blocks/intermediates in analogy to the methods S and U as described before.*

| Int. | Systematic Name | Building blocks / intermediates | Method | MS, m/z |
|---|---|---|---|---|
| INT11e | 2-[4-Bromo-2-oxo-1'-(1H-pyrazolo[4,3-b]pyridine-5-carbonyl)spiro[indoline-3,4'-piperidine]-1-yl]acetic acid | INT10d | U | MS (ESI): m/z = 484.2 [M + H]$^+$ |
| INT12e | 2-[4-Chloro-5-fluoro-2-oxo-1'-(1H-pyrazolo[4,3-b]pyridine-5-carbonyl)spiro[indoline-3,4'-piperidine]-1-yl]acetic acid | INT12d | U | MS (ESI): m/z = 472.2 [M + H]$^+$ |
| INT13e | 3-[1'-(1H-Indazole-5-carbonyl)-4-methyl-2-oxo-spiro[indoline-3,4'-piperidine]-1-yl]propanoic acid | INT13d | S | MS (EI): m/z = 433.2 [M + H]$^+$ |
| INT14e | 2-[5'-Chloro-1-(1H-indazole-5-carbonyl)-2'-oxo-spiro[piperidine-4,3'-pyrrolo[3,2-b]pyridine]-1'-yl]acetic acid | INT15d | S | MS (EI): m/z = 440.2 [M + H]$^+$ |

TABLE 5-continued

The following intermediates were synthesized from the suitable building blocks/intermediates in analogy to the methods S and U as described before.

| Int. | Systematic Name | Building blocks / intermediates | Method | MS, m/z |
|------|-----------------|--------------------------------|--------|---------|
| INT15e | 2-[4,5-Dichloro-2-oxo-1'-(1H-pyrazolo[4,3-b]pyridine-5-carbonyl)spiro[indoline-3,4'-piperidine]-1-yl]acetic acid | INT16d | U | MS (EI): m/z = 474.2 [M + H]+ |
| INT16e | 2-{4-Chloro-5-fluoro-1'-[(1H-indazol-5-yl)carbonyl]-2-oxo-1,2-dihydrospiro[indole-3,4'-piperidine]-1-yl}acetic acid | INT17d | U | MS (EI): m/z = 457.0 [M + H]+ |

Intermediate INT1f (Method G)

a) 4-Bromo-7-fluoro-1,3-dihydro-indol-2-one

10% aqueous NaOH solution (300 mL) was added to 4-bromo-7-fluoro-3-hydrazono-1,3-dihydro-indol-2-one (3.3 g, 12.79 mmol) at 25° C. and reaction mixture was stirred at 100° C. for 1 h. The reaction mixture was cooled to 10° C. and then acidified to pH 2 using hydrochloric acid. The mixture was extracted with EtOAc (2×200 mL) and the combined organic layers were dried over Na$_2$SO$_4$, filtered and the filtrate was evaporated under vacuum. The resulting crude product was purified by column chromatography over silica gel (25-31% EtOAc/n-hexane) to get the desired compound as a light brown solid (1.9 g, 65%). MS (ESI): m/z=228.2 [M−H]−.

b) 4-Bromo-7-fluoro-3-hydrazono-1,3-dihydro-indol-2-one

To a stirred solution of 4-bromo-7-fluoro-1H-indole-2,3-dione (4 g, 16.39 mmol) in acetic acid (150 mL, CAS RN 64-19-7) was added hydrazine hydrate (15.93 mL, 327.87 mmol, CAS RN 10217-52-4) at 50° C. and the reaction mixture was stirred at 110° C. for 1 h. The reaction mixture was poured onto ice. The precipitate was filtered off, washed with water and dried under vacuum to give the title compound as a light yellow solid (3.3 g, 78%) as. MS: (ESI): m/z=257.8 [M+H]+.

c) 4-Bromo-7-fluoro-1H-indole-2,3-dione

To a stirred solution of concentrated H$_2$SO$_4$ (51 mL) was added in portions N-(5-bromo-2-fluoro-phenyl)-2-[hydroxyimino]-acetamide (12.6 g, 48.27 mmol) at 60° C. and the reaction mixture was stirred at 85° C. for 20 min. The reaction mixture was cooled to 25° C., poured onto ice and the resulting solid was filtered off. The residue was purified by column chromatography over silica gel (35-45% EtOAc/n-hexane) to yield the desired product as a yellow solid (5.1 g, 45%). $^1$H NMR (400 MHz, DMSO-d$_6$) δ 7.20-7.24 (1H, m), 7.44-7.49 (1H, m), 11.68 (1H, s).

d) N-(5-Bromo-2-fluoro-phenyl)-2-[hydroxyimino]-acetamide

To a stirred solution of chloral hydrate (6.28 g, 37.97 mmol, CAS RN 302-17-0) in water (40 mL) was added Na₂SO₄ (43.73 g, 473.68 mmol, CAS RN 7757-82-6) at 25° C. and the reaction mixture was heated to 35° C. Then a warmed mixture of 5-bromo-2-fluoro-phenylamine (6.5 g, 34.21 mmol, CAS RN 2924-09-6), water (40 mL) and concentrated HCl (6.5 mL) followed by hydroxyl amine hydrochloride (8.08 g, 116.32 mmol, CAS RN 5470-11-1) in water (20 mL) were added to reaction mixture at 35° C. and reaction mixture was stirred at 90° C. for 3 h. After cooling to 25° C. the reaction mixture was filtered, dried and azeotroped with toluene to get the title compound as an off-white solid (7.6 g, 85%). MS (ESI): m/z=263.1 [M−H]⁻.

TABLE 6

The following examples were synthesized in analogy to method G from the suitable building blocks/intermediates and using the chemical transformations as described above.

| INT. | Systematic Name | Building blocks/ | method | MS, m/z |
|---|---|---|---|---|
| INT2f | 4-Trifluoromethyl-1,3-dihydro-indol-2-one | 3-Trifluoromethyl-phenylamine (CAS RN 98-16-8) | G | MS (ESI): m/z = 199.7 [M − H]⁻ |
| INT3f | 4-Bromo-5-fluoro-2,3-dihydro-1H-indol-2-one | 3-Bromo-4-fluoroaniline (CAS RN 656-64-4) | G | MS (EI): m/z = 230.0 [M + H]⁺ |
| INT4f | 4,5-Dichloro-1,3-dihydro-indol-2-one | 3,4-Dichloro-phenylamine (CAS RN 95-76-1) | G | MS (EI): m/z = 200.0 [M − H]⁻ |
| INT5f | 4-Chloro-5-fluoro-1,3-dihydro-indol-2-one | 4-Chloro-5-fluoro-1H-indole-2,3-dione (CAS RN 84378-94-9) | G starting with step b | MS (EI): m/z = 186.0 [M + H]⁺ |

131

Intermediate INT12 (Method I)

1'-Benzyl-4-ethenyl-1,2-dihydrospiro[indole-3,4'-piperidine]-2-one

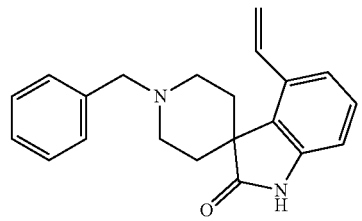 [SMILES: C=Cc1cccc2c1C1(CCN(Cc3ccccc3)CC1)C(=O)N2]

To a solution of 1'-benzyl-4-bromo-1,2-dihydrospiro[indole-3,4'-piperidine]-2-one (800 mg, 2.15 mmol, intermediate INT3c) in toluene (20 mL) was added LiCl (274 mg, 6.46 mmol, CAS RN 7447-41-8) and tributyl(vinyl)tin (1.26 mL, 4.3 mmol, CAS RN 7486-35-3). It was then purged with nitrogen for 20 min at 25° C. To this mixture was added Pd(PPh$_3$)$_4$ (249 mg, 0.22 mmol, CAS RN 14221-01-3) and the reaction mixture was heated to 100° C. for 16 h. After cooling to 25° C., the mixture was filtered through celite bed and the residue was washed with EtOAc (2×100 mL). The filtrate was evaporated under reduced pressure. The resulting crude product was purified by flash column chromatography (70-100% EtOAc/n-hexane) to afford the desired product (417 mg, 61%) as a brown solid. MS (EI) m/z=518.8 [M+H]$^+$.

Intermediate INT2g (Method J)

1'-Benzyl-2-oxo-1,2-dihydrospiro

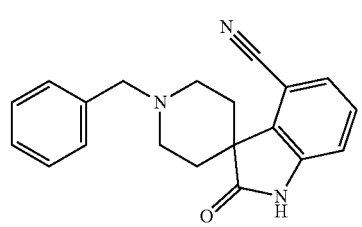 [SMILES: N#Cc1cccc2c1C1(CCN(Cc3ccccc3)CC1)C(=O)N2]

To a stirred solution of 1'-benzyl-4-bromo-1,2-dihydrospiro[indole-3,4'-piperidine]-2-one (900 mg, 2.42 mmol, intermediate INT3c) in DMF (8 mL) were added Zn(CN)$_2$ (569 mg, 4.84 mmol, CAS RN 557-21-1), dppf (268 mg, 0.48 mmol, CAS RN 12150-46-8) and Zinc powder (39 mg, 0.61 mmol, CAS RN 7440-66-6) and the mixture was purged with argon for 15 min. Then Pd$_2$(dba)$_3$ (443 mg, 0.48 mmol, CAS RN 12364-51-3) was added and reaction mixture was again purged with argon for 10 min. Reaction mixture was the heated to 100° C. and stirred at this temperature for 16 h. The reaction mixture was diluted with EtOAc (50 mL), filtered through a celite pad and then washed with EtOAc (2×30 mL). The filtrate was concentrated under reduced pressure and the crude product was purified by silica gel flush chromatography (50-70% EtOAc/n-hexane) to afford the title product (416 mg, 52%) as a yellow solid. MS (EI): m/z=318.3 [M+H]$^-$.

132

Intermediate INT32 (Method N)

1'-Benzyl-4-cyclopropyl-1,2-dihydrospiro[indole-3,4'-piperidine]-2-one

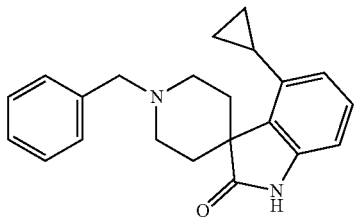 [SMILES: O=C1Nc2cccc(C3CC3)c2C12CCN(Cc1ccccc1)CC2]

To a solution of 1'-benzyl-4-bromo-1,2-dihydrospiro[indole-3,4'-piperidine]-2-one (790 mg, 2.13 mmol, intermediate INT3c) in toluene (17 mL) and water (1 mL) were added cyclopropyl boronic acid (475 mg, 5.53 mmol, CAS RN 411235-57-9), K$_3$PO$_4$ (1.49 g, 7.02 mmol, CAS RN 7778-53-2) and the solution was purged with argon for 20 min. Then tricyclohexylphosphine (101 mg, 0.36 mmol, CAS RN 2622-14-2) and Pd(OAc)$_2$ (38 mg, 0.17 mmol, CAS RN 3375-31-3) were added and the reaction mixture again degassed for another 10 min. The reaction mixture was stirred at 100° C. for 16 h, then cooled down to 25° C. and filtered through a celite pad. The filtrate was concentrated and the residue dissolved in EtOAc (30 mL) and washed with water (30 mL) and brine (20 mL). The organic layer was dried over Na$_2$SO$_4$, filtered and concentrated. The crude product was purified by flash chromatography over silica gel (10-25% EtOAc/n-hexane) to get the title product as a brown solid (603 mg, 85%). MS (EI): m/z=333.0 [M+H]$^+$.

Intermediate INT4 (Method O)

Methyl 1'-benzyl-2-oxospiro[indoline-3,4'-piperidine]-4-carboxylate

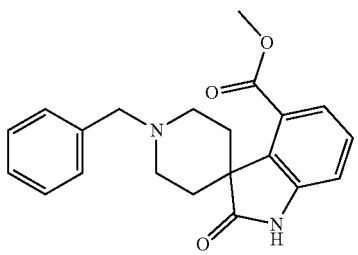 [SMILES: COC(=O)c1cccc2c1C1(CCN(Cc3ccccc3)CC1)C(=O)N2]

To a solution of 1'-benzyl-4-bromo-1,2-dihydrospiro[indole-3,4'-piperidine]-2-one (1.4 g, 3.77 mmol, INT3c) in MeOH (21.4 mL) and EtOAc (10.7 mL) were added TEA (788 µL, 5.66 mmol). 1,1'-Bis(diphenylphosphino)ferrocene palladium(II) chloride (140 mg, 170 µmol, CAS RN 95464-05-4) was added under an argon atmosphere. The mixture was heated at 110° C. for 20 h under a carbon monoxide (106 mg, 3.77 mmol, CAS RN 630-08-0) atmosphere at 20 bar in an autoclave. After cooling down to RT the reaction mixture was filtered over dicalite and the filtrate was concentrated. The crude product was purified by silica gel chromatography on a 40 g column using a MPLC system eluting with a gradient of DCM:MeOH (100:0 to 90:10) to give the desired compound as a brown solid (762 mg, 57.7%). MS (EI): m/z=351.2 [M+H]⁺.

Intermediate INT52 (Method W)

2-{1'-Benzyl-4-hydroxy-2-oxo-1,2-dihydrospiro[indole-3,4'-piperidine]-1-yl}-N-(2,2,2-trifluoroethyl)acetamide

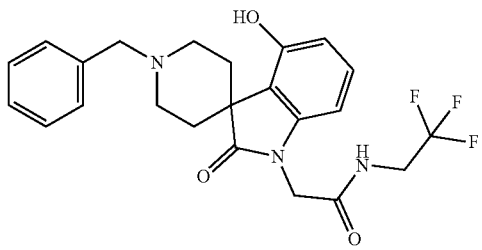 [SMILES: O=C(CN1C(=O)C2(CCN(Cc3ccccc3)CC2)c2c(O)cccc21)NCC(F)(F)F]

To a solution of 2-{1'-benzyl-4-methoxy-2-oxo-1,2-dihydrospiro[indole-3,4'-piperidine]-1-yl}-N-(2,2,2-trifluoroethyl)acetamide (400 mg, 0.80 mmol, intermediate INT12b) in DMF (10 mL) was added BBr₃ (3 mL, 1M solution in DCM, CAS RN 10294-33-4) and the mixture was stirred at 25° C. for 16 h. DCM (20 mL) was added to the reaction mixture which was quenched with a saturated NH₄HCO₃ solution and the layers were separated. The organic layer was dried with Na₂SO₄ and evaporated to get the title product as a yellow solid (280 mg, 72%). MS (ESI): m/z=448.4 [M+H]⁺.

Intermediate INT62 (Method V)

2-{1'-Benzyl-4-ethoxy-2-oxo-1,2-dihydrospiro[indole-3,4'-piperidine]-1-yl}-N-(2,2,2-trifluoroethyl)acetamide

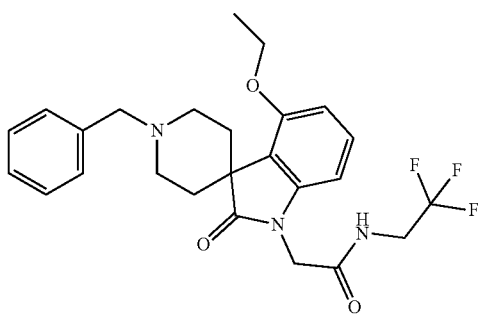 [SMILES: CCOc1cccc2c1C1(CCN(Cc3ccccc3)CC1)C(=O)N2CC(=O)NCC(F)(F)F]

To a solution of 2-{1'-benzyl-4-hydroxy-2-oxo-1,2-dihydrospiro[indole-3,4'-piperidine]-1-yl}-N-(2,2,2-trifluoroethyl)acetamide (150 mg, 0.34 mmol, intermediate INT5g) in ACN (30 mL) were added Cs₂CO₃ (218 mg, 0.67 mmol, CAS RN 534-17-8) and the mixture was stirred at 25° C. for 5 min. Iodoethane (0.5 mL, 1M in ACN, CAS RN 75-03-6) was added and the mixture was stirred at 25° C. for 1 h. The reaction mixture was filtered and the filtrate was evaporated under reduced pressure. The resulting crude product was purified by flash chromatography using silica gel (40-50% EtOAc/n-hexane) to yield the title product as a brown solid (135 mg, 84%). MS (ESI): m/z=476.0 [M+H]⁺.

Intermediate INT39

1H-Pyrazolo[4,3-d]pyrimidine-5-carboxylic acid

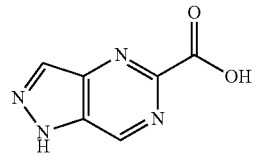 [SMILES: O=C(O)c1ncc2[nH]ncc2n1]

To a stirred solution of 1-(oxan-2-yl)-1H-pyrazolo[4,3-d]pyrimidine-5-carboxylic acid (1.4 g, 5.645 mmol) in DCM (14 mL) was added 4M HCl in dioxane solution (14 mL) and the reaction mixture was stirred at 25° C. for 3 h. After completion of reaction, it was evaporated to dryness and was triturated with pentane to get the title compound as an off-white solid (920 mg, 99%). MS (ESI): m/z=163.0 [M−H]⁻.

a) N-(2-Chloro-4-methylpyrimidin-5-yl)acetamide

To a stirred solution of 2-chloro-4-methylpyrimidin-5-amine (2 g, 14.706 mmol, CAS RN 20090-69-1) in DCM (50 mL) was added acetic anhydride (2.96 mL, 29.412 mmol) followed by triethyl amine (6.15 mL, 44.118 mmol) and reaction mixture was stirred at 25° C. for 16 h. After completion of the reaction, the mixture was evaporated. The crude product was purified by chromatography over silica gel (23-26% EtOAc/n-hexane) to afford the compound as an off white solid (2.49 g, 91%). MS (ESI): m/z=186.1 [M+H]⁺.

b) 1-{5-Chloro-1H-pyrazolo[4,3-d]pyrimidin-1-yl}ethan-1-one

To a stirred solution of N-(2-chloro-4-methylpyrimidin-5-yl)acetamide (2.5 g, 13.51 mmol) in chloroform (50 mL) in a sealed tube were added potassium acetate (955 mg, 9.73 mmol), acetic anhydride (4.59 mL, 48.65 mmol) and iso-amyl nitrite (4.57 mL, 34.054 mmol) at 25° C. and reaction mixture was stirred at 80° C. for 16 h. After completion of reaction, the reaction was quenched with H₂O and extracted with DCM (3×100 mL). The combined organic layers were dried over Na₂SO₄, filtered and concentrated under reduced pressure. The residue was purified by silica gel column chromatography over silica gel (10-15% EtOAc/hexane) to afford the desired compound as an off-white solid (2.1 g, 82%) which was used for the next step without further purification.

c) 5-Chloro-1H-pyrazolo[4,3-d]pyrimidine

To a stirred solution of 1-(5-chloro-pyrazolo[4,3-d]pyrimidin-1-yl)-ethanone (1.5 g, 7.65 mmol) in THF (15 mL) was added 8% aqueous HCl (14.46 mL) at 50° C. and reaction mixture was refluxed for 30 min. After completion of the reaction, it was cooled to 25° C. and was extracted with EtOAc (2×50 mL). The combined organic layers were dried over Na₂SO₄, filtered and concentrated under reduced pressure to yield the title compound as an off-white solid (1.1 g, 93%). MS (ESI): m/z=153.0 [M−H]⁻.

d) 5-Chloro-1-(oxan-2-yl)-1H-pyrazolo[4,3-d]pyrimidine

To a stirred solution of 5-chloro-1H-pyrazolo[4,3-d]pyrimidine (2.5 g, 16.234 mmol) in THF (20 mL) was added dihydropyran (2.22 mL, 24.351 mmol) and 4-methylbenzenesulfonic acid (28 mg, 0.162 mmol) at 0° C. and the reaction mixture was stirred at 60° C. for 16 h. After completion of the reaction, it was extracted with DCM (2×100 mL) and the combined organic layers were washed with water and brine. The organic layer was dried over Na₂SO₄, evaporated and the resulting crude product was purified by silica gel column chromatography (10-12% EtOAc/n-hexane) to afford the desired compound as a light yellow liquid (2.6 g, 67%). The product was used without further purification for the next step.

e) Methyl 1-(oxan-2-yl)-1H-pyrazolo[4,3-d]pyrimidine-5-carboxylate

To a stirred solution of 5-chloro-1-(oxan-2-yl)-1H-pyrazolo[4,3-d]pyrimidine (2.6 g, 10.924 mmol) in DMF (40 mL) and MeOH (40 mL) was added TEA (6.06 mL, 43.697 mmol) and the resulting solution was purged with nitrogen for 15 min. Then Pd(OAc)₂ (49 mg, 0.218 mmol) and 1,3-bis(diphenylphosphino)propane (180 mg, 0.437 mmol, CAS RN 6737-42-4) were added and the resulting reaction mixture was stirred at 70° C. for 16 h under carbon monoxide atmosphere in an autoclave. The reaction mixture was filtered through a celite bed and the resulting filtrate was evaporated. The residue was purified by silica gel column chromatography (26-30% EtOAc/n-hexane) to furnish the desired compound as an off-white solid (2 g, 70%). MS (ESI): m/z=263.1 [M+H]⁺.

d) 1-(Oxan-2-yl)-1H-pyrazolo[4,3-d]pyrimidine-5-carboxylic acid

To a stirred solution of methyl 1-(oxan-2-yl)-1H-pyrazolo[4,3-d]pyrimidine-5-carboxylate (1 g, 3.817 mmol) in THF (9 mL), H₂O (3 mL) and MeOH (3 mL) was added LiOH.H₂O (480 mg, 11.45 mmol) and the reaction mixture was stirred at 25° C. for 5 h. After completion of the reaction the mixture was evaporated to dryness. The residue was diluted with water, neutralized with 1N aqueous HCl solution and extracted with EtOAc (3×50 mL). The combined organic layers were washed with water and brine, dried over Na₂SO₄ and evaporated to yield the title compound as an off-white solid (900 mg, 100%). MS (ESI): m/z=249.1 [M+H]⁺.

Intermediate INT40

3-(Fluoromethyl)-4-(trifluoromethyl)pyrrolidine hydrochloride

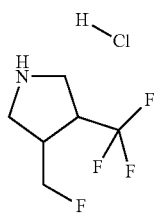

To a stirred solution of tert-butyl 3-(fluoromethyl)-4-(trifluoromethyl)pyrrolidine-1-carboxylate (210 mg, 0.775 mmol) in DCM (5 mL) at 0° C. was added 4 M HCl in dioxane (2 mL, CAS RN 38078-09-0) and the solution was stirred at 25° C. for 3 h. After completion of the reaction, the solvent was evaporated to get the desired compound as HCl salt as a brown sticky solid (130 mg, 98%) which was used in the next step without further purification.

a) tert-Butyl 3-(fluoromethyl)-4-(trifluoromethyl)pyrrolidine-1-carboxylate To a stirred solution of tert-butyl 3-(hydroxymethyl)-4-(trifluoromethyl)pyrrolidine-1-carboxylate (200 mg, 0.743 mmol, MFCD11848057) in DCM (5 mL) at 0° C. was added N,N-diethylaminosuflur trifluoride (0.15 mL, 1.115 mmol, CAS RN 38078-09-0) and the reaction mixture was stirred at 25° C. for 16 h. The reaction mixture was quenched with aqueous NaHCO₃ solution (20 mL) and extracted with DCM (3×30 mL). The organic layer was washed with water (20 mL) and brine (20 mL), dried over Na₂SO₄ and concentrated. The crude product was purified by silica gel column chromatography by using 15-20% EtOAc/n-hexane to furnish the desired compound as a light yellow liquid (198 mg, 98%) which was used in the following step without further purification.

Intermediate INT41

(3R,4S)-4-Fluoro-N,N-dimethyl-pyrrolidin-3-amine; 2,2,2-trifluoroacetic acid

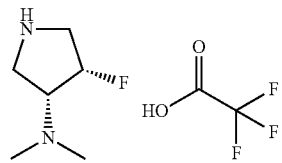

To a solution of (3R,4S)-tert-butyl 3-(dimethylamino)-4-fluoropyrrolidine-1-carboxylate (40.6 mg, 175 μmol) in DCM (0.3 mL) was added TFA (199 mg, 135 μL, 1.75 mmol) and the mixture was stirred at RT for 2.5 h. The reaction mixture was completely evaporated to give the compound as its TFA salt which was used without further purification in the next step.

a) (3R,4R)-tert-Butyl-3-(dimethylamino)-4-hydroxypyrrolidine-1-carboxylate

To a solution of (3R,4R)-tert-butyl-3-hydroxy-4-(methylamino)pyrrolidine-1-carboxylate (0.6 g, 2.77 mmol, CAS RN 859212-58-1) in formic acid (3.83 g, 3.19 mL, 83.2 mmol) and formaldehyde 37% solution in water (3.38 g, 3.1 mL, 41.6 mmol) was added sodium cyanoborohydride 1M solution in THF (2.77 mL, 2.77 mmol) dropwise. The reaction mixture was stirred at RT for 2.5 h, then poured on NaOH 1M solution and DCM and the layers were separated. The aqueous layer was extracted twice with DCM. The organic layers were washed with brine, dried over MgSO₄, filtered and evaporated. The compound was purified by silica gel chromatography on a 4 g column using an MPLC (ISCO) system eluting with a gradient of DCM:MeOH (100:0 to 90:10) to give a colorless oil (0.448 g; 70.1%). MS (ESI): m/z=213.2 [M+H]$^+$.

b) (3R,4S)-tert-Butyl-3-(dimethylamino)-4-fluoropyrrolidine-1-carboxylate

To a solution of (3R,4S)-tert-butyl 3-(dimethylamino)-4-hydroxypyrrolidine-1-carboxylate (300 mg, 1.3 mmol) in DCM (6 mL) at −78° C. was added N,N-diethylaminosulfur trifluoride (315 mg, 258 μL, 1.95 mmol) and the solution was stirred at this temperature for 2.75 h. The cooling bath was removed and the solution was allowed to stir at RT for 26 h. The reaction mixture was poured on saturated aqueous NH$_4$Cl solution and DCM and the layers were separated. The aqueous layer was extracted twice with DCM. The combined organic layers were dried over MgSO$_4$, filtered and evaporated to give a brown solid (0.140 g; 46.3%). MS (ESI): m/z=232.16 [M+H]$^+$.

Example 1 (Method A)

2-{1'-[(1H-Indazol-5-yl)carbonyl]-2-oxo-1,2-dihydrospiro[indole-3,4'-piperidine]-1-yl}-N-(2,2,2-trifluoroethyl)acetamide

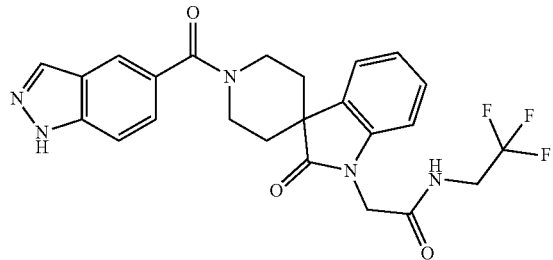 [SMILES: O=C(CN1C(=O)C2(CCN(C(=O)c3ccc4[nH]ncc4c3)CC2)c2ccccc21)NCC(F)(F)F]

To a solution of 2-{2-oxo-1,2-dihydrospiro[indole-3,4'-piperidine]-1-yl}-N-(2,2,2-trifluoroethyl)acetamide (120 mg, 0.37 mmol, intermediate INT1a) and 1H-indazole-5-carboxylic acid (60 mg, 0.37 mmol, CAS RN 61700-61-6) in DMF (25 mL) were added HBTU (210 mg, 0.55 mmol, CAS RN 94790-37-1) and DIPEA (0.24 mL, 1.47 mmol, CAS RN 7087-68-5) and the mixture was stirred at 25° C. for 16 h. DMF was evaporated off. The residue was dissolved in EtOAc (50 mL) and washed with water (30 mL). The combined organic part was dried (Na$_2$SO$_4$) and evaporated. The resulting crude was purified by prep. HPLC (NH$_4$OAc/ACN) to get the title product (40 mg, 22%) as a white solid. MS (ESI): m/z=486.3 [M+H]$^+$.

Example 4 (Method B)

2-[4-Fluoro-2-oxo-1'-(1H-pyrazolo[3,4-b]pyridine-5-carbonyl)spiro[indole-3,4'-piperidine]-1-yl]-N-(2,2,2-trifluoroethyl)acetamide

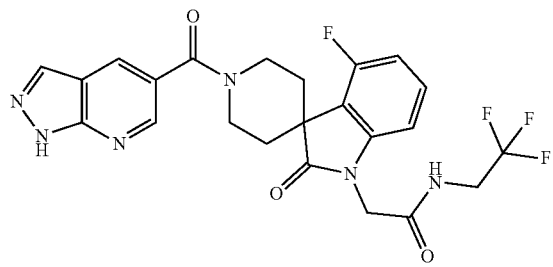 [SMILES: O=C(CN1C(=O)C2(CCN(C(=O)c3cnc4[nH]ncc4c3)CC2)c2c(F)cccc21)NCC(F)(F)F]

To a solution of 2-{4-fluoro-2-oxo-1,2-dihydrospiro[indole-3,4'-piperidine]-1-yl}-N-(2,2,2-trifluoroethyl)acetamide (229 mg, 0.64 mmol, intermediate INT4a) and 1H-pyrazolo[3,4-b]pyridine-5-carboxylic acid (104 mg, 0.64 mmol, CAS RN 952182-02-4) in anhydrous DCM (10 mL) were added PyBOP (497 mg, 0.96 mmol, CAS RN 128625-52-5) and DIPEA (0.21 mL, 1.28 mmol, CAS RN 7087-68-5) under N$_2$ atmosphere at 25° C. The mixture was stirred at 25° C. for 16 h. The reaction mixture was diluted with DCM (20 mL), washed with water (30 mL) and brine (20 mL). The organic part was dried over Na$_2$SO$_4$, filtered and concentrated under reduced pressure. The resulting crude product was purified by flash chromatography using silica gel (50-80% EtOAc/n-hexane) to afford the title product (43 mg, 13%) as a white solid. MS (EI): m/z=503.2 [M−H]$^+$.

Example 7 (Method C)

2-[5-Bromo-2-oxo-1'-(1H-pyrazolo[3,4-b]pyridine-5-carbonyl)spiro[indole-3,4'-piperidine]-1-yl]-N-(2,2,2-trifluoroethyl)acetamide

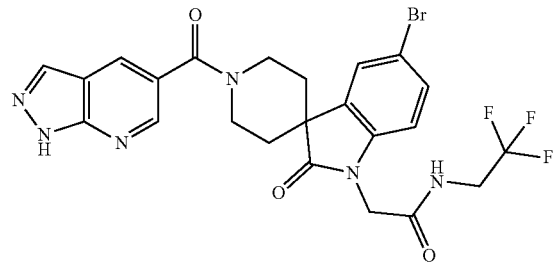 [SMILES: O=C(CN1C(=O)C2(CCN(C(=O)c3cnc4[nH]ncc4c3)CC2)c2cc(Br)ccc21)NCC(F)(F)F]

To a solution of 2-{5-bromo-2-oxo-1,2-dihydrospiro[indole-3,4'-piperidine]-1-yl}-N-(2,2,2-trifluoroethyl)-acetamide (121 mg, 0.29 mmol, intermediate INT6a) and 1H-pyrazolo[3,4-b]pyridine-5-carboxylic acid (47 mg, 0.28 mmol, CAS RN 952182-02-4) in anhydrous DMF (10 mL) were added HOBt (58 mg, 0.43 mmol, CAS RN 2592-95-2), EDC (81 mg, 0.42 mmol, CAS RN 25952-53-8) and DIPEA (83 mg, 0.432 mmol, CAS RN 7087-68-5) under N$_2$ atmosphere at 25° C. The mixture was stirred at 25° C. for 16 h. The solvent was removed under vacuum and the residue was diluted with EtOAc (30 mL), washed with water (30 mL) and brine (20 mL). The organic layer was dried over Na$_2$SO$_4$, filtered and concentrated. The resulting crude product was purified by prep. HPLC (NH$_4$OAc/ACN) to get the title product (28 mg, 17%) as a white solid. MS (EI): m/z=567.0 [M+H]$^+$.

Example 25 (Method D)

2-[1'-(1H-Indazole-5-carbonyl)-4-methyl-2-oxospiro[indole-3,4'-piperidine]-1-yl]-N-[1-(trifluoromethyl)cyclopropyl]acetamide

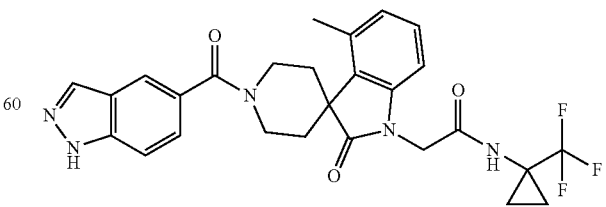

To a solution of 2-{1'-[(1H-indazol-5-yl)carbonyl]-4-methyl-2-oxo-1,2-dihydrospiro-[indole-3,4'-piperidine]-1- yl}acetic acid (200 mg, 0.48 mmol, intermediate INT1e) and 1-trifluoromethyl-cyclopropylamine hydrochloride (154 mg, 0.96 mmol, CAS RN 112738-68-8) in anhydrous THF (15 mL) were added T$_3$P (0.6 mL, 0.96 mmol, 50% solution in EtOAc, CAS RN 68957-94-8) and DIPEA (0.24 mL, 1.43 mmol, CAS RN 7087-68-5) under N$_2$ atmosphere at 25° C. The mixture was stirred at 50° C. for 16 h. It was diluted with EtOAc (40 mL), washed with water (40 mL) and brine (30 mL). The organic part was dried over Na$_2$SO$_4$, filtered and concentrated. The resulting crude was purified by prep HPLC to afford the title product (29 mg, 12%) as white solid. MS (EI): m/z=526.3 [M+H]$^+$.

Example 5 (Method E)

2-[1-(1H-Indazole-5-carbonyl)-5'-methoxy-2'-oxospiro[piperidine-4,3'-pyrrolo[3,2-b]pyridine]-1'-yl]-N-(2,2,2-trifluoroethyl)acetamide

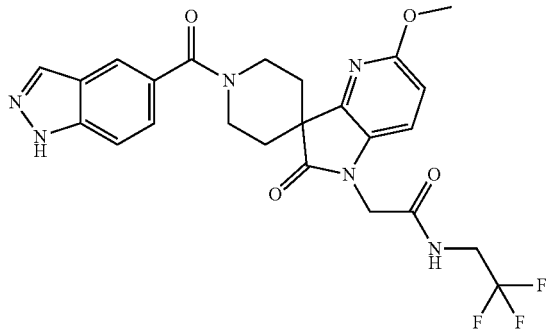 [SMILES: COc1ccc2c(n1)C1(CCN(C(=O)c3ccc4[nH]ncc4c3)CC1)C(=O)N2CC(=O)NCC(F)(F)F]

To a solution of 2-(1-benzyl-5'-methoxy-2'-oxospiro[piperidine-4,3'-pyrrolo[3,2-b]pyridin]-1'(2'H)-yl)-N-(2,2,2-trifluoroethyl)acetamide (48 mg, 104 µmol, intermediate INT1b) in MeOH (1 mL) and EtOAc (0.5 mL) was added palladium 10% on carbon (11 mg, 10.4 µmol) and the suspension was hydrogenated under a hydrogen atmosphere of 1.7 bar for 5.5 h. The resulting mixture was filtered over a microfilter and the filtrate was evaporated. The intermediate was dissolved in DMF (0.5 mL) and 1H-indazole-5-carboxylic acid (16.8 mg, 104 µmol, CAS RN 61700-61-6), HBTU (39.4 mg, 104 µmol, CAS RN 94790-37-1) and NEt$_3$ (43.4 µL, 311 µmol) were added. The clear solution was stirred at RT for 20 h. The product was purified on a prep. HPLC (Gemini NX column) using a gradient of ACN:water (containing 0.1% NEt$_3$) (20:80 to 98:2) to afford the title product as colorless solid (0.016 g; 29.8%). MS (ESI): m/z=517.18 [M+H]$^+$.

Example 11 (Method F)

Methyl 2-oxo-1-(2-oxo-2-((2,2,2-trifluoroethyl)amino)ethyl)-1'-(1H-pyrazolo[3,4-b]pyridine-5-carbonyl)spiro[indoline-3,4'-piperidine]-4-carboxylate

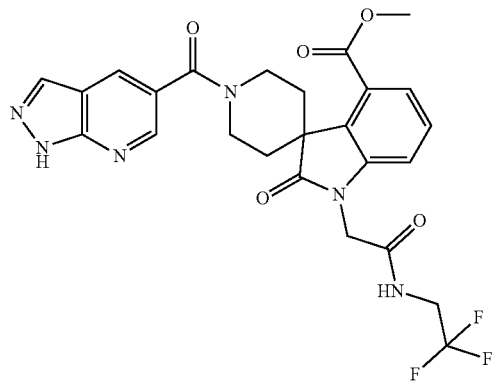 [SMILES: COC(=O)c1cccc2c1C1(CCN(C(=O)c3cnc4[nH]ncc4c3)CC1)C(=O)N2CC(=O)NCC(F)(F)F]

Methyl 2-oxo-1-(2-oxo-2-((2,2,2-trifluoroethyl)amino)ethyl)spiro[indoline-3,4'-piperidine]-4-carboxylate (43 mg, 79 µmol, intermediate INT9a), 1H-pyrazolo[3,4-b]pyridine-5-carboxylic acid (20.4 mg, 125 µmol, CAS RN 952182-02-4), HATU (47.6 mg, 125 µmol, CAS RN 148893-10-1) were suspended in DCM (750 µL) and TEA (359 µmol) was added. The suspension turned into a yellow solution after adding DMF (100 µL). The reaction mixture was stirred at RT for 72 h. The reaction mixture was filtered over a syringe filter. The filtrate was purified by prep. HPLC to give a light yellow solid (43 mg, 63.1%). MS (ESI): m/z=545.2 [M+H]$^-$.

Example 44 (Method H)

(S)-Methyl 4,4-difluoro-1-(2-(4-methyl-2-oxo-1'-(1H-pyrazolo[3,4-b]pyridine-5-carbonyl)spiro[indoline-3,4'-piperidin]-1-yl)acetyl)pyrrolidine-2-carboxylate

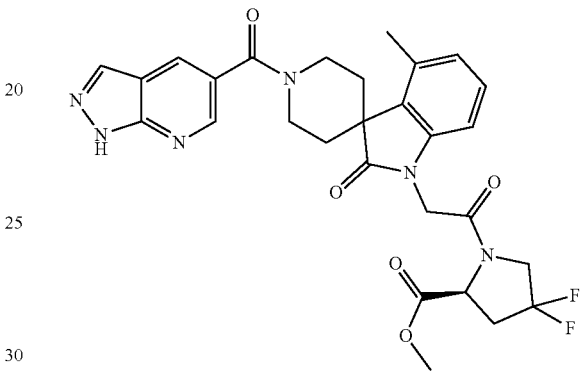

2-(4-Methyl-2-oxo-1'-(1H-pyrazolo[3,4-b]pyridine-5-carbonyl)spiro[indoline-3,4'-piperidin]-1-yl)acetic acid (30 mg, 71.5 µmol, intermediate INT5e) was suspended in DCM (1.2 mL). Oxalyl chloride (13.6 mg, 9.39 µl, 107 µmol, CAS RN 79-37-8) was added followed by DMF (5.66 mg, 6 µL, 77.5 µmol). The reaction mixture was stirred at RT for 1 h, then concentrated in vacuo. The crude product was added to a stirred solution of (S)-methyl 4,4-difluoropyrrolidine-2-carboxylate hydrochloride (23 mg, 114 µmol, CAS RN 126111-14-6) and TEA (34.7 mg, 47.7 µL, 343 µmol) in DCM (2 mL). The reaction mixture was stirred at RT overnight under an argon atmosphere. The reaction mixture was filtered and concentrated in vacuo. The crude product was purified by prep. HPLC to give a white solid (1.7 mg, 4.2%). MS (ESI): m/z=567.3 [M+H]$^+$.

Example 53 (Method R)

2-[4-(Hydroxymethyl)-1'-(1H-indazole-5-carbonyl)-2-oxo-spiro[indoline-3,4'-piperidine]-1-yl]-N-(2,2,2-trifluoroethyl)acetamide

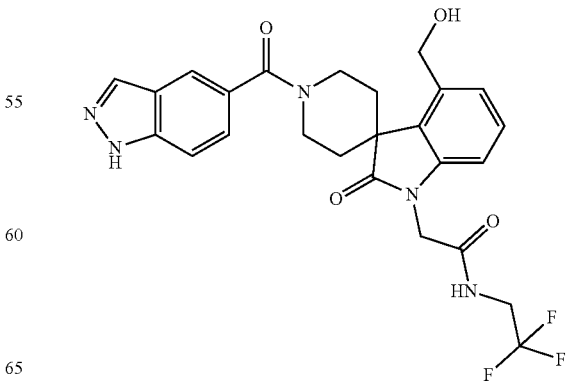

Methyl 1'-(1H-indazole-5-carbonyl)-2-oxo-1-(2-oxo-2-((2,2,2-trifluoroethyl)amino) ethyl)spiro[indoline-3,4'-piperidine]-4-carboxylate (22.1 mg, 40.7 μmol, Example 15) was dissolved in THF (3 mL). The reaction mixture was cooled to 0° C. LiAlH$_4$ (3.86 mg, 102 μmol) was added. The reaction mixture was stirred at RT for 2 h. Water (200 μL) followed by 4 M NaOH solution (200 μL) were added. The reaction mixture was stirred at 0° C. for 1 h, then filtered and washed with THF. The filtrate was concentrated in vacuo. The crude solid was purified by prep. HPLC to give a white solid (1.4 mg, 6.7%). MS (ESI): m/z=516.2 [M+H]$^+$.

Examples 112 and 113 (Method X)

(−)-4-Chloro-5-fluoro-1-[2-oxo-2-(2,2,2-trifluoroethyl)pyrrolidin-1-yl]ethyl]-1'-(1H-pyrazolo[4,3-b]pyridine-5-carbonyl)spiro[indole-3,4'-piperidine]-2-one and (+)-4-Chloro-5-fluoro-1-[2-oxo-2-[2-(2,2,2-trifluoroethyl)pyrrolidin-1-yl]ethyl]-1'-(1H-pyrazolo[4,3-b]pyridine-5-carbonyl)spiro[indole-3,4'-piperidine]-2-one

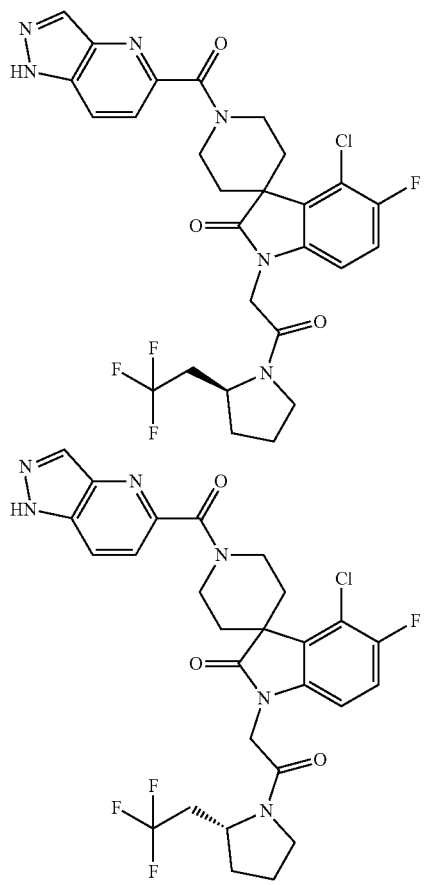

Racemic 4-chloro-5-fluoro-1-(2-oxo-2-(2-(2,2,2-trifluoroethyl)pyrrolidin-1-yl)ethyl)-1'-(1H-pyrazolo[4,3-b]pyridine-5-carbonyl)spiro[indoline-3,4'-piperidin]-2-one (20 mg, 33.7 μmol, example 99) was separated by preparative chiral HPLC (Chiralpak-AD column) using an isocratic mixture of EtOH (containing 0.5% NH$_4$OAc):n-heptane (40:60).

Example 112: (−)-4-Chloro-5-fluoro-1-[2-oxo-2-[2-(2,2,2-trifluoroethyl)pyrrolidin-1-yl]ethyl]-1'-(1H-pyrazolo[4,3-b]pyridine-5-carbonyl)spiro[indole-3,4'-piperidine]-2-one White solid (5.7 mg, 28.5%). MS (ESI): m/z=593.3 [M+H]$^+$.

Example 113: (+)-4-Chloro-5-fluoro-1-[2-oxo-2-[2-(2,2,2-trifluoroethyl)pyrrolidin-1-yl]ethyl]-1'-(1H-pyrazolo[4,3-b]pyridine-5-carbonyl)spiro[indole-3,4'-piperidine]-2-one White solid (7.3 mg, 36.5%). MS (ESI): m/z=593.3 [M+H]$^+$.

Example 131 (Method Y)

4-Chloro-5-fluoro-1-(2-((3aR,6aS)-hexahydrocyclopenta[c]pyrrol-2(1H)-yl)-2-oxoethyl)-1'-(1H-pyrazolo[4,3-b]pyridine-5-carbonyl)spiro[indoline-3,4'-piperidin]-2-one

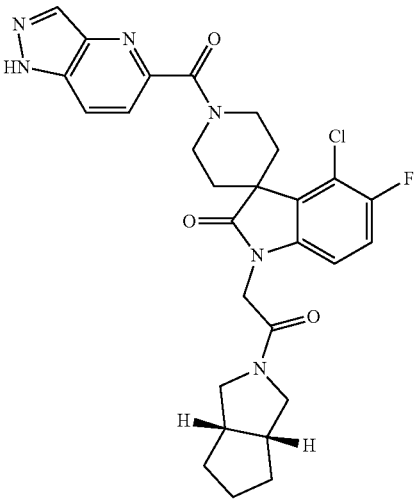 [SMILES: O=C(CN1C(=O)C2(CCN(C(=O)c3ccc4[nH]ncc4n3)CC2)c2c1ccc(F)c2Cl)N1C[C@H]2CCC[C@H]2C1]

2-(4-chloro-5-fluoro-2-oxo-1'-(1H-pyrazolo[4,3-b]pyridine-5-carbonyl)spiro[indoline-3,4'-piperidin]-1-yl)acetic acid (40 mg, 87.4 μmol, INT12e) was dissolved in DMF (1 mL). HOBT (20.1 mg, 131 μmol) and EDC (25.1 mg, 131 μmol) were added, and the reaction solution was stirred for another 10 min. (3aR,6aS)-Octahydrocyclopenta[c]pyrrole (19.4 mg, 175 μmol, CAS RN 1037834-39-1) followed by TEA (35.4 mg, 48.7 μL, 349 μmol) were added and the reaction mixture was stirred at RT for 24 h. The reaction mixture was filtered through a syringe filter and purified by prep. HPLC to give a light brown solid (25 mg, 51.9%). MS (ESI): m/z=551.2 [M+H]$^+$.

Example 161

Methyl 5-[4-chloro-5-fluoro-2-oxo-1-[2-oxo-2-(2,2,2-trifluoroethylamino)ethyl]spiro[indole-3,4'-piperidine]-1'-carbonyl]-1H-indazole-3-carboxylate

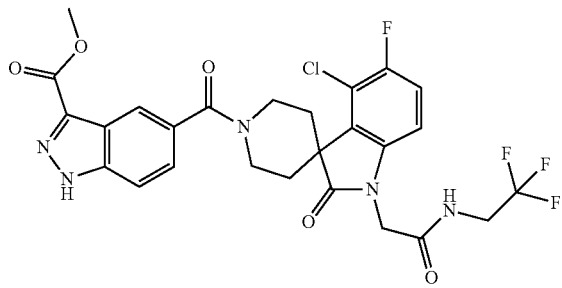 [SMILES: COC(=O)c1n[nH]c2ccc(C(=O)N3CCC4(CC3)C(=O)N(CC(=O)NCC(F)(F)F)c3ccc(F)c(Cl)c34)cc12]

To a stirred solution of methyl 5-[(4-chloro-5-fluoro-2-oxo-1-{[(2,2,2-trifluoroethyl) carbamoyl]methyl}-1,2-dihydrospiro[indole-3,4'-piperidine]-1'-yl)carbonyl]-1-(oxan-2-yl)-1H-indazole-3-carboxylate (600 mg, 0.884 mmol) in DCM (15 mL) was added TFA (6 mL, CAS RN 76-05-1) and the reaction mixture was stirred at 25° C. for 16 h. The solvent was evaporated under reduced pressure and the residue diluted with DCM (100 mL) and washed with saturated aqueous NaHCO₃ solution (2×20 mL). The organic layer was dried over Na₂SO₄, filtered and filtrate was concentrated to afford the desired compound as an off-white solid (450 mg, 85%). MS (EI): m/z=595.9 [M+H]⁺.

a) Methyl 3-iodo-1-(oxan-2-yl)-1H-indazole-5-carboxylate

To a solution of methyl 3-iodo-1H-indazole-5-carboxylate (2 g, 6.623 mmol, CAS RN 885271-25-0) in anhydrous THF (20 mL) were added dihydropyran (0.91 mL, 9.934 mmol, CAS RN 110-87-2) and 4-methylbenzenesulfonic acid. H₂O (13 mL, 0.066 mmol, CAS RN 6192-52-5) was added and the reaction mixture was stirred at 60° C. for 16 h. The reaction mixture was diluted with EtOAc (100 mL) and washed with water and brine. The organic layer was dried over Na₂SO₄, filtered and concentrated. The resulting crude product was purified over silica gel column chromatography (20-25% EtOAc/n-hexane) to yield the desired compound as an off-white solid (2.2 g, 86%). MS (EI): m/z=386.9 [M+H]⁺.

b) 3-Iodo-1-(oxan-2-yl)-1H-indazole-5-carboxylic acid

To a stirred solution of methyl 3-iodo-1-(oxan-2-yl)-1H-indazole-5-carboxylate (2.2 g, 5.699 mmol) in a mixture of THF (30 mL), MeOH (10 mL) and water (10 mL) was added LiOH.H₂O (717 mg, 17.098 mmol) at 25° C. and the reaction mixture was stirred at this temperature for 2 h. The organic solvent was evaporated under reduced pressure, the remaining aqueous layer was acidified to pH 2 using 1N aqueous HCl and the resulting solid was filtered, washed with EtOAc (2×10 mL) and dried under high vacuum to yield the title compound as an off-white solid (2.0 g, 95%). MS (EI): m/z=371.0 [M−H]⁺.

c) 2-(4-Chloro-5-fluoro-1'-{[3-iodo-1-(oxan-2-yl)-1H-indazol-5-yl]carbonyl}-2-oxo-1,2-dihydrospiro[indole-3,4'-piperidine]-1-yl)-N-(2,2,2-trifluoroethyl)acetamide To a solution of 2-{4-chloro-5-fluoro-2-oxo-1,2-dihydrospiro[indole-3,4'-piperidine]-1-yl}-N-(2,2,2-trifluoroethyl)acetamide (2 g, 5.089 mmol, INT17a) and 3-iodo-1-(oxan-2-yl)-1H-indazole-5-carboxylic acid (2 g, 5.344 mmol) in DMF (4 mL) was added EDC.HCl (1.1 g, 5.598 mmol, CAS RN 7087-68-5), HOBt (722 mg, 5.344 mmol, CAS RN 7087-68-5) and DIPEA (2.7 mL, 15.267 mmol, CAS RN 7087-68-5). The reaction mixture was stirred at 25° C. for 16 h. DMF was evaporated off and the residue was dissolved in EtOAc (150 mL) and washed with water (2×50 mL) and brine (50 mL). The organic layer was dried over Na₂SO₄, filtered and concentrated. The resulting crude product was purified over silica gel column chromatography using 3-4% MeOH/DCM to afford the desired compound (3.6 g, 95%) as an off-white solid. MS (EI): m/z=747.8 [M+H]⁺.

d) Methyl 5-[(4-chloro-5-fluoro-2-oxo-1-{[(2,2,2-trifluoroethyl)carbamoyl]methyl}-1,2-dihydrospiro[indole-3,4'-piperidine]-1'-yl)carbonyl]-1-(oxan-2-yl)-1H-indazole-3-carboxylate To a stirred solution of 2-(4-chloro-5-fluoro-1'-{[3-iodo-1-(oxan-2-yl)-1H-indazol-5-yl]carbonyl}-2-oxo-1,2-dihydrospiro[indole-3,4'-piperidine]-1-yl)-N-(2,2,2-trifluoroethyl) acetamide (1.5 g, 2.01 mmol) in DMF (15 mL) and MeOH (15 mL) was added TEA (1.12 mL, 8.032 mmol) and reaction mixture was purged with nitrogen for 15 min. Then Pd(OAc)₂ (9 mg, 0.04 mmol, CAS RN 3375-31-3) and 1,3-bis(diphenylphosphino)propane (33 mg, 0.08 mmol, CAS RN 6737-42-4) were added and reaction mixture was stirred at 80° C. for 16 h under CO atmosphere (80 psi). The reaction mixture was filtered through celite and washed with 10% MeOH in DCM (50 mL) and the filtrate was evaporated. The resulting crude product was purified over silica gel column chromatography (2-3% MeOH/DCM) to give the desired compound as a brown sticky solid (910 mg, 67%). MS (EI): m/z=679.9 [M+H]⁺.

Example 162

5-(4-Chloro-5-fluoro-2-oxo-1-{[(2,2,2-trifluoroethyl)carbamoyl methyl}-1,2-dihydrospiro[indole-3,4'-piperidine]-1'-yl)carbonyl]-1H-indazole-3-carboxylic acid

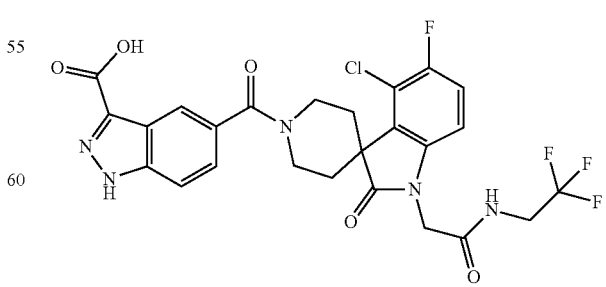

To a stirred solution of methyl 5-[(4-chloro-5-fluoro-2-oxo-1-{[(2,2,2-trifluoroethyl)-carbamoyl]methyl}-1,2-dihydrospiro[indole-3,4'-piperidine]-1'-yl)carbonyl]-1H-indazole-3-carboxylate (600 mg, 1.008 mmol, example 161) in THF (3 mL), MeOH (1 mL) and water (1 mL) was added LiOH.H$_2$O (43 mg, 1.008 mmol) at 25° C. and reaction mixture was stirred at 25° C. for 48 h. The organic solvent was evaporated under reduced pressure, the remaining aqueous layer was acidified to pH 2 using 1N aqueous HCl and the resulting solid was filtered through sintered glass. The solid was washed with EtOAc (2×5 mL) and dried under vacuum to yield the title compound as an off-white solid (440 mg, 75%). MS (EI): m/z=581.8 [M+H]$^+$.

TABLE 7

(Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 2 | 2-[1'-(1H-Indazole-5-carbonyl)-4-methyl-2-oxospiro[indole-3,4'-piperidine]-1-yl]-N-(2,2,2-trifluoroethyl)acetamide | 1H-Indazole-5-carboxylic acid (CAS RN 61700-61-6) INT2a | A | MS (EI): m/z = 500.3 [M + H]$^+$ |
| 3 | 2-[1'-(1H-Indazole-5-carbonyl)-4-methyl-2-oxospiro[indole-3,4'-piperidine]-1-yl]-N-(2,2,2-trifluoroethyl)acetamide | 1H-Indazole-5-carboxylic acid (CAS RN 61700-61-6) INT3a | A | MS (EI): m/z = 566.6 [M + H]$^+$ |
| 6 | 2-[4-Chloro-2-oxo-1'-(1H-pyrazolo[3,4-b]pyridine-5-carbonyl)spiro[indole-3,4'-piperidine]-1-yl]-N-(2,2,2-trifluoroethyl)acetamide | 1H-Pyrazolo[3,4-b]pyridine-5-carboxylic acid (CAS RN 952182-02-4) INT5a | B | MS (EI): m/z = 519.3 [M − H]$^-$ |

TABLE 7-continued (Examples 2 to 168)

The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 8 | 2-[5-Fluoro-2-oxo-1'-(1H-pyrazolo[3,4-b]pyridine-5-carbonyl)spiro[indole-3,4'-piperidine]-1-yl]-N-(2,2,2-trifluoroethyl)acetamide | 1H-Pyrazolo[3,4-b]pyridine-5-carboxylic acid (CAS RN 952182-02-4) INT7a | C | MS (EI): m/z = 505.0 [M + H]+ |
| 9 | 2-[4-Methoxy-2-oxy-1'-(1H-pyrazolo[3,4-b]pyridine-5-carbonyl)spiro[indole-3,4'-piperidine]-1-yl]-N-(2,2,2-trifluoroethyl)acetamide | 1H-Pyrazolo[3,4-b]pyridine-5-carboxylic acid (CAS RN 952182-02-4) INT8a | C | MS (EI): m/z = 517.2 [M + H]+ |
| 10 | 2-[4-Bromo-2-oxo-1'-(1H-pyrazolo[3,4-b]pyridine-5-carbonyl)spiro[indole-3,4'-piperidine]-1-yl]-N-(2,2,2-trifluoroethyl)acetamide | 1H-Pyrazolo[3,4-b]pyridine-5-carboxylic acid (CAS RN 952182-02-4) INT3a | C | MS (EI): m/z = 567.1 [M + H]+ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 12 | 2-[4-Ethyl-2-oxo-1'-(1H-pyrazolo[3,4-b]pyridine-5-carbonyl)spiro[indole-3,4'-piperidine]-1-yl]-N-(2,2,2-trifluoroethyl)acetamide | 1H-Pyrazolo[3,4-b]pyridine-5-carboxylic acid (CAS RN 952182-02-4) INT10a | C | MS (EI): m/z = 515.0 [M + H]$^+$ |
| 13 | 2-[4,5-Difluoro-2-oxo-1'-(1H-pyrazolo[3,4-b]pyridine-5-carbonyl)spiro[indole-3,4'-piperidine]-1-yl]-N-(2,2,2-trifluoroethyl)acetamide | 1H-Pyrazolo[3,4-b]pyridine-5-carboxylic acid (CAS RN 952182-02-4) INT11a | C | MS (EI): m/z = 523.2 [M + H]$^+$ |
| 14 | 2-[4-Methyl-2-oxo-1'-(1H-pyrazolo[3,4-b]pyridine-5-carbonyl)spiro[indole-3,4'-piperidine]-1-yl]-N-(2,2,2-trifluoroethyl)acetamide | 1H-Pyrazolo[3,4-b]pyridine-5-carboxylic acid (CAS RN 952182-02-4) INT2a | C | MS (EI): m/z = 500.8 [M + H]$^+$ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 15 | Methyl 1'-(1H-indazole-5-carbonyl)-2-oxo-1-(2-oxo-2-((2,2,2-trifluoroethyl)amino)ethyl)spiro[indoline-3,4'-piperidine]-4-carboxylate | 1H-Indazole-5-carboxylic acid (CAS RN 61700-61-6) INT9a | F | MS (ESI): m/z = 544.2 [M + H]⁺ |
| 16 | (S)-4-Methyl-1-(2-oxo-2-(2-(trifluoromethyl)pyrrolidin-1-yl)ethyl)-1'-(1H-pyrazolo[3,4-b]pyridine-5-carbonyl)spiro[indoline-3,4'-piperidin]-2-one | 1H-Pyrazolo[3,4-b]pyridine-5-carboxylic acid (CAS RN 952182-02-4) INT5e | F | MS (ESI): m/z = 541.2 [M + H]⁺ |
| 17 | 2-[4-Cyano-2-oxo-1'-(1H-pyrazolo[3,4-b]pyridine-5-carbonyl)spiro[indole-3,4'-piperidine]-1-yl]-N-(2,2,2-trifluoroethyl)acetamide | 1H-Pyrazolo[3,4-b]pyridine-5-carboxylic acid (CAS RN 952182-02-4) INT12a | C | MS (EI): m/z = 512.2 [M + H]⁺ |

TABLE 7-continued (Examples 2 to 168)

The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 18 | 2-[5-Chloro-2-oxo-1'-(1H-pyrazolo[3,4-b]pyridine-5-carbonyl)spiro[indole-3,4'-piperidine]-1-yl]-N-(2,2,2-trifluoroethyl)acetamide | 1H-Pyrazolo[3,4-b]pyridine-5-carboxylic acid (CAS RN 952182-02-4) INT13a | C | MS (EI): m/z = 521.1 [M + H]+ |
| 19 | 2-[6-Fluoro-2-oxo-1'-(1H-pyrazolo[3,4-b]pyridine-5-carbonyl)spiro[indole-3,4'-piperidine]-1-yl]-N-(2,2,2-trifluoroethyl)acetamide | 1H-Pyrazolo[3,4-b]pyridine-5-carboxylic acid (CAS RN 952182-02-4) INT14a | C | MS (EI): m/z = 505.2 [M + H]+ |
| 20 | 2-[4-Bromo-7-fluoro-2-oxo-1'-(1H-pyrazolo[3,4-b]pyridine-5-carbonyl)spiro[indole-3,4'-piperidine]-1-yl]-N-(2,2,2-trifluoroethyl)acetamide | 1H-Pyrazolo[3,4-b]pyridine-5-carboxylic acid (CAS RN 952182-02-4) INT15a | C | MS (EI): m/z = 585.2 [M + H]+ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
| --- | --- | --- | --- | --- |
| 21 | 2-[4,5-Dichloro-2-oxo-1'-(1H-pyrazolo[3,4-b]pyridine-5-carbonyl)spiro[indole-3,4'-piperidine]-1-yl]-N-(2,2,2-trifluoroethyl)acetamide | 1H-Pyrazolo[3,4-b]pyridine-5-carboxylic acid (CAS RN 952182-02-4) INT 16a | C | MS (EI): m/z = 555.2 [M + H]$^+$ |
| 22 | 2-[4-Bromo-2-oxo-1'-(1H-pyrazolo[3,4-c]pyridine-5-carbonyl)spiro[indole-3,4'-piperidine]-1-yl]-N-(2,2,2-trifluoroethyl)acetamide | 1H-Pyrazolo[3,4-b]pyridine-5-carboxylic acid (CAS RN 1256824-45-9) INT3a | C | MS (EI): m/z = 567.1 [M + H]$^+$ |
| 23 | 2-[4-Bromo-2-oxo-1'-(1H-pyrazolo[4,3-b]pyridine-5-carbonyl)spiro[indole-3,4'-piperidine]-1-yl]-N-(2,2,2-trifluoroethyl)acetamide | 1H-Pyrazolo[4,3-b]pyridine-5-carboxylic acid (CAS RN 1260670-03-8) INT 3a | C | MS (EI): m/z = 567.1 [M + H]$^+$ |

TABLE 7-continued (Examples 2 to 168)

The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 24 | 4-Methyl-1-(2-oxo-2-(2-(trifluoromethyl)morpholino)ethyl)-1'-(1H-pyrazolo[3,4-b]pyridine-5-carbonyl)spiro[indoline-3,4'-piperidin]-2-one | 2-(Trifluoromethyl)morpholine (CAS RN 1196532-95-2) INT5e | F | MS (ESI): m/z = 557.3 [M + H]+ |
| 26 | N-tert-Butyl-2-[1'-(1H-indazole-5-carbonyl)-4-methyl-2-oxospiro[indole-3,4'-piperidine]-1-yl]acetamide | tert-Butyl amine (CAS RN 76-05-1) INT1e | A | MS (EI): m/z = 474.3 [M + H]+ |
| 27 | N-(1-Hydroxy-2-methylpropan-2-yl)-2-[1'-(1H-indazole-5-carbonyl)-4-methyl-2-oxospiro[indole-3,4'-piperidine]-1-yl]acetamide | 2-Amino-2-methyl-propan-1-ol (CAS RN 124-68-5) INT1e | A | MS (EI): m/z = 490.3 [M + H]+ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 28 | (Rac, cis)-1-[2-[2,6-dimethylmorpholin-4-yl]-2-oxoethyl]-1'-(1H-indazole-5-carbonyl)-4-methylspiro[indole-3,4'-piperidine]-2-one | (cis)-2,6-Dimethyl-morpholine (CAS RN 6485-55-8) INT1e | A | MS (EI): m/z = 516.3 [M + H]+ |
| 29 | N-tert-Butyl-2-[1'-(1H-indazole-5-carbonyl)-4-methyl-2-oxospiro[indole-3,4'-piperidine]-1-yl]-N-methylacetamide | tert-Butyl-methyl-amine (CAS RN 14610-37-8) INT1e | D | MS (EI): m/z = 488.2 [M + H]+ |
| 30 | 2-[1'-(1H-Indazole-5-carbonyl)-4-methyl-2-oxospiro[indole-3,4'-piperidine]-1-yl]-N-[(2R)-1,1,1-trifluoropropan-2-yl]acetamide | (R)-2,2,2-Trifluoro-1-methyl-ethylamine hydrochloride (CAS RN 177469-12-4) INT1e | D | MS (EI): m/z = 514.2 [M + H]+ |
| 31 | 2-[4,5-Dichloro-2-oxo-1'-(1H-pyrazolo[3,4-c]pyridine-5-carbonyl)spiro[indole-3,4'-piperidine]-1-yl]-N-(2,2,2-trifluoroethyl)acetamide | 1H-Pyrazolo[3,4-c]pyridine-5-carboxylic acid (CAS RN 1256824-45-9) INT16a | C | MS (EI): m/z = 555.2 [M + H]+ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
| --- | --- | --- | --- | --- |
| 32 | 2-[4-Chloro-5-fluoro-2-oxo-1'-(1H-pyrazolo[3,4-c]pyridine-5-carbonyl)spiro[indole-3,4'-piperidine]-1-yl]-N-(2,2,2-trifluoroethyl)acetamide | 1H-Pyrazolo[3,4-c]pyridine-5-carboxylic acid (CAS RN 1256824-45-9) INT17a | C | MS (EI): m/z = 539.1 [M + H]$^+$ |
| 33 | 2-[4-Chloro-5-fluoro-1'-(1H-indazole-5-carbonyl)-2-oxospiro[indole-3,4'-piperidine]-1-yl]-N-(2,2,2-trifluoroethyl)acetamide | 1H-Indazole-5-carboxylic acid (CAS RN 61700-61-6) INT17a | C | MS (EI): m/z = 539.1 [M + H]$^+$ |
| 34 | 2-[4,5-Dichloro-2-oxo-1'-(1H-pyrazolo[4,3-b]pyridine-5-carbonyl)spiro[indole-3,4'-piperidine]-1-yl]-N-(2,2,2-trifluoroethyl)acetamide | 1H-Pyrazolo[4,3-b]pyridine-5-carboxylic acid (CAS RN 1260670-03-8) INT16a | C | MS (EI): m/z = 555.2 [M + H]$^+$ |

TABLE 7-continued (Examples 2 to 168)
The following examples were synthesized from the suitable building blocks/intermediates in
analogy to the methods from A to F, H to J, N, Q, R and V to Y as described before.

| Ex. | Systematic Name | Building blocks / intermediates | Method | MS, m/z |
|---|---|---|---|---|
| 35 | 2-[4-Chloro-5-fluoro-2-oxo-1'-(1H-pyrazolo[4,3-b]pyridine-5-carbonyl)spiro[indole-3,4'-piperidine]-1-yl]-N-(2,2,2-trifluoroethyl)acetamide | 1H-pyrazolo[4,3-b]pyridine-5-carboxylic acid (CAS RN 1260670-03-8) INT17a | C | MS (EI): m/z = 539.1 [M + H]$^+$ |
| 36 | 2-[4-Chloro-5-fluoro-2-oxo-1'-(1H-pyrazolo[3,4-b]pyridine-5-carbonyl)spiro[indole-3,4'-piperidine]-1-yl-N-(2,2,2-trifluoroethyl)acetamide | 1H-Pyrazolo[3,4-b]pyridine-5-carboxylic acid (CAS RN 952182-02-4) INT17a | C | MS (EI): m/z = 539.1 [M + H]$^+$ |
| 37 | 2-[4,5-Dichloro-1'-(1H-indazole-5-carbonyl)-2-oxospiro[indole-3,4'-piperidine]-1-yl]-N-(2,2,2-trifluoroethyl)acetamide | 1H-Indazole-5-carboxylic acid (CAS RN 61700-61-6) INT 16a | C | MS (EI): m/z = 556 [M + H]$^+$ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 38 | 2-[2-Oxo-1'-(1H-pyrazolo[3,4-b]pyridine-5-carbonyl)-4-(trifluoromethyl)spiro[indole-3,4'-piperidine]-1-yl]-N-(2,2,2-trifluoroethyl)acetamide | 1H-Pyrazolo[3,4-b]pyridine-5-carboxylic acid (CAS RN 952182-02-4) INT18a | C | MS (EI): m/z = 555.2 [M + H]$^+$ |
| 39 | 1-[2-(4-Hydroxy-3,3-dimethylpyrrolidin-1-yl)-2-oxoethyl]-1'-(1H-indazole-5-carbonyl)-4-methylspiro[indole-3,4'-piperidine]-2-one | 4,4-Dimethylpyrrolidin-3-ol (CAS RN 1186299-11-5) INT1e | A using TEA instead of DIPEA | MS (ESI): m/z = 516.3 [M + H]$^+$ |
| 40 | 1-[2-(3,3-Difluoro-4-hydroxypyrrolidin-1-yl)-2-oxoethyl]-1'-(1H-indazole-5-carbonyl)-4-methylspiro[indole-3,4'-piperidine]-2-one | 4,4-Difluoropyrrolidin-3-ol hydrochloride (CAS RN 1638764-82-5) INT1e | A using TEA instead of DIPEA | MS (ESI): m/z = 524.2 [M + H]$^+$ |

TABLE 7-continued (Examples 2 to 168)

The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 41 | 1-[2-(3,3-Difluoropyrrolidin-1-yl)-2-oxoethyl]-1'-(1H-indazole-5-carbonyl)-4-methylspiro[indole-3,4'-piperidine]-2-one | 3,3-Difluoropyrrolidine hydrochloride (CAS RN 163457-23-6) | A using TEA instead of DIPEA | MS (ESI): m/z = 508.2 [M + H]$^+$ |
| 42 | 1-[2-(3-Fluoro-3-methylpyrrolidin-1-yl)-2-oxoethyl]-1'-(1H-indazole-5-carbonyl)-4-methylspiro[indole-3,4'-piperidine]-2-one | 3-Fluoro-3-methylpyrrolidine hydrochloride (supplier Zylexa Pharma) | A using TEA instead of DIPEA | MS (ESI): m/z = 504.2 [M + H]$^+$ |
| 43 | 1-[2-[3-Hydroxy-3-(trifluoromethyl)pyrrolidin-1-yl]-2-oxoethyl]-1'-(1H-indazole-5-carbonyl)-4-methylspiro[indole-3,4'-piperidine]-2-one | 3-(Trifluoromethyl)pyrrolidin-3-ol hydrochloride (CAS RN 1334147-81-7) | A using TEA instead of DIPEA | MS (ESI): m/z = 556.2 [M + H]$^+$ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 45 | (S)-4-Bromo-1'-(1H-indazole-5-carbonyl)-1-(2-oxo-2-(2-(trifluoromethyl)pyrrolidin-1-yl)ethyl)spiro[indoline-3,4'-piperidin]-2-one | (S)-2-(Trifluoromethyl) pyrrolidine (CAS RN 119580-41-5) INT6e | C | MS (ESI): m/z = 601.1 [M + H]+ |
| 46 | (S)-4-Methyl-1-(2-oxo-2-(2-(trifluoromethyl)pyrrolidin-1-yl)ethyl)-1'-(1H-pyrazolo[4,3-b]pyridine-5-carbonyl)spiro[indoline-3,4'-piperidin]-2-one | (S)-2-(Trifluoromethyl) pyrrolidine (CAS RN 119580-41-5) INT7e | C | MS (ESI): m/z = 541.3 [M + H]+ |
| 47 | 2-[1'-(1H-Indazole-5-carbonyl)-4-methyl-2-oxospiro[indole-3,4'-piperidine]-1-yl]-N-[(2S)-1,1,1-trifluoropropan-2-yl]acetamide | (S)-2,2,2-Trifluoro-1-methyl-ethylamine hydrochloride (CAS RN 125353-44-8) INT1e | D | MS (EI): m/z = 514.2 [M + H]+ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 48 | 2-[1'-(1H-Indazole-5-carbonyl)-4-methyl-2-oxospiro[indole-3,4'-piperidine]-1-yl]-N-(3-methyloxetan-3-yl)acetamide | 3-Methyl-oxetan-3-ylamine (CAS RN 874473-14-0) INT1e | D | MS (EI): m/z = 488.2 [M + H]⁺ |
| 49 | 1-[(3-Cyclopropyl-1,2,4-oxadiazol-5-yl)methyl]-1'-(1H-indazole-5-carbonyl)-4-methylspiro[indole-3,4'-piperidine]-2-one | 1H-Indazole-5-carboxylic acid (CAS RN 61700-61-6) INT2b | Method L followed by method A | MS (ESI): m/z = 483.2 [M + H]⁺ |
| 50 | 2-(4-Methyl-2-oxo-1'-(1H-pyrazolo[4,3-b]pyridine-5-carbonyl)spiro[indoline-3,4'-piperidin]-1-yl)-N-(2,2,2-trifluoroethyl)acetamide | 2,2,2-Trifluoroethanamine (CAS RN 753-90-2) INT7e | C | MS (ESI): m/z = 501.3 [M + H]⁺ |
| 51 | N-(2-(Cyanopropan-2-yl)-2-[1'-(1H-indazole-5-carbonyl)-4-methyl-2-oxospiro[indole-3,4'-piperidine]-1-yl]acetamide | 2-Amino-2-methyl-propionitrile (CAS RN 19355-69-2) INT1e | D | MS (EI): m/z = 485.2 [M + H]⁺ |

TABLE 7-continued (Examples 2 to 168)

The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 52 | (S)-4-Methyl-1-(2-oxo-2-(2-(trifluoromethyl)pyrrolidin-1-yl)ethyl)-1'-(1H-pyrazolo[3,4-c]pyridine-5-carbonyl)spiro[indoline-3,4'-piperidin]-2-one 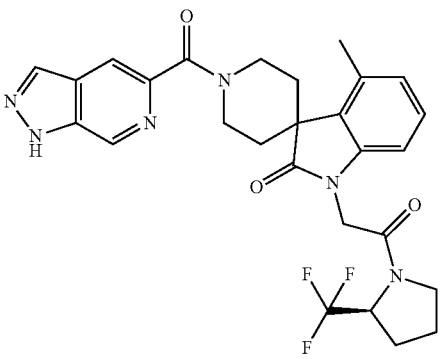 | 1H-Pyrazolo[3,4-c]pyridine-5-carboxylic acid (CAS RN 1256824-45-9) INT8e | C | MS (ESI): m/z = 541.3 [M + H]⁺ |
| 54 | N-(2,3-Dihydro-1H-inden-1-yl)-2-[1'-(1H-indazole-5-carbonyl)-4-methyl-2-oxospiro[indole-3,4'-piperidine]-1-yl]acetamide 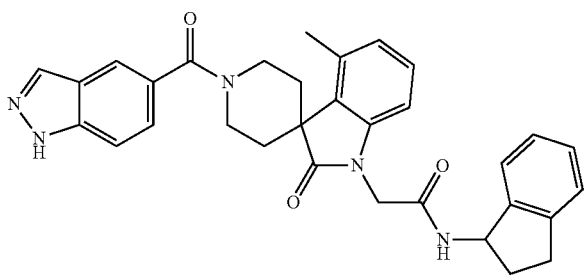 | 2,3-Dihydro-1H-inden-1-amine (CAS RN 34698-41-4) INT1e | A using TEA instead of DIPEA | MS (ESI): m/z = 534.2 [M + H]⁺ |
| 55 | 2-[1'-(1H-Indazole-5-carbonyl)-4-methyl-2-oxospiro[indole-3,4'-piperidine]-1-yl]-N-(1,2,3,4-tetrahydronaphthalen-1-yl)acetamide 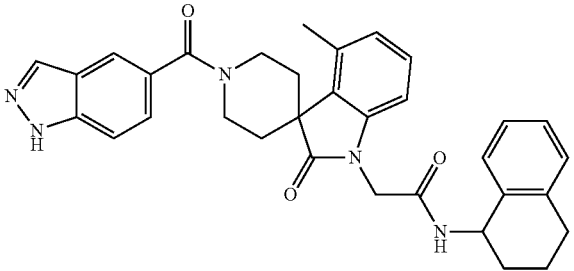 | 1,2,3,4-Tetrahydronaphthalen-1-amine (CAS RN 2217-40-5) INT1e | A using TEA instead of DIPEA | MS (ESI): m/z = 548.2 [M + H]⁺ |

TABLE 7-continued (Examples 2 to 168)
The following examples were synthesized from the suitable building blocks/intermediates in
analogy to the methods from A to F, H to J, N, Q, R and V to Y as described before.

| Ex. | Systematic Name | Building blocks / intermediates | Method | MS, m/z |
|---|---|---|---|---|
| 56 | N-(2,2-Difluorocyclohexyl)-2-[1'-(1H-indazole-5-carbonyl)-4-methyl-2-oxospiro[indole-3,4'-piperidine]-1-yl]acetamide | 2,2-Difluorocyclohex anamine hydrocloride (CAS RN 921602-83-7) INT1e | A using TEA instead of DIPEA | MS (ESI): m/z = 536.3 [M + H]+ |
| 57 | 1-[2-[1'-(1H-Indazole-5-carbonyl)-4-methyl-2-oxospiro[indole-3,4'-piperidine]-1-yl]acetyl]pyrrolidine-3-carbonitrile | Pyrrolidine-3-carbonitrile hydrochloride (CAS RN 10603-53-9) INT1e | A using TEA instead of DIPEA | MS (ESI): m/z = 497.2 [M + H]+ |
| 58 | 2-[4-Chloro-1'-(1H-indazole-5-carbonyl)-2-oxospiro[indole-3,4'-piperidine]-1-yl]-N-(2,2,2-trifluoroethyl)acetamide | 2,2,2-Trifluoroethanamine (CAS RN 753-90-2)) INT2e | A using TEA instead of DIPEA | MS (ESI): m/z = 520.1 [M + H]+ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 59 | 2-[4-Cyclopropyl-1'-(1H-indazole-5-carbonyl)-2-oxospiro[indole-3,4'-piperidine]-1-yl]-N-(2,2,2-trifluoroethyl)acetamide | 1H-Indazole-5-carboxylic acid (CAS RN 61700-61-6) INT21a | A | MS (EI): m/z = 526.3 [M + H]$^+$ |
| 60 | 4-Chloro-1'-(1H-indazole-5-carbonyl)-1-[2-oxo-2-[(2S)-2-(trifluoromethyl)pyrrolidin-1-yl]ethyl]spiro[indole-3,4'-piperidine]-2-one | (S)-2-(Trifluoromethyl) pyrrolidine (CAS RN 119580-41-5) INT2e | A using TEA instead of DIPEA | MS (ESI): m/z = 560.17 [M + H]$^+$ |
| 61 | 4-Bromo-1'-(1H-indazole-5-carbonyl)-1-[2-(3-oxa-8-azabicyclo[3.2.1]octan-8-yl)-2-oxo-ethyl]spiro[indoline-3,4'-piperidine]-2-one | 3-Oxa-8-azabicyclo[3.2.1] octane hydrochloride (CAS RN 904316-92-3) INT6e | A using TEA instead of DIPEA | MS (ESI): m/z = 578.2 [M + H]$^+$ |

TABLE 7-continued (Examples 2 to 168)

The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 62 | 4-Bromo-1'-(1H-indazole-5-carbonyl)-1-(2-oxo-2-(2-(trifluoromethyl)morpholino)ethyl)spiro[indoline-3,4'-piperidin]-2-one | 2-(Trifluoromethyl)morpholine (CAS RN 1196532-95-2) INT6e | A using TEA instead of DIPEA | MS (ESI): m/z = 622.1 [M + H]+ |
| 63 | 4-Bromo-1-(2-(3,3-difluoropyrrolidin-1-yl)-2-oxoethyl)-1'-(1H-indazole-5-carbonyl)spiro[indoline-3,4'-piperidin]-2-one | 3,3-Difluoropyrrolidine hydrochloride (CAS RN 163457-23-6) INT 6e | A using TEA instead of DIPEA | MS (ESI): m/z = 572.3 [M + H]+ |
| 64 | 4-Bromo-1'-(1H-indazole-5-carbonyl)-1-(2-oxo-2-(3-(trifluoromethyl)pyrrolidin-1-yl)ethyl)spiro[indoline-3,4'-piperidin]-2-one | 3-(Trifluoromethyl)pyrrolidine hydrochloride (CAS RN 1189485-03-7) INT6e | A using TEA instead of DIPEA | MS (ESI): m/z = 604.3 [M + H]+ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 65 | 4-Bromo-1-(2-oxo-2-(3-(trifluoromethyl)pyrrolidin-1-yl)ethyl)-1'-(1H-pyrazolo[4,3-b]pyridine-5-carbonyl)spiro[indoline-3,4'-piperidin]-2-one | 3-(Trifluoromethyl) pyrrolidine hydrochloride (CAS RN 1189485-03-7) INT11e | A using TEA instead of DIPEA | MS (ESI): m/z = 607.1 [M + H]⁺ |
| 66 | 4-Bromo-1-(2-(3,3-difluoropyrrolidin-1-yl)-2-oxoethyl)-1'-(1H-pyrazolo[3,4-b]pyridine-5-carbonyl)spiro[indoline-3,4'-piperidin]-2-one | 3,3-Difluoropyrrolidine hydrochloride (CAS RN 163457-23-6) INT11e | A with TEA instead of DIPEA | MS (ESI): m/z = 575.1 [M + H]⁺ |
| 67 | 4-Bromo-1-(2-oxo-2-(3-(trifluoromethyl)pyrrolidin-1-yl)ethyl)-1'-(1H-pyrazolo[3,4-b]pyridine-5-carbonyl)spiro[indoline-3,4'-piperidin]-2-one | 3-(Trifluoromethyl) pyrrolidine hydrochloride (CAS RN 1189485-03-7) INT9e | A using TEA instead of DIPEA | MS (ESI): m/z = 607.1 [M + H]⁺ |

TABLE 7-continued (Examples 2 to 168)
The following examples were synthesized from the suitable building blocks/intermediates in
analogy to the methods from A to F, H to J, N, Q, R and V to Y as described before.

| Ex. | Systematic Name | Building blocks / intermediates | Method | MS, m/z |
|---|---|---|---|---|
| 68 | 4-Bromo-1-(2-(3,3-difluoropyrrolidin-1-yl)-2-oxoethyl)-1'-(1H-pyrazolo[3,4-b]pyridine-5-carbonyl)spiro[indoline-3,4'-piperidin]-2-one | 3,3-Difluoropyrrolidine hydrochloride (CAS RN 163457-23-6) INT9e | A using TEA instead of DIPEA | MS (ESI): m/z = 575.1 [M + H]$^+$ |
| 69 | 4-Bromo-1-(2-oxo-2-(3-(trifluoromethyl)pyrrolidin-1-yl)ethyl)-1'-(1H-pyrazolo[3,4-c]pyridine-5-carbonyl)spiro[indoline-3,4'-piperidin]-2-one | 2-(Trifluoromethyl)morpholine (CAS RN 1196532-95-2) INT10e | A using TEA instead of DIPEA | MS (ESI): m/z = 607.1 [M + H]$^+$ |
| 70 | 4-Bromo-1-(2-(3,3-difluoropyrrolidin-1-yl)-2-oxoethyl)-1'-(1H-pyrazolo[3,4-c]pyridine-5-carbonyl)spiro[indoline-3,4'-piperidin]-2-one | 3,3-Difluoropyrrolidine hydrochloride (CAS RN 163457-23-6) INT10e | A using TEA instead of DIPEA | MS (ESI): m/z = 575.1 [M + H]$^+$ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 71 | (S)-4-Bromo-1-(2-oxo-2-(2-(trifluoromethyl)pyrrolidin-1-yl)ethyl)-1'-(1H-pyrazolo[3,4-c]pyridine-5-carbonyl)spiro[indoline-3,4'-piperidin]-2-one | (S)-2-(Trifluoromethyl)pyrrolidine (CAS RN 119580-41-5) INT10e | A using TEA instead of DIPEA | MS (ESI): m/z = 605.2 [M + H]+ |
| 72 | (S)-4-Bromo-1-(2-oxo-2-(2-(trifluoromethyl)pyrrolidin-1-yl)ethyl)-1'-(1H-pyrazolo[4,3-b]pyridine-5-carbonyl)spiro[indoline-3,4'-piperidin]-2-one | (S)-2-(Trifluoromethyl)pyrrolidine (CAS RN 119580-41-5) INT11e | A using TEA instead of DIPEA | MS (ESI): m/z = 607.1 [M + H]+ |

TABLE 7-continued (Examples 2 to 168)

The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 73 | 4-Bromo-1-(2-oxo-2-(2-(trifluoromethyl)morpholino)ethyl)-1'-(1H-pyrazolo[4,3-b]pyridine-5-carbonyl)spiro[indoline-3,4'-piperidin]-2-one | 2-(Trifluoromethyl)morpholine (CAS RN 1196532-95-2) INT11e | A using TEA instead of DIPEA | MS (ESI): m/z = 621.2 [M + H]+ |
| 74 | 4-Bromo-1-[2-(3-oxa-8-azabicyclo[3.2.1]octan-8-yl)-2-oxoethyl]-1'-(1H-pyrazolo[4,3-b]pyridine-5-carbonyl)spiro[indole-3,4'-piperidine]-2-one | 3-Oxa-8-azabicyclo[3.2.1]octane hydrochloride (CAS RN 9004316-92-3) INT11e | A using TEA instead of DIPEA | MS (ESI): m/z = 581.1 [M + H]+ |

TABLE 7-continued (Examples 2 to 168)

The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 75 | (S)-4-Bromo-1-(2-oxo-2-(2-(trifluoromethyl)pyrrolidin-1-yl)ethyl)-1'-(1H-pyrazolo[3,4-b]pyridine-5-carbonyl)spiro[indoline-3,4'-piperidin]-2-one | (S)-2-(Trifluoromethyl)pyrrolidine (CAS RN 119580-41-5) INT9e | A using TEA instead of DIPEA | MS (ESI): m/z = 607.1 [M + H]+ |
| 76 | 4-Bromo-1-(2-oxo-2-(2-(trifluoromethyl)morpholino)ethyl)-1'-(1H-pyrazolo[3,4-b]pyridine-5-carbonyl)spiro[indoline-3,4'-piperidin]-2-one | 2-(Trifluoromethyl)morpholine (CAS RN 1196532-95-2) INT9e | A using TEA instead of DIPEA | MS (ESI): m/z = 623.1 [M + H]+ |

TABLE 7-continued (Examples 2 to 168)

The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 77 | 1-(2-(3-Oxa-8-azabicyclo[3.2.1]octan-8-yl)-2-oxoethyl)-4-bromo-1'-(1H-pyrazolo[3,4-b]pyridine-5-carbonyl)spiro[indoline-3,4'-piperidin]-2-one | 3-Oxa-8-azabicyclo[3.2.1]octane hydrochloride (CAS RN 904316-92-3) INT9e | A using TEA instead of DIPEA | MS (ESI): m/z = 581.1 [M + H]$^+$ |
| 78 | 4-Chloro-1-[(3-cyclopropyl-1,2,4-oxadiazol-5-yl)methyl]-1'-(1H-indazole-5-carbonyl)spiro[indole-3,4'-piperidine]-2-one | 1H-Indazole-5-carboxylic acid (CAS RN 61700-61-6) INT22a | D | MS (ESI): m/z = 503.1 [M + H]$^+$ |
| 79 | 4-Bromo-1'-(1H-indazole-5-carbonyl)-1-(2-oxo-2-(3,3,4-trimethylpiperazin-1-yl)ethyl)spiro[indoline-3,4'-piperidin]-2-one | 1,2,2-Trimethylpiperazine hydrochloride (CAS RN 932047-03-5) INT6e | A using TEA instead of DIPEA | MS (ESI): m/z = 595.3 [M + H]$^+$ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 80 | 1-(1H-Indazole-5-carbonyl)-5'-methoxy-1'-[2-oxo-2-[(2S)-2-(trifluoromethyl)pyrrolidin-1-yl]ethyl]spiro[piperidine-4,3'-pyrrolo[3,2-b]pyridine]-2'-one | 1H-Indazole-5-carboxylic acid (CAS RN 61700-61-6) INT3d | Method L, followed by method A | MS (ESI): m/z = 557.2 [M + H]+ |
| 81 | 2-[1'-(1H-Indazole-5-carbonyl)-4-methyl-2-oxospiro[indole-3,4'-piperidine]-1-yl]-N-methyl-N-[(2S)-1,1,1-trifluoropropan-2-yl]acetamide | 1H-Indazole-5-carboxylic acid (CAS RN 61700-61-6) INT23a | C | MS (EI): m/z = 528.3 [M + H]+ |
| 82 | 2-[4-Bromo-5-fluoro-2-oxo-1'-(1H-pyrazolo[3,4-b]pyridine-5-carbonyl)spiro[indole-3,4'-piperidine]-1-yl]-N-(2,2,2-trifluoroethyl)acetamide | 1H-Pyrazolo[3,4-b]pyridine-5-carboxylic acid (CAS RN 952182-02-4) INT26a | C | MS (EI): m/z = 582.9 [M + H]+ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 83 | 2-[4-Bromo-5-fluoro-1'-(1H-indazole-5-carbonyl)-2-oxospiro[indole-3,4'-piperidine]-1-yl]-N-(2,2,2-trifluoroethyl)acetamide | 1H-Indazole-5-carboxylic acid (CAS RN 61700-61-6) INT26a | C | MS (EI): m/z = 582.0 [M + H]$^+$ |
| 84 | 4-Bromo-1-(2-(3,3-dimethylmorpholino)-2-oxoethyl)-1'-(1H-indazole-5-carbonyl)spiro[indoline-3,4'-piperidin]-2-one | 3,3-Dimethylmorpholine (CAS RN 59229-63-9) INT6e | A using TEA instead of DIPEA | MS (ESI): m/z = 582.2 [M + H]$^+$ |
| 85 | 1-(2-(2H-Benzo[b][1,4]oxazin-4(3H)-yl)-2-oxoethyl)-4-bromo-1'-(1H-indazole-5-carbonyl)spiro[indoline-3,4'-piperidin]-2-one | 3,4-Dihydro-2H-benzo[b][1,4]oxazine (CAS RN 5735-53-5) INT6e | H | MS (ESI): m/z = 602.1 [M + H]$^+$ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 86 | 2-(4-Bromo-1'-(1H-indazole-5-carbonyl)-2-oxospiro[indoline-3,4'-piperidin]-1-yl)-N-(pyridin-2-yl)acetamide | Pyridin-2-amine (CAS RN 504-29-0) INT6e | H | MS (ESI): m/z = 559.1 [M + H]$^+$ |
| 87 | 2-(4-Bromo-1'-(1H-indazole-5-carbonyl)-2-oxospiro[indoline-3,4'-piperidin]-1-yl)-N-(2-(morpholinomethyl)phenyl)acetamide | 2-(Morpholinomethyl) aniline (CAS RN 95539-61-0) INT6e | A using TEA instead of DIPEA | MS (ESI): m/z = 659.2 [M + H]$^+$ |
| 88 | 2-(4-Bromo-1'-(1H-indazole-5-carbonyl)-2-oxospiro[indoline-3,4'-piperidin]-1-yl)-N-phenylacetamide | Aniline (CAS RN 62-53-3) INT6e | A using TEA instead of DIPEA | MS (ESI): m/z = 558.2 [M + H]$^+$ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 89 | 2-[4-Ethoxy-1'-(1H-indazole-5-carbonyl)-2-oxospiro[indole-3,4'-piperidine]-1-yl]-N-(2,2,2-trifluoroethyl)acetamide | 1H-Indazole-5-carboxylic acid (CAS RN 61700-61-6) INT29a | A | MS (ESI): m/z = 530.2 [M + H]⁺ |
| 90 | 2-[1'-(1H-Indazole-5-carbonyl)-4-methyl-2-oxospiro[indole-3,4'-piperidine]-1-yl]-N-(3,3,3-trifluoropropyl)acetamide | 3,3,3-Trifluoropropylamine (CAS RN 460-39-9) INT1e | D | MS (EI): m/z = 514.2 [M + H]⁺ |
| 91 | 2-[1'-(1H-Indazole-5-carbonyl)-4-methyl-2-oxospiro[indole-3,4'-piperidine]-1-yl]-N-methyl-N-[(2R)-1,1,1-trifluoropropan-2-yl]acetamide | 1H-Indazole-5-carboxylic acid (CAS RN 61700-61-6) INT31a | C | MS (EI): m/z = 528.2 [M + H]⁺ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 92 | 3-[1'-(1H-Indazole-5-carbonyl)-4-methyl-2-oxospiro[indole-3,4'-piperidine]-1-yl]-N-(2,2,2-trifluoroethyl)propanamide | 2,2,2-Trifluoro-ethylamine hydrochloride (CAS RN 373-88-6) INT13e | D | MS (EI): m/z = 514.3 [M + H]+ |
| 93 | 2-[4-Hydroxy-1'-(1H-indazole-5-carbonyl)-2-oxospiro[indole-3,4'-piperidine]-1-yl]-N-(2,2,2-trifluoroethyl)acetamide | 1H-Indazole-5-carboxylic acid (CAS RN 61700-61-6) INT28a | C | MS (EI): m/z = 502.2 [M + H]+ |
| 94 | 5'-Chloro-1-(1H-indazole-5-carbonyl)-1'-[2-oxo-2-[(2S)-2-(trifluoromethyl)pyrrolidin-1-yl]ethyl]spiro[piperidine-4,3'-pyrrolo[3,2-b]pyridine]-2'-one | 1H-Indazole-5-carboxylic acid (CAS RN 61700-61-6) INT14e | D | MS (EI): m/z = 561.1 [M + H]+ |

TABLE 7-continued (Examples 2 to 168)

The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 95 | 4-Bromo-1'-(1H-indazole-5-carbonyl)-1-[2-oxo-2-[2-(2,2,2-trifluoroethyl)pyrrolidin-1-yl]ethyl]spiro[indoline-3,4'-piperidine]-2-one | 2-(2,2,2-Trifluoroethyl)pyrrolidine hydrochloride (supplier: Enamine, catalog N° BBV-56260027) INT6e | A using TEA instead of DIPEA | MS (ESI): m/z = 618.3 [M + H]$^+$ |
| 96 | 4-Bromo-1-[2-(4,4-difluoro-1-piperidyl)-2-oxo-ethyl]-1'-(1H-indazole-5-carbonyl)spiro[indoline-3,4'-piperidine]-2-one | 4,4-Difluoropiperidine hydrochloride (CAS RN 144230-52-4) INT6e | C using TEA instead of DIPEA | MS (ESI): m/z = 588.1 [M + H]$^+$ |

TABLE 7-continued (Examples 2 to 168)

The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 97 | 4-Bromo-1'-(1H-indazole-5-carbonyl)-1-[2-oxo-2-(1-piperidyl)ethyl]spiro[indoline-3,4'-piperidine]-2-one | Piperidine (CAS RN 110-89-4) INT6e | C using TEA instead of DIPEA | MS (ESI): m/z = 552.1 [M + H]+ |
| 98 | 1-[2-(3,3a,4,5,6,6a-hexahydro-2H-cyclopenta[b]pyrrol-1-yl)-2-oxo-ethyl]-4-bromo-1'-(1H-indazole-5-carbonyl)spiro[indoline-3,4'-piperidine]-2-one | Octahydrocyclopenta[b]pyrrole (CAS RN 5661-02-9) INT6e | C using TEA instead of DIPEA | MS (ESI): m/z = 578.2 [M + H]+ |

TABLE 7-continued (Examples 2 to 168)

The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 99 | 4-Chloro-5-fluoro-1-[2-oxo-2-[2-(2,2,2-trifluoroethyl)pyrrolidin-1-yl]ethyl]-1'-(1H-pyrazolo[4,3-b]pyridine-5-carbonyl)spiro[indoline-3,4'-piperidine]-2-one | 2-(2,2,2-Trifluoroethyl) pyrrolidine hydrochloride (Supplier: Enamine, catalog # BBV-56260027) INT12e | C using TEA instead of DIPEA | MS (ESI): m/z = 593.3 [M + H]+ |
| 100 | 1-[2-(3,3a,4,5,6,6a-Hexahydro-2H-cyclopenta[b]pyrrol-1-yl)-2-oxo-ethyl]-4-chloro-5-fluoro-1'-(1H-pyrazolo[4,3-b]pyridine-5-carbonyl)spiro[indoline-3,4'-piperidine]-2-one | Octahydrocyclopenta[b]pyrrole (CAS RN 5661-02-9) INT12e | C using TEA instead of DIPEA | MS (ESI): m/z = 551.3 [M + H]+ |

TABLE 7-continued (Examples 2 to 168)

The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 101 | 4-Chloro-5-fluoro-1-[2-oxo-2-[(2S)-2-(trifluoromethyl)pyrrolidin-1-yl]ethyl]-1'-(1H-pyrazolo[4,3-b]pyridine-5-carbonyl)spiro[indoline-3,4'-piperidine]-2-one | (S)-2-(Trifluoromethyl)pyrrolidine (CAS RN 119580-41-5) INT12e | C using TEA instead of DIPEA | MS (ESI): m/z = 579.3 [M + H]+ |
| 102 | 4-Chloro-5-fluoro-1-[2-oxo-2-[2-(trifluoromethyl)morpholine-4-yl]ethyl]-1'-(1H-pyrazolo[4,3-b]pyridine-5-carbonyl)spiro[indoline-3,4'-piperidine]-2-one | 2-(Trifluoromethyl)morpholine (CAS RN 1196532-95-2) INT12e | C using TEA instead of DIPEA | MS (ESI): m/z = 595.3 [M + H]+ |

TABLE 7-continued (Examples 2 to 168)

The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 103 | 2-[1'-(3-Amino-1H-indazole-6-carbonyl)-4-chloro-5-fluoro-2-oxospiro[indole-3,4'-piperidine]-1-yl]-N-(2,2,2-trifluoroethyl)acetamide | 3-Amino-1H-indazole-6-carboxylic acid (CAS RN 871709-92-1) INT17a | C using DCM instead of DMF, and TEA instead of DIPEA | MS (ESI): m/z = 553.3 [M + H]+ |
| 104 | (-)-4-Chloro-1-[2-oxo-1-(2,2,2-trifluoroethyl)piperidin-3-yl]-1'-(1H-pyrazolo[3,4-b]pyridine-5-carbonyl)spiro[indole-3,4'-piperidine]-2-one | 1H-Pyrazolo[3,4-b]pyridine-5-carboxylic acid (CAS RN 952182-02-4) INT34a | C | MS (ESI): m/z = 561.0 [M + H]+ |

TABLE 7-continued (Examples 2 to 168)

The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 105 | (+)-4-Chloro-1-[2-oxo-1-(2,2,2-trifluoroethyl)piperidin-3-yl]-1'-(1H-pyrazolo[3,4-b]pyridine-5-carbonyl)spiro[indole-3,4'-piperidine]-2-one | 1H-Pyrazolo[3,4-b]pyridine-5-carboxylic acid (CAS RN 952182-02-4) INT35a | C | MS (ESI): m/z = 561.1 [M + H]+ |
| 106 | 4-Bromo-1'-(1H-indazole-5-carbonyl)-1-[2-(2-methylthiomorpholin-4-yl)-2-oxoethyl]spiro[indole-3,4'-piperidine]-2-one | 2-Methylthiomorpholine (CAS RN 3970-88-5) INT6e | Y | MS (ESI): m/z = 581.8 [M + H]+ |
| 107 | 1-[2-(5-Azaspiro[2.5]octan-5-yl)-2-oxoethyl]-4-bromo-1'-(1H-indazole-5-carbonyl)spiro[indole-3,4'-piperidine]-2-one | 5-Azaspiro[2.5]octane HCl salt (CAS RN 25337-01-3) INT6e | Y | MS (ESI): m/z = 575.9 [M + H]+ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 108 | 4-Bromo-1'-(1H-indazole-5-carbonyl)-1-[2-oxo-2-(4-oxo-1,3,6,7,8,8a-hexahydropyrrolo[1,2-a]pyrazin-2-yl)ethyl]spiro[indole-3,4'-piperidine]-2-one | Octahydropyrrolo[1,2-a]piperazin-4-one HCl salt (MFCD20278321) INT6e | Y | MS (ESI): m/z = 605.1 [M + H]+ |
| 109 | 4-Bromo-1-[2-(3-fluoropyrrolidin-1-yl)-2-oxoethyl]-1'-(1H-indazole-5-carbonyl)spiro[indole-3,4'-piperidine]-2-one | 3-Fluoro pyrrolidine (CAS RN 116574-74-4) INT6e | Y | MS (ESI): m/z = 554.2 [M + H]+ |
| 110 | (−)-4,5-Dichloro-1-[2-oxo-2-[2-(2,2,2-trifluoroethyl)pyrrolidin-1-yl]ethyl]-1'-(1H-pyrazolo[4,3-b]pyridine-5-carbonyl)spiro[indole-3,4'-piperidine]-2-one | Example 168 | X | MS (ESI): m/z = 609.3 [M + H]+ |

TABLE 7-continued (Examples 2 to 168)

The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 111 | (+)-4,5-Dichloro-1-[2-oxo-2-[2-(2,2,2-trifluoroethyl)pyrrolidin-1-yl]ethyl]-1'-(1H-pyrazolo[4,3-b]pyridine-5-carbonyl)spiro[indole-3,4'-piperidine]-2-one | Example 168 | X | MS (ESI): m/z = 609.3 [M + H]+ |
| 114 | (cis)-(+)-4-Chloro-5-fluoro-1-(2-(-hexahydrocyclopenta[b]pyrrol-1(2H)-yl)-2-oxoethyl)-1'-(1H-pyrazolo[4,3-b]pyridine-5-carbonyl)spiro[indoline-3,4'-piperidin]-2-one | Example 100 | X | MS (ESI): m/z = 551.3 [M + H]+ |

TABLE 7-continued (Examples 2 to 168)

The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 115 | (cis)-(-)-4-Chloro-5-fluoro-1-(2-(-hexahydrocyclopenta[b]pyrrol-1(2H)-yl)-2-oxoethyl)-1'-(1H-pyrazolo[4,3-b]pyridine-5-carbonyl)spiro[indoline-3,4'-piperidin]-2-one | Example 100 | X | MS (ESI): m/z = 551.3 [M + H]+ |
| 116 | (+) or (-)-4-Chloro-5-fluoro-1-[2-oxo-2-[2-(trifluoromethyl)morpholin-4-yl]ethyl]-1'-(1H-pyrazolo[4,3-b]pyridine-5-carbonyl)spiro[indole-3,4'-piperidine]-2-one | Example 102 | X (First eluting peak) | MS (ESI): m/z = 595.3 [M + H]+ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 117 | (−) or (+)-4-Chloro-5-fluoro-1-[2-oxo-2-[2-(trifluoromethyl)morpholin-4-yl]ethyl]-1′-(1H-pyrazolo[4,3-b]pyridine-5-carbonyl)spiro[indole-3,4′-piperidine]-2-one | Example 102 | X (Second eluting peak) | MS (ESI): m/z = 595.3 [M + H]+ |
| 118 | 2-[4′-Bromo-1-(1H-indazole-5-carbonyl)-2′-oxospiro[azetidine-3,3′-indole]-1′-yl]-N-(2,2,2-trifluoroethyl)acetamide | 1H-Indazole-5-carboxylic acid (CAS RN 61700-61-6) INT37a | C | MS (ESI): m/z = 538.1 [M + H]+ |
| 119 | 2-[4-Bromo-2-oxo-1′-(1H-pyrazolo[4,3-d]pyrimidine-5-carbonyl)spiro[indole-3,4′-piperidine]-1-yl]-N-(2,2,2-trifluoroethyl)acetamide | INT39 INT3a | C useing TEA instead of DIPEA | MS (ESI): m/z = 568.1 [M + H]+ |

TABLE 7-continued (Examples 2 to 168)
The following examples were synthesized from the suitable building blocks/intermediates in
analogy to the methods from A to F, H to J, N, Q, R and V to Y as described before.

| Ex. | Systematic Name | Building blocks / intermediates | Method | MS, m/z |
|---|---|---|---|---|
| 120 | 2-[4-Chloro-5-fluoro-2-oxo-1'-(1H-pyrazolo[4,3-d]pyrimidine-5-carbonyl)spiro[indole-3,4'-piperidine]-1-yl]-N-(2,2,2-trifluoroethyl)acetamide | INT39 INT17a | C useing TEA instead of DIPEA | MS (ESI): m/z = 540.2 [M + H]$^+$ |
| 121 | 2-[4-Bromo-1'-(1H-indazole-5-carbonyl)-2-oxospiro[indole-3,4'-piperidine]-1-yl]-N-methyl-N-(oxetan-3-ylmethyl)acetamide | Methyl(oxetan-3-ylmethyl)amine (CAS RN 1408076-16-3) INT6e | Y | MS (ESI): m/z = 566.2 [M + H]$^+$ |
| 122 | 2-[4-Bromo-1'-(1H-indazole-5-carbonyl)-2-oxospiro[indole-3,4'-piperidine]-1-yl]-N-(cyanomethyl)-N-methylacetamide | 2-(Methylamino)acetonitrile (CAS RN 5616-32-0) INT6e | Y | MS (ESI): m/z = 534.9 [M + H]$^+$ |
| 123 | 2-[4-Bromo-1'-(1H-indazole-5-carbonyl)-2-oxospiro[indole-3,4'-piperidine]-1-yl]-N-methyl-N-(5-methyl-1,2-oxazol-3-yl)acetamide | N,5-dimethyl-1,2-oxazol-3-amine (CAS RN 55809-40-0) INT6e | Y | MS (ESI): m/z = 577.2 [M + H]$^+$ |

TABLE 7-continued (Examples 2 to 168)
The following examples were synthesized from the suitable building blocks/intermediates in
analogy to the methods from A to F, H to J, N, Q, R and V to Y as described before.

| Ex. | Systematic Name | Building blocks / intermediates | Method | MS, m/z |
|---|---|---|---|---|
| 124 | 4-Bromo-1'-(1H-indazole-5-carbonyl)-1-[2-oxo-2-(1,4,6,7-tetrahydropyrrolo[3,2-c]pyridin-5-yl)ethyl]spiro[indole-3,4'-piperidine]-2-one | 4,5,6,7-Tetrahydro-5-azaindole (CAS RN 1176405-02-9) INT6e | Y | MS (ESI): m/z = 587.2 [M + H]+ |
| 125 | 4-Bromo-1'-(1H-indazole-5-carbonyl)-1-[2-(3-methyl-2,3-dihydroindol-1-yl)-2-oxoethyl]spiro[indole-3,4'-piperidine]-2-one | 3-Methyl-2,3-dihydro-1H-indole (CAS RN 4375-15-9) INT6e | Y | MS (ESI): m/z = 598.2 [M + H]+ |
| 126 | 4-Bromo-1-[2-(5-fluoro-2,3-dihydroindol-1-yl)-2-oxoethyl]-1'-(1H-indazole-5-carbonyl)spiro[indole-3,4'-piperidine]-2-one | 5-Fluoro-2,3-dihydro-1H-indole (CAS RN 2343-22-8) INT6e | Y | MS (ESI): m/z = 602.2 [M + H]+ |
| 127 | (2S)-1-[2-[4-Bromo-1'-(1H-indazole-5-carbonyl)-2-oxospiro[indole-3,4'-piperidine]-1-yl]acetyl]pyrrolidine-2-carbonitrile | (2S)-Pyrrolidine-2-carbonitrile (CAS RN 65732-69-6) INT6e | Y | MS (ESI): m/z = 561.1 [M + H]+ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 128 | 2-[4-Chloro-2-oxo-1'-(1H-pyrazolo[3,4-b]pyridine-5-carbonyl)spiro[indole-3,4'-piperidine]-1-yl]-3-morpholin-4-yl-N-(2,2,2-trifluoroethyl)propanamide | 1H-Pyrazolo[3,4-b]pyridine-5-carboxylic acid (CAS RN 952182-02-4) INT36a | Y | MS (ESI): m/z = 620.2 [M + H]$^+$ |
| 129 | 4-Chloro-1-[2-(2,2-dimethylpyrrolidin-1-yl)-2-oxoethyl]-5-fluoro-1'-(1H-pyrazolo[4,3-b]pyridine-5-carbonyl)spiro[indole-3,4'-piperidine]-2-one | 2,2-Dimethylpyrrolidine (CAS RN 35018-15-6) INT12e | Y | MS (ESI): m/z = 539.2 [M + H]$^+$ |
| 130 | 4-Chloro-5-fluoro-1-[2-oxo-2-[3-(trifluoromethyl)azetidin-1-yl]ethyl]-1'-(1H-pyrazolo[4,3-b]pyridine-5-carbonyl)spiro[indole-3,4'-piperidine]-2-one | 3-(Trifluoromethyl)azetidine (CAS RN 1221349-18-3) INT12e | Y | MS (ESI): m/z = 565.1 [M + H]$^+$ |

TABLE 7-continued (Examples 2 to 168)

The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 132 | 1-[2-[(3aR,6aS)-3,3a,4,5,6,6a-Hexahydro-1H-cyclopenta[c]pyrrol-2-yl]-2-oxoethyl]-4-bromo-1'-(1H-indazole-5-carbonyl)spiro[indole-3,4'-piperidine]-2-one | (3aR,6aS)-Octahydrocyclopenta[c]pyrrole (CAS RN 1037834-39-1) INT6e | Y | MS (ESI): m/z = 578.2 [M + H]+ |
| 133 | 1-[2-(3,4,6,7,8,8a-Hexahydro-1H-pyrrolo[1,2-a]pyrazin-2-yl)-2-oxoethyl]-4-bromo-1'-(1H-indazole-5-carbonyl)spiro[indole-3,4'-piperidine]-2-one | Octahydropyrrolo[1,2-a]pyrazine (CAS RN 5654-83-1) INT6e | Y | MS (ESI): m/z = 589.4 [M − H]− |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 134 | 1-[2-(3,4,5,7,8,8a-Hexahydro-1H-pyrrolo[1,2-a]pyrazin-2-yl)-2-oxoethyl]-4-chloro-5-fluoro-1'-(1H-pyrazolo[4,3-b]pyridine-5-carbonyl)spiro[indole-3,4'-piperidine]-2-one | Octahydro pyrrollo[1,2-a] pyrazine (CAS RN 5654-83-1) INT12e | Y | MS (ESI): m/z = 564.4 [M − H]− |
| 135 | 4-Chloro-1-[2-(7,7-difluoro-2-azaspiro[3.3]heptan-2-yl)-2-oxoethyl]-5-fluoro-1'-(1H-pyrazolo[4,3-b]pyridine-5-carbonyl)spiro[indole-3,4'-piperidine]-2-one | 5,5-Difluoro-2-azaspiro[3.3]heptane 2,2,2-trifluoroacetate (CAS RN 1330765-36-0) | Y | MS (ESI): m/z = 573.2 [M + H]+ |
| 136 | 2-[1-(3-Amino-1H-indazole-6-carbonyl)-4'-bromo-2'-oxospiro[azetidine-3,3'-indole]-1'-yl]-N-(2,2,2-trifluoroethyl)acetamide | 3-Amino-1H-indazole-6-carboxylic acid (CAS RN 871709-92-1) INT37a | C | MS (ESI): m/z = 553.1 [M + H]+ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 137 | 2-[4'-Bromo-2'-oxo-1-(1H-pyrazolo[4,3-b]pyridine-5-carbonyl)spiro[azetidine-3,3'-indole]-1'-yl]-N-(2,2,2-trifluoroethyl)acetamide | 1H-Pyrazolo[4,3-b]pyridine-5-carboxylic acid (CAS RN 1260670-03-8) INT37a | C | MS (ESI): m/z = 539.2 [M + H]$^+$ |
| 138 | 4-Chloro-1-[2-(3,3-difluoroazetidin-1-yl)-2-oxoethyl]-5-fluoro-1'-(1H-indazole-5-carbonyl)spiro[indole-3,4'-piperidine]-2-one | 3,3-Difluoroazetidine•HCl (CAS RN 288315-03-7) INT16e | D | MS (ESI): m/z = 532.2 [M + H]$^+$ |
| 139 | 4-Bromo-1-[2-(2,3-dihydroindol-1-yl)-2-oxoethyl]-1'-(1H-indazole-5-carbonyl)spiro[indole-3,4'-piperidine]-2-one | 2,3-Dihydro-1H-indole (CAS RN 30922-25-9) INT6e | D | MS (ESI): m/z = 584.1 [M + H]$^+$ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 140 | 5-[4-chloro-2-oxo-1-[2-oxo-2-(2,2,2-trifluoroethylamino)ethyl]spiro[indole-3,4'-piperidine]-1'-carbonyl]-1H-indazole-3-carboxamide | 3-Carbamoyl-1H-indazole-5-carboxylic acid (MFCD24502734) INT5a | C | MS (ESI): m/z = 563.0 [M + H]$^+$ |
| 141 | 4-Chloro-5-fluoro-1'-(1H-indazole-5-carbonyl)-1-[2-oxo-2-(3,3,4,4-tetrafluoropyrrolidin-1-yl)ethyl]spiro[indole-3,4'-piperidine]-2-one | 3,3,4,4-Tetrafluoropyrrolidine (CAS RN 1841-00-5) INT16e | D | MS (ESI): m/z = 582.0 [M + H]$^+$ |
| 142 | 4-Chloro-5-fluoro-1'-(1H-indazole-5-carbonyl)-1-[2-(3-methoxypyrrolidin-1-yl)-2-oxoethyl]spiro[indole-3,4'-piperidine]-2-one | 3-Methoxypyrrolidine (CAS RN 62848-20-8) INT16e | D | MS (ESI): m/z = 539.9 [M + H]$^+$ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 143 | 1-[2-[4-Chloro-5-fluoro-1'-(1H-indazole-5-carbonyl)-2-oxospiro[indole-3,4'-piperidine]-1-yl]acetyl]pyrrolidine-2-carbonitrile | Pyrrolidine-2-carbonitrile (CAS RN 65732-69-6) INT16e | D | MS (ESI): m/z = 534.9 [M + H]+ |
| 144 | 1-[2-(3,3a,4,5,6,6a-Hexahydro-1H-cyclopenta[c]pyrrol-2-yl)-2-oxoethyl]-4-chloro-5-fluoro-1'-(1H-indazole-5-carbonyl)spiro[indole-3,4'-piperidine]-2-one | Octahydrocyclopenta[c]pyrrole (CAS RN 1260788-72-4) INT16e | D | MS (ESI): m/z = 550.0 [M + H]+ |
| 145 | 2-[4-Chloro-5-fluoro-1'-(1H-indazole-5-carbonyl)-2-oxospiro[indole-3,4'-piperidine]-1-yl]-N-(1-cyanocyclopropyl)acetamide | 1-Aminocyclopropane-1-carbonitrile (CAS RN 127946-77-4) INT16e | D | MS (ESI): m/z = 521.0 [M + H]+ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 146 | 4-Chloro-5-fluoro-1'-(1H-indazole-5-carbonyl)-1-[2-[2-(methoxymethyl)pyrrolidin-1-yl]-2-oxoethyl]spiro[indole-3,4'-piperidine]-2-one 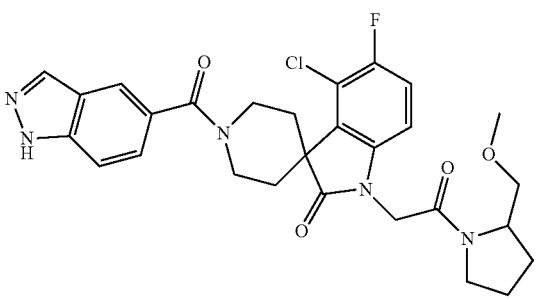 | 2-(Methoxymethyl)pyrrolidine (CAS RN 76946-27-5) INT16e | D | MS (ESI): m/z = 554.1 [M + H]+ |
| 147 | 4-Chloro-5-fluoro-1-[2-(3-fluoropyrrolidin-1-yl)-2-oxoethyl]-1'-(1H-indazole-5-carbonyl)spiro[indole-3,4'-piperidine]-2-one 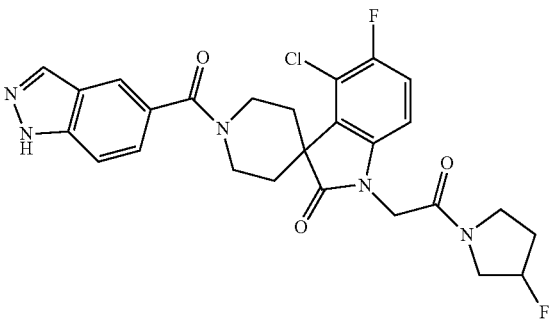 | 3-Fluoropyrrolidine (CAS RN 116574-74-4) INT16e | D | MS (ESI): m/z = 528.1 [M + H]+ |
| 148 | 4-Chloro-5-fluoro-1'-(1H-indazole-5-carbonyl)-1-[2-oxo-2-[(2S)-2-(trifluoromethyl)pyrrolidin-1-yl]ethyl]spiro[indole-3,4'-piperidine]-2-one 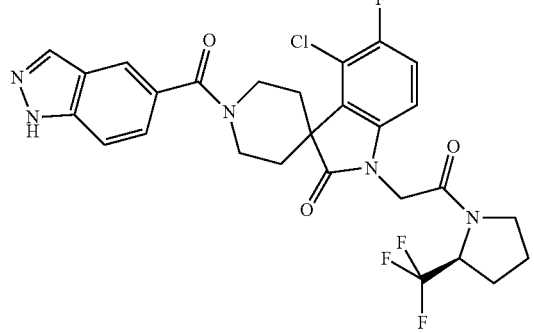 | (2S)-2-(Trifluoromethyl)pyrrolidine (CAS RN 119580-41-5) INT16e | D | MS (ESI): m/z = 578.1 [M + H]+ |

TABLE 7-continued (Examples 2 to 168)
The following examples were synthesized from the suitable building blocks/intermediates in
analogy to the methods from A to F, H to J, N, Q, R and V to Y as described before.

| Ex. | Systematic Name | Building blocks / intermediates | Method | MS, m/z |
|---|---|---|---|---|
| 149 | 4-Chloro-5-fluoro-1'-(1H-indazole-5-carbonyl)-1-[2-oxo-2-[(2R)-2-(trifluoromethyl)pyrrolidin-1-yl]ethyl]spiro[indole-3,4'-piperidine]-2-one | (2R)-2-(Trifluoromethyl)pyrrolidine (CAS RN 119618-29-0) | D | MS (ESI): m/z = 578.1 [M + H]⁺ |
| 150 | (-)-2-[4-Chloro-2-oxo-1'-(1H-pyrazolo[3,4-b]pyridine-5-carbonyl)spiro[indole-3,4'-piperidine]-1-yl]-3-morpholin-4-yl-N-(2,2,2-trifluoroethyl)propanamide | Example 128 | X (First eluting peak) | MS (ESI): m/z = 620.2 [M + H]⁺ |
| 151 | (+)-2-[4-Chloro-2-oxo-1'-(1H-pyrazolo[3,4-b]pyridine-5-carbonyl)spiro[indole-3,4'-piperidine]-1-yl]-3-morpholin-4-yl-N-(2,2,2-trifluoroethyl)propanamide | Example 128 | X (Second eluting peak) | MS (ESI): m/z = 620.2 [M + H]⁺ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 152 | (+) or (−)-4-Bromo-1′-(1H-indazole-5-carbonyl)-1-[2-[3-methyl-2,3-dihydroindol-1-yl]-2-oxoethyl]spiro[indole-3,4′-piperidine]-2-one | Example 125 | X (First eluting peak) | MS (ESI): m/z = 600.1 [M + H]⁺ |
| 153 | (−) or (+)-4-Bromo-1′-(1H-indazole-5-carbonyl)-1-[2-[3-methyl-2,3-dihydroindol-1-yl]-2-oxoethyl]spiro[indole-3,4′-piperidine]-2-one | Example 125 | X (Second eluting peak) | MS (ESI): m/z = 600.1 [M + H]⁺ |
| 154 | 4-Chloro-1-[2-[(3R,4S)-3-(dimethylamino)-4-fluoro-pyrrolidin-1-yl]-2-oxo-ethyl]-5-fluoro-1′-(1H-pyrazolo[4,3-b]pyridine-5-carbonyl)spiro[indoline-3,4′-piperidine]-2-one | INT41 INT12e | Y | MS (ESI): m/z = 570.2 [M + H]⁺ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 155 | 2-[4-Chloro-5-fluoro-1'-(1H-indazole-5-carbonyl)-2-oxospiro[indole-3,4'-piperidine]-1-yl]-N-(2,2-difluorocyclopropyl)acetamide | 2,2-Difluorocyclopropan-1-amine•HCl (CAS RN 105614-25-3) INT16e | D | MS (ESI): m/z = 532.2 [M + H]$^+$ |
| 156 | 4-Bromo-1-[2-[3-(fluoromethyl)-4-(trifluoromethyl)pyrrolidin-1-yl]-2-oxoethyl]-1'-(1H-indazole-5-carbonyl)spiro[indole-3,4'-piperidine]-2-one | INT40 INT6e | D | MS (ESI): m/z = 636.1 [M + H]$^+$ |
| 157 | 4-Chloro-5-fluoro-1'-(1H-indazole-5-carbonyl)-1-[2-(2-oxa-7-azaspiro[3.4]octan-7-yl)-2-oxoethyl]spiro[indole-3,4'-piperidine]-2-one | 2-Oxa-6-azaspiro[3.4]octane•oxalate salt (CAS RN 220290-68-6) INT16e | D | MS (ESI): m/z = 551.9 [M + H]$^+$ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 158 | 4-Bromo-1-[2-[(3R,4S)-3,4-difluoropyrrolidin-1-yl]-2-oxoethyl]-1'-(1H-indazole-5-carbonyl)spiro[indole-3,4'-piperidine]-2-one | (3R,4S)-3,4-difluoro-pyrrolidine (MFCD19220622; Enamine Ltd) INT6e | D | MS (ESI): m/z = 571.9 [M + H]+ |
| 159 | 4-Bromo-1-[2-(3,4-dihydro-1H-pyrrolo[1,2-a]pyrazin-2-yl)-2-oxoethyl]-1'-(1H-indazole-5-carbonyl)spiro[indole-3,4'-piperidine]-2-one | 1H,2H,3H,4H-Pyrrolo[1,2-a]pyrazine (CAS RN 71257-38-0) INT6e | D | MS (ESI): m/z = 586.8 [M + H]+ |
| 160 | 4-Bromo-1-[2-[(2S)-4,4-difluoro-2-(fluoromethyl)pyrrolidin-1-yl]-2-oxoethyl]-1'-(1H-indazole-5-carbonyl)spiro[indole-3,4'-piperidine]-2-one | (S)-4,4-Difluoro-2-(fluoromethyl)pyrrolidine hydrochloride (MFCD28119141) INT6e | D | MS (ESI): m/z = 604.1 [M + H]+ |

TABLE 7-continued (Examples 2 to 168)
The following examples were synthesized from the suitable building blocks/intermediates in analogy to the methods from A to F, H to J, N, Q, R and V to Y as described before.

| Ex. | Systematic Name | Building blocks / intermediates | Method | MS, m/z |
|---|---|---|---|---|
| 163 | 2-[4-Chloro-2-oxo-1'-(1H-pyrazolo[3,4-b]pyridine-5-carbonyl)spiro[indole-3,3'-pyrrolidine]-1-yl]-N-(2,2,2-trifluoroethyl)acetamide | 1H-Pyrazolo[3,4-b]pyridine-5-carboxylic acid (CAS RN 952182-02-4) INT38a | C | MS (ESI): m/z = 507.2 [M + H]$^+$ |
| 164 | 2-[4-Chloro-1'-(1H-indazole-5-carbonyl)-2-oxospiro[indole-3,3'-pyrrolidine]-1-yl]-N-(2,2,2-trifluoroethyl)acetamide | 1H-Indazole-5-carboxylic acid (CAS RN 61700-61-6) INT38a | C | MS (ESI): m/z = 506.2 [M + H]$^+$ |
| 165 | 2-[4-Chloro-2-oxo-1'-(1H-pyrazolo[4,3-b]pyridine-5-carbonyl)spiro[indole-3,3'-pyrrolidine]-1-yl]-N-(2,2,2-trifluoroethyl)acetamide | 1H-Pyrazolo[4,3-b]pyridine-5-carboxylic acid (CAS RN 1260670-03-8) INT38a | C | MS (ESI): m/z = 507.2 [M + H]$^+$ |
| 166 | (+) or (-)-2-[4-Chloro-1'-(1H-indazole-5-carbonyl)-2-oxospiro[indole-3,3'-pyrrolidine]-1-yl]-N-(2,2,2-trifluoroethyl)acetamide | Example 164 | X (First eluting peak) | MS (ESI): m/z = 506.1 [M + H]$^+$ |

TABLE 7-continued (Examples 2 to 168)
The following examples were synthesized from the suitable building blocks/intermediates in
analogy to the methods from A to F, H to J, N, Q, R and V to Y as described before.

| Ex. | Systematic Name | Building blocks / intermediates | Method | MS, m/z |
|---|---|---|---|---|
| 167 | (-) or (+)-2-[4-Chloro-1'-(1H-indazole-5-carbonyl)-2-oxospiro[indole-3,3'-pyrrolidine]-1-yl]-N-(2,2,2-trifluoroethyl)acetamide | Example 164 | X (Second eluting peak) | MS (ESI): m/z = 506.1 [M + H]$^+$ |
| 168 | 4,5-Dichloro-1-(2-oxo-2-(2-(2,2,2-trifluoroethyl)pyrrolidin-1-yl)ethyl)-1'-(1H-pyrazolo[4,3-b]pyridine-5-carbonyl)spiro[indoline-3,4'-piperidin]-2-one | 2-(2,2,2-Trifluoro-ethyl)pyrrolidine hydrochloride (CAS RN 1795277-48-3) INT15e | Y | MS (ESI): m/z = 609.2 [M + H]$^+$ |

Example 169

In Vitro Binding Assay for DDR1

An in vitro binding competition assay was performed to evaluate the effect of the compounds of present invention on DDR1 protein.

Binding Competition Assay:

This assay is based on the intracellular domain of the DDR1 protein which contains the kinase active site. The recombinant protein additionally carries a GST-tag that can be recognized by an Eu-labeled anti-GST antibody. A tracer compound binding to the active site is labeled with a dye so that a FRET donor acceptor pair can be formed. Excitation energy absorbed by the Europium complex (350 nm flash light or pulsed laser) is transferred to a suitable fluorescent dye, if it is in close proximity. Compounds binding competitively with the tracer molecule will displace the bound tracer molecules and reduce the FRET signal in a dose dependent manner. Due to the long lifetime of the Eu excited state, the emission of the donor and the acceptor can be measured in time-gated mode such that most of the intrinsic fluorescence contributions have already decayed. This results in high sensitivity, excellent reproducibility and high data quality. This sensitive detection method enables protein concentrations below 20 nM.

Protein, tracer and labeled antibody were obtained from commercial sources. The assay was performed in 384 low volume microtiter-plates with a final volume of 15 al. Dose response curves were generated from 16 compound dilutions in DMSO as solvent compound dilutions, a solution containing protein and labeled antibody, and a solution containing the tracer which is added in the last step. The fluorescence of donor and acceptor were then measured after one hour incubation at room temperature. Every assay run was quality-controlled with dose response curves for two reference compounds.

Table 9 provides IC50 values for DDR1 inhibition obtained according to the above binding competition assay for particular compounds of the present invention. Particular compounds of the present invention exhibit IC50 values for DDR1 inhibition ≤5000 nM, obtained according to the above binding competition assay. More particular compounds of the present invention exhibit IC50 values for DDR1 inhibition ≤1000 nM, obtained according to the above binding competition assay. Even more particular compounds of the present invention exhibit IC50 values for DDR1 inhibition ≤500 nM, obtained according to the above binding competition assay. Most particular compounds of the present invention exhibit IC50 values for DDR1 inhibition ≤100 nM, obtained according to the above binding competition assay.

TABLE 9

IC50 values for DDR1 inhibition measured using binding competition assay.

| Example | Binding IC50 [nM] DDR1 |
|---|---|
| 1 | 407.5 |
| 2 | 30.3 |
| 3 | 16.7 |
| 4 | 153.6 |
| 5 | 410.1 |
| 6 | 59.7 |
| 7 | 1589.1 |
| 8 | 1123.6 |
| 9 | 121.2 |
| 10 | 36.6 |
| 11 | 431.7 |
| 12 | 4362.2 |
| 13 | 104.5 |
| 14 | 260.8 |
| 15 | 468.3 |
| 16 | 38.9 |
| 17 | 89.3 |
| 18 | 258.3 |
| 19 | 2955.9 |
| 20 | 432.0 |
| 21 | 32.2 |
| 22 | 129.7 |
| 23 | 25.6 |
| 24 | 60.5 |
| 25 | 136.6 |
| 26 | 222.4 |
| 27 | 2988.1 |
| 28 | 129.7 |
| 29 | 397.5 |
| 30 | 597.0 |
| 31 | 55.7 |
| 32 | 84.9 |
| 33 | 29.5 |
| 34 | 22.6 |
| 35 | 29.6 |
| 36 | 48.4 |
| 37 | 43.9 |
| 38 | 1354.5 |
| 39 | 410.7 |
| 40 | 528.1 |
| 41 | 95.2 |
| 42 | 122.6 |
| 43 | 110.1 |
| 44 | 260.6 |
| 45 | 44.3 |
| 46 | 40.7 |
| 47 | 53.3 |
| 48 | 2199.2 |
| 49 | 101.8 |
| 50 | 89.5 |
| 51 | 278.9 |
| 52 | 204.5 |
| 53 | 4503.6 |
| 54 | 449.6 |
| 55 | 620.3 |
| 56 | 159.3 |
| 57 | 878.3 |
| 58 | 36.4 |
| 59 | 2155.1 |
| 60 | 103.5 |
| 61 | 387.5 |
| 62 | 46.9 |
| 63 | 37.8 |
| 64 | 80.1 |
| 65 | 64.8 |
| 66 | 57.0 |
| 67 | 62.4 |
| 68 | 104.5 |
| 69 | 72.8 |
| 70 | 288.0 |
| 71 | 57.3 |
| 72 | 17.6 |
| 73 | 16.6 |
| 74 | 312.1 |
| 75 | 28.2 |
| 76 | 41.3 |
| 77 | 3100.3 |
| 78 | 80.2 |
| 79 | 117.2 |
| 80 | 119.6 |
| 81 | 67.7 |
| 82 | 22.9 |
| 83 | 22.4 |
| 84 | 54.9 |
| 85 | 46.2 |
| 86 | 90.5 |
| 87 | 66.8 |
| 88 | 35.4 |
| 89 | 512.2 |
| 90 | 80.9 |
| 91 | 431.1 |
| 92 | 1119.0 |
| 93 | 963.7 |
| 94 | 44.6 |
| 95 | 26.8 |
| 96 | 44.5 |
| 97 | 130.8 |
| 98 | 18.2 |
| 99 | 30.1 |
| 100 | 27.9 |
| 101 | 34.7 |
| 102 | 53.0 |
| 103 | 50.3 |
| 104 | 211.95 |
| 105 | 3429.55 |
| 106 | 31.8 |
| 107 | 18.1 |
| 108 | 134.9 |
| 109 | 97.9 |
| 110 | 49.6 |
| 111 | 60.1 |
| 112 | 36.1 |
| 113 | 30.1 |
| 114 | 39.5 |
| 115 | 30.9 |
| 116 | 59.7 |
| 117 | 42 |
| 118 | 81.4 |
| 119 | 59.25 |
| 120 | 36.45 |
| 121 | 52.9 |
| 122 | 89.6 |
| 123 | 33.2 |
| 124 | 60.4 |
| 125 | 26.8 |
| 126 | 22.6 |
| 127 | 30.9 |
| 128 | 171.1 |
| 129 | 32.6 |
| 130 | 43.6 |
| 131 | 23.7 |
| 132 | 19 |
| 133 | 130 |
| 134 | 67.9 |

TABLE 9-continued

IC50 values for DDR1 inhibition measured using binding competition assay.

| Example | Binding IC50 [nM] DDR1 |
|---|---|
| 135 | 34.7 |
| 136 | 52.5 |
| 137 | 34.45 |
| 138 | 98.55 |
| 139 | 43.3 |
| 140 | 2739 |
| 141 | 34.2 |
| 142 | 80.4 |
| 143 | 64.5 |
| 144 | 21.2 |
| 145 | 57.2 |
| 146 | 48.4 |
| 147 | 96.1 |
| 148 | 47.2 |
| 149 | 102.5 |
| 150 | 226.55 |
| 151 | 160.75 |
| 152 | 40 |
| 153 | 53.8 |
| 154 | 119.7 |
| 155 | 38.3 |
| 156 | 18.5 |
| 157 | 34.4 |
| 158 | 64.9 |
| 159 | 30.5 |
| 160 | 15.8 |
| 161 | 263.6 |
| 162 | 110 |
| 163 | 3019.2 |
| 164 | 2342.8 |
| 165 | 2947 |
| 166 | 799 |
| 167 | 47593 |
| 168 | 26.8 |

The invention claimed is:
1. A compound of formula (I)

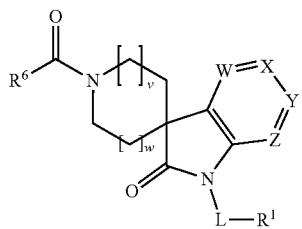

(I)

wherein
W is $CHR^2$ or N;
X is $CHR^3$ or N;
Y is $CHR^4$ or N;
Z is $CHR^5$ or N;
with the proviso that not more than two of W, X, Y and Z are N,
L is $-(CHR^7)_m-(CHR^8)_n-(CO)_q-$;
$R^1$ is $NR^9R^{10}$, aryl, heteroaryl, $C_{3-7}$ cycloalkyl, heterocycloalkyl, aryl annelated to cycloalkyl, aryl annelated to heterocycloalkyl, or heteroaryl annelated to heterocycloalkyl, wherein each of aryl, heteroaryl, $C_{3-7}$ cycloalkyl and heterocycloalkyl are optionally substituted with one or more $R^{1'}$;
each $R^{1'}$ is independently selected from halogen, cyano, $C_{1-7}$ alkyl, halo-$C_{1-7}$ alkyl, $C_{3-7}$ cycloalkyl, $C_{3-7}$ cycloalkyl-$C_{1-7}$ alkyl, heterocycloalkyl, heterocloalkyl-$C_{1-7}$ alkyl, phenyl, benzyl, heteroaryl, amino, hydroxy, $C_{1-7}$ alkoxy, halo-$C_{1-7}$ alkoxy, $C_{1-7}$ alkoxy-$C_{1-7}$ alkyl, oxo, $-CH_2-OR^{11}$, $-C(O)-OR^{11}$, and $-C(O)-NHR^{11}$;
or if $R^1$ is $C_{3-7}$ cycloalkyl or heterocycloalkyl then two $R^{1'}$ together are forming $-(CR^{12}R^{13})_s-$ or $-(CR^{12}R^{13})_t-O-(CR^{14}R^{15})_u-$;
$R^2$ is hydrogen, halogen, cyano, $C_{1-7}$ alkyl, halo-$C_{1-7}$ alkyl, hydroxy-$C_{1-7}$ alkyl, $C_{3-7}$ cycloalkyl, $C_{3-7}$ cycloalkyl-$C_{1-7}$ alkyl, amino, hydroxy, $C_{1-7}$ alkoxy, halo-$C_{1-7}$ alkoxy, $C_{1-7}$ alkoxy-$C_{1-7}$ alkyl, $-C(O)-C_{1-7}$ alkoxy or $-C(O)$-amino;
$R^3$ is hydrogen, halogen, cyano, $C_{1-7}$ alkyl, halo-$C_{1-7}$ alkyl, hydroxy-$C_{1-7}$ alkyl, $C_{3-7}$ cycloalkyl, $C_{3-7}$ cycloalkyl-$C_{1-7}$ alkyl, amino, hydroxy, $C_{1-7}$ alkoxy, halo-$C_{1-7}$ alkoxy, $C_{1-7}$ alkoxy-$C_{1-7}$ alkyl, $-C(O)-C_{1-7}$ alkoxy or $-C(O)$-amino;
$R^4$ is hydrogen, halogen, cyano, $C_{1-7}$ alkyl, halo-$C_{1-7}$ alkyl, hydroxy-$C_{1-7}$ alkyl, $C_{3-7}$ cycloalkyl, $C_{3-7}$ cycloalkyl-$C_{1-7}$ alkyl, amino, hydroxy, $C_{1-7}$ alkoxy, halo-$C_{1-7}$ alkoxy, $C_{1-7}$ alkoxy-$C_{1-7}$ alkyl, $-C(O)-C_{1-7}$ alkoxy or $-C(O)$-amino;
$R^5$ is hydrogen, halogen, cyano, $C_{1-7}$ alkyl, halo-$C_{1-7}$ alkyl, hydroxy-$C_{1-7}$ alkyl, $C_{3-7}$ cycloalkyl, $C_{3-7}$ cycloalkyl-$C_{1-7}$ alkyl, amino, hydroxy, $C_{1-7}$ alkoxy, halo-$C_{1-7}$ alkoxy, $C_{1-7}$ alkoxy-$C_{1-7}$ alkyl, $-C(O)-C_{1-7}$ alkoxy or $-C(O)$-amino;
$R^6$ is mono- or bicyclic heteroaryl comprising 2 to 5 heteroatoms selected from N, O or S, wherein $R^6$ is optionally substituted with one or more $R^{6'}$;
each $R^{6'}$ is independently selected from halogen, cyano, $C_{1-7}$ alkyl, halo-$C_{1-7}$ alkyl, $C_{3-7}$ cycloalkyl, amino, hydroxy, $C_{1-7}$ alkoxy, $-C(O)OH$, $-C(O)OCH_3$ and $-C(O)NH_2$;
$R^7$ is hydrogen, $C_{1-7}$ alkyl, hydroxy-$C_{1-7}$ alkyl, $C_{1-7}$ alkoxy-$C_{1-7}$ alkyl, halo-$C_{1-7}$ alkoxy-$C_{1-7}$ alkyl, $-(CH_2)_r$-phenyl, $-(CH_2)_r$-heteroaryl, $-(CH_2)_x-NR^{16}R^{17}$ or $R^7$ is forming $C_{1-7}$ alkylene with $R^{10}$;
$R^8$ is hydrogen, $C_{1-7}$ alkyl, or halo-$C_{1-7}$ alkyl;
$R^9$ is $C_{1-7}$ alkyl, $C_{3-7}$ cycloalkyl, heterocycloalkyl, heterocycloalkyl-$C_{1-7}$ alkyl, aryl, aryl annelated to $C_{5-6}$ cycloalkyl, heteroaryl, or $-CH_2-CH_2-NR^{18}R^{19}$, wherein $C_{1-7}$ alkyl, is optionally substituted with one or more $R^{9'}$, and wherein $C_{3-7}$ cycloalkyl, heterocycloalkyl, aryl annelated to $C_{5-6}$ cycloalkyl, aryl, benzyl, and heteroaryl are optionally substituted with one or more $R^{9''}$;
each $R^{9'}$ is independently selected from halogen, cyano, amino, hydroxy, $C_{1-7}$ alkoxy, $C_{1-7}$ alkyl, halo-$C_{1-7}$ alkoxy, $C_{3-7}$ cycloalkyl, halo-$C_{3-7}$ cycloalkyl, heterocycloalkyl, phenyl, and heteroaryl;
each $R^{9'''}$ is independently selected from halogen, cyano, $C_{1-7}$ alkyl, halo-$C_{1-7}$ alkyl, $C_{3-7}$ cycloalkyl, amino, hydroxy, $C_{1-7}$ alkoxy, halo-$C_{1-7}$ alkoxy, $C_{1-7}$ alkoxy-$C_{1-7}$ alkyl, oxo, $-CH_2-C(O)-NHC_{1-7}$ alkyl, heterocycloalkyl, phenyl, benzyl, heteroaryl and $C_{1-7}$ alkyl-heteroaryl;
$R^{10}$ is hydrogen, $C_{1-7}$ alkyl, $C_{3-7}$ cycloalkyl, halo-$C_{1-7}$ alkyl, or $R^{10}$ is forming $C_{1-7}$ alkylene with $R^7$;
$R^{11}$ is hydrogen, $C_{1-7}$alkyl, halo-$C_{1-7}$ alkyl, $C_{3-7}$ cycloalkyl, or heterocycloalkyl bound via C-atom;
$R^{12}$, $R^{13}$, $R^{14}$ and $R^{15}$ are each independently selected from hydrogen, halogen and $C_{1-7}$ alkyl;
$R^{16}$ and $R^{17}$ are independently selected from hydrogen and $C_{1-7}$ alkyl or $R^{16}$ and $R^{17}$ together with the nitrogen to which they are bound form heterocycloalkyl optionally substituted by $R^{21}$;

R¹⁸ and R¹⁹ are independently selected from hydrogen and $C_{1-7}$ alkyl or R¹⁸ and R¹⁹ together with the nitrogen to which they are bound form heterocycloalkyl;

R²¹ is $C_{1-7}$ alkyl, $C_{3-7}$ cycloalkyl, halo-$C_{1-7}$ alkyl;

m is 0, 1 or 2;
n is 0, 1 or 2;
q is 0 or 1;
r is 0, 1 or 2;
s is 2, 3 or 4;
t is 1 or 2;
u is 1 or 2;
v is 0 or 1;
w is 0 or 1;
x is 1 or 2;

or a pharmaceutically acceptable salt thereof;

with the proviso that if m=n=q=0 then R¹ is not heterocycloalkyl bound via a nitrogen ring atom or —NR⁹R¹⁰;

with the proviso that if R¹ is heterocycloalkyl bound to L via a nitrogen ring atom or R¹ is —NR⁹R¹⁰ then m+n≥2 if q=0;

with the proviso that 1'-(1-methylimidazole-2-carbonyl)-1-(3-quinolyl)spiro[indoline-3,4'-piperidine]-2-one and salts thereof are excluded.

2. The compound of formula (I) according to claim 1, wherein W is C<u>H</u>R².

3. The compound of formula (I) according to claim 1, wherein X is C<u>H</u>R³.

4. The compound of formula (I) according to claim 1, wherein Y is C<u>H</u>R⁴.

5. The compound of formula (I) according to claim 1, wherein Z is C<u>H</u>R⁵.

6. The compound of formula (I) according to claim 1, wherein L is —CH₂—, —CH₂—C(O)—, —CH(CH₂-morpholinyl)-C(O)—, —CH(R⁷)—C(O)— or —CH₂—CH₂—C(O)—; wherein R⁷ is forming ethylene with R¹⁰.

7. The compound of formula (I) according to claim 1, wherein R¹ is —NR⁹R¹⁰, aryl, heteroaryl, heterocycloalkyl, aryl annelated to heterocycloalkyl, or heteroaryl annelated to heterocycloalkyl, wherein each of aryl, heteroaryl, and heterocycloalkyl are optionally substituted with one or more R¹'.

8. The compound of formula (I) according to claim 1, wherein R¹ is —NR⁹R¹⁰, phenyl, oxadiazolyl, pyridinyl, azetidinyl, pyrrolidinyl, piperidinyl, piperazinyl, morpholinyl, thiomorpholinyl, 3-oxa-8-azabicyclo[3.2.1]octanyl, hexahydrocyclopenta[b]pyrrolyl, hexahydrocyclopenta[c]pyrrolyl, hexahydropyrrolo[1,2-a]pyrazinyl, 2-azaspiro[3.3]heptanyl, 5-azaspiro[2.5]octanyl, 2-oxa-7-azaspiro[3.4]octanyl, dihydroindolyl, benzo[b][1,4]oxazinyl, dihydropyrrolo[1,2-a]pyrazinyl, or tetrahydropyrrolo[3,2-c]pyridinyl, each except —NR⁹R¹⁰ optionally substituted with one, two, three or four R¹'.

9. The compound of formula (I) according to claim 1, wherein each R¹' is independently selected from halogen, cyano, $C_{1-7}$ alkyl, halo-$C_{1-7}$ alkyl, $C_{3-7}$ cycloalkyl, heterocycloalkyl-$C_{1-7}$ alkyl, hydroxy, $C_{1-7}$ alkoxy, $C_{1-7}$ alkoxy-$C_{1-7}$ alkyl, oxo, amino and —C(O)—OR¹¹.

10. The compound of formula (I) according to claim 1, wherein each R¹' is independently selected from fluoro, cyano, methyl, —CH₂F, —CF₃, —CH₂—CF₃, cyclopropyl, morpholinyl-CH₂—, hydroxy, methoxy, methoxy-methyl, oxo, dimethylamino and —C(O)—OCH₃.

11. The compound of formula (I) according to claim 1, wherein R² is hydrogen, halogen, cyano, $C_{1-7}$ alkyl, halo-$C_{1-7}$ alkyl, hydroxy-$C_{1-7}$ alkyl, $C_{3-7}$ cycloalkyl, hydroxy, $C_{1-7}$ alkoxy, or —C(O)—$C_{1-7}$alkoxy.

12. The compound of formula (I) according to claim 1, wherein R² is hydrogen, fluoro, chloro, bromo, cyano, methyl, ethyl, —CF₃, —CH₂OH, cyclopropyl, hydroxy, methoxy, ethoxy, or —C(O)—OCH₃.

13. The compound of formula (I) according to claim 1, wherein R³ is hydrogen, halogen, or $C_{1-7}$ alkoxy.

14. The compound of formula (I) according to claim 1, wherein R³ is hydrogen, fluoro, chloro, bromo, or methoxy.

15. The compound of formula (I) according to claim 1, wherein R⁴ is hydrogen or halogen.

16. The compound of formula (I) according to claim 1, wherein R⁵ is hydrogen or halogen.

17. The compound of formula (I) according to claim 1, wherein R⁶ is bicyclic heteroaryl comprising 2, 3 or 4 nitrogen atoms, wherein R⁶ is optionally substituted with one or more R⁶'.

18. The compound of formula (I) according to claim 1, wherein R⁶ is indazolyl, pyrazolo[3,4-b]pyridinyl, pyrazolo[3,4-c]pyridinyl, pyrazolo[4,3-b]pyridinyl, or 1H-pyrazolo[4,3-d]pyrimidinyl.

19. The compound of formula (I) according to claim 1, wherein R⁶' is —NH₂, —C(O)NH₂, —C(O)OH, or —C(O)OCH₃.

20. The compound of formula (I) according to claim 1, wherein R⁷ is hydrogen, —CH₂-morpholinyl, or R⁷ is forming $C_{1-7}$ alkylene with R¹⁰.

21. The compound of formula (I) according to claim 1, wherein R⁸ is hydrogen.

22. The compound of formula (I) according to claim 1, wherein R⁹ is $C_{1-7}$ alkyl, $C_{3-7}$ cycloalkyl, heterocycloalkyl, heterocycloalkyl-alkyl, heteroaryl or aryl annelated to $C_{5-6}$ cycloalkyl, wherein $C_{1-7}$ alkyl is optionally substituted with one, two or three R⁹', and wherein $C_{3-7}$ cycloalkyl, heterocycloalkyl, and aryl annelated to $C_{5-6}$ cycloalkyl are optionally substituted with one or two R⁹'''.

23. The compound of formula (I) according to claim 1, wherein R⁹ is methyl, ethyl, n-propyl, isopropyl, tert-butyl, cyclopropyl, cyclohexyl, oxetanyl, oxetanyl-methyl, oxazolyl, dihydroindenyl or tetrahydronaphthalenyl, wherein methyl, ethyl, n-propyl, isopropyl and tert-butyl are optionally substituted with one, two or three R⁹', and wherein cyclopropyl, cyclohexyl, oxetanyl, oxazolyl, dihydroindenyl and tetrahydronaphthalenyl are optionally substituted with one or two R⁹'''.

24. The compound of formula (I) according to claim 1, wherein each R⁹' is independently selected from halogen, cyano, oxetanyl or hydroxy.

25. The compound of formula (I) according to claim 1, wherein each R⁹''' is independently selected from halogen, cyano, $C_{1-7}$ alkyl and halo-$C_{1-7}$ alkyl.

26. The compound of formula (I) according to claim 1, wherein R¹⁰ is hydrogen, $C_{1-7}$ alkyl, or R¹⁰ is forming $C_{1-7}$ alkylene with R⁷.

27. The compound of formula (I) according to claim 1, wherein R¹¹ is $C_{1-7}$ alkyl.

28. The compound of formula (I) according to claim 1, wherein R¹⁶ and R¹⁷ together with the nitrogen to which they are bound form morpholinyl.

29. The compound of formula (I) according to claim 1, wherein m is 1.

30. The compound of formula (I) according to claim 1, wherein n is 0 or 1.

31. The compound of formula (I) according to claim 1, wherein q is 0 or 1.

32. The compound of formula (I) according to claim 1 selected from the group consisting of:

2-[1'-(1H-Indazole-5-carbonyl)-2-oxospiro[indole-3,4'-piperidine]-1-yl]-N-(2,2,2-trifluoroethyl)acetamide;

2-[1'-(1H-Indazole-5-carbonyl)-4-methyl-2-oxospiro[indole-3,4'-piperidine]-1-yl]-N-(2,2,2-trifluoroethyl)acetamide;

2-[4-Bromo-1'-(1H-indazole-5-carbonyl)-2-oxospiro[indole-3,4'-piperidine]-1-yl]-N-(2,2,2-trifluoroethyl)acetamide;

2-[4-Fluoro-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[1-(1H-Indazole-5-carbonyl)-5'-methoxy-2'-oxospiro[piperidine-4,3'-pyrrolo[3,2-b]pyridine]-1'-yl]-N-(2,2,2-trifluoroethyl)acetamide;

2-[4-Chloro-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[5-Bromo-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[5-Fluoro-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[4-Methoxy-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[4-Bromo-2-oxo-1'-(1H-pyrazolo[3,4-b]pyridine-5-carbonyl)spiro[indole-3,4'-piperidine]-1-yl]-N-(2,2,2-trifluoroethyl)acetamide;

Methyl 2-oxo-1-(2-oxo-2-((2,2,2-trifluoroethyl)amino)ethyl)-1'-(1H-pyrazolo[3,4-b]pyridine-5-carbonyl)spiro[indoline-3,4'-piperidine]-4-carboxylate;

2-[4-Ethyl-2-oxo-1'-(1-pyrazolo[3,4-b]pyridine-5-carbonyl)spiro[indole-3,4'-piperidine]-1-yl]-N-(2,2,2-trifluoroethyl)acetamide;

2-[4,5-Difluoro-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[4-Methyl-2-oxo-1'-(1H-pyrazolo[3,4-b]pyridine-5-carbonyl)spiro[indole-3,4'-piperidine]-1-yl]-N-(2,2,2-trifluoroethyl)acetamide;

Methyl 1'-(1H-indazole-5-carbonyl)-2-oxo-1-(2-oxo-2-((2,2,2-trifluoroethyl)amino)ethyl)spiro[indoline-3,4'-piperidine]-4-carboxylate;

(S)-4-Methyl-1-(2-oxo-2-(2-(trifluoromethyl)pyrrolidin-1-yl)ethyl)-1'-(1H-pyrazolo[3,4-b]pyridine-5-carbonyl)spiro[indoline-3,4'-piperidin]-2-one;

2-[4-Cyano-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[5-Chloro-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[6-Fluoro-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[4-Bromo-7-fluoro-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[4,5-Dichloro-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[4-Bromo-2-oxo-1'-(1H-pyrazolo[3,4-c]pyridine-5-carbonyl)spiro[indole-3,4'-piperidine]-1-yl]-N-(2,2,2-trifluoroethyl)acetamide;

2-[4-Bromo-2-oxo-1'-(1H-pyrazolo[4,3-b]pyridine-5-carbonyl)spiro[indole-3,4'-piperidine]-1-yl]-N-(2,2,2-trifluoroethyl)acetamide;

4-Methyl-1-(2-oxo-2-(2-(trifluoromethyl)morpholino)ethyl)-1'-(1H-pyrazolo[3,4-b]pyridine-5-carbonyl)spiro[indoline-3,4'-piperidin]-2-one;

2-[1'-(1H-Indazole-5-carbonyl)-4-methyl-2-oxospiro[indole-3,4'-piperidine]-1-yl]-N-[1-(trifluoromethyl)cyclopropyl]acetamide;

N-tert-Butyl-2-[1'-(1H-indazole-5-carbonyl)-4-methyl-2-oxospiro[indole-3,4'-piperidine]-1-yl]acetamide;

N-(1-Hydroxy-2-methylpropan-2-yl)-2-[1'-(1H-indazole-5-carbonyl)-4-methyl-2-oxospiro[indole-3,4'-piperidine]-1-yl]acetamide;

(rac, cis)-1-[2-[2,6-Dimethylmorpholin-4-yl]-2-oxoethyl]-1'-(1H-indazole-5-carbonyl)-4-methylspiro[indole-3,4'-piperidine]-2-one;

N-tert-Butyl-2-[1'-(1H-indazole-5-carbonyl)-4-methyl-2-oxospiro[indole-3,4'-piperidine]-1-yl]-N-methylacetamide;

2-[1'-(1H-Indazole-5-carbonyl)-4-methyl-2-oxospiro[indole-3,4'-piperidine]-1-yl]-N-[(2R)-1,1,1-trifluoropropan-2-yl]acetamide;

2-[4,5-Dichloro-2-oxo-1'-(1H-pyrazolo[3,4-c]pyridine-5-carbonyl)spiro[indole-3,4'-piperidine]-1-yl]-N-(2,2,2-trifluoroethyl)acetamide;

2-[4-Chloro-5-fluoro-2-oxo-1'-(1H-pyrazolo[3,4-c]pyridine-5-carbonyl)spiro[indole-3,4'-piperidine]-1-yl]-N-(2,2,2-trifluoroethyl)acetamide;

2-[4-Chloro-5-fluoro-1'-(1H-indazole-5-carbonyl)-2-oxospiro[indole-3,4'-piperidine]-1-yl]-N-(2,2,2-trifluoroethyl)acetamide;

2-[4,5-Dichloro-2-oxo-1'-(1H-pyrazolo[4,3-b]pyridine-5-carbonyl)spiro[indole-3,4'-piperidine]-1-yl]-N-(2,2,2-trifluoroethyl)acetamide;

2-[4-Chloro-5-fluoro-2-oxo-1'-(1H-pyrazolo[4,3-b]pyridine-5-carbonyl)spiro[indole-3,4'-piperidine]-1-yl]-N-(2,2,2-trifluoroethyl)acetamide;

2-[4-Chloro-5-fluoro-2-oxo-1'-(1H-pyrazolo[3,4-b]pyridine-5-carbonyl)spiro[indole-3,4'-piperidine]-1-yl]-N-(2,2,2-trifluoroethyl)acetamide;

2-[4,5-Dichloro-1'-(1H-indazole-5-carbonyl)-2-oxospiro[indole-3,4'-piperidine]-1-yl]-N-(2,2,2-trifluoroethyl)acetamide;

2-[2-Oxo-1'-(1H-pyrazolo[3,4-b]pyridine-5-carbonyl)-4-(trifluoromethyl)spiro[indole-3,4'-piperidine]-1-yl]-N-(2,2,2-trifluoroethyl)acetamide;

1-[2-(4-Hydroxy-3,3-dimethylpyrrolidin-1-yl)-2-oxoethyl]-1'-(1H-indazole-5-carbonyl)-4-methylspiro[indole-3,4'-piperidine]-2-one;

1-[2-(3,3-Difluoro-4-hydroxypyrrolidin-1-yl)-2-oxoethyl]-1'-(1H-indazole-5-carbonyl)-4-methylspiro[indole-3,4'-piperidine]-2-one;

1-[2-(3,3-Difluoropyrrolidin-1-yl)-2-oxoethyl]-1'-(1H-indazole-5-carbonyl)-4-methylspiro[indole-3,4'-piperidine]-2-one;

1-[2-(3-Fluoro-3-methylpyrrolidin-1-yl)-2-oxoethyl]-1'-(1H-indazole-5-carbonyl)-4-methylspiro[indole-3,4'-piperidine]-2-one;

1-[2-[3-Hydroxy-3-(trifluoromethyl)pyrrolidin-1-yl]-2-oxoethyl]-1'-(1H-indazole-5-carbonyl)-4-methylspiro[indole-3,4'-piperidine]-2-one;

(S)-Methyl 4,4-difluoro-1-(2-(4-methyl-2-oxo-1'-(1H-pyrazolo[3,4-b]pyridine-5-carbonyl)spiro[indoline-3,4'-piperidin]-1-yl)acetyl)pyrrolidine-2-carboxylate;

(S)-4-Bromo-1'-(1H-indazole-5-carbonyl)-1-(2-oxo-2-(2-(trifluoromethyl)pyrrolidin-1-yl)ethyl)spiro[indoline-3,4'-piperidin]-2-one;
(S)-4-Methyl-1-(2-oxo-2-(2-(trifluoromethyl)pyrrolidin-1-yl)ethyl)-1'-(1H-pyrazolo[4,3-b]pyridine-5-carbonyl)spiro[indoline-3,4'-piperidin]-2-one;
2-[1'-(1H-Indazole-5-carbonyl)-4-methyl-2-oxospiro[indole-3,4'-piperidine]-1-yl]-N-[(2S)-1,1,1-trifluoropropan-2-yl]acetamide;
2-[1'-(1H-Indazole-5-carbonyl)-4-methyl-2-oxospiro[indole-3,4'-piperidine]-1-yl]-N-(3-methyloxetan-3-yl)acetamide;
1-[(3-Cyclopropyl-1,2,4-oxadiazol-5-yl)methyl]-1'-(1H-indazole-5-carbonyl)-4-methylspiro[indole-3,4'-piperidine]-2-one;
2-(4-Methyl-2-oxo-1'-(1H-pyrazolo[4,3-b]pyridine-5-carbonyl)spiro[indoline-3,4'-piperidin]-1-yl)-N-(2,2,2-trifluoroethyl)acetamide;
N-(2-Cyanopropan-2-yl)-2-[1'-(1H-indazole-5-carbonyl)-4-methyl-2-oxospiro[indole-3,4'-piperidine]-1-yl]acetamide;
(S)-4-Methyl-1-(2-oxo-2-(2-(trifluoromethyl)pyrrolidin-1-yl)ethyl)-1'-(1H-pyrazolo[3,4-c]pyridine-5-carbonyl)spiro[indoline-3,4'-piperidin]-2-one;
2-(4-(Hydroxymethyl)-1'-(1H-indazole-5-carbonyl)-2-oxospiro[indoline-3,4'-piperidin]-1-yl)-N-(2,2,2-trifluoroethyl)acetamide;
N-(2,3-Dihydro-1H-inden-1-yl)-2-[1'-(1H-indazole-5-carbonyl)-4-methyl-2-oxospiro[indole-3,4'-piperidine]-1-yl]acetamide;
2-[1'-(1H-Indazole-5-carbonyl)-4-methyl-2-oxospiro[indole-3,4'-piperidine]-1-yl]-N-(1,2,3,4-tetrahydronaphthalen-1-yl)acetamide;
N-(2,2-Difluorocyclohexyl)-2-[1'-(1H-indazole-5-carbonyl)-4-methyl-2-oxospiro[indole-3,4'-piperidine]-1-yl]acetamide;
1-[2-[1'-(1H-Indazole-5-carbonyl)-4-methyl-2-oxospiro[indole-3,4'-piperidine]-1-yl]acetyl]pyrrolidine-3-carbonitrile;
2-[4-Chloro-1'-(1H-indazole-5-carbonyl)-2-oxospiro[indole-3,4'-piperidine]-1-yl]-N-(2,2,2-trifluoroethyl)acetamide;
2-[4-Cyclopropyl-1'-(1H-indazole-5-carbonyl)-2-oxospiro[indole-3,4'-piperidine]-1-yl]-N-(2,2,2-trifluoroethyl)acetamide;
4-Chloro-1'-(1H-indazole-5-carbonyl)-1-[2-oxo-2-[2S)-2-(trifluoromethyl)pyrrolidin-1-yl]ethyl]spiro[indole-3,4'-piperidine]-2-one;
1-(2-(3-Oxa-8-azabicyclo[3.2.1]octan-8-yl)-2-oxoethyl)-4-bromo-1'-(1H-indazole-5-carbonyl)spiro[indoline-3,4'-piperidin]-2-one;
4-Bromo-1'-(1H-indazole-5-carbonyl)-1-(2-oxo-2-(2-(trifluoromethyl)morpholino)ethyl)spiro[indoline-3,4'-piperidin]-2-one;
4-Bromo-1-(2-(3,3-difluoropyrrolidin-1-yl)-2-oxoethyl)-1'-(1H-indazole-5-carbonyl)spiro[indoline-3,4'-piperidin]-2-one;
4-Bromo-1'-(1H-indazole-5-carbonyl)-1-(2-oxo-2-(3-(trifluoromethyl)pyrrolidin-1-yl)ethyl)spiro[indoline-3,4'-piperidin]-2-one;
4-Bromo-1-(2-oxo-2-(3-(trifluoromethyl)pyrrolidin-1-yl)ethyl)-1'-(1H-pyrazolo[4,3-b]pyridine-5-carbonyl)spiro[indoline-3,4'-piperidin]-2-one;
4-Bromo-1-(2-(3,3-difluoropyrrolidin-1-yl)-2-oxoethyl)-1'-(1H-pyrazolo[4,3-b]pyridine-5-carbonyl)spiro[indoline-3,4'-piperidin]-2-one;

4-Bromo-1-(2-oxo-2-(3-(trifluoromethyl)pyrrolidin-1-yl)ethyl)-1'-(1H-pyrazolo[3,4-b]pyridine-5-carbonyl)spiro[indoline-3,4'-piperidin]-2-one;
4-Bromo-1-(2-(3,3-difluoropyrrolidin-1-yl)-2-oxoethyl)-1'-(1H-pyrazolo[3,4-b]pyridine-5-carbonyl)spiro[indoline-3,4'-piperidin]-2-one;
4-Bromo-1-(2-oxo-2-(3-(trifluoromethyl)pyrrolidin-1-yl)ethyl)-1'-(1H-pyrazolo[3,4-c]pyridine-5-carbonyl)spiro[indoline-3,4'-piperidin]-2-one;
4-Bromo-1-(2-(3,3-difluoropyrrolidin-1-yl)-2-oxoethyl)-1'-(1H-pyrazolo[3,4-c]pyridine-5-carbonyl)spiro[indoline-3,4'-piperidin]-2-one;
(S)-4-Bromo-1-(2-oxo-2-(2-(trifluoromethyl)pyrrolidin-1-yl)ethyl)-1'-(1H-pyrazolo[3,4-c]pyridine-5-carbonyl)spiro[indoline-3,4'-piperidin]-2-one;
(S)-4-Bromo-1-(2-oxo-2-(2-(trifluoromethyl)pyrrolidin-1-yl)ethyl)-1'-(1H-pyrazolo[4,3-b]pyridine-5-carbonyl)spiro[indoline-3,4'-piperidin]-2-one;
4-Bromo-1-(2-oxo-2-(2-(trifluoromethyl)morpholino)ethyl)-1'-(1H-pyrazolo[4,3-b]pyridine-5-carbonyl)spiro[indoline-3,4'-piperidin]-2-one;
4-Bromo-1-[2-(3-oxa-8-azabicyclo[3.2.1]octan-8-yl)-2-oxoethyl]-1'-(1H-pyrazolo[4,3-b]pyridine-5-carbonyl)spiro[indole-3,4'-piperidine]-2-one;
(S)-4-Bromo-1-(2-oxo-2-(2-(trifluoromethyl)pyrrolidin-1-yl)ethyl)-1'-(1H-pyrazolo[3,4-b]pyridine-5-carbonyl)spiro[indoline-3,4'-piperidin]-2-one;
4-Bromo-1-(2-oxo-2-(2-(trifluoromethyl)morpholino)ethyl)-1'-(1H-pyrazolo[3,4-b]pyridine-5-carbonyl)spiro[indoline-3,4'-piperidin]-2-one;
1-(2-(3-Oxa-8-azabicyclo[3.2.1]octan-8-yl)-2-oxoethyl)-4-bromo-1'-(1H-pyrazolo[3,4-b]pyridine-5-carbonyl)spiro[indoline-3,4'-piperidin]-2-one;
4-Chloro-1-[(3-cyclopropyl-1,2,4-oxadiazol-5-yl)methyl]-1'-(1H-indazole-5-carbonyl)spiro[indole-3,4'-piperidine]-2-one;
4-Bromo-1'-(1H-indazole-5-carbonyl)-1-(2-oxo-2-(3,3,4-trimethylpiperazin-1-yl)ethyl)spiro[indoline-3,4'-piperidin]-2-one;
1-(1H-Indazole-5-carbonyl)-5'-methoxy-1[2-oxo-2-[(2S)-2-(trifluoromethyl)pyrrolidin-1-yl]ethyl]spiro[piperidine-4,3'-pyrrolo[3,2-b]pyridine]-2'-one;
2-[1'-(1H-Indazole-5-carbonyl)-4-methyl-2-oxospiro[indole-3,4'-piperidine]-1-yl]-N-methyl-N-[(2S)-1,1,1-trifluoropropan-2-yl]acetamide;
2-[4-Bromo-5-fluoro-2-oxo-1'-(1H-pyrazolo[3,4-b]pyridine-5-carbonyl)spiro[indole-3,4'-piperidine]-1-yl]-N-(2,2,2-trifluoroethyl)acetamide;
2-[4-Bromo-5-fluoro-1'-(1H-indazole-5-carbonyl)-2-oxospiro[indole-3,4'-piperidine]-1-yl]-N-(2,2,2-trifluoroethyl)acetamide;
4-Bromo-1-(2-(3,3-dimethylmorpholino)-2-oxoethyl)-1'-(1H-indazole-5-carbonyl)spiro[indoline-3,4'-piperidin]-2-one;
1-(2-(2H-Benzo[b][1,4]oxazin-4(3H)-yl)-2-oxoethyl)-4-bromo-1'-(1H-indazole-5-carbonyl)spiro[indoline-3,4'-piperidin]-2-one;
2-(4-Bromo-1'-(1H-indazole-5-carbonyl)-2-oxospiro[indoline-3,4'-piperidin]-1-yl)-N-(pyridin-2-yl)acetamide;
2-(4-Bromo-1'-(1H-indazole-5-carbonyl)-2-oxospiro[indoline-3,4'-piperidin]-1-yl)-N-(2-(morpholinomethyl)phenyl)acetamide;
2-(4-Bromo-1'-(1H-indazole-5-carbonyl)-2-oxospiro[indoline-3,4'-piperidin]-1-yl)-N-phenylacetamide;

2-[4-Ethoxy-1'-(1H-indazole-5-carbonyl)-2-oxospiro[indole-3,4'-piperidine]-1-yl]-N-(2,2,2-trifluoroethyl)acetamide;

2-[1'-(1H-Indazole-5-carbonyl)-4-methyl-2-oxospiro[indole-3,4'-piperidine]-1-yl]-N-(3,3,3-trifluoropropyl) acetamide;

2-[1'-(1H-Indazole-5-carbonyl)-4-methyl-2-oxospiro[indole-3,4'-piperidine]-1-yl]-N-methyl-N-[(2R)-1,1,1-trifluoropropan-2-yl]acetamide;

3-[1'-(1H-Indazole-5-carbonyl)-4-methyl-2-oxospiro[indole-3,4'-piperidine]-1-yl]-N-(2,2,2-trifluoroethyl)propanamide;

2-[4-Hydroxy-1'-(1H-indazole-5-carbonyl)-2-oxospiro[indole-3,4'-piperidine]-1-yl]-N-(2,2,2-trifluoroethyl)acetamide;

5'-Chloro-1-(1H-indazole-5-carbonyl)-1 [2-oxo-2-[(2S)-2-(trifluoromethyl)pyrrolidin-1-yl]ethyl]spiro[piperidine-4,3'-pyrrolo[3,2-b]pyridine]-2'-one;

4-Bromo-1'-(1H-indazole-5-carbonyl)-1-[2-oxo-2-[2-(2,2,2-trifluoroethyl)pyrrolidin-1-yl]ethyl]spiro[indoline-3,4'-piperidine]-2-one;

4-Bromo-1-[2-(4,4-difluoro-1-piperidyl)-2-oxo-ethyl]-1'-(1H-indazole-5-carbonyl)spiro[indoline-3,4'-piperidine]-2-one;

4-Bromo-1'-(1H-indazole-5-carbonyl)-1-[2-oxo-2-(1-piperidyl)ethyl]spiro[indoline-3,4'-piperidine]-2-one;

1-[2-(3,3a,4,5,6,6a-Hexahydro-2H-cyclopenta[b]pyrrol-1-yl)-2-oxo-ethyl]-4-bromo-1'-(1H-indazole-5-carbonyl)spiro[indoline-3,4'-piperidine]-2-one;

4-Chloro-5-fluoro-1-[2-oxo-2-[2-(2,2,2-trifluoroethyl)pyrrolidin-1-yl]ethyl]-1'-(1H-pyrazolo[4,3-b]pyridine-5-carbonyl)spiro[indoline-3,4'-piperidine]-2-one;

1-[2-(3,3a,4,5,6,6a-Hexahydro-2H-cyclopenta[b]pyrrol-1-yl)-2-oxo-ethyl]-4-chloro-5-fluoro-1'-(1H-pyrazolo[4,3-b]pyridine-5-carbonyl)spiro[indoline-3,4'-piperidine]-2-one;

4-Chloro-5-fluoro-1-[2-oxo-2-[(2S)-2-(trifluoromethyl)pyrrolidin-1-yl]ethyl]-1'-(1H-pyrazolo[4,3-b]pyridine-5-carbonyl)spiro[indoline-3,4'-piperidine]-2-one;

4-Chloro-5-fluoro-1-[2-oxo-2-[(trifluoromethyl)morpholin-4-yl]ethyl]-1'-(1H-pyrazolo[4,3-b]pyridine-5-carbonyl)spiro[indoline-3,4'-piperidine]-2-one;

2-[1'-(3-Amino-1H-indazole-6-carbonyl)-4-chloro-5-fluoro-2-oxospiro[indole-3,4'-piperidine]-1-yl]-N-(2,2,2-trifluoroethyl)acetamide;

(−)-4-Chloro-1-[2-oxo-1-(2,2,2-trifluoroethyl)piperidin-3-yl]-1'-(1H-pyrazolo[3,4-b]pyridine-5-carbonyl)spiro[indole-3,4'-piperidine]-2-one;

(+)-4-Chloro-1-[2-oxo-1-(2,2,2-trifluoroethyl)piperidin-3-yl]-1'-(1H-pyrazolo[3,4-b]pyridine-5-carbonyl)spiro[indole-3,4'-piperidine]-2-one;

4-Bromo-1'-(1H-indazole-5-carbonyl)-1-[2-(2-methylthiomorpholin-4-yl)-2-oxoethyl]spiro[indole-3,4'-piperidine]-2-one;

1-[2-(5-Azaspiro[2.5]octan-5-yl)-2-oxoethyl]-4-bromo-1'-(1H-indazole-5-carbonyl)spiro[indole-3,4'-piperidine]-2-one;

4-Bromo-1'-(1H-indazole-5-carbonyl)-1-[2-oxo-2-(4-oxo-1,3,6,7,8,8a-hexahydropyrrolo[1,2-a]pyrazin-2-yl)ethyl]spiro[indole-3,4'-piperidine]-2-one;

4-Bromo-1-[2-(3-fluoropyrrolidin-1-yl)-2-oxoethyl]-1'-(1H-indazole-5-carbonyl)spiro[indole-3,4'-piperidine]-2-one;

(−)-4,5-Dichloro-1-[2-oxo-2-[2-(2,2,2-trifluoroethyl)pyrrolidin-1-yl]ethyl]-1'-(1H-pyrazolo[4,3-b]pyridine-5-carbonyl)spiro[indole-3,4'-piperidine]-2-one;

(+)-4,5-Dichloro-1-[2-oxo-2-[2-(2,2,2-trifluoroethyl)pyrrolidin-1-yl]ethyl]-1'-(1H-pyrazolo[4,3-b]pyridine-5-carbonyl)spiro[indole-3,4'-piperidine]-2-one;

(−)-4-Chloro-5-fluoro-1-[2-oxo-2-[2-(2,2,2-trifluoroethyl)pyrrolidin-1-yl]ethyl]-1'-(1H-pyrazolo[4,3-b]pyridine-5-carbonyl)spiro[indole-3,4'-piperidine]-2-one;

(+)-4-Chloro-5-fluoro-1-[2-oxo-2-[2-(2,2,2-trifluoroethyl)pyrrolidin-1-yl]ethyl]-1'-(1H-pyrazolo[4,3-b]pyridine-5-carbonyl)spiro[indole-3,4'-piperidine]-2-one;

(+)-1-[2-[3,3a,4,5,6,6a-Hexahydro-2H-cyclopenta[b]pyrrol-1-yl]-2-oxoethyl]-4-chloro-5-fluoro-1'-(1H-pyrazolo[4,3-b]pyridine-5-carbonyl)spiro[indole-3,4'-piperidine]-2-one;

(−)-1-[2-[3,3a,4,5,6,6a-Hexahydro-2H-cyclopenta[b]pyrrol-1-yl]-2-oxoethyl]-4-chloro-5-fluoro-1'-(1H-pyrazolo[4,3-b]pyridine-5-carbonyl)spiro[indole-3,4'-piperidine]-2-one;

(+) or (−)-4-Chloro-5-fluoro-1-[2-oxo-2-[2-(trifluoromethyl)morpholin-4-yl]ethyl]-1'-(1H-pyrazolo[4,3-b]pyridine-5-carbonyl)spiro[indole-3,4'-piperidine]-2-one;

(−) or (+)-4-Chloro-5-fluoro-1-[2-oxo-2-[2-(trifluoromethyl)morpholin-4-yl]ethyl]-1'-(1H-pyrazolo[4,3-b]pyridine-5-carbonyl)spiro[indole-3,4'-piperidine]-2-one;

2-[4'-Bromo-1-(1H-indazole-5-carbonyl)-2'-oxospiro[azetidine-3,3'-indole]-1'-yl]-N-(2,2,2-trifluoroethyl)acetamide;

2-[4-Bromo-2-oxo-1'-(1H-pyrazolo[4,3-d]pyrimidine-5-carbonyl)spiro[indole-3,4'-piperidine]-1-yl]-N-(2,2,2-trifluoroethyl)acetamide;

2-[4-Chloro-5-fluoro-2-oxo-1'-(1H-pyrazolo[4,3-d]pyrimidine-5-carbonyl)spiro[indole-3,4'-piperidine]-1-yl]-N-(2,2,2-trifluoroethyl)acetamide;

2-[4-Bromo-1'-(1H-indazole-5-carbonyl)-2-oxospiro[indole-3,4'-piperidine]-1-yl]-N-methyl-N-(oxetan-3-ylmethyl)acetamide;

2-[4-Bromo-1'-(1H-indazole-5-carbonyl)-2-oxospiro[indole-3,4'-piperidine]-1-yl]-N-(cyanomethyl)-N-methylacetamide;

2-[4-Bromo-1'-(1H-indazole-5-carbonyl)-2-oxospiro[indole-3,4'-piperidine]-1-yl]-N-methyl-N-(5-methyl-1,2-oxazol-3-yl)acetamide;

4-Bromo-1'-(1H-indazole-5-carbonyl)-1-[2-oxo-2-(1,4,6,7-tetrahydropyrrolo[3,2-c]pyridin-5-yl)ethyl]Spiro[indole-3,4'-piperidine]-2-one;

4-Bromo-1'-(1H-indazole-5-carbonyl)-1-[2-(3-methyl-2,3-dihydroindol-1-yl)-2-oxoethyl]spiro[indole-3,4'-piperidine]-2-one;

4-Bromo-1-[2-(5-fluoro-2,3-dihydroindol-1-yl)-2-oxoethyl]-1'-(1H-indazole-5-carbonyl)spiro[indole-3,4'-piperidine]-2-one;

(2S)-1-[2-[4-Bromo-1'-(1H-indazole-5-carbonyl)-2-oxospiro[indole-3,4'-piperidine]-1-yl]acetyl]pyrrolidine-2-carbonitrile;

2-[4-Chloro-2-oxo-1'-(1H-pyrazolo[3,4-b]pyridine-5-carbonyl)spiro[indole-3,4'-piperidine]-1-yl]-3-morpholin-4-yl-N-(2,2,2-trifluoroethyl)propanamide;

4-Chloro-1-[2-(2,2-dimethylpyrrolidin-1-yl)-2-oxoethyl]-5-fluoro-1'-(1H-pyrazolo[4,3-b]pyridine-5-carbonyl)spiro[indole-3,4'-piperidine]-2-one;

4-Chloro-5-fluoro-1-[2-oxo-2-[3-(trifluoromethyl)azetidin-1-yl]ethyl]-1'-(1H-pyrazolo[4,3-b]pyridine-5-carbonyl)spiro[indole-3,4'-piperidine]-2-one;

1-[2-[(3aR,6aS)-3,3a,4,5,6,6a-Hexahydro-1H-cyclopenta[c]pyrrol-2-yl]-2-oxoethyl]-4-chloro-5-fluoro-1'-(1H-pyrazolo[4,3-b]pyridine-5-carbonyl)spiro[indole-3,4'-piperidine]-2-one;

1-[2-[(3aR,6aS)-3,3a,4,5,6,6a-Hexahydro-1H-cyclopenta[c]pyrrol-2-yl]-2-oxoethyl]-4-bromo-1'-(1H-indazole-5-carbonyl)spiro[indole-3,4'-piperidine]-2-one;

1-[2-(3,4,6,7,8,8a-Hexahydro-1H-pyrrolo[1,2-a]pyrazin-2-yl)-2-oxoethyl]-4-bromo-1'-(1H-indazole-5-carbonyl)spiro[indole-3,4'-piperidine]-2-one;

1-[2-(3,4,6,7,8,8a-Hexahydro-1H-pyrrolo[1,2-a]pyrazin-2-yl)-2-oxoethyl]-4-chloro-5-fluoro-1'-(1H-pyrazolo[4,3-b]pyridine-5-carbonyl)spiro[indole-3,4'-piperidine]-2-one;

4-Chloro-1-[2-(7,7-difluoro-2-azaspiro[3.3]heptan-2-yl)-2-oxoethyl]-5-fluoro-1'-(1H-pyrazolo[4,3-b]pyridine-5-carbonyl)spiro[indole-3,4'-piperidine]-2-one;

2-[1-(3-Amino-1H-indazole-6-carbonyl)-4'-bromo-2'-oxospiro[azetidine-3,3'-indole]-1'-yl]-N-(2,2,2-trifluoroethyl)acetamide;

2-[4'-Bromo-2'-oxo-1-(1H-pyrazolo[4,3-b]pyridine-5-carbonyl)spiro[azetidine-3,3'-indole]-1'-yl]-N-(2,2,2-trifluoroethyl)acetamide;

4-Chloro-1-[2-(3,3-difluoroazetidin-1-yl)-2-oxoethyl]-5-fluoro-1'-(1H-indazole-5-carbonyl)spiro[indole-3,4'-piperidine]-2-one;

4-Bromo-1-[2-(2,3-dihydroindol-1-yl)-2-oxoethyl]-1'-(1H-indazole-5-carbonyl)spiro[indole-3,4'-piperidine]-2-one;

5-[4-Chloro-2-oxo-1-[2-oxo-2-(2,2,2-trifluoroethylamino)ethyl]spiro[indole-3,4'-piperidine]-1'-carbonyl]-1H-indazole-3-carboxamide;

4-Chloro-5-fluoro-1'-(1H-indazole-5-carbonyl)-1-[2-oxo-2-(3,3,4,4-tetrafluoropyrrolidin-1-yl)ethyl]spiro[indole-3,4'-piperidine]-2-one;

4-Chloro-5-fluoro-1'-(1H-indazole-5-carbonyl)-1-[2-(3-methoxypyrrolidin-1-yl)-2-oxoethyl]Spiro[indole-3,4'-piperidine]-2-one;

1-[2-[4-Chloro-5-fluoro-1'-(1H-indazole-5-carbonyl)-2-oxospiro[indole-3,4'-piperidine]-1-yl]acetyl]pyrrolidine-2-carbonitrile;

1-[2-(3,3a,4,5,6,6a-Hexahydro-1H-cyclopenta[c]pyrrol-2-yl)-2-oxoethyl]-4-chloro-5-fluoro-1'-(1H-indazole-5-carbonyl)spiro[indole-3,4'-piperidine]-2-one;

2-[4-Chloro-5-fluoro-1'-(1H-indazole-5-carbonyl)-2-oxospiro[indole-3,4'-piperidine]-1-yl]N-(1-cyanocyclopropyl)acetamide;

4-Chloro-5-fluoro-1'-(1H-indazole-5-carbonyl)-1-[2-[2-(methoxymethyl)pyrrolidin-1-yl]-2-oxoethyl]Spiro[indole-3,4'-piperidine]-2-one;

4-Chloro-5-fluoro-1-[2-(3-fluoropyrrolidin-1-yl)-2-oxoethyl]-1'-(1H-indazole-5-carbonyl)spiro[indole-3,4'-piperidine]-2-one;

4-Chloro-5-fluoro-1'-(1H-indazole-5-carbonyl)-1-[2-oxo-2-[(2S)-2-(trifluoromethyl)pyrrolidin-1-yl]ethyl]spiro[indole-3,4'-piperidine]-2-one;

4-Chloro-5-fluoro-1'-(1H-indazole-5-carbonyl)-1-[2-oxo-2-[(2R)-2-(trifluoromethyl)pyrrolidin-1-yl]ethyl]spiro[indole-3,4'-piperidine]-2-one;

(−)-2-[4-Chloro-2-oxo-1'-(1H-pyrazolo[3,4-b]pyridine-5-carbonyl)spiro[indole-3,4'-piperidine]-1-yl]-3-morpholin-4-yl-N-(2,2,2-trifluoroethyl)propanamide;

(+)-2-[4-Chloro-2-oxo-1'-(1H-pyrazolo[3,4-b]pyridine-5-carbonyl)spiro[indole-3,4'-piperidine]-1-yl]-3-morpholin-4-yl-N-(2,2,2-trifluoroethyl)propanamide;

(+) or (−)-4-Bromo-1'-(1H-indazole-5-carbonyl-1-[2-[3-methyl-2,3-dihydroindol-1-yl]-2-oxoethyl]spiro[indole-3,4'-piperidine]-2-one;

(−) or (+)-4-Bromo-1'-(1H-indazole-5-carbonyl)-1-[2-[3-methyl-2,3-dihydroindol-1-yl]-2-oxoethyl]spiro[indole-3,4'-piperidine]-2-one;

4-Chloro-1-[2-[(3R,4S)-3-(dimethylamino)-4-fluoropyrrolidin-1-yl]-2-oxoethyl]-5-fluoro-1'-(1H-pyrazolo[4,3-b]pyridine-5-carbonyl)spiro[indole-3,4'-piperidine]-2-one;

2-[4-Chloro-5-fluoro-1'-(1H-indazole-5-carbonyl)-2-oxospiro[indole-3,4'-piperidine]-1-yl]-N-(2,2-difluorocyclopropyl)acetamide;

4-Bromo-1-[2-[3-(fluoromethyl)-4-(trifluoromethyl)pyrrolidin-1-yl]-2-oxoethyl]-1'-(1H-indazole-5-carbonyl)spiro[indole-3,4'-piperidine]-2-one;

4-Chloro-5-fluoro-1'-(1H-indazole-5-carbonyl)-1-[2-(2-oxa-7-azaspiro[3.4]octan-7-yl)-2-oxoethyl]spiro[indole-3,4'-piperidine]-2-one;

4-Bromo-1-[2-[(3R,4S)-3,4-difluoropyrrolidin-1-yl]-2-oxoethyl]-1'-(1H-indazole-5-carbonyl)spiro[indole-3,4'-piperidine]-2-one;

4-Bromo-1-[2-(3,4-dihydro-1H-pyrrolo[1,2-a]pyrazin-2-yl)-2-oxoethyl]-1'-(1H-indazole-5-carbonyl)spiro[indole-3,4'-piperidine]-2-one;

4-Bromo-1-[2-[(2S)-4,4-difluoro-2-(fluoromethyl)pyrrolidin-1-yl]-2-oxoethyl]-1'-(1H-indazole-5-carbonyl)spiro[indole-3,4'-piperidine]-2-one;

Methyl 5-[4-chloro-5-fluoro-2-oxo-1-[2-oxo-2-(2,2,2-trifluoroethylamino)ethyl]spiro[indole-3,4'-piperidine]-1'-carbonyl]-1H-indazole-3-carboxylate;

5-[4-Chloro-5-fluoro-2-oxo-1-[2-oxo-2-(2,2,2-trifluoroethylamino)ethyl]spiro[indole-3,4'-piperidine]-1'-carbonyl]-1H-indazole-3-carboxylic acid;

2-[4-Chloro-2-oxo-1'-(1H-pyrazolo[3,4-b]pyridine-5-carbonyl)spiro[indole-3,3'-pyrrolidine]-1-yl]-N-(2,2,2-trifluoroethyl)acetamide;

2-[4-Chloro-1'-(1H-indazole-5-carbonyl)-2-oxospiro[indole-3,3'-pyrrolidine]-1-yl]-N-(2,2,2-trifluoroethyl)acetamide;

2-[4-Chloro-2-oxo-1'-(1H-pyrazolo[4,3-b]pyridine-5-carbonyl)spiro[indole-3,3'-pyrrolidine]-1-yl]-N-(2,2,2-trifluoroethyl)acetamide;

(+) or (−)-2-[4-Chloro-1'-(1H-indazole-5-carbonyl)-2-oxospiro[indole-3,3'-pyrrolidine]-1-yl]-N-(2,2,2-trifluoroethyl)acetamide;

(−) or (+)-2-[4-Chloro-1'-(1H-indazole-5-carbonyl)-2-oxospiro[indole-3,3'-pyrrolidine]-1-yl]-N-(2,2,2-trifluoroethyl)acetamide; and 4,5-Dichloro-1-(2-oxo-2-(2-(2,2,2-trifluoroethyl)pyrrolidin-1-yl)ethyl)-1'-(1H-pyrazolo[4,3-b]pyridine-5-carbonyl)spiro[indoline-3,4'-piperidin]-2-one, or a pharmaceutically acceptable salt thereof.

33. A process for the manufacture of a compound of formula (I), or a pharmaceutically acceptable salt thereof, according to claim 1, comprising the amide coupling of a compound of formula (III) with an optionally protected carboxylic acid of formula $R^6COOH$, wherein L, W, X, Y, Z, v, w, $R^1$ and $R^6$ are according to claim 1

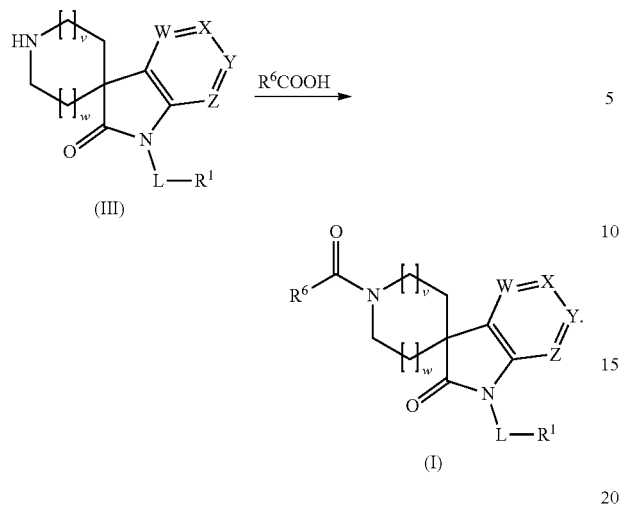
34. A pharmaceutical composition comprising a compound of formula (I), or a pharmaceutically acceptable salt thereof, according to claim 1 and at least one pharmaceutically acceptable excipient.
* * * * *